United States Patent
Lacy et al.

(10) Patent No.: US 9,670,276 B2
(45) Date of Patent: Jun. 6, 2017

(54) IL-1 BINDING PROTEINS

(71) Applicant: AbbVie Inc., North Chicago, IL (US)

(72) Inventors: Susan E. Lacy, Westborough, MA (US); Lorenzo Benatuil, Northborough, MA (US); Meha Chhaya, Strewsbury, MA (US); Emma Fung, Northborough, MA (US); Renee Miller, N. Grosvenordale, CT (US); Ravi Chari, Norwich, CT (US); Sarah J. Heighton, Leominster, MA (US); Jacqueline G. Bixby, Auburn, MA (US)

(73) Assignee: AbbVie Inc., North Chicago, IL (US)

( * ) Notice: Subject to any disclaimer, the term of this patent is extended or adjusted under 35 U.S.C. 154(b) by 58 days.

(21) Appl. No.: 13/940,506

(22) Filed: Jul. 12, 2013

(65) Prior Publication Data
US 2014/0178389 A1     Jun. 26, 2014

Related U.S. Application Data

(60) Provisional application No. 61/670,834, filed on Jul. 12, 2012.

(51) Int. Cl.
C12P 21/08     (2006.01)
A61K 39/395    (2006.01)
(Continued)

(52) U.S. Cl.
CPC ...... *C07K 16/245* (2013.01); *A61K 2039/505* (2013.01); *C07K 2317/24* (2013.01);
(Continued)

(58) Field of Classification Search
None
See application file for complete search history.

(56) References Cited

U.S. PATENT DOCUMENTS 4,526,938 A    7/1985  Churchill et al.
4,554,101 A   11/1985  Hopp
(Continued)

FOREIGN PATENT DOCUMENTS

AU    2012200225 A1    2/2012
EP    0 471 293 A2     2/1992
(Continued)

OTHER PUBLICATIONS

Rudikoff et al., Proc Natl Acad Sci USA 79: 1979-1983, 1982.*
(Continued)

*Primary Examiner* — Christine J Saoud
*Assistant Examiner* — Jegatheesan Seharaseyon
(74) *Attorney, Agent, or Firm* — Sterne, Kessler, Goldstein & Fox P.L.L.C.

(57) ABSTRACT

The disclosure provides binding proteins that specifically bind to IL-1α and IL-1β. These binding proteins can be organized into DVD-Igs. These proteins can be used to modulate the activity of IL-1α and/or IL-1β and can be used for the treatment immunological diseases such as rheumatoid arthritis, osteoarthritis, psoriasis, multiple sclerosis, and other autoimmune diseases. In addition, their uses in the amelioration and/or treatment of pain in an individual suffering from a disease or disorder associated with IL-1 accumulation.

24 Claims, 5 Drawing Sheets

(51) Int. Cl.
  *C07K 16/24* (2006.01)
  *A61K 39/00* (2006.01)
(52) U.S. Cl.
  CPC ...... C07K 2317/33 (2013.01); C07K 2317/56 (2013.01); C07K 2317/60 (2013.01); C07K 2317/622 (2013.01); C07K 2317/76 (2013.01); C07K 2317/92 (2013.01)

(56) References Cited

U.S. PATENT DOCUMENTS

| | | |
|---|---|---|
| 4,699,784 A | 10/1987 | Shih et al. |
| 4,753,894 A | 6/1988 | Frankel et al. |
| 4,816,397 A | 3/1989 | Boss et al. |
| 4,816,567 A | 3/1989 | Cabilly et al. |
| 4,943,533 A | 7/1990 | Mendelsohn et al. |
| 4,946,778 A | 8/1990 | Ladner et al. |
| 4,980,286 A | 12/1990 | Morgan et al. |
| 5,006,309 A | 4/1991 | Khalil et al. |
| 5,063,081 A | 11/1991 | Cozzette et al. |
| 5,089,424 A | 2/1992 | Khalil et al. |
| 5,128,326 A | 7/1992 | Balazs et al. |
| 5,135,875 A | 8/1992 | Meucci et al. |
| 5,223,409 A | 6/1993 | Ladner et al. |
| 5,225,539 A | 7/1993 | Winter |
| 5,241,070 A | 8/1993 | Law et al. |
| 5,242,828 A | 9/1993 | Bergstrom et al. |
| 5,258,498 A | 11/1993 | Huston et al. |
| 5,290,540 A | 3/1994 | Prince et al. |
| 5,294,404 A | 3/1994 | Grandone et al. |
| 5,352,803 A | 10/1994 | Mattingly |
| 5,359,093 A | 10/1994 | Adamczyk et al. |
| 5,403,484 A | 4/1995 | Ladner et al. |
| 5,427,908 A | 6/1995 | Dower et al. |
| 5,468,646 A | 11/1995 | Mattingly et al. |
| 5,496,925 A | 3/1996 | Mattingly |
| 5,500,362 A | 3/1996 | Robinson et al. |
| 5,516,637 A | 5/1996 | Huang et al. |
| 5,530,101 A | 6/1996 | Queen et al. |
| 5,543,524 A | 8/1996 | Mattingly et al. |
| 5,558,864 A | 9/1996 | Bendig et al. |
| 5,565,332 A | 10/1996 | Hoogenboom et al. |
| 5,565,352 A | 10/1996 | Hochstrasser et al. |
| 5,571,698 A | 11/1996 | Ladner et al. |
| 5,573,904 A | 11/1996 | Mattingly |
| 5,580,717 A | 12/1996 | Dower et al. |
| 5,585,089 A | 12/1996 | Queen et al. |
| 5,593,896 A | 1/1997 | Adamczyk et al. |
| 5,624,821 A | 4/1997 | Winter et al. |
| 5,627,052 A | 5/1997 | Schrader et al. |
| 5,641,870 A | 6/1997 | Rinderknecht et al. |
| 5,648,260 A | 7/1997 | Winter et al. |
| 5,658,727 A | 8/1997 | Barbas et al. |
| 5,677,171 A | 10/1997 | Hudziak et al. |
| 5,679,377 A | 10/1997 | Bernstein et al. |
| 5,693,762 A | 12/1997 | Queen et al. |
| 5,698,426 A | 12/1997 | Huse et al. |
| 5,714,350 A | 2/1998 | Co et al. |
| 5,714,352 A | 2/1998 | Jakobovits et al. |
| 5,723,323 A | 3/1998 | Kauffman et al. |
| 5,733,743 A | 3/1998 | Johnson et al. |
| 5,736,137 A | 4/1998 | Anderson et al. |
| 5,763,192 A | 6/1998 | Kauffman et al. |
| 5,766,886 A | 6/1998 | Studnicka et al. |
| 5,780,225 A | 7/1998 | Wigler et al. |
| 5,783,699 A | 7/1998 | Mattingly et al. |
| 5,789,554 A | 8/1998 | Leung et al. |
| 5,807,715 A | 9/1998 | Morrison et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,855,913 A | 1/1999 | Hanes et al. |
| 5,874,064 A | 2/1999 | Edwards et al. |
| 5,891,996 A | 4/1999 | Mateo de Acosta del Rio et al. |
| 5,912,015 A | 6/1999 | Bernstein et al. |
| 5,916,597 A | 6/1999 | Lee et al. |
| 5,916,771 A | 6/1999 | Hori et al. |
| 5,934,272 A | 8/1999 | Lloyd et al. |
| 5,939,598 A | 8/1999 | Kucherlapati et al. |
| 5,959,083 A | 9/1999 | Bosslet et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,615 A | 11/1999 | Jakobovits et al. |
| 5,989,463 A | 11/1999 | Tracy et al. |
| 5,998,209 A | 12/1999 | Jakobovits et al. |
| 6,019,968 A | 2/2000 | Platz et al. |
| 6,075,181 A | 6/2000 | Kucherlapati et al. |
| 6,091,001 A | 7/2000 | Jakobovits et al. |
| 6,114,598 A | 9/2000 | Kucherlapati et al. |
| 6,130,364 A | 10/2000 | Jakobovits et al. |
| 6,180,370 B1 | 1/2001 | Queen et al. |
| 6,204,023 B1 | 3/2001 | Robinson et al. |
| 6,225,047 B1 | 5/2001 | Hutchens et al. |
| 6,235,883 B1 | 5/2001 | Jakobovits et al. |
| 6,258,562 B1 | 7/2001 | Salfeld et al. |
| 6,329,209 B1 | 12/2001 | Wagner et al. |
| 6,350,861 B1 | 2/2002 | Co et al. |
| 6,506,883 B2 | 1/2003 | Meteo de Acosta del Rio et al. |
| 6,660,843 B1 | 12/2003 | Feige et al. |
| 6,699,658 B1 | 3/2004 | Wittrup et al. |
| 6,914,128 B1 | 7/2005 | Salfeld et al. |
| 7,247,301 B2 | 7/2007 | van de Winkel et al. |
| 7,262,028 B2 | 8/2007 | Van Berkel et al. |
| 7,491,516 B2 | 2/2009 | Collinson et al. |
| 7,612,181 B2 * | 11/2009 | Wu ...... C07K 16/245 424/178.1 |
| 8,258,268 B2 | 9/2012 | Wu et al. |
| 8,398,966 B2 * | 3/2013 | Wu ...... A61K 39/3955 424/85.2 |
| 8,664,367 B2 * | 3/2014 | Wu ...... A61K 9/0019 530/387.3 |
| 8,735,546 B2 | 5/2014 | Ghayur et al. |
| 8,841,417 B2 * | 9/2014 | Wu ...... A61K 9/0019 424/133.1 |
| 8,853,365 B2 | 10/2014 | Wu et al. |
| 9,035,027 B2 | 5/2015 | Ghayur et al. |
| 9,303,085 B2 | 4/2016 | Wu et al. |
| 9,409,986 B2 | 8/2016 | Wu et al. |
| 9,441,038 B2 | 9/2016 | Wu et al. |
| 9,447,183 B2 | 9/2016 | Wu et al. |
| 9,447,184 B2 | 9/2016 | Wu et al. |
| 2002/0137134 A1 | 9/2002 | Gerngross |
| 2003/0091561 A1 | 5/2003 | van de Winkel et al. |
| 2003/0170881 A1 | 9/2003 | Davis et al. |
| 2003/0186374 A1 | 10/2003 | Hufton et al. |
| 2004/0018577 A1 | 1/2004 | Emerson Campbell et al. |
| 2004/0018590 A1 | 1/2004 | Gerngross |
| 2005/0042664 A1 | 2/2005 | Wu et al. |
| 2005/0054078 A1 | 3/2005 | Miller et al. |
| 2005/0147610 A1 | 7/2005 | Ghayur et al. |
| 2006/0104968 A1 | 5/2006 | Bookbinder et al. |
| 2006/0160164 A1 | 7/2006 | Miller et al. |
| 2006/0228358 A1 | 10/2006 | Lawson et al. |
| 2007/0041905 A1 | 2/2007 | Hoffman et al. |
| 2007/0071675 A1 | 3/2007 | Wu et al. |
| 2007/0081996 A1 | 4/2007 | Hoffman et al. |
| 2008/0020401 A1 | 1/2008 | Grenier et al. |
| 2008/0118506 A1 | 5/2008 | Wu et al. |
| 2008/0248493 A1 | 10/2008 | Mattingly et al. |
| 2009/0215992 A1 | 8/2009 | Wu et al. |
| 2009/0232736 A1 | 9/2009 | Collinson et al. |
| 2009/0291081 A1 | 11/2009 | Hsieh et al. |
| 2009/0311253 A1 | 12/2009 | Ghayur et al. |
| 2010/0047239 A1 | 2/2010 | Wu et al. |
| 2010/0099103 A1 | 4/2010 | Hsieh et al. |
| 2010/0167301 A1 | 7/2010 | Collier et al. |
| 2010/0221179 A1 | 9/2010 | Wu et al. |
| 2011/0016506 A1 | 1/2011 | Lu et al. |
| 2011/0076722 A1 | 3/2011 | Takahashi |
| 2011/0280800 A1 | 11/2011 | Wu et al. |
| 2013/0004416 A1 | 1/2013 | Wu et al. |

(56) References Cited

U.S. PATENT DOCUMENTS

| | | |
|---|---|---|
| 2013/0295004 A1 | 11/2013 | Hsieh et al. |
| 2014/0100359 A1 | 4/2014 | Wu et al. |
| 2014/0154256 A1 | 6/2014 | Wu et al. |
| 2014/0213768 A1 | 7/2014 | Wu et al. |
| 2014/0219912 A1 | 8/2014 | Ghayur et al. |
| 2014/0220019 A1 | 8/2014 | Ghayur et al. |
| 2014/0234208 A1 | 8/2014 | Ghayur et al. |
| 2014/0296493 A1 | 10/2014 | Hoffman et al. |
| 2014/0335014 A1 | 11/2014 | Ghayur et al. |
| 2014/0377805 A1 | 12/2014 | Wu et al. |
| 2014/0377858 A1 | 12/2014 | Wu et al. |
| 2015/0004167 A1 | 1/2015 | Wu et al. |
| 2015/0056202 A1 | 2/2015 | Wu et al. |
| 2015/0086554 A1 | 3/2015 | Wu et al. |
| 2015/0093387 A1 | 4/2015 | Wu et al. |
| 2015/0147327 A1 | 5/2015 | Wu et al. |
| 2015/0315283 A1 | 11/2015 | Ghayur et al. |

FOREIGN PATENT DOCUMENTS

| | | |
|---|---|---|
| EP | 0 517 024 A2 | 12/1992 |
| EP | 0 592 106 A1 | 4/1994 |
| EP | 0 239 400 B1 | 8/1994 |
| EP | 1 176 195 A2 | 1/2002 |
| EP | 1 444 268 A2 | 5/2003 |
| EP | 0 592 106 B1 | 11/2004 |
| EP | 0 519 596 B1 | 2/2005 |
| JP | 2009504191 A | 2/2009 |
| WO | 90/02809 A1 | 3/1990 |
| WO | 90/05144 A1 | 5/1990 |
| WO | 90/14424 A1 | 11/1990 |
| WO | 90/14430 A1 | 11/1990 |
| WO | 90/14443 A2 | 11/1990 |
| WO | 91/05548 A1 | 5/1991 |
| WO | 91/09967 A1 | 7/1991 |
| WO | 91/10737 A1 | 7/1991 |
| WO | 91/10741 A1 | 7/1991 |
| WO | 91/17271 A1 | 11/1991 |
| WO | 92/01047 A1 | 1/1992 |
| WO | 92/02551 A1 | 2/1992 |
| WO | 92/03461 A1 | 3/1992 |
| WO | 92/09690 A1 | 6/1992 |
| WO | 92/11272 A1 | 7/1992 |
| WO | 92/15679 A1 | 9/1992 |
| WO | 92/18619 A1 | 10/1992 |
| WO | 92/19244 A1 | 11/1992 |
| WO | 92/20791 A1 | 11/1992 |
| WO | 92/22324 A1 | 12/1992 |
| WO | 93/01288 A1 | 1/1993 |
| WO | 93/06213 A1 | 4/1993 |
| WO | 93/11236 A1 | 6/1993 |
| WO | 94/02602 A1 | 2/1994 |
| WO | 94/18219 A1 | 8/1994 |
| WO | 95/01997 A1 | 1/1995 |
| WO | 95/15982 A2 | 6/1995 |
| WO | 95/20045 A1 | 7/1995 |
| WO | 95/20401 A1 | 8/1995 |
| WO | 96/20698 A2 | 7/1996 |
| WO | 96/33735 A1 | 10/1996 |
| WO | 96/34096 A1 | 10/1996 |
| WO | 96/40210 A1 | 12/1996 |
| WO | 97/20032 A1 | 6/1997 |
| WO | 97/29131 A1 | 8/1997 |
| WO | 97/32572 A2 | 9/1997 |
| WO | 97/44013 A1 | 11/1997 |
| WO | 98/16654 A1 | 4/1998 |
| WO | 98/24893 A2 | 6/1998 |
| WO | 98/31346 A1 | 7/1998 |
| WO | 98/31700 A1 | 7/1998 |
| WO | 98/50433 A1 | 11/1998 |
| WO | 99/06834 A2 | 2/1999 |
| WO | 99/15154 A1 | 4/1999 |
| WO | 99/20253 A1 | 4/1999 |
| WO | 99/45031 A2 | 9/1999 |
| WO | 99/51773 A1 | 10/1999 |
| WO | 99/53049 A1 | 10/1999 |
| WO | 99/54342 A1 | 10/1999 |
| WO | 99/66903 A2 | 12/1999 |
| WO | 00/09560 A2 | 2/2000 |
| WO | 00/34337 A1 | 6/2000 |
| WO | 00/37504 A2 | 6/2000 |
| WO | 00/56772 A1 | 9/2000 |
| WO | 00/56934 A1 | 9/2000 |
| WO | 01/62931 A2 | 8/2001 |
| WO | 01/77342 A1 | 10/2001 |
| WO | 01/83525 A2 | 11/2001 |
| WO | 01/88138 A1 | 11/2001 |
| WO | 02/02773 A2 | 1/2002 |
| WO | 02/072636 A2 | 9/2002 |
| WO | 03/016466 A2 | 2/2003 |
| WO | 03/035835 A2 | 5/2003 |
| WO | 03/039486 A2 | 5/2003 |
| WO | 2004/056312 A2 | 7/2004 |
| WO | 2004/078140 A2 | 9/2004 |
| WO | 2005/100584 A2 | 10/2005 |
| WO | 2005/111082 A1 | 11/2005 |
| WO | 2007/024715 A9 | 3/2007 |
| WO | 2007/124299 A2 | 11/2007 |
| WO | 2008/082984 A2 | 7/2008 |
| WO | WO2008/055206 A2 | 8/2008 |
| WO | 2009/131239 A1 | 10/2009 |
| WO | 2010/078443 A1 | 7/2010 |
| WO | WO2011047266 A1 | 4/2011 |
| WO | WO2014011955 A2 | 1/2014 |

OTHER PUBLICATIONS

Colman, Research in Immunology 145: 33-36, 1994.*
Kussie et al., J. Immunol. 152: 146-152, 1994.*
Chen et al., EMBO J., 14: 2784-2794, 1995.*
U.S. Appl. No. 13/775,540, filed Feb. 25, 2013, Chung-ming Hsieh.
U.S. Appl. No. 13/940,506, filed Jul. 12, 2013, Susan E. Lacy.
Adamczyk and Mattingly, "Chemiluminescent N-Sulfonylacridinium-9-Carboxamides and Their Application in Clinical Assays," Chapter 5, In Luminescence Biotechnology: Instruments and Applications; (Dyke, K.V., ed.) (CRC Press LLC, Boca Raton, 2002) pp. 77-105.
Adamczyk et al., "Homogeneous chemiluminescent assays for free choline in human plasma and whole blood," Anal. Chim. Acta, 579(1): 61-67 (2006).
Adamczyk et al., "Linker-mediated modulation of the chemiluminescent signal from N10-(3-sulfopropyl)-N-sulfonylacridinium-9-carboxamide tracers," Bioconjugate Chem., 11: 714-724 (2000).
Adamczyk et al., "Chemiluminescent acridinium-9-carboxamide boronic acid probes: Application to a homogeneous glycated hemoglobin assay," Bioorg. Med. Chem. Lett., 16: 1324-1328 (2006).
Adamczyk et al., "Chemiluminescence quenching of pteroic acid-N-sulfonyl-acridinium-9-carboxamide conjugates by folate binding protein," Bioorg. Med. Chem. Lett., 14: 2313-2317 (2004).
Adamczyk et al., "Intrinsic factor-mediated modulation of cyanocobalamin-N-sulfonyl-acridinium-9-carboxamide chemiluminescence," Biorg. Med. Chem. Lett., 14: 3917-3921 (2004).
Adamczyk et al., "Neopentyl 3-triflyloxypropanesulfonate. A reactive sulfopropylation reagent for the preparation of chemiluminescent labels," J. Org. Chem., 63: 5636-5639 (1998).
Adamczyk et al., "Synthesis of a chemiluminescent acridinium hydroxylamine (AHA) for the direct detection of abasic sites in DNA," Org. Lett., 1: 779-781 (1999).
Adamczyk et al., "Regiodependent luminescence quenching of biotinylated N-sulfonyl-acridinium-9-carboxamides by avidin," Org. Lett., 5: 3779-3782 (2003).
Adamczyk et al., "Modulation of the chemiluminescent signal from N10-(3-sulfopropyl)-N-sulfonylacridinium-9-carboxamides," Tetrahedron, 55: 10899-10914 (1999).
Ames et al., "Conversion of murine Fabs isolated from a combinatorial phage display library to full length immunoglobulins," J. Immunol. Methods, 184: 177-186 (1995).

(56) References Cited

OTHER PUBLICATIONS

Anthony et al., "Recapitulation of IVIG anti-inflammatory activity with a recombinant IgG Fc," Science, 320: 373-376 (2008).
Aoki et al., "Endothelial Progenitor Cell Capture by Stents Coated with Antibody Against CD34," J. Am. Coll. Cardiol., 45(10): 1574-1579 (2005).
Arancio et al., "RAGE potentiates AP-induced perturbation of neuronal function in transgenic mice," EMBO J., 23: 4096-4105 (2004).
Auron et al., "Human and murine interleukin 1 possess sequence and structural similarities," J. Mol. Cell Immunol., 2: 169-177 (1985).
Auron et al., "Nucleotide sequence of human monocyte interleukin 1 precursor cDNA," Proc. Natl. Acad. Sci. USA, 81: 7907-7911 (1984).
Azzazy et al., "Phage display technology: clinical applications and recent innovations," Clin. Biochem., 35: 425-445 (2002).
Babcook et al., "A novel strategy for generating monoclonal antibodies from single, isolated lymphocytes producing antibodies of defined specificities," Proc. Natl. Acad. Sci. USA, 93: 7843-7848 (1996).
Barbas et al., "Assembly of combinatorial antibody libraries on phage surfaces: The gene III site," Proc. Natl. Acad. Sci. USA, 88: 7978-7982 (1991).
Barbas et al., "In vitro evolution of a neutralizing human antibody to human immunodeficiency virus type 1 to enhance affinity and broaden strain cross-reactivity," Proc. Natl. Acad. Sci. USA, 91: 3809-3813 (1994).
Baslund, Bo et al., "Targeting interleukin-15 in patients with rheumatoid arthritis," Arthritis Rheum., 52(9): 2686-2692 (2005).
Baumgartner et al., "Double blind, placebo controlled trial of tumor necrosis factor receptor fusion protein (TNFR:Fc) in active rheumatoid arthritis," J. Invest. Med.,vol. 44, No. 3, 235A (Saturday Morning Concurrent Sessions) (Mar. 1996).
Bessis et al., "Use of hollow fibers filled with cells engineered to secrete IL-4 or IL-13 for treatment of experimental arthritis," (Abstract No. 1681), Arthritis Rheum., vol. 39, No. 9 (supplement), S308 (1996).
Better et al., "*Escherichia coli* Secretion of an Active Chimeric Antibody Fragment," Science, 240: 1041-1043 (1988).
Biewenga et al., "IgAl half molecules in human multiple myeloma and the in vitro production of similar fragments from intact IgAl molecules," Clin. Exp. Immunol., 51: 395-400 (1983).
Bird et al., "Single-Chain Antigen-Binding Proteins," Science, 242: 423-426 (1988).
Boado et al., "Fusion antibody for Alzheimer's Disease with bidirectional transport across the blood-brain barrier and A6 fibril disaggregation," Bioconjug. Chem., 18(2): 447-455 (2007).
Bornemann et al., "AP-Induced Inflammatory Processes in Microglia Cells of APP23 Transgenic Mice," Am. J. Pathol., 158(1): 63-73 (2001).
Boyce et al., "No audible wheezing: nuggets and conundrums from mouse asthma models," J. Exp. Med., 201(12): 1869-1873 (2005).
Brand, D.D., "Rodent Models of Rheumatoid Arthritis," Comparative Medicine, 55(2): 114-122 (2005).
Brinkmann et al., "Phage display of disulfide-stabilized Fv fragments," J. Immunol. Methods, 182: 41-50 (1995).
Bruncko et al., "Studies leading to potent, dual inhibitors of Bcl-2 and Bcl-xL," J. Med. Chem., 50(4): 641-662 (2007).
Buchwald et al., "Long-term, continuous intravenous heparin administration by an implantable infusion pump in ambulatory patients with recurrent venous thrombosis," Surgery, 88: 507-516 (1980).
Buras et al., "Animal Models of Sepsis: Setting the Stage," Nat. Rev. Drug. Discovery, 4: 854-865 (2005).
Burke et al., "Zotarolimus (ABT-578) eluting stents," Adv. Drug Del. Rev., 58: 437-446 (2006).
Burton et al., "Human Antibodies from Combinatorial Libraries," Adv. Immunol., 57: 191-280 (1994).

Calandra et al., "Protection from septic shock by neutralization of macrophage migration inhibitory factor," Nature Med., 6(2): 164-170 (2000).
Carroll et al., "The selection of high-producing cell lines using flow cytometry and cell sorting," Expert Opin. Biol. Ther., 4: 1821-1829 (2004).
Carter et al., "Humanization of an anti-p185HER2antibody for human cancer therapy," Proc. Natl. Acad. Sci. USA, 89: 4285-4289 (1992).
Chakravarty et al., "Thermal ablation of tumor cells with antibody-functionalized single-walled carbon nanotubes," Proc. Natl. Acad. Sci. USA, 105: 8697-8702 (2008).
Chikanza et al., "Treatment of patients with rheumatoid arthritis with RP73401 phosphodiesterase Type IV inhibitor," (Abstract No. 1527), Arthritis Rheum., vol. 39, No. 9 (supplement), S282 (1996).
Choi et al., "Recombinant chimeric OKT3 scFv IgM antibodies mediate immune suppression while reducing T cell activation in vitro," Eur. J. Immunol., 31(1): 94-106 (2001).
Chothia et al., "Canonical Structures for the Hypervariable Regions of Immunoglobulins," J. Mol. Biol., 196: 901-917 (1987).
Chothia et al., "Structural repertoire of the human VH segments," J. Mol. Biol., 227: 799-817 (1992).
Chothia et al., "Conformations of immunoglobulin hypervariable regions," Nature, 342: 877-883 (1989).
Clackson et al., "Making antibody fragments using phage display libraries," Nature, 352: 624-628 (1991).
Cleek et al., "Biodegradable Polymeric Carriers for a bFGF Antibody for Cardiovascular Application," Proceed. Intl. Symp. Control. Rel. Bioact. Mater., 24: 853-854 (1997).
Co et al., "Genetically Engineered Deglycosylation of the Variable Domain Increases the Affinity of an Anti-CD33 Monoclonal Antibody," Mol. Immunol., 30(15): 1361-1367 (1993).
Coffman et al., "Nonhuman primate models of asthma," J. Exp. Med., 201(12): 1875-1879 (2005).
Coloma et al., "Transport across the primate blood-brain barrier of a genetically engineered chimeric monoclonal antibody to the human insulin receptor," Pharm Res., 17(3): 266-274 (2000).
Cox et al., "Measurement of cytokine release at the single cell level using the ELISPOT assay," Methods, 38(4): 274-282 (2006).
Dall'Acqua et al., "Contribution of Domain Interface Residues to the Stability of Antibody CH3 Domain Homodimers," Biochemistry, 37: 9266-9273 (1998).
Dall'Acqua et al., "Increasing the affinity of a human IgG1 for the neonatal Fc receptor: biological consequences," J. Immunol., 169(9): 5171-5180 (2002).
Dall'Acqua et al., "Properties of human IgGls engineered for enhanced binding to the neonatal Fc receptor (FcRn)," J. Biol. Chem., 281: 23514-23524 (2006).
Deane et al., "RAGE mediates amyloid-I3 peptide transport across the blood-brain barrier and accumulation in brain," Nature Med., 9(7): 907-913 (2003).
DeLuca et al., "Marine and botanical lipids as immunomodulatory and therapeutic agents in the treatment of rheumatoid arthritis," Rheum. Dis. Clin. North Am., 21: 759-777 (1995).
Descotes J., "Immunotoxicology of Immunomodulators," Develop. Biol. Standard, 77: 99-102 (1992).
Desmet et al., "Anchor profiles of HLA-specific peptides: analysis by a novel affinity scoring method and experimental validation," Proteins, 58: 53-69 (2005).
Dickson, B.J., "Molecular Mechanisms of Axon Guidance," Science, 298: 1959-1964 (2002).
Dinarello et al., "Measurement of soluble and membrane-bound interleukin 1 using a fibroblast bioassay," Unit 6.2, In Current Protocols in Immunology, 6:1 (2000).
Dinarello, C.A., "The interleukin-1 family: 10 years of discovery," FASEB J., 8(15): 1314-1325 (1994).
Domeniconi et al., "Overcoming inhibitors in myelin to promote axonal regeneration," J. Neurological Sciences, 233: 43-47 (2005).
Dunn et al., "Annotating genes with potential roles in the immune system: six new members of the IL 1 family," Trends Immunol., 22(10): 533-536 (2001).

(56) References Cited

OTHER PUBLICATIONS

During et al., "Controlled Release of Dopamine from a Polymeric Brain Implant: In Vivo Characterization," Ann. Neurol., 25(4): 351-356 (1989).
Durocher et al., "High-level and high-throughput recombinant protein production by transient transfection of suspension-growing human 293-EBNA1 cells," Nucl. Acids Res., 30(2e9): 1-9 (2002).
Economides et al., "Cytokine traps: multi-component, high-affinity blockers of cytokine action," Nature Med., 9(1): 47-52 (2003).
Ehrich et al., "Demonstration of selective COX-2 inhibition by MK-966 in humans," (Abstract No. 328), Arthritis Rheum., vol. 39, No. 9 (supplement), S81 (1996).
Ehrich et al., "Efficacy of MK-966, a highly selective inhibitor of COX-2, in the treatment of postoperative dental pain," (Abstract No. 329), Arthritis Rheum., vol. 39, No. 9 (supplement), S81 (1996).
Evans et al., "Efficacy of tumor necrosis factor binding protein (TNF-bp) in the streptococcal cell wall-induced reactivation model of arthritis," (Abstract No. 1540), Arthritis Rheum., vol. 39, No. 9 (supplement), S284 (1996).
Farr et al., "Sulphasalazine (SASP) in rheumatoid arthritis (RA): a 5 year prospective study," (Abstract No. 1519), Arthritis Rheum., vol. 39, No. 9 (supplement), S281 (1996).
Fiebich et al., "Effects of NSAIDs on IL-1-beta-induced IL-6 mRNA and protein synthesis in human astrocytoma cells," NeuroReport, vol. 7, 1209-1213 (1996).
Finnegan et al., "Leflunomide inhibits immunoglobulin production by two separate mechanisms," (Abstract No. 627), Arthritis Rheum., vol. 39, No. 9 (supplement), S131 (1996).
Foote and Winter, "Antibody framework residues affecting the conformation of the hypervariable loops," J. Mol. Biol., 224: 487-499 (1992).
Fuchs et al., "Targeting Recombinant Antibodies to the Surface of *Escherichia coli*: Fusion to a Peptidoglycan Associated Lipoprotein," Bio/Technology, 9: 1369-1372 (1991).
Garrard et al., "FAB Assembly and Enrichment in a Monovalent Phage Display System," Bio/Technology, 9: 1373-1377 (1991).
Gavilondo et al., "Antibody Engineering at the Millennium," BioTechniques, 29: 128-145 (2000).
Genain et al., "Creation of a model for multiple sclerosis in *Callithrix jacchus* marmosets," J. Mol. Med., 75(3): 187-197 (1997).
Genovese et al., "Abatacept for Rheumatoid Arthritis Refractory to Tumor Necrosis Factor a Inhibition," N. Engl. J. Med., 353: 1114-1123 (2005).
Ghetie et al., "Increasing the serum persistence of an IgG fragment by random mutagenesis," Nature Biotechnol., 15(7): 637-640 (1997).
Giege et al., Chapter 1, In Crystallization of Nucleic Acids and Proteins, A Practical Approach, 2nd ed., (Ducruix and Giege, eds.) (Oxford University Press, New York, 1999) pp. 1-16.
Gillies et al., "High-level expression of chimeric antibodies using adapted cDNA variable region cassettes," J. Immunol. Methods, 125: 191-202 (1989).
Goldspiel et al., "Human Gene Therapy," Clin. Pharm., 12: 488-505 (1993).
Goodson, J.M., Chapter 6, In Medical Applications of Controlled Release, vol. II, Applications and Evaluation, (Langer and Wise, eds.) (CRC Press, Inc., Boca Raton, 1984), pp. 115-138.
Gram et al., "In vitro selection and affinity maturation of antibodies from a naive combinatorial immunoglobulin library," Proc. Natl. Acad. Sci. USA, 89: 3576-3580 (1992).
Green et al., "Antigen-specific human monoclonal antibodies from mice engineered with human Ig heavy and light chain YACs," Nature Genetics, 7: 13-21 (1994).
Green et al., "Regulation of B Cell Development by Variable Gene Complexity in Mice Reconstituted with Human Immunoglobulin Yeast Artificial Chromosomes," J. Exp. Med., 188(3): 483-495 (1998).
Griffiths et al., "Human anti-self antibodies with high specificity from phage display libraries," EMBO J., 12(2): 725-734 (1993).
Guttadauria, M., "Tenidap in Rheumatoid Arthritis Collaborative International Study (TRACIS): a 6-month interim analysis," (Abstract No. 1516), Arthritis Rheum., vol. 39, No. 9 (supplement), S280 (1996).
Hammerling et al., eds., "Monoclonal Antibodies and T-Cell Hybridomas," In Research Monographs in Immunology, vol. 3 (J.L. Turk, General Editor) (Elsevier, New York, 1981), pp. 563-587.
Hara et al., "Therapeutic effect of T-614, a new anti-arthritic agent, on rheumatoid arthritis," (Abstract No. 1526), Arthritis Rheum., vol. 39, No. 9 (supplement), S282 (1996).
Harriman et al., "Summary of clinical trials in rheumatoid arthritis using infliximab, an anti-TNFa treatment," Ann. Rheum. Dis., 58: (Suppl. I) I 61-I 64 (1999).
Hart et al., "Preclinical efficacy and safety of mepolizumab (SB-240563), a humanized monoclonal antibody to IL-5, in cynomolgus monkeys," J. Allergy Clin. Immunol., 108(2): 250-257 (2001).
Hawkins et al., "Selection of Phage Antibodies by Binding Affinity Mimicking Affinity Maturation," J. Mol. Biol., 226: 889-896 (1992).
Hay et al., "Bacteriophage cloning and *Escherichia coli* expression of a human IgM Fab," Hum. Antibod. Hybridomas, 3: 81-85 (1992).
Hickey et al., "The Rheumatoid Arthritis Azathioprine Registry (RAAR)—interim analysis of malignancy and mortality," (Abstract No. 1521), Arthritis Rheum., vol. 39, No. 9 (supplement), S281 (1996).
Hildebrand et al., "Surface coatings for biological activation and functionalization of medical devices," Surface & Coatings Technology, 200: 6318-6324 (2006).
Hinton et al., "Engineered human IgG antibodies with longer serum half-lives in primates," J. Biol. Chem. 279(8): 6213-6216 (2004).
Holliger et al., "'Diabodies': Small bivalent and bispecific antibody fragments," Proc. Natl. Acad. Sci. USA, 90: 6444-6448 (1993).
Holliger et al., "Diabodies: small bispecific antibody fragments," Cancer Immunol. Immunother., 45: 128-130 (1997).
Hoogenboom et al., "Multi-subunit proteins on the surface of filamentous phage: methodologies for displaying antibody (Fab) heavy and light chains," Nucl. Acids Res., 19(15): 4133-4137 (1991).
Hoogenboom et al., "Natural and designer binding sites made by phage display technology," Immunol. Today, 21(8): 371-378(2000).
Hoogenboom, H.R., "Designing and optimizing library selection strategies for generating high-affinity antibodies," Trends Biotechnol., 15: 62-70 (1997).
Hoogenboom, H.R., "Mix and match: Building manifold binding sites," Nature Biotechnol., 15: 126 (1997).
Howard et al., "Intracerebral drug delivery in rats with lesion-induced memory deficits," J. Neurosurg., 71: 105-112 (1989).
Huber et al., "Crystallographic structure studies of an IgG molecule and an Fc fragment," Nature, 264: 415-420 (1976).
Huising et al., "The molecular evolution of the interleukin-1 family of cytokines; IL-18 in teleost fish," Dev. Comp. Immunol., 28(5): 395-413 (2004).
Huse et al., "Generation of a Large Combinatorial Library of the Immunoglobulin Repertoire in Phage Lambda," Science, 246: 1275-1281 (1989).
Huston, et al., "Protein engineering of antibody binding sites: Recovery of specific activity in an anti-digoxin single-chain Fv analogue produced in *Escherichia coli*," Proc. Natl. Acad. Sci. USA, 85: 5879-5883 (1988).
Huston, et al., "Protein Engineering of Single-Chain Fv Analogs and Fusion Proteins," Methods Enzymol., 203: 46-88 (1991).
Jackson et al., "In Vitro Antibody Maturation, Improvement of a High Affinity, Neutralizing Antibody Against IL-1I3," J. Immunol., 154(7): 3310-3319 (1995).
Janelsins et al., "Early correlation of microglial activation with enhanced tumor necrosis factor-alpha and monocyte chemoattractant protein-I expression specifically within the entorhinal cortex of triple transgenic Alzheimer's disease mice," J. Neuroinflammation, 2(23): 1-12 (2005).
Jefferis, R., "Glycosylation of Recombinant Antibody Therapuetics," Biotechnol. Prog., 21: 11-16 (2005).

(56) References Cited

OTHER PUBLICATIONS

Jiang et al., "Regulation of recombinant monoclonal antibody production in Chinese hampster ovary cells: a comparative study of gene copy number, mRNA level, and protein expression" Biotechnol. Prog., 22(1): 313-318 (2006).
Johnsson et al., "Immobilization of Proteins to a Carboxymethyldextran-Modified Gold Surface for Biospecific Interaction Analysis in Surface Plasmon Resonance Sensors," Anal. Biochem., 198: 268-277 (1991).
Johnsson et al., "Comparison of Methods for Immobilization to Carboxymethyl Dextran Sensor Surfaces by Analysis of the Specific Activity of Monoclonal Antibodies," J. Mol. Recognit., 8: 125-131 (1995).
Joliot et al., "Antennapedia homeobox peptide regulates neural morphogenesis," Proc. Natl. Acad. Sci. USA, 88: 1864-1868 (1991).
Jones, A.G., Dept. Chem. Biochem. Eng., Univ. Coll. London, "Particle formation and separation in suspension crystallization processes," Chapter 4, In Process. Solid-Liq. Suspensions, (P. Ayazi Shamlou, ed.) (Butterworth-Heinemann, Oxford, UK, 1993) pp. 93-117.
Jones, A.J.S., "Analytical methods for the assessment of protein formulations and delivery systems," Chapter 2, In Formulation and Delivery of Peptides and Proteins, 1st ed., (Cleland and Langer, eds.) (American Chemical Society, Washington, D.C., 1994) pp. 22-45.
Jones et al., "Replacing the complementarity-determining regions in a human antibody with those from a mouse," Nature, 321: 522-525 (1986).
Jones, R., "Rovelizumab—ICOS Corp," IDrugs, 3(4): 442-446 (2000).
Jonsson, et al., "Real-Time Biospecific Interaction Analysis Using Surface Plasmon Resonance and a Sensor Chip Technology," BioTechniques, 11(5): 620-627 (1991).
Jonsson et al., "Introducing a biosensor based technology for real-time biospecific interaction analysis," Ann. Biol. Clin., 51: 19-26 (1993).
Joosten et al., "Anticytokine Treatment of Established Type II Collagen-Induced Arthritis in DBA/1 Mice," Arthritis Rheum., 39(5): 797-809 (1996).
Jungbluth et al., "A monoclonal antibody recognizing human cancers with amplification/overexpression of the human epidermal growth factor receptor," Proc. Natl. Acad. Sci. USA, 100(2): 639-644 (2003).
Kabat et al., "Attempts to Locate Complementarity-Determining Residues in the Variable Positions of Light and Heavy Chains," Ann. NY Acad. Sci., 190: 382-391 (1971).
Kaine et al., "Results of a multi-dose protocol 7002 using an immunomodulating, non-depleting PrimatizedTM anti-CD4 monoclonal antibody in rheumatoid arthritis (RA)," (Abstract No. 195), Arthritis Rheum., vol. 38, S185 (1995).
Kanda et al., "Establishment of a GDP-mannose 4,6-dehydratase (GMD) knockout host cell line: a new strategy for generating completely non-fucosylated recombinant therapeutics," J. Biotechnol., 130(3): 300-310 (2007).
Kapadia et al., "Soluble TNF binding proteins modulate the negative inotropic properties of TNF-alpha in vitro," Am. J. Physiol. 268 (Heart Circ. Physiol. 37): H517-H525 (1995).
Karnezis et al., "The neurite outgrowth inhibitor Nogo A is involved in autoimmune-mediated demyelination," Nature Neurosci., 7: 736 (2004).
Karni et al., IL-18 is linked to raised IFN-y in multiple sclerosis and is induced by activated CD4+ T cells via CD4O-CD40 ligand interactions, J. Neuroimmunol., 125: 134-140 (2002).
Kashmiri et al., "SDR grafting—a new approach to antibody humanization," Methods, 36(1): 25-34 (2005).
Kaufman and Sharp, "Amplification and expression of sequences cotransfected with a modular dihydrofolate reductase complementary DNA gene," J. Mol. Biol., 159(4): 601-621 (1982).
Keith Jr., et al., "Recombinant human interleukin eleven decreases arthritis in HLA-B27 transgenic rats," (Abstract No. 1613), Arthritis Rheum., vol. 39, No. 9 (supplement), S296 (1996).
Kellermann et al., "Antibody discovery: the use of transgenic mice to generate human monoclonal antibodies for therapeutics," Curr. Opin. Biotechnol., 13: 593-597 (2002).
Kettleborough et al., "Humanization of a mouse monoclonal antibody by CDR-grafting: the importance of framework residues on loop conformation," Protein Eng., 4(7): 773-783 (1991).
Kettleborough et al., "Isolation of tumor cell-specific single-chain Fv from immunized mice using phage-antibody libraries and the re-construction of whole antibodies from these antibody fragments," Eur. J. Immunol., 24: 952-958 (1994).
Kim et al., "Identifying amino acid residues that influence plasma clearance of murine IgG1 fragments by site-directed mutagenesis," Eur. J. Immunol., 24: 542-548 (1994).
Kipriyanov et al., "Generation of recombinant antibodies," Mol. Biotechnol., 12: 173-201 (1999).
Kipriyanov et al., "Recombinant single-chain FV fragments carrying C-terminal cysteine residues: Production of bivalent and biotinylated miniantibodies," Mol. Immunol., 31: 1047-1058 (1994).
Kipriyanov et al., "Single-chain antibody streptavidin fusions: Tetrameric bifunctional scFv-complexes with biotin binding activity and enhanced affinity to antigen," Hum. Antibod. Hybridomas, 6: 93-101 (1995).
Klein, W. L., "Al3 toxicity in Alzheimer's disease: globular oligomers (ADDLs) as new vaccine and drug targets," Neurochem. Int., 41: 345-352 (2002).
Klyubin et al., "Amyloid 13 protein immunotherapy neutralizes Al3 oligomers that disrupt synaptic plasticity in vivo," Nature Med., 11: 556-561 (2005).
Kyte et al., "A simple method for displaying the hydropathic character of a protein," J. Mol. Biol., 157: 105-132 (1982).
Lam et al., "Microencapsulation of Recombinant Humanized Monoclonal Antibody for Local Delivery," Proceed. Intl Symp. Control Rel. Bioact. Mater., 24: 759-760 (1997).
Langer et al., "Chemical and Physical Structure of Polymers as Carriers for Controlled Release of Bioactive Agents: A Review," J. Macromol. Sci. Rev. Macromol. Chem. Phys., C23(1): 61-126 (1983).
Langer, R., "New Methods of Drug Delivery," Science, 249: 1527-1533 (1990).
Lee et al., "Treatment of rheumatoid arthritis (RA) with thalidomide," (Abstract No. 1524), Arthritis Rheum., vol. 39, No. 9 (supplement), S282 (1996).
Legros et al., "Characterization of an anti-Borrelia burgdorferi OspA conformational epitope by limited proteolysis of monoclonal antibody-bound antigen and mass spectrometric peptide mapping," Protein Science, 9: 1002-1010 (2000).
Levy et al., "Inhibition of Calcification of Bioprosthetic Heart Valves by Local Controlled-Release Diphosphonate," Science, 228: 190-192 (1985).
Li et al., "Genetically engineered brain drug delivery vectors: cloning, expression and in vivo application of an anti-transferrin receptor single chain antibody-streptavidin fusion gene and protein," Protein Eng., 12(9): 787-796 (1999).
Little et al., "Of mice and men: hybridoma and recombinant antibodies," Immunol. Today, 21(8): 364-370 (2000).
Lloyd et al., "Mouse Models of Allergic Airway Disease," Adv. Immunol., 77: 263-295 (2001).
Lomedico et al., "Cloning and expression of murine interleukin-1 cDNA in *Escherichia coli*," Nature, 312: 458-462 (1984).
Lotz et al., "IL-17 promotes cartilage degradation," (Abstract No. 559), Arthritis Rheum., vol. 39, No. 9 (supplement), S120 (1996).
Lublin, F.D., "Relapsing Experimental Allergic Encephalomyelitis an Autoimmune Model of Multiple Sclerosis," Springer Semin. Immunopathol., 8: 197-208 (1985).
Luster et al., "Use of animal studies in risk assessment for immunotoxicology," Toxicology, 92(1-3): 229-243 (1994).
MacCallum et al., "Antibody-antigen Interactions: Contact Analysis and Binding Site Topography," J. Mol. Biol., 262: 732-745 (1996).

(56) References Cited

OTHER PUBLICATIONS

Madhusudan et al., "A phase II study of etanercept (Enbrel), a tumor necrosis factor alpha inhibitor in patients with metastatic breast cancer," Clin. Cancer Res., 10(19): 6528-6534 (2004).
Makwana et al., "Molecular mechanisms in successful peripheral regeneration," FEBS J., 272: 2628-2638 (2005).
Marchalonis et al., "Evolutionary Factors in the Emergence of the Combinatorial Germline Antibody Repertoire," Adv. Exp. Med. Biol., 484: 13-30 (2001).
Margolin et al., "Protein crystals as novel catalytic materials," Angew. Chem. Int. Ed., vol. 40, pp. 2204-2222 (2001).
Marks et al., "By-Passing Immunization: Building High Affinity Human Antibodies by Chain Shuffling," BioTechnology, 10: 779-783 (1992).
Marques et al., "Mediation of the Cytokine Network in the Implantation of Orthopedic Devices," Chapter 21, In Biodegradable Systems in Tissue Engineering and Regenerative Medicine, (Reis et al., eds.) (CRC Press LLC, Boca Raton, 2005) pp. 377-397.
Marquina et al., "Inhibition of B cell death causes the development of an IgA nephropathy in (New Zealand White x C57BL/6)F1-bcl-2 transgenic mice," J. Immunol., 172(11): 7177-7185 (2004).
Martin, A.C.R., "Protein Sequence and Structure Analysis of Antibody Variable Domains," In Kontermann and DUbel, eds., Antibody Engineering (Springer-Verlag, Berlin, 2001), chapter 31, pp. 422-439.
Masliah et al., "Effects of cc-Synuclein Immunization in a Mouse Model of Parkinson's Disease," Neuron, 46: 857-868 (2005).
Mateo et al., "Humanization of a mouse monoclonal antibody that blocks the epidermal growth factor receptor: recovery of antagonistic activity," Immunotechnology, 3: 71-81 (1997).
Mattingly, P.G., "Chemiluminescent 10-methyl-acridinium-9-(N-sulphonylcarboxamide) salts. Synthesis and kinetics of light emission," J. Biolumin. Chemilumin., 6: 107-114 (1991).
McCafferty et al., "Phage antibodies: filamentous phage displaying antibody variable domains," Nature, 348: 552-554 (1990).
McCarpa et al., "Chemiluminescence involving peroxide decompositions," Photochem. Photobiol., 4: 1111-1121 (1965).
McGee et al., "The Nogo-66 receptor: focusing myelin inhibition of axon regeneration," Trends Neurosciences, 26(4): 193-198 (2003).
Mendez et al., "Functional transplant of megabase human immunoglobulin loci recapitulates human antibody response in mice," Nature Genet., 15: 146-156 (1997).
Milstein et al., "Hybrid hybridomas and their use in immunohistochemistry," Nature, 305: 537-540 (1983).
Mizushima et al., "pEF-B OS, a powerful mammalian expression vector," Nucl. Acids Res., 18(17): 5322 (1990).
Modjtahedi et al., "Antitumor Activity of Combinations of Antibodies Directed Against Different Epitopes on the Extracellular Domain of the Human EGF Receptor," J. Cell Biophys., 22(1-3): 129-146 (1993).
Modjtahedi et al., "Phase I trial and tumour localisation of the anti-EGFR monoclonal antibody 1CR62 in head and neck or lung cancer," Br. J. Cancer, 73: 228-235 (1996).
Modjtahedi et al., "Targeting of Cells Expressing Wild-Type EGFR and Type-III Mutant EGFR (EGFRVIII) by Anti-EGFR MAB ICR62: A Two-Pronged Attack for Tumour Therapy," Int. J. Cancer, 105: 273-280 (2003).
Modjtahedi et al., "The human EGF receptor as a target for cancer therapy: six new rat mAbs against the receptor on the breast carcinoma MDA-MB 468", Br. J. Cancer, 67: 247-253 (1993).
Moreland et al., "Soluble tumor necrosis factor receptors (sTNFR): results of a phase I dose-escalation study in patients with rheumatoid arthritis," (Abstract No. 813), Arthritis Rheum., vol. 37, 5295 (1994).
Morgan and Anderson, "Human Gene Therapy," Ann. Rev. Biochem., 62: 191-217 (1993).
Morgan et al., "Dissociation of hyperalgesia from fever following intracerebroventricular administration of interleukin-113 in the rat," Brain Res., 1022: 96-100 (2004).
Moriuchi et al., "Treatment of established collagen-induced arthritis with PGE1 incorporated in lipid microspheres," (Abstract No. 1528), Arthritis Rheum., vol. 39, No. 9 (supplement), 5282 (1996).
Morrison and Schlom, "Recombinant Chimeric Monoclonal Antibodies," Chapter 1, In Important Advances in Oncology 1990 (J.B. Lippincott Company, Philadelphia, 1990), pp. 3-18.
Morrison et al., "Chimeric human antibody molecules: Mouse antigen-binding domains with human constant region domains," Proc. Natl. Acad. Sci. USA, 81: 6851-6855 (1984).
Morrison, S.L., "Transfectomas provide novel chimeric antibodies," Science, 229: 1202-1207 (1985).
Mulligan, R.C., "The Basic Science of Gene Therapy," Science, 260: 926-932 (1993).
Mullinax et al., "Expression of a Heterodimeric Fab Antibody Protein in One Cloning Step," BioTechniques, 12(6): 864-869 (1992).
Murthy et al., "Binding of an Antagonistic Monoclonal Antibody to an Intact and Fragmented EGF-Receptor Polypeptide," Arch. Biochem. Biophys., 252(2): 549-560 (1987).
Nelson, R.B. "The Dualistic Nature of Immune Modulation in Alzheimer's Disease: Lessons from the Transgenic Models," Curr. Pharm. Des., 11: 3335-3352 (2005).
Neuberger et al., "Recombinant antibodies possessing novel effector functions," Nature, 312: 604-608 (1984).
Ning et al., "Intratumoral radioimmunotherapy of a human colon cancer xenograft using a sustained-release gel," Radiotherapy Oncol., 39: 179-189 (1996).
Nishimoto et al., "Treatment of rheumatoid arthritis with humanized anti-interleukin-6 receptor antibody," Arthritis Rheum., 50(6): 1761-1769 (2004).
O'Connor et al., "Requirement of multiple phage displayed peptide libraries for optimal mapping of a conformational antibody epitope on CCR5," J. Immunol. Methods, 299: 21-35 (2005).
Oi et al., "Chimeric Antibodies," BioTechniques, 4: 214-221 (1986).
Okamoto et al., "Rituximab for Rheumatoid Arthritis," N. Engl. J. Med., 351: 1909 (2004).
Owens et al., "The Immunology of Multiple Sclerosis and its Animal Model, Experimental Allergic Encephalomyelitis," Neurol. Clin., 13(1): 51-73 (1995).
Padlan, E.A., "A Possible Procedure for Reducing the Immunogenicity of Antibody Variable Domains While Preserving Their Ligand-Binding Properties," Mol. Immunol., 28(4/5): 489-498 (1991).
Padlan et al., "Identification of specificity-determining residues in antibodies," FASEB J., 9: 133-139 (1995).
Pearlman and Nguyen, "Analysis of protein drugs," Chapter 6, In Peptide and Protein Drug Delivery, 1st ed., [In Advances in Parenteral Sciences, vol. 4] (Lee, ed.) (Marcel Dekker, Inc., New York, 1991) pp. 247-301.
Peng, S.L., "Experimental Use of Murine Lupus Models," Methods Mol. Med., 102: 227-272 (2004).
Persic et al., "An integrated vector system for the eukaryotic expression of antibodies or their fragments after selection from phage display libraries," Gene, 187: 9-18 (1997).
Petkova et al., "Enhanced half-life of genetically engineered human IgG1 antibodies in a humanized FcRn mouse model: potential application in humorally mediated autoimmune disease," Int. Immunol., 18: 1759-1769 (2006).
Poljak, R.J., "Production and structure of diabodies," Structure, 2: 1121-1123 (1994).
Presta et al., "Humanization of an Antibody Directed Against IgE," J. Immunol., 151(5): 2623-2632 (1993).
Presta, L.G., "Engineering of therapeutic antibodies to minimize immunogenicity and optimize function," Adv. Drug Del. Rev., 58: 640-656 (2006).
Presta , L.G., "Selection, design, and engineering of therapeutic antibodies," J. Allergy Clin. Immunol., 116: 731-736 (2005).
Razavi et al., "Stable and versatile active acridinium esters I," Luminescence, 15: 239-244 (2000).
Razavi et al., "Stable and versatile active acridinium esters II," Luminescence, 15: 245-249 (2000).
Riechmann et al., "Reshaping human antibodies for therapy," Nature, 332: 323-327 (1988).

(56) References Cited

OTHER PUBLICATIONS

Roberts et al., "RNA-peptide fusions for the in vitro selection of peptides and proteins," Proc. Natl. Acad. Sci. USA, 94: 12297-12302 (1997).
Robinson, C., "Gene therapy—proceeding from laboratory to clinic," Trends Biotechnol., 11(5): 155 (1993).
Rodeck et al., "Interations Between Growth Factor Receptors and Corresponding Monoclonal Antibodies in Human Tumors," J. Cell Biochem., 35: 315-320 (1987).
Roguska et al., "A comparison of two murine monoclonal antibodies humanized by CDR-grafting and variable domain resurfacing," Protein Eng., 9(10): 895-904 (1996).
Roguska et al., "Humanization of murine monoclonal antibodies through variable domain resurfacing," Proc. Natl. Acad. Sci. USA, 91: 969-973 (1994).
Ronday et al., "Tranexamic acid (TEA), an inhibitor of plasminogen activation, reduces collagen crosslink excretion in arthritis," (Abstract No. 1541), Arthritis Rheum., vol. 39, No. 9 (supplement), 5284 (1996).
Satoh et al., "Non-fucosylated therapeutic antibodies as next-generation therapeutic antibodies," Expert Opin. Biol. Ther., 6(11): 1161-1173 (2006).
Saudek et al., "A Preliminary Trial of the Programmable Implantable Medication System for Insulin Delivery," N. Engl. J. Med., 321: 574-579 (1989).
Sawai et al., "Direct Production of the Fab Fragment Derived From the Sperm immobilizing Antibody Using Polymerase Chain Reaction and cDNA Expression Vectors," Am. J. Reprod. Immunol., 34: 26-34 (1995).
Schier et al., "Identification of functional and structural amino-acid residues by parsimonious mutagenesis," Gene, 169: 147-155 (1995).
Scholz, P., "Inhibition of the production and effect of TNF-alpha by iloprost: possible impact for treatment of rheumatoid arthritis," (Abstract No. 336), Arthritis Rheum., vol. 39, No. 9 (supplement), S82 (1996).
Sefton, M.V., "Implantable Pumps," CRC Crit. Rev. Biomed. Eng., 14(3): 201-240 (1987).
Seligmann et al., "Immunochemical Study of a Human Myeloma IgG1 Half Molecule," Ann. Immunol., 129 C: 855-870 (1978).
Sewell et al., "DAB486IL-2 fusion toxin in refractory rheumatoid arthritis," Arthritis Rheum., vol. 36, No. 9, pp. 1223-1233 (Sep. 1993).
Sfikakis et al., "Rituximab anti-B-cell therapy in systemic lupus erythematosus: pointing to the future," Curr. Opin. Rheumatol., 17: 550-557 (2005).
Shapiro et al., "DNA Target Motifs of Somatic Mutagenesis in Antibody Genes," Crit. Rev. Immunol., 22(3): 183-200 (2002).
Shepherd et al., "Novel 'inflammatory plaque' pathology in presenilin-1 Alzheimer's disease," Neuropathol. Appl. Neurobiol., 31: 503-511 (2005).
Shields et al., "Lack of Fucose on Human IgG1 N-Linked Oligosaccharide Improves Binding to Human FcγRIII and Antibody-dependent Cellular Toxicity," J. Biol. Chem., 277(30): 26733-26740 (2002).
Shu et al., "Secretion of a single-gene-encoded immunoglobulin from myeloma cells," Proc. Natl. Acad. Sci. USA, 90: 7995-7999 (1993).
Sims et al., "A Humanized CD18 Antibody Can Block Function without Cell Destruction," J. Immunol., 151(4): 2296-2308 (1993).
Sims et al., "A new nomenclature for IL-1-family genes," Trends Immunol., 22(1): 536-537 (2001).
Skerra et al., "Assembly of a Functional Immunoglobulin Fv Fragment in *Escherichia coli*," Science, 240: 1038-1041 (1988).
Snibson et al., "Airway remodelling and inflammation in sheep lungs after chronic airway challenge with house dust mite," Clin. Exp. Allergy, 35: 146-152 (2005).
Soloman, B., "Alzheimer's Disease and Immunotherapy," Curr. Alzheimer. Res., 1: 149-163 (2004).

Song et al., "Antibody Mediated Lung Targeting of Long-Circulating Emulsions," PDA J. Pharm. Sci. Technol., 50: 372-377 (1996).
Staerz et al., "Hybrid antibodies can target sites for attack by T cells," Nature, 314: 628-631 (1985).
Steinman et al., "Virtues and pitfalls of EAE for the development of therapies for multiple sclerosis," Trends Immunol., 26(11):565-571 (2005).
Stickler et al., "CD4+ T-cell epitope determination using unexposed human donor peripheral blood mononuclear cells," J. Immunotherapy, 23: 654-660 (2000).
Studnicka et al., "Human-engineered monoclonal antibodies retain full specific binding activity by preserving non-CDR complementarity-modulating residues," Protein Eng., 7(6): 805-814 (1994).
't Hart et al., "Suppression of Ongoing Disease in a Nonhuman Primate Model of Multiple Sclerosis by a Human-Anti-Human IL-12p40 Antibody," J. Immunol., 175(7): 4761-4768 (2005).
Takeda et al., "Construction of chimaeric processed immunoglobulin genes containing mouse variable and human constant region sequences," Nature, 314: 452-454 (1985).
Taylor et al., "A transgenic mouse that expresses a diversity of human sequence heavy and light chain immunoglobulins," Nucl. Acids Res., 20: 6287-6295 (1992).
Teng et al., "Nogo Signaling and Non-Physical Injury-Induced Nervous System Pathology," J. Neurosci. Res., 79: 273-278 (2005).
Thies et al., "Folding and Association of the Antibody Domain CH3: Prolyl Isomerization Preceeds Dimerization," J. Mol. Biol., 293: 67-79 (1999).
Thoss et al., "Immunomodulation of rat antigen-induced arthritis by leflunomide alone and in combination with cyclosporin A," Inflamm. Res., vol. 45, 103-107 (1996).
Tolstoshev, P., "Gene Therapy, Concepts, Current Trials and Future Directions," Ann. Rev. Pharmacol. Toxicol., 32: 573-596 (1993).
Tuohy et al., "Spontaneous Regression of Primary Autoreactivity during Chronic Progression of Experimental Autoimmune Encephalomyelitis and Multiple Sclerosis," J. Exp. Med., 189(7): 1033-1042 (1999).
Umana et al., "Engineered glycoforms of an antineuroblastoma IgG1 with optimized antibody-dependent cellular cytotoxic activity," Nature Biotechnol., 17: 176-180 (1999).
Urlaub et al., "Isolation of Chinese hamster cell mutants deficient in dihydrofolate reductase activity," Proc. Natl. Acad. Sci. USA, 77: 4216-4220 (1980).
Vaccaro et al., "Divergent activities of an engineered antibody in murine and human systems have implications for therapeutic antibodies," Proc. Natl. Acad. Sci. USA, 103: 18709-18714 (2006).
Verhoeyen et al., "Reshaping Human Antibodies: Grafting an Antilysozyme Activity," Science, 239: 1534-1536 (1988).
von Mehren et al., "Monoclonal Antibody Therapy for Cancer," Ann. Rev. Med., 54: 343-369 (2003).
Wallemacq et al., "Evaluation of the new AxSYM cyclosporine assay: Comparison with TDx monoclonal whole blood and Emit cyclosporine assays," Clin. Chem., 45: 432-435 (1999).
Wallick et al., "Glycosylation of a VH Residue of a Monoclonal Antibody Against all -p6) Dextran Increases its Affinity for Antigen," J. Exp. Med., 168: 1099-1109 (1988).
Ward et al., "Binding activities of a repertoire of single immunoglobulin variable domains secreted from *Escheria coli*," Nature, 341: 544-546 (1989).
West et al., "Crystal Structure and Immunoglobulin G Binding Properties of the Human Major Histocompatibility Complex-Related Fc Receptor," Biochemistry, 39: 9698-9708 (2000).
Wing et al., "Ex-vivo whole blood cultures for predicting cytokine-release syndrome: dependence on target antigen and antibody isotype," Therapeutic Immunol., 2(4): 183-190 (1995).
Wright et al., "Antibody variable region glycosylation: position effects on antigen binding and carbohydrate structure," EMBO J., 10(10): 2717-2723 (1991).
Wu et al., "Delivery systems for gene therapy," Biotherapy, 3: 87-95 (1991).
Wu et al., "Drug/device combinations for local drug therapies and infection prophylaxis," Biomaterials, 27: 2450-2467 (2006).

(56) References Cited

OTHER PUBLICATIONS

Wu et al., "IL-18 receptor {beta}-induced changes in the presentation of IL-18 binding sites affect ligand binding and signal transduction," J. Immunol., 170: 5571-5577 (2003).

Wu et al., "Molecular construction and optimization of anti-human IL-Ialpha/beta dual variable domain immunoglobulin (DVD-IgTM) molecules," mAbs., 1(4): 339-347 (Jul.-Aug. 2009).

Wu et al., "Receptor-mediated in vitro Gene Transformation by a Soluble DNA Carrier System," J. Biol. Chem., 262 (10): 4429-4432 (1987).

Wu et al., "Simultaneous targeting of multiple disease mediators by a dual-variable-domain immunoglobulin," Nature Biotechnology (advance online publication), 2007 Nature Publishing Group, 1-8 (ht_t_pl/www.nature.coirinaturebiotechnolugy) published online Oct. 14, 2007.

Wu et al., "Simultaneous targeting of multiple disease mediators by a dual-variable-domain immunoglobulin," Nature Biotechnol., 25(11): 1290-1297 (2007).

Wurm, F.M., "Production of recombinant protein therapeutics in cultivated mammalian cells," Nature Biotechnol., 22 (11): 1393-1398 (2004).

Xu et al., "Recombinant DNA vaccine encoding multiple domains related to inhibition of neurite outgrowth: a potential strategy for axonal regeneration," J. Neurochem., 91: 1018-1023 (2004).

Yatscoff et al., "Abbott TDx Monoclonal Antibody Assay Evaluated for Measuring Cyclosporine in Whole Blood," Clin. Chem., 36: 1969-1973 (1990).

Yelton et al., "Affinity Maturation of the BR96 Anti-Carcinoma Antibody by Codon-Based Mutagenesis," J. Immunol., 155: 1994-2004 (1995).

Zapata et al., "Engineering linear F(ab')2 fragments for efficient production in *Escherichia coli* and enhanced antiproliferative activity," Protein Eng., 8(10): 1057-1062 (1995).

Zola et al., "CD molecules 2005: human cell differentiation molecules," Blood, 106: 3123-3126 (2005).

International Search Report and Written Opinion, PCT/US2011/036444, dated Jan. 5, 2012.

International Preliminary Report on Patentability, PCT/US2011/036444, dated May 3, 2012.

International Search Report and Written Opinion, PCT/US2010/052849, dated Apr. 15, 2012, 5 pages.

International Search Report and Written Opinion, PCT/US2010/052849, dated Nov. 16, 2011, 3 pages.

International Search Report and Written Opinion, PCTUS2013/050197, dated Jan. 3, 2014, 15 pages.

Beck et al: Strategies and challenges for the next generation of therapeutic antibodies; Nature Reviews Immunology; 2010, vol. 10, No. 5, pp. 345-352.

Konterman: Dual targeting strategies with bispecific antibodies; MABS, Landes Bioscience; 2012, vol. 4, No. 2, pp. 182-197.

Co-pending, U.S. Appl. No. 15/270,945, inventors Ghayur, T., et al., filed Sep. 20, 2016 (Not Published).

Co-pending, U.S. Appl. No. 15/156,261, inventors Wu, C., et al., filed May 16, 2016 (Not Published).

Fernandez-Bolanos et al. 'Synthesis and Crystal Structure of methyl 2-amino-2,6-dideoxy-α-d-glucopyranoside-6-sulfonic acid'. Carbohydrate Research. 1993, vol. 248, pp. 1-14.

\* cited by examiner

| | 1 | 10 | 20 | 30 | 40 | 50 | 60 | 70 | 80 | 90 | 100 | 110 | 122 |
|---|---|---|---|---|---|---|---|---|---|---|---|---|---|
| h1B12 | EVQLQESGPGLVKPSETLSLTCTVSGFSLSDYGVSWIRQPPGKGLEWLGLIWGGDTYYNSPLKSRLTISKDTYYNSKSQVSLKLSSVTAADTAVYYCAKQRTIWGYDLGMDYWGQGTLVTVSS |
| 21tr | EVQLQESGPGLVKPSEFTLSLTCTVSGFSLSDYGVSWIRQPPGKGLEWIGLIWGGDTYYNSPLKSRLTISKDNSKSQVSLKLSSVTAADTAVYYCAKQENIWAYDLGMDYWGQGTLVTVSS |
| A6tr | EVQLQESGPGLVKPSETLSLTCTVSGFSLSEFGVSWIRQPPGKGLEWIGLIWGGDTYYNSPLKSRLTISKDNSKSQVSLKLSSVTAADTAVYYCAKQRNIWAYDLGMDYWGQGTLVTVSS |
| 25tr | EVQLQESGPGLVKPSETLSLTCTVSGFSLSEFGVSWIRQPPGKGLEWIGLIWGGDTYYNSPLKSRLTISKDNSKSQVSLKLSSVTAADTAVYYCAKQRNIWAYDLGMDYWGQGTLVTVSS |
| A8tr | EVQLQESGPGLVKPSEITLSLTCTVSGFSLSDYGVSWIRQPPGKGLEWIGLIWGGDTYYNSPLKSRLTISKDNSKSQVSLKLSSVTAADTAVYYCAKQRNIWGYDLGMDYWGQGTLVTVSS |
| 8Atr | EVQLQESGPGLVKPSETLSLTCTVSGFSLSDYGVSWIRQPPGKGLEWLGLIWGGDTYYNSPLKSRLTISKDNSKSQVSLKLSSVTAADTAVYYCAKQNIWGYDLGMDYWGQGTLVTVSS |
| 10tr | EVQLQESGPGLVKPSETLSLTCTVSGFSLSEYGVSWIRQPPGKGLEWIGLIWGGDTYYNSPLKSRLTISKDNSKSQVSLKLSSVTAADTAVYYCAKQNVWGYDLGMDYWGQGTLVTVSS |
| A1tr | EVQLQESGPGLVKPSETLSLTCTVSGFSLSLRDYGVSWIRQPPGKGLEWIGLIWGGDTYYNSPLKSRLTISKINSKSQVSLKLSSVTAADTAVYYCAKQTNIWAYDLGMDYWGQGTLVTVSS |
| 11Gtr | EVQLQESGPGLVKPSETLSLTCTVSGFSLSEFGVSWIRQPPGKGLEWIGLIWGGDTYYNSPLKSRLTISKDTSKSQVSLKLSSVTAADTAVYYCAKQRNIWAYDLSMDYWGQGTLVTVSS |
| A3tr | EVQLQESGPGLVKPSETLSLTCTVSGFSLSDYGVSWIRQPPGKGLEWIGLIWGSGDTYYNSPLKSRLTISKINSKSQVSLKLSSVTAADTAVYYCAKQRNIWAYDLSMDYWGQGTLVTVSS |
| 13tr | EVQLQESGPGLVKPSETLSLTCTVSGFSLSDYGVSWIRQPPGKGLEWIGLIWGSGDTYYNSPLKSRLTISKDNSKSQVSLKLSSVTAADTAVYYCAKQNIWAYDLSMDYWGQGTLVTVSS |
| 34tr | EVQLQESGPGLVKPSETLSLTCTVSGFSLSDYGVSWIRQPPGKGLEWLGLIWGGDTYYNSPLKSRLTISKDTSKSQVSLKLSSVTAADTAVYYCAKQNIWGYDLSMDYWGQGTLVTVSS |
| A4tr | EVQLQESGPGLVKPSETLSLTCTVSGFSLSDYGVSWIRQPPGKGLEWLGLIWGGDTYYNSPLKSRLTISKDNSKSQVSLKLSSVTAADTAVYYCAKQNIWGYDLGMDYWGQGTLVTVSS |

IL-1 BINDING PROTEINS

CROSS-REFERENCE TO RELATED APPLICATION

This application claims priority to U.S. Provisional Patent Application Ser. No. 61/670,834, filed Jul. 12, 2012, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Mar. 16, 2015, is named 548441BBI-332US_SL.txt and is 427,081 bytes in size.

FIELD

The present disclosure provides IL-1 binding proteins, and specifically their uses in the prevention and/or treatment of acute and chronic immunological diseases such as rheumatoid arthritis, osteoarthritis, psoriasis, multiple sclerosis, and other autoimmune diseases. Uses of the IL-1 binding proteins in the amelioration and/or treatment of pain in an individual suffering from a disease or disorder associated with IL-1 accumulation are also described.

BACKGROUND

Cytokines, such as interleukin-1 (IL-1) and tumor necrosis factor (TNF), are molecules produced by a variety of cells, such as monocytes and macrophages, that are mediators of inflammatory processes. Interleukin-1 is a cytokine with a wide range of biological and physiological effects, including fever, prostaglandin synthesis (e.g., fibroblasts, muscle cells and endothelial cells), T-lymphocyte activation, and interleukin-2 production.

Both IL-1α and IL-1β are produced by macrophages, monocytes and dendritic cells. They form an important part of the inflammatory response of the body against infection. These cytokines increase the expression of adhesion factors on endothelial cells to enable transmigration of leukocytes, the cells that fight pathogens, to sites of infection and re-set the hypothalamus thermoregulatory center, leading to an increased body temperature which expresses itself as fever. IL-1 is therefore called an endogenous pyrogen. The increased body temperature helps the body's immune system to fight infection. IL-1 is also important in the regulation of hematopoiesis. IL-1β production in peripheral tissue has also been associated with hyperalgesia (increased sensitivity to pain) associated with fever (Morgan et al., Brain Res., 1022 (1-2): 96-100 (2004)). For the most part, these two forms of IL-1 bind to the same cellular receptor. This receptor is composed of two related, but non-identical, subunits that transmit intracellular signals via a pathway that is mostly shared with certain other receptors. These include the Toll family of innate immune receptors and the receptor for IL-18. IL-1α and IL-1β also possess similar biological properties, including induction of fever, slow wave sleep, and neutrophilia, T- and B-lymphocyte activation, fibroblast proliferation, cytotoxicity for certain cells, induction of collagenases, synthesis of hepatic acute phase proteins, and increased production of colony stimulating factors and collagen.

cDNAs encoding the two distinct forms of IL-1 have been isolated and expressed; these cDNAs represent two different gene products, termed IL-1β (Auron et al., Proc. Natl. Acad. Sci. USA, 81: 7907-7911 (1984)) and IL-1α (Lomedico et al., Nature, 312: 458-462 (1984)). IL-1β is the predominant form produced by human monocytes both at the mRNA and protein levels. The two forms of human IL-1 share only 26% amino acid homology. Despite their distinct polypeptide sequences, the two forms of IL-1 have structural similarities (Auron et al., J. Mol. Cell. Immunol., 2: 169-177 (1985)), in that the amino acid homology is confined to discrete regions of the IL-1 molecule.

IL-1α and IL-1β are produced as precursor peptides. In other words they are made as a long protein that is then processed to release a shorter, active molecule, which is called the mature protein. Mature IL-1β, for example, is released from Pro-IL-1β following cleavage by a certain member of the caspase family of proteins, called caspase-1 or the interleukin-1 converting enzyme (ICE). The 3-dimensional structure of the mature forms of each member of the human IL-1 superfamily is composed of 12-14 β-strands producing a barrel-shaped protein.

Although a variety of antibodies to IL-1 have been described in the nearly two decades of work since the discovery of this critical proinflammatory cytokine, there remains a need for improved binding proteins that can effectively mediate or neutralize the activity of IL-1 in the inflammatory response and autoimmune disorders and for use in detecting IL-1β in samples and tissues.

SUMMARY

This disclosure provides proteins that bind human IL-1α and IL-1β. Binding proteins of the disclosure include but are not limited to antibodies, antigen binding portions thereof, and multivalent, multispecific binding proteins such as DVD-Ig™ binding proteins that can bind human IL-1α and IL-1β. The disclosure also provides methods of making and using the IL-1α and IL-1β binding proteins described herein as well as various compositions that may be used in methods of detecting IL-1α and IL-1β in a sample or in methods of treating or preventing a disorder in an individual that is associated with or suspected to be associated with IL-1 activity.

The disclosure also provides a binding protein comprising an antigen binding domain, wherein the binding protein is capable of binding human IL-1β and the antigen-binding domain comprises six CDRs, i.e., CDR-H1, CDR-H2, CDR-H3, CDR-L1, CDR-L2, and CDR-L3, as defined below: CDR-H1: $X_1$-$X_2$-G-V-S(SEQ ID NO:1), wherein; $X_1$ is D or E and $X_2$ is Y or F; CDR-H2: L-I-W-G-$X_3$-G-D-T-Y-Y-N-S-P-L-K-S (SEQ ID NO:2), wherein; $X_3$ is S or G; CDR-H3: Q-$X_4$-N-$X_5$-W-$X_6$-Y-D-L-Y-$X_7$-M-D-Y (SEQ ID NO:3), wherein; $X_4$ is T or R; $X_5$ is L or I; $X_6$ is A or G and $X_7$ is S or G; CDR-L1: Q-$X_8$-S-$X_9$-D-I-D-$X_{10}$-D-$X_{11}$—N(SEQ ID NO: 4), wherein; $X_8$ is A or T; $X_9$ is Q or T; $X_{10}$ is D or M; and $X_{11}$ is L or M; CDR-L2: $X_{12}$-$X_{13}$-$X_{14}$-$X_{15}$-L-$X_{16}$-P (SEQ ID NO: 5), wherein; $X_{12}$ is L or Q; $X_{13}$ is A or G; $X_{14}$ is S or M; $X_{15}$ is I, K or T; and $X_{16}$ is R, W or P; and CDR-L3: L-Q-$X_{17}$-D-$X_{18}$-$X_{19}$-P-L-T (SEQ ID NO: 6), wherein; $X_{17}$ is S or T; $X_{18}$ is S, W or R; and $X_{19}$ is F or L.

In an embodiment, an isolated binding protein described above comprises at least one CDR comprising an amino acid sequence selected from the group consisting of: residues 31-35 of SEQ ID NOs:30, 31, 32, 33 and 34; residues 50-65 of SEQ ID NOs:30, 31, 32, 33 and 34; residues 98-111 of SEQ ID NOs:30, 31, 32, 33 and 34; residues 24-34 of SEQ ID NOs: 36, 37, 38, 39 and 40; residues 50-56 of SEQ ID NOs: 36, 37, 38, 39 and 40; and residues 89-97 of SEQ ID NOs: 36, 37, 38, 39 and 40. In other embodiments, the binding protein described above can have 1, 2, 3, 4, 5, 6 or more CDRs. In various embodiments, these CDRs can comprise 1, 2, 3, 4, 5, 6 or more of the CDRs described above. In certain embodiments, the binding proteins comprise three CDRs from residues 31-35 of SEQ ID NOs:30, 31, 32, 33 and 34; residues 50-65 of SEQ ID NOs:30, 31, 32, 33 and 34; and residues 98-111 of SEQ ID NOs:30, 31, 32, 33 and 34; as well as three CDRs from residues 24-34 of SEQ ID NOs: 36, 37, 38, 39 and 40; residues 50-56 of SEQ ID NOs: 36, 37, 38, 39 and 40; and residues 89-97 of SEQ ID NOs: 36, 37, 38, 39 and 40. In other embodiments, the binding proteins comprise one CDR from each of residues 31-35 of SEQ ID NOs:30, 31, 32, 33 and 34; residues 50-65 of SEQ ID NOs:30, 31, 32, 33 and 34; residues 98-111 of SEQ ID NOs:30, 31, 32, 33 and 34; residues 24-34 of SEQ ID NOs: 36, 37, 38, 39 and 40; residues 50-56 of SEQ ID NOs: 36, 37, 38, 39 and 40; and residues 89-97 of SEQ ID NOs: 36, 37, 38, 39 and 40.

In another embodiment, the binding protein is capable of modulating a biological function of IL-1 or neutralizing IL-1. In another embodiment, the binding protein specifically binds both IL-1α and IL-1β. In another embodiment, the binding protein has an IC50 of between 30 and 60 pM using the MRC-5 bioassay.

In another embodiment, the binding protein according claim 1, further includes an IL-1α antigen binding domain comprising a CDR-H1 comprising an amino acid sequence of SEQ ID NO:132, a CDR-H2 comprising an amino acid sequence of SEQ ID NO:133, and a CDR-H3 comprising an amino acid sequence of SEQ ID NO:134, a CDR-L1 comprising an amino acid sequence of SEQ ID NO:135, a CDR-L2 comprising an amino acid sequence of SEQ ID NO:136, and a CDR-L3 comprising an amino acid sequence of SEQ ID NO:137.

In other embodiments, the binding protein is cleared from a CD-1 mouse subject at between 0.16 and 0.19 mL/h/kg when administered at 4-5 mg/kg, the volume of distribution of the binding protein is between 94 and 109 mL/kg when the binding protein is administered to a CD-1 mouse subject at 4-5 mg/kg and/or the half-life of the binding protein is between 14 and 19 days when the binding protein is administered to a CD-1 mouse subject at 4-5 mg/kg. In other embodiments, the binding protein is cleared from a Sprague-Dawley rat subject at 0.21 and 0.24 mL/h/kg when administered at 4-5 mg/kg; the volume of distribution of the binding protein is between 71 and 78 mL/kg when the binding protein is administered to a Sprague-Dawley rat subject at 4-5 mg/kg; and/or the half-life of the binding protein is between 12 and 19 days when the binding protein is administered to a Sprague-Dawley rat subject at 4-5 mg/kg.

The disclosure further provides a binding protein that specifically binds to both IL-1α and IL-1β, said binding protein comprising an IL-1β antigen binding domain comprising six CDRs:
CDR-H1, CDR-H2, CDR-H3, CDR-L1, CDR-L2, and CDR-L3, as defined below:
CDR-H1: $X_1$-$X_2$-G-V-S (SEQ ID NO:146), wherein;
$X_1$ is D, E, H, Y, N, G, V or Q and
$X_2$ is Y, F, D, N, H or S;
CDR-H2: $X_3$-I-$X_4$-$X_5$-$X_6$-G-$X_7$-T-$X_8$-Y-N-S-P-L-K-S (SEQ ID NO:147), wherein;
$X_3$ is L, V, R, G, F, W, M or I;
$X_4$ is W, G, L, Y, S, R, E or A;
$X_5$ is G, V, R, W, L, D or S;
$X_6$ is G, R, V, W, S, L, I, E or D;
$X_7$ is D, G, E, V, S, A, K, D, Y or Q; and
$X_8$ is Y, F, S, D, V, T or H;
CDR-H3: $X_9$-$X_{10}$-$X_{11}$-$X_{12}$-$X_{13}$-$X_{14}$-$X_{15}$-$X_{16}$-$X_{17}$-$X_{18}$-$X_{19}$-M-D-Y (SEQ ID NO:148), wherein;
$X_9$ is Q, D, K, P, H, A, Y, V or T;
$X_{10}$ is R, T, M, S, I, W, P, N or K;
$X_{11}$ is T, R, N, Y, W, V, M or K;
$X_{12}$ is L, M, R, I, G, W, Q, H F or A;
$X_{13}$ is W, S, G, R, V, L, K, A, Y or T;
$X_{14}$ is G, A, R, V, T, P, N, E or D;
$X_{15}$ is Y, F, N, D, H or S;
$X_{16}$ is D, Q, H, A, V, L or K;
$X_{17}$ is L, I, F, S, M or G;
$X_{18}$ is Y, N, D, V or D; and
$X_{19}$ is G, A, R, D or W;
CDR-L1: $X_{20}$-$X_{21}$-S-$X_{22}$-D-I-$X_{23}$-$X_{24}$-$X_{25}$-M-N (SEQ ID NO:149), wherein;
$X_{20}$ is I or Q;
$X_{21}$ is T or A;
$X_{22}$ is T or Q;
$X_{23}$ is D, P, Y, N, Q or L;
$X_{24}$ is V, P, A or F; and
$X_{25}$ is D, A, P, N, Y or V;
CDR-L2 have the sequence $X_{26}$-$X_{27}$-$X_{28}$-$X_{29}$-L-$X_{30}$-$X_{31}$ (SEQ ID NO:150), wherein;
$X_{26}$ is S or Y;
$X_{27}$ is Q, H, P, K or R;
$X_{28}$ is G or A;
$X_{29}$ is N or S;
$X_{30}$ is T, S, I, M or A; and
$X_{31}$ is P, L, S or T; and
CDR-L3: $X_{32}$-Q-$X_{33}$-$X_{34}$-$X_{35}$-$X_{36}$-$X_{37}$-L-T (SEQ ID NO:151), wherein;
$X_{32}$ is L or Q;
$X_{33}$ is 5, W, R, K, G or V;
$X_{34}$ is D, G, K or V;
$X_{35}$ is N, E, R, M or G;
$X_{36}$ is L, G, D or F; and
$X_{37}$ is P or A.

In another embodiment, the binding protein is capable of modulating a biological function of IL-1 or neutralizing IL-1. In another embodiment, the binding protein specifically binds both IL-1α and IL-1β. In another embodiment, the binding protein has an IC50 of between 30 and 60 pM using the MRC-5 bioassay.

In another embodiment, the binding protein further includes an IL-1α antigen binding domain comprising a CDR-H1 comprising an amino acid sequence of SEQ ID NO:132, a CDR-H2 comprising an amino acid sequence of SEQ ID NO:133, and a CDR-H3 comprising an amino acid sequence of SEQ ID NO:134, a CDR-L1 comprising an amino acid sequence of SEQ ID NO:135, a CDR-L2 comprising an amino acid sequence of SEQ ID NO:136, and a CDR-L3 comprising an amino acid sequence of SEQ ID NO:137.

In other embodiments, the binding protein is cleared from a CD-1 mouse subject at between 0.16 and 0.19 mL/h/kg when administered at 4-5 mg/kg, the volume of distribution of the binding protein is between 109 and 94 mL/kg when the binding protein is administered to a CD-1 mouse subject at 4-5 mg/kg and/or the half-life of the binding protein is between 19 and 14 days when the binding protein is administered to a CD-1 mouse subject at 4-5 mg/kg. In other embodiments, the binding protein is cleared from a Sprague-Dawley rat subject at 0.21 and 0.24 mL/h/kg when administered at 4-5 mg/kg; the volume of distribution of the binding protein is between 78 and 71 mL/kg when the binding protein is administered to a Sprague-Dawley rat subject at 4-5 mg/kg; and/or the half-life of the binding protein is between 19 and 12 days when the binding protein is administered to a Sprague-Dawley rat subject at 4-5 mg/kg.

The disclosure further provides a binding protein comprising first and second polypeptide chains, wherein said first polypeptide chain comprises a first VD1-(X1)n-VD2-C-(X2)$_n$, wherein: VD1 is a first heavy chain variable domain; VD2 is a second heavy chain variable domain; C is a heavy chain constant domain; X1 is a linker with the proviso that it is not CH1; X2 is an Fc region; and n is independently 0 or 1; and wherein said second polypeptide chain comprises a second VD1-(X1)n-VD2-C-(X$_2$)n, wherein: VD1 is a first light chain variable domain; VD2 is a second light chain variable domain; C is a light chain constant domain; X1 is a linker with the proviso that it is not CH1; X2 does not comprise an Fc region; and n is independently 0 or 1; wherein, in said first polypeptide chain, VD1 comprises an amino acid sequence 95, 96, 97, 98, 99 or 100% identical to an amino acid sequence selected from the group consisting of SEQ ID NOs: 30, 31, 32, 33, 34, 420, 421, 422, 423, 424, 425, 426 and 427; and VD2 comprises an amino acid sequence 95, 96, 97, 98, 99 or 100% identical to the amino acid sequence SEQ ID NO: 128 wherein, in said second polypeptide chain, VD1 comprises an amino acid sequence 95, 96, 97, 98, 99 or 100% identical to an amino acid sequence selected from the group consisting of SEQ ID NOs: 36, 37, 38, 39, 40, 138, 139, 140, 141, 142, 143, 144 and 145; and VD2 comprises an amino acid sequence 95, 96, 97, 98, 99 or 100% identical to the amino acid sequence SEQ ID NO: 129.

In an embodiment, a binding protein described above comprises a first polypeptide chain that comprises an amino acid sequence 95, 96, 97, 98, 99 or 100% identical to an amino acid sequence selected from the group consisting of SEQ ID NOs: 44, 46, 48, 50, 52, and 54.

In another embodiment, a binding protein described above comprises a second polypeptide chain that comprises an amino acid sequence 95, 96, 97, 98, 99 or 100% identical to an amino acid sequence selected from the group consisting of SEQ ID NOs: 45, 47, 49, 51, 53, and 55.

In an embodiment, a binding protein of the disclosure described above comprises two first polypeptide chains and two second polypeptide chains.

In another aspect, in a binding protein described above X1 or X2 is an amino acid sequence selected from the group consisting of SEQ ID NOs: 42, 43, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110 and 111. X1 or X2 can also be an amino acid sequence selected from the group consisting of SEQ ID NOs:42 and 43. In certain embodiments, X1 is an amino acid sequence comprising SEQ ID NO:42 and X2 is an amino acid sequence comprising SEQ ID NO:43.

In another embodiment, the disclosure provides a binding protein described above wherein the Fc region is selected from the group consisting of a native sequence Fc region and a variant sequence Fc region. In another embodiment, the Fc region is selected from the group consisting of an Fc region from an IgG1, IgG2, IgG3, IgG4, IgA, IgM, IgE, and IgD.

The disclosure further provides a binding protein that specifically binds to both IL-1α and IL-1β, comprising first and second polypeptide chains, wherein said first polypeptide chain comprises a first VD1-(X1)n-VD2-C-(X2)n, wherein: VD1 is a first heavy chain variable domain; VD2 is a second heavy chain variable domain; C is a heavy chain constant domain; X1 is a linker with the proviso that it is not CH1; X2 is an Fc region; and n is independently 0 or 1; wherein said second polypeptide chain comprises a second VD1-(X1)n-VD2-C-(X2)n, wherein: VD1 is a first light chain variable domain; VD2 is a second light chain variable domain; C is a light chain constant domain; X1 is a linker with the proviso that it is not CH1; X2 does not comprise an Fc region; and n is independently 0 or 1; wherein, in said first polypeptide chain, VD1 comprises a VH amino acid sequence found in Table 3b; wherein, in said second polypeptide chain, comprises a VL amino acid sequence found in Table 3b; wherein the VD1 of the first polypeptide chain and the VD1 of the second polypeptide chain form a IL-1β antigen binding domain; and wherein the VD2 of the first polypeptide chain and the VD2 of the second polypeptide chain form a IL-1α antigen binding domain.

In another aspect, in a binding protein described above X1 or X2 is an amino acid sequence selected from the group consisting of SEQ ID NOs: 42, 43, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110 and 111. X1 or X2 can also be an amino acid sequence selected from the group consisting of SEQ ID NOs:42 and 43. In certain embodiments, X1 is an amino acid sequence comprising SEQ ID NO:42 and X2 is an amino acid sequence comprising SEQ ID NO:43.

In another embodiment, the disclosure provides a binding protein described above wherein the Fc region is selected from the group consisting of a native sequence Fc region and a variant sequence Fc region. In another embodiment, the Fc region is selected from the group consisting of an Fc region from an IgG1, IgG2, IgG3, IgG4, IgA, IgM, IgE, and IgD.

In another embodiment, the disclosure provides a binding protein conjugate that comprises a binding protein described above and further comprises an agent. Such agents include, but are not limited to, an immunoadhesion molecule, an imaging agent, a therapeutic agent, and a cytotoxic agent. Preferred imaging agents include, but are not limited to, a radiolabel, an enzyme, a fluorescent label, a luminescent label, a bioluminescent label, a magnetic label, and biotin. Preferred radiolabels include, but are not limited to, $^3$H $^{14}$C, $^{35}$S, $^{90}$Y, $^{99}$Tc, $^{111}$In, $^{125}$I, $^{131}$I, $^{177}$Lu, $^{166}$Ho and $^{153}$Sm. A preferred therapeutic or cytotoxic agent includes, but is not limited to, an anti-metabolite, an alkylating agent, an antibiotic, a growth factor, a cytokine, an anti-angiogenic agent, an anti-mitotic agent, an anthracycline, toxin, and an apoptotic agent.

In one aspect, the disclosure provides a binding protein construct that comprises a binding protein described herein and further comprises a linker or an immunoglobulin constant domain. In an embodiment, the binding protein construct comprises a binding protein, wherein the binding protein is selected from the group consisting of: an immunoglobulin molecule, a disulfide linked Fv, a monoclonal antibody, an scFv, a chimeric antibody, a CDR-grafted antibody, a diabody, a humanized antibody, a multispecific antibody, an Fab, a dual specific antibody, a Fab', a bispecific antibody, and a F(aN)$_2$, a DVD-Ig™, and an Fv.

In another embodiment, a binding protein conjugate comprises an agent that is a therapeutic or cytotoxic agent selected from the group consisting of: an anti-metabolite, an alkylating agent, an antibiotic, a growth factor, a cytokine, an anti-angiogenic agent, an anti-mitotic agent, an anthracycline, toxin, and an apoptotic agent.

In an embodiment, a binding protein, binding protein construct, or binding protein conjugate described herein possesses a human glycosylation pattern.

Binding proteins, binding protein constructs, and binding protein conjugates described herein may exist as soluble proteins or as crystals. In an embodiment, such crystals are carrier-free pharmaceutical controlled released crystals. In another embodiment, a crystalline form of a binding protein, binding protein construct, or binding protein conjugate described herein has a greater in vivo half-life than its soluble counterpart. In another embodiment, a crystal of a binding protein, binding protein construct, or binding protein conjugate described herein retains biological activity of its soluble counterpart.

Compositions of the disclosure include a composition for the release of a crystallized binding protein, binding protein construct, or binding protein conjugate described herein, comprising:

(a) a formulation, wherein said formulation comprises a crystallized binding protein, binding protein construct, or binding protein conjugate described herein, and an ingredient; and (b) at least one polymeric carrier.

Polymeric carriers useful in compositions of the disclosure include, without limitation, one or more of the group consisting of: poly (acrylic acid), poly (cyanoacrylates), poly (amino acids), poly (anhydrides), poly (depsipeptide), poly (esters), poly (lactic acid), poly (lactic-co-glycolic acid) or PLGA, poly (b-hydroxybutryate), poly (caprolactone), poly (dioxanone); poly (ethylene glycol), poly ((hydroxypropyl)methacrylamide, poly[(organo) phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof.

In another aspect, an ingredient of a composition of the disclosure is selected from the group consisting of albumin, sucrose, trehalose, lactitol, gelatin, hydroxypropyl-β-cyclodextrin, methoxypolyethylene glycol and polyethylene glycol.

The disclosure also provides pharmaceutical compositions comprising a binding protein, a binding protein construct, or binding protein conjugate described herein, and a pharmaceutically acceptable carrier. Pharmaceutical compositions of the disclosure may further comprise at least one additional agent. In an embodiment, such an additional agent includes, but is not limited to, therapeutic agent, imaging agent, cytotoxic agent, angiogenesis inhibitors; kinase inhibitors; co-stimulation molecule blockers; adhesion molecule blockers; anti-cytokine antibody or functional fragment thereof; methotrexate; cyclosporin; rapamycin; FK506; detectable label or reporter; a TNF antagonist; an antirheumatic; a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteroid, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, and a cytokine antagonist.

In an embodiment, a pharmaceutical composition of the disclosure comprises a pharmaceutically acceptable carrier, wherein the carrier also serves as an adjuvant to increase the absorption or dispersion of the binding protein, binding protein construct, or binding protein conjugate in the composition. An exemplary adjuvant is hyaluronidase.

In an embodiment of the pharmaceutical, the binding protein conjugate comprises an imaging agent selected from the group consisting of: a radiolabel, an enzyme, a fluorescent label, a luminescent label, a bioluminescent label, a magnetic label, and biotin. In one aspect of this embodiment, said imaging agent is a radiolabel selected from the group consisting of: $^{3}$H $^{14}$C, $^{35}$S, $^{90}$Y, $^{99}$Tc, $^{111}$In, $^{125}$I, $^{131}$I, $^{177}$Lu, $^{166}$Ho and $^{153}$Sm.

In another embodiment, said binding protein conjugate comprises a therapeutic or cytotoxic agent selected from the group consisting of: an anti-metabolite, an alkylating agent, an antibiotic, a growth factor, a cytokine, an anti-angiogenic agent, an anti-mitotic agent, an anthracycline, a toxin, and an apoptotic agent.

In an embodiment, the disclosure provides isolated nucleic acids encoding one or more amino acid sequences of a binding protein described herein. Such nucleic acids may be inserted into a vector for carrying out various genetic analyses or for expressing, characterizing, or improving one or more properties of a binding protein described herein. A vector may comprise a one or more nucleic acid molecules encoding one or more amino acid sequences of a binding protein described herein in which the one or more nucleic acid molecules is operably linked to appropriate transcriptional and/or translational sequences that permit expression of the binding protein in a particular host cell carrying the vector. Examples of vectors for cloning or expressing nucleic acids encoding amino acid sequences of binding proteins described herein include, but are not limited, pcDNA, pTT, pTT3, pEFBOS, pBV, pJV, and pBJ.

The disclosure also provides a host cell comprising a vector comprising a nucleic acid encoding one or more amino acid sequences of a binding protein described herein. Host cells useful according to the disclosure may be prokaryotic or eukaryotic. An exemplary prokaryotic host cell is *Escherichia coli*. Eukaryotic cells useful as host cells according to the disclosure include protist cell, animal cell, plant cell, and fungal cell. An exemplary fungal cell is a yeast cell, including *Saccharomyces cerevisiae*. An exemplary animal cell useful as a host cell according to the disclosure includes, but is not limited to, a mammalian cell, an avian cell, and an insect cell. Preferred mammalian cells include CHO and COS cells. An insect cell useful as a host cell according to the disclosure is an insect Sf9 cell.

In another aspect, the disclosure provides a method of producing a binding protein described herein comprising culturing a host cell comprising a vector encoding the binding protein in culture medium under conditions sufficient to produce the binding protein capable of binding IL-1α and/or IL-1β. The protein so produced can be isolated and used in various compositions and methods described herein.

In another embodiment, the disclosure provides a method for reducing human IL-1 activity comprising contacting human IL-1 with a binding protein described herein, such that human IL-1 activity is reduced.

Another embodiment of the disclosure provides a method for treating a subject for a disorder by administering to the subject a binding protein described herein such that treatment is achieved.

In a further embodiment of a method of treatment described herein, the step of administering to the subject a binding protein or binding protein construct or binding protein conjugate described herein is by at least one mode selected from parenteral, subcutaneous, intramuscular, intravenous, intra-articular, intrabronchial, intraabdominal, intracapsular, intracartilaginous, intracavitary, intracelial, intracerebellar, intracerebroventricular, intracolic, intracervical, intragastric, intrahepatic, intramyocardial, intrao steal, intrapelvic, intrapericardiac, intraperitoneal, intrapleural, intrapro static, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

Another aspect of the disclosure is a method of treating a patient suffering from a disorder in which IL-1 is detrimental comprising the step of administering a binding protein, binding protein construct, or binding protein conjugate described herein before, concurrently with, or after the administration of a second agent, wherein the second agent is selected from the group consisting of inhaled steroids; beta-agonists; short-acting or long-acting beta-agonists; antagonists of leukotrienes or leukotriene receptors; ADVAIR; IgE inhibitors; anti-IgE antibodies; XOLAIR; phosphodiesterase inhibitors; PDE4 inhibitors; xanthines; anticholinergic drugs; mast cell-stabilizing agents; Cromolyn; IL-4 inhibitors; IL-5 inhibitors; eotaxin/CCR3 inhibitors; antagonists of histamine or its receptors including H1, H2, H3, and H4; antagonists of prostaglandin D or its receptors DP1 and CRTH2; TNF antagonists; a soluble fragment of a TNF receptor; ENBREL®; TNF enzyme antagonists; TNF converting enzyme (TACE) inhibitors; muscarinic receptor antagonists; TGF-beta antagonists; interferon gamma; perfenidone; chemotherapeutic agents, methotrexate; leflunomide; sirolimus (rapamycin) or an analog thereof, CCI-779; COX2 or cPLA2 inhibitors; NSAIDs; immunomodulators; p38 inhibitors; TPL-2, MK-2 and NFkB inhibitors; budenoside; epidermal growth factor; corticosteroids; cyclosporine; sulfasalazine; amino salicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β antibodies; anti-IL-6 antibodies; growth factors; elastase inhibitors; pyridinyl-imidazole compounds; antibodies or agonists of TNF, LT, IL-1, IL-2, IL-3, IL-4, IL-5, IL-6, IL-7, IL-8, IL-9, IL-10, IL-11, IL-12, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, EMAP-II, GM-CSF, FGF, or PDGF; antibodies of CD2, CD3, CD4, CD8, CD25, CD28, CD30, CD40, CD45, CD69, CD90 or their ligands; FK506; rapamycin; mycophenolate mofetil; ibuprofen; prednisolone; phosphodiesterase inhibitors; adenosine agonists; antithrombotic agents; complement inhibitors; adrenergic agents; IRAK, NIK, IKK, p38, or MAP kinase inhibitors; IL-1β converting enzyme inhibitors; TNF-α converting enzyme inhibitors; T-cell signaling inhibitors; metalloproteinase inhibitors; 6-mercaptopurines; angiotensin converting enzyme inhibitors; soluble cytokine receptors; soluble p55 TNF receptor; soluble p75 TNF receptor; sIL-1RI; sIL-1RII; sIL-6R; anti-inflammatory cytokines; IL-4; IL-10; IL-11; and TGF-β.

Another aspect of the disclosure provides at least one IL-1 anti-idiotype antibody to at least one IL-1 binding protein described herein. The anti-idiotype antibody includes any protein or peptide containing molecule that comprises at least a portion of an immunoglobulin molecule such as, but not limited to, at least one CDR of a heavy or light chain or ligand binding portion thereof, a heavy chain or light chain variable region, a heavy chain or light chain constant region, a framework region, or any portion thereof, that can be incorporated into a binding protein of the disclosure.

BRIEF DESCRIPTION OF THE DRAWINGS

FIG. 2 shows VH sequences of h1B12.1 final variants aligned with h1B12 parental. From top to bottom the sequences are SEQ ID NOs:420, 31, 421, 422, 423, 424, 425, 33, 426, 34, 30, 32 and 427.

FIG. 3 shows VL sequences of the final affinity-matured variants (following sorting of h1B12.1 libraries) aligned with h1B12.1. From top to bottom the sequences are SEQ ID NOs:138, 37, 139, 140, 141, 142, 143, 39, 433, 144, 36, 38 and 145.

DETAILED DESCRIPTION

Figure 1:
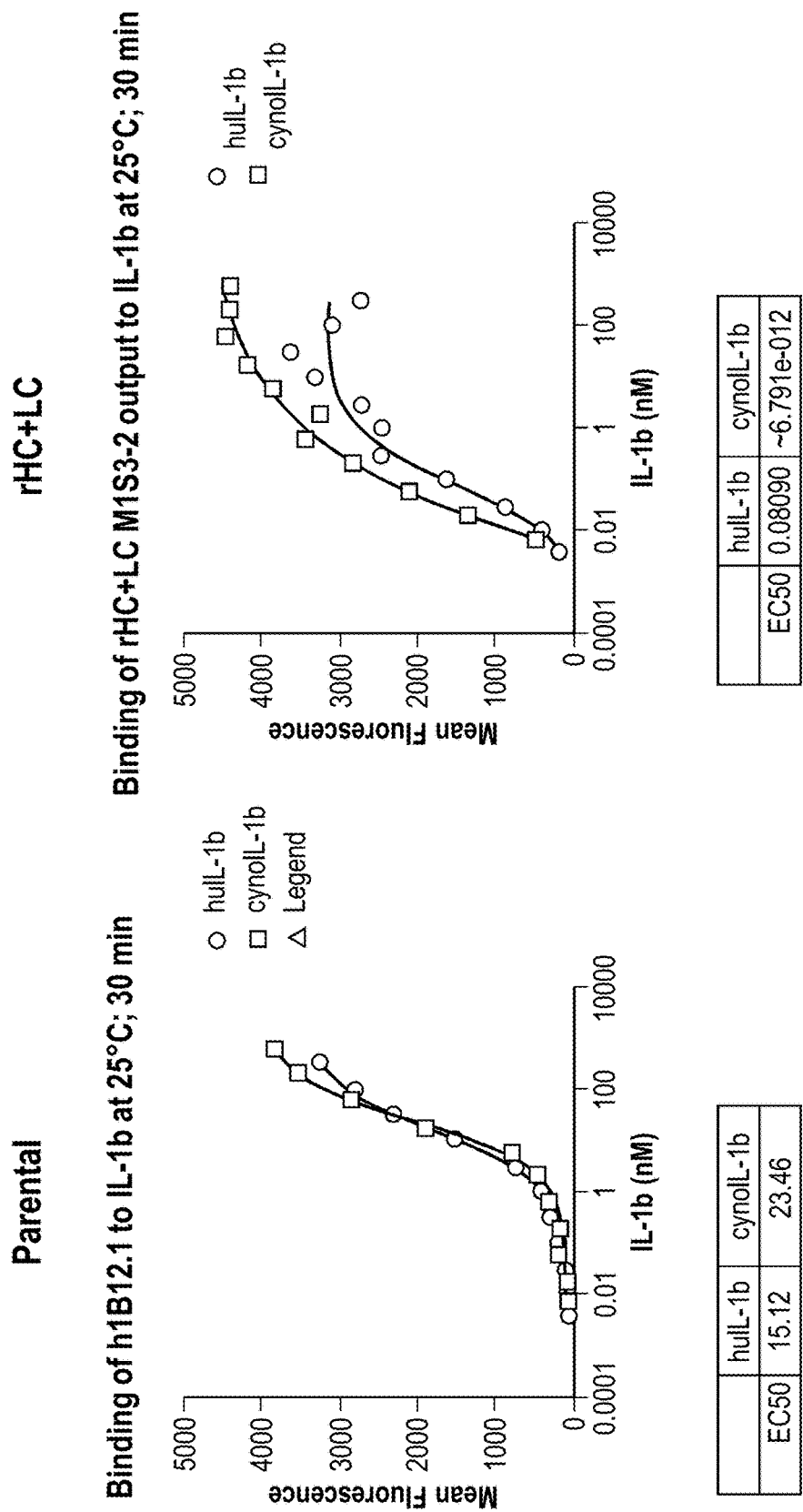
FIG. 1 shows line graphs depicting binding analyses of h1B12.1 scFv and rHC+LC M1S3-2 library output.

This disclosure provides IL-1α and β binding proteins, including, but not limited to, anti-IL-1 α and/or β antibodies, or antigen-binding portions thereof, that bind IL-1α and/or β and multivalent, multispecific binding proteins such as DVD-Ig™ that bind IL-1β and/or IL-1α. Various aspects of the disclosure relate to antibodies and antibody fragments, DVD-Ig binding proteins, and pharmaceutical compositions thereof, as well as nucleic acids, recombinant expression vectors and host cells for making such IL-1α/β binding proteins, including antibodies, DVD-Ig binding proteins, and fragments thereof. Methods of using the IL-1α/β binding proteins of the disclosure to detect human IL-1α/β; to inhibit human IL-1α/β, either in vitro or in vivo; and to regulate gene expression are also encompassed by the disclosure. The disclosure also encompasses any binding protein or antibody capable of competing with an IL-1α or β binding protein described herein.

In certain embodiments, this disclosure provides binding proteins that specifically bind IL-1α and/or IL-1β. In certain embodiments, the binding proteins have homology to VH and VL domains of antibodies that specifically bind IL-1α and/or IL-1β. In other embodiments, the binding proteins have sequences that correspond to the complementarity determining regions (CDRs) of these VH and VL domains. Each of the VH and VL domains contains three CDR domains: CDR-H1, CDR-H2, CDR-H3, CDR-L1, CDR-L2, and CDR-L3. According to certain embodiments, the binding proteins described herein can contain 1, 2, 3, 4, 5 or 6 of these CDRs. One binding protein can comprise a sequence with high homology to a VH or a VL domain, or it can include sequences that are homologous to a VH and a VL domain in the same binding protein.

In certain embodiments, binding proteins with sequences homologous to CDR-H1 have the sequence $X_1$-$X_2$-G-V-S (SEQ ID NO:1), wherein; $X_1$ is D or E and $X_2$ is Y or F. In other embodiments, binding proteins with sequences homologous to CDR-H2 have the sequence L-I-W-G-$X_3$-G-D-T-Y-Y-N-S-P-L-K-S (SEQ ID NO:2), wherein; $X_3$ is S or G. In other embodiments, binding proteins with sequences homologous to CDR-H3 have the sequence Q-$X_4$-N-$X_5$-W-$X_6$Y-D-L-Y-$X_7$-M-D-Y (SEQ ID NO:3), wherein; $X_4$ is T or R; $X_5$ is L or I; $X_6$ is A or G and $X_7$ is S or G. In other embodiments, binding proteins with sequences homologous to CDR-L1 have the sequence Q-$X_8$-S-$X_9$-D-I-D-$X_{10}$-D-$X_{11}$-N(SEQ ID NO:4), wherein; $X_8$ is A or T; $X_9$ is Q or T; $X_{10}$ is D or M; and $X_{11}$ is L or M. In other embodiments, binding proteins with sequences homologous to CDR-L2 have the sequence $X_{12}$-$X_{13}$-$X_{14}$-$X_{15}$-L-$X_{16}$-P (SEQ ID NO:5), wherein; $X_{12}$ is L or Q; $X_{13}$ is A or G; $X_{14}$ is S or M; $X_{15}$ is I, K or T; and $X_{16}$ is R, W or P. In other embodiments, binding proteins with sequences homologous to CDR-L3 have the sequence: L-Q-$X_{17}$-D-$X_{18}$-$X_{19}$-P-L-T (SEQ ID NO:6), wherein; $X_{17}$ is S or T; $X_{18}$ is 5, W or R; and $X_{19}$ is F or L.

According to certain embodiments, the binding proteins can include sequences homologous to the following CDR sequences in Table 1.

TABLE 1

Sequence of CDRs

| Domain Type | Sequence Identifier | Sequence 123456789012345678901234567890 |
|---|---|---|
| CDR-H1 | SEQ ID NO: 7 | DYGVS |
| CDR-H2 | SEQ ID NO: 8 | LIWGGGDTYYNSPLKS |
| CDR-H3 | SEQ ID NO: 9 | QTNIWAYDLYSMDY |
| CDR-H1 | SEQ ID NO: 10 | EFGVS |
| CDR-H3 | SEQ ID NO: 11 | QRNLWAYDLYGMDY |
| CDR-H2 | SEQ ID NO: 12 | LIWGSGDTYYNSPLKS |
| CDR-H3 | SEQ ID NO: 13 | QTNLWAYDLYSMDY |
| CDR-H3 | SEQ ID NO: 14 | QTNIWGYDLYGMDY |
| CDR-H3 | SEQ ID NO: 15 | QTNLWAYDLYSMDY |
| CDR-H1 | SEQ ID NO: 132 | MFGVH |
| CDR-H2 | SEQ ID NO: 133 | AVSYDGSNKYYAESVKG |
| CDR-H3 | SEQ ID NO: 134 | GRPKVVIPAPLAH |
| CDR-L1 | SEQ ID NO: 16 | QTSTDIDDDLN |
| CDR-L2 | SEQ ID NO: 17 | LASTLRP |
| CDR-L3 | SEQ ID NO: 18 | LQSDRLPLT |
| CDR-L1 | SEQ ID NO: 19 | QTSQDIDMDLN |
| CDR-L2 | SEQ ID NO: 20 | QGSTLWP |
| CDR-L3 | SEQ ID NO: 21 | LQTDSFPLT |
| CDR-L1 | SEQ ID NO: 22 | QASQDIDDDLN |
| CDR-L2 | SEQ ID NO: 23 | LASILRP |
| CDR-L3 | SEQ ID NO: 24 | LQSDSFPLT |
| CDR-L1 | SEQ ID NO: 25 | QASQDIDMDLN |
| CDR-L2 | SEQ ID NO: 26 | QANTLPP |
| CDR-L3 | SEQ ID NO: 27 | LQSDWLPLT |
| CDR-L1 | SEQ ID NO: 28 | QASTDIDDDMN |
| CDR-L2 | SEQ ID NO: 29 | LANKLRP |
| CDR-L1 | SEQ ID NO: 135 | RASQGISSWLA |
| CDR-L2 | SEQ ID NO: 136 | EASNLET |
| CDR-L3 | SEQ ID NO: 137 | QQTSSFLLS |

In other embodiments, binding proteins with sequences homologous to CDR-H1 have the sequence $X_1$-$X_2$-G-V-S (SEQ ID NO:146), wherein; $X_1$ is D, E, H, Y, N, G, V or Q and $X_2$ is Y, F, D, N, H or S. In other embodiments, binding proteins with sequences homologous to CDR-H2 have the sequence $X_3$-I-$X_4$-$X_5$-$X_6$-G-$X_7$-T-$X_8$-Y-N-S-P-L-K-S (SEQ ID NO:147), wherein; $X_3$ is L, V, R, G, F, W, M or I; $X_4$ is W, G, L, Y, S, R, E or A; $X_5$ is G, V, R, W, L, D or S; $X_6$ is G, R, V, W, S, L, I, E or D; $X_7$ is D, G, E, V, S, A, K, D, Y or Q; and $X_8$ is Y, F, S, D, V, T or H. In other embodiments, binding proteins with sequences homologous to CDR-H3 have the sequence $X_9$-$X_{10}$-$X_{11}$-$X_{12}$-$X_{13}$-$X_{14}$-$X_{15}$-$X_{16}$-$X_{17}$-$X_{18}$-$X_{19}$-M-D-Y (SEQ ID NO:148), wherein; $X_9$ is Q, D, K, P, H, A, Y, V or T; $X_{10}$ is R, T, M, S, I, W, P, N or K; $X_{11}$ is T, R, N, Y, W, V, M or K; $X_{12}$ is L, M, R, I, G, W, Q, H F or A; $X_{13}$ is W, S, G, R, V, L, K, A, Y or T; $X_{14}$ is G, A, R, V, T, P, N, E or D; $X_{15}$ is Y, F, N, D, H or S; $X_{16}$ is D, Q, H, A, V, L or K; $X_{17}$ is L, I, F, S, M or G; $X_{18}$ is Y, N, D, V or D; and $X_{19}$ is G, A, R, D or W. In other embodiments, binding proteins with sequences homologous to CDR-L1 have the sequence $X_{20}$-$X_{21}$-S-$X_{22}$-D-I-$X_{23}$-$X_{24}$-$X_{25}$-M-N (SEQ ID NO:149), wherein; $X_{20}$ is I or Q; $X_{21}$ is T or A; $X_{22}$ is T or Q; $X_{23}$ is D, P, Y, N, Q or L; $X_{24}$ is V, P, A or F; and $X_{25}$ is D, A, P, N, Y or V. In other embodiments, binding proteins with sequences homologous to CDR-L2 have the sequence $X_{26}$-$X_{27}$-$X_{28}$-$X_{29}$-L-$X_{30}$-$X_{31}$ (SEQ ID NO:150), wherein; $X_{26}$ is S or Y; $X_{27}$ is Q, H, P, K or R; $X_{28}$ is G or A; $X_{29}$ is N or S; $X_{30}$ is T, S, I, M or A; and $X_{31}$ is P, L, S or T. In other embodiments, binding proteins with sequences homologous to CDR-L3 have the sequence: $X_{32}$-Q-$X_{33}$-$X_{34}$-$X_{35}$-$X_{36}$-$X_{37}$-L-T (SEQ ID NO:151), wherein; $X_{32}$ is L or Q; $X_{33}$ is S, W, R, K, G or V; $X_{34}$ is D, G, K or V; $X_{35}$ is N, E, R, M or G; $X_{36}$ is L, G, D or F; and X37 is P or A.

In certain embodiments, the binding proteins disclosed herein contain sequences that have high homology to VH or VL domains of antibodies that specifically binds to IL-1α or IL-1β. These sequences can be 70, 75, 80, 85, 90, 91, 92, 93, 94, 95, 96, 97, 98, 99 or 100% identical to a VH or VL domain of an antibody that specifically binds to IL-1α or IL-1β. In other embodiments, the biding proteins described herein contain sequences that have high homology to VH or VL domains of antibodies that specifically binds to IL-1α or IL-1β wherein these sequences have the same number of amino acids as the VH or VL domain or fewer amino acids. Sequences that have fewer amino acids than the VH or VL domain—that they have identity to or have homology to—can have 121 or fewer amino acids. In other embodiments, the sequences have 107 or fewer amino acids. In other embodiments, the sequences have 5, 10, 15, 20, 25, 30, 35, 40, 45, 50, 55, 60, 65, 70, 75, 80, 85, 90, 95, 100, 105 or fewer amino acids.

In certain embodiments, the binding proteins disclosed herein contain sequences that have high homology to VH or VL domains or fragments thereof, wherein the sequences are selected from those shown below in Table 2.

TABLE 2

Sequence of VH and VL Domains

| Domain Name | Sequence Identifier | Sequence 123456789012345678901234567890 |
|---|---|---|
| 13 VH | SEQ ID NO: 30 | EVQLQESGPGLVKPSETLSLTCTVSGFSLS DYGVSWIRQPPGKGLEWIGLIWGSGDTYYN SPLKSRLTISKDNSKSQVSLKLSSVTAADT AVYYCAKQTNIWAYDLYSMDYWGQGTLVTV SS |
| 21 VH | SEQ ID NO: 31 | EVQLQESGPGLVKPSETLSLTCTVSGFSLS EFGVSWIRQPPGKGLEWIGLIWGGGDTYYN SPLKSRLTISKDNSKSQVSLKLSSVTAADT AVYYCAKQRNLWAYDLYGMDYWGQGTLVTV SS |

TABLE 2-continued

Sequence of VH and VL Domains

| Domain Name | Sequence Identifier | Sequence 12345678901234567890123456789 0 |
|---|---|---|
| 34 VH | SEQ ID NO: 32 | EVQLQESGPGLVKPSETLSLTCTVSGFSLS DYGVSWIRQPPGKGLEWIGLIWGSGDTYYN SPLKSRLTISKDTSKSQVSLKLSSVTAADT AVYYCAKQTNLWAYDLYSMDYWGQGTLVTV SS |
| A1 VH | SEQ ID NO: 33 | EVQLQESGPGLVKPSETLSLTCTVSGFSLR DYGVSWIRQPPGKGLEWLGLIWGSGDTYYN SPLKSRLTISKDTSKSQVSLKLSSVTAADT AVYYCAKQTNIWGYDLYGMDYWGQGTLVTV SS |
| A3 VH | SEQ ID NO: 34 | EVQLQESGPGLVKPSETLSLTCTVSGFSLS DYGVSWIRQPPGKGLEWIGLIWGSGDTYYN SPLKSRLTISKDNSKSQVSLKLSSVTAADT AVYYCARQTNLWAYDLYSMDYWGQGTLVTV SS |
| 1B12.9 VH | SEQ ID NO: 35 | EVQLQESGPGLVKPSETLSLTCTVSGFSLS DYGVSWIRQPPGKGLEWLGLIWGGGDTYYN SPLKSRLTISKDNSKSQVSLKLSSVTAADT AVYYCAKQRTLWGYDLYGMDYWGQGTLVTV SS |
| X3 VH | SEQ ID NO: 128 | QVQLVESGGGVVQPGRSLRLSCTASGFTFS MFGVHWVRQAPGKGLEWVAAVSYDGSNKYY AESVKGRFTISRDNSKNILFLQMDSLRLED TAVYYCARGRPKVVIPAPLAHWGQGTLVTF SS |
| 13 VL | SEQ ID NO: 36 | DIQMTQSPSSLSASVGDRVTITCQTSTDID DDLNWYQQKPGKAPKLLISLASTLRPGVPS RFSGSGSGTDFTFTISSLQPEDFATYYCLQ SDRLPLTFGQGTKLEIKR |
| 21 VL | SEQ ID NO: 37 | DIQMTQSPSSLSASVGDRVTITCQTSQDID MDLNWYQQKPGKAPKLLISQGSTLWPGVPS RFSGSGSGTDFTFTISSLQPEDFATYYCLQ TDSFPLTFGQGTKLEIKR |
| 34 VL | SEQ ID NO: 38 | DIQMTQSPSSLSASVGDRVTITCQASQDID DDLNWYQQKPGKAPKLLISLASILRPGVPS RFSGSGSGTDFTFTISSLQPEDFATYYCLQ SDSFPLTFGQGTKLEIKR |
| A1 VL | SEQ ID NO: 39 | DIQMTQSPSSLSASVGDRVTITCQASQDID MDLNWYQQKPGKAPKLLISQANTLPPGVPS RFSGSGSGTDFTFTISSLQPEDFATYYCLQ SDWLPLTFGQGTKLEIKR |
| A3 VL | SEQ ID NO: 40 | DIQMTQSPSSLSASVGDRVTITCQASTDID DDMNWYQQKPGKAPKLLISLANKLRPGVPS RFSGSGSGTDFTFTISSLQPEDFATYYCLQ TDSFPLTFGQGTKLEIKR |
| 1B12.9 VL | SEQ ID NO: 41 | DTQMTQSPSSLSASVGDRVTITCITSTDID VDMNWYQQKPGKPPKLLISQGNTLRPGVPS RFSSSGSGTDFTFTISSLQPEDFATYYCLQ SDNLPLTFGQGTKLEIKR |
| X3VL | SEQID NO: 129 | DIQMTQSPSSVSASVGDRVTITCRASQGIS SWLAWYQQKPGKAPKLLIYEASNLETGVPS RFSGSGSGSDFTLTISSLQPEDFATYYCQQ TSSFLLSFGGGTKVEHKR |

In other embodiments, the VH or VL sequences can be selected from any of the mutants shown in Table 3a. Table 3a shows potential mutations at various positions of the h1B121 VH and VL sequences. Any one or more of the mutations can be made to construct a VH or VL domain that will specifically bind to IL-1β.

TABLE 3a

H1B12 Heavy chain variable region

```
                1234567890123456789012345678901234567890123456789012 h1B12VH.1a    EVQLQESGPGLVKPSETLSLTCTVSGFSLSDYGVSWIRQPPGKGLEWLGLIWGGGDTYYN
(SEQ                                         G   RED                I V GVR G F
ID                                                GHN                 R LRV E S
NO: 428)                                          NYH                 G YWW V D
                                                  INS                 F SLS S V
                                                  TGF                 W RDL A T
                                                  MV                  M ESI K H
                                                  KQ                  I A E Q
                                                                        D Y

SPLKSRLTISKDNSKSQVSLKLSSVTAADTAVYYCAKQRTLWGYDLYGMDYWGQGTLVTVSS
                V T                              RTTKASAFQGNA
                                                 DMRMGRNKIDR
                                                 KSNRRVDHFVD
                                                 PIYIVTHASSW
                                                 HWWGLPSVM
                                                 APVWKN L
                                                 YNMQAE
                                                 VK HYD
                                                   FT
```

H1B12 Light chain variable region

```
              123456789012345678901234567890123456789012345678901234567890 h1B12VL.1a    DTQVTQSPSSLSASVGDRVTITCITSTDIDVDMNWYQQKPGKPPKLLISQGNTLRPGVPS
(SEQ            I M                     QA Q  PPAM         A        YHASS LL
ID                                              YAP                 P   I  PS
NO: 429)                                        NFN                 K   M  WT
```

TABLE 3a-continued

|   |   |   |   |   |
|---|---|---|---|---|
| Q Y |   | R | A | Q |
| L V |   |   |   | H |

H1B12 Heavy chain variable region

123456789012345678901234567890123456789012345678901234567890123456789012

RFSSSGSGTDFTFTISSLQPEDFATYYCLQSDNLPLTFGQGTKLEIK
G                           Q  WGEGA
                                 RKRD
                                 KVMF
                                 G G
                                 V

In other embodiments, the VH and/or VL sequences of a binding protein of the invention can be independently selected from Table 3b. Table 3b lists exemplary affinity-matured clones comprising mutations at one or more of the positions depicted in Table 3a supra.

TABLE 3b

VH/VL sequences of affinity matured H1B12.1 clones

VH SEQUENCE

>Lib1_D4 (SEQ ID NO: 152)
EVQLQESGPGLVKPSETLSLTCTVSGFSLGDYGVSWIR
QPPGKGLEWIGLIWGGGDTYYNSPLKSRLTISKDNSKS
QVSLKLSSVTAADTAVYYCAKQRTLWGYDLYGMDYWGQ
GTLVTVSS

>Lib2_H8 (SEQ ID NO: 153)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQTNLWGYDLYSMDYWGQ
GTLVTVSS

>Lib1_G2 (SEQ ID NO: 154)
EVQLQESGPGLVKPSETLSLTCTVSGFSLSEFGVSWIR
QPPGKGLEWIGLIWGSGDTYYNSPLKSRLTISKDTSKS
QVSLKLSSVTAADTAVYYCAKQRTLWGYDLYGMDYWGQ
GTLVTVSS

>Lib1_B6 (SEQ ID NO: 155)
EVQLQESGPGLVKPSETLSLTCTVSGFSLSNFGVSWIR
QPPGKGLEWIGLIWGGGDTYYNSPLKSRLTISKDNSKS
QVSLKLSSVTAADTAVYYCAKQRTLWGYDLYGMDYWGQ
GTLVTVSS

>Lib4_12E (SEQ ID NO: 156)
EVQLQESGPGLVKPSETLSLTCTVSGFSLSGYGVSWIR
QPPGKGLEWLGLIWGSGDTYYNSPLKSRLTISKDNSKS
QVSLKLSSVTAADTAVYYCAKQRNLWGYDLYGMDYWGQ
GTLVTVSS

>Lib4_5C (SEQ ID NO: 157)
EVQLQESGPGLVKPSETLSLTCTVSGFSLSKYGVSWIR
QPPGKGLEWLGLIWGGGDTYYNSPLKSRLTISKDNSKS
QVSLKLSSVTAADTAVYYCAKQTNTwAyDLySMDYWGQ
GTLVTVSS

>Lib2_H1 (SEQ ID NO: 158)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQRNLwGyDmyGmDYWGQ
GTLVTVSS

>Lib4_12D (SEQ ID NO: 159)
EVQLQESGPGLVKPSETLSLTCTVSGFSLSDFGVSWIR
QPPGKGLEWLGLIWGGGDTYYNSPLKSRLTISKDNSKS
QVSLKLSSVTAADTAVYYCAKQTNLWAYDLYSMDYWGQ
GTLVTVSS

TABLE 3b-continued

VH/VL sequences of affinity matured H1B12.1 clones

>Lib1_H6 (SEQ ID NO: 160)
EVQLQESGPGLVKPSETLSLTCTVSGFSLSGYGVSWIR
QPPGKGLEWIGLIWGSGDTYYNSPLKSRLTISKDNSKS
QVSLKLSSVTAADTAVYYCAKQRTLWGYDLYGMDYWGQ
GTLVTVSS

>Lib4_3A (SEQ ID NO: 161)
EVQLQESGPGLVKPSETLSLTCTVSGFSLSDYGVSWIR
QPPGKGLEWIGLIWGGGDTYYNSPLKSRLTISKDNSKS
QVSLKLSSVTAADTAVYYCARQRNIWAYDLYGMDYWGQ
GTLVTVSS

>Lib2_G5 (SEQ ID NO: 162)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQNNLWGYDLYGMDYWGQ
GTLVTVSS

>Lib2_B6 (SEQ ID NO: 163)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQRNVWGYDLYGMDYWGQ
GTLVTVSS

>Lib2_B1 (SEQ ID NO: 164)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKHRNIWGYDLYGMDYWGQ
GTLVTVSS

>Lib1_A7 (SEQ ID NO: 165)
EVQLQESGPGLVKPSETLSLTCTVSGFSLSEFGVSWIR
QPPGKGLEWLGLIWGGGDTYYNSPLKSRLTISKDTSKS
QVSLKLSSVTAADTAVYYCAKQRTLWGYDLYGMDYWGQ
GTLVTVSS

>Lib4_6C (SEQ ID NO: 166)
EVQLQESGPGLVKPSETLSLTCTVSGFSLSDFGVSWIR
QPPGKGLEWLGLIWGGGDTYYNSPLKSRLTISKDNSKS
QVSLKLSSVTAADTAVYYCAKQRNLWGYDLYGMDYWGQ
GTLVTVSS

>Lib4_3 (SEQ ID NO: 167)
EVQLQESGPGLVKPSETLSLTCTVSGFSLSDYGVSWIR
QPPGKGLEWIGLIWGGGDTYYNSPLKSRLTISKDNSKS
QVSLKLSSVTAADTAVYYCAKQSNVWGYDLYSMDYWGQ
GTLVTVSS

>Lib2_E9 (SEQ ID NO: 168)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQINIWGYDLYGMDYWGQ
GTLVTVSS

TABLE 3b-continued

VH/VL sequences of affinity
matured H1B12.1 clones

>Lib2_D6 (SEQ ID NO: 169)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCARQNTRWGDDLYGMDYWGQ
GTLVTVSS

>Lib4_29 (SEQ ID NO: 170)
EVQLQESGPGLVKPSETLSLTCTVSGFSLSDYGVSWIR
QPPGKGLEWIGLIWGGGDTYYNSPLKSRLTISKDTSKS
QVSLKLSSVTAADTAVYYCAKQRNLWGYDLYSMDYWGQ
GTLVTVSS

>Lib1_D8 (SEQ ID NO: 171)
EVQLQESGPGLVKPSETLSLTCTVSGFSLSYGVSWIR
QPPGKGLEWLGLIWGSGDTYYNSPLKSRLTISKDTSKS
QVSLKLSSVTAADTAVYYCAKQRTLWGYDLYGMDYWGQ
GTLVTVSS

>Lib4_72 (SEQ ID NO: 172)
EVQLQESGPGLVKPSETLSLTCTVSGFSLRDYGVSWIR
QPPGKGLEWIGLIWGSGDTYYNSPLKSRLTISKDNSKS
QVSLKLSSVTAADTAVYYCAKQRNLWGYDLYGMDYWGQ
GTLVTVSS

>Lib4_11H (SEQ ID NO: 173)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQNNVWGYDLYGMDYWGQ
GTLVTVSS

>Lib2_H11 (SEQ ID NO: 174)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKHRNLWGYDLYGMDYWGQ
GTLVTVSS

>Lib4_58 (SEQ ID NO: 175)
EVQLQESGPGLVKPSETLSLTCTVSGFSLSEYGVSWIR
QPPGKGLEWIGLIWGSGDTYYNSPLKSRLTISKDNSKS
QVSLKLSSVTAADTAVYYCAKQRNLWGYDLYGMDYWGQ
GTLVTVSS

>Lib4_5B (SEQ ID NO: 176)
EVQLQESGPGLVKPSETLSLTCTVSGFSLSDYGVSWIR
QPPGKGLEWIGLIWGGGDTYYNSPLKSRLTISKDNSKS
QVSLKLSSVTAADTAVYYCARQTNLWAYDLYSMDYWGQ
GTLVTVSS

>Lib2_H3 (SEQ ID NO: 177)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQRTLWGYDLYGMDYWGQ
GTLVTVSS

>Lib1_D5 (SEQ ID NO: 178)
EVQLQESGPGLVKPSETLSLTCTVSGFSLREYGVSWIR
QPPGKGLEWIGLIWGGGDTYYNSPLKSRLTISKDTSKS
QVSLKLSSVTAADTAVYYCAKQRTLWGYDLYGMDYWGQ
GTLVTVSS

>Lib1_G7 (SEQ ID NO: 179)
EVQLQESGPGLVKPSETLSLTCTVSGFSLIDYGVSWIR
QPPGKGLEWIGLIWGGGDTYYNSPLKSRLTISKDNSKS
QVSLKLSSVTAADTAVYYCAKQRNLWGYDLYGMDYWGQ
GTLVTVSS

>Lib4_2C (SEQ ID NO: 180)
EVQLQESGPGLVKPSETLSLTCTVSGFSLSDYGVSWIR
QPPGKGLEWIGLIWGGGDTYYNSPLKSRLTISKDTSKS
QVSLKLSSVTAADTAVYYCAKQINLWGYDLYGMDYWGQ
GTLVTVSS

TABLE 3b-continued

VH/VL sequences of affinity
matured H1B12.1 clones

>Lib2_H10 (SEQ ID NO: 181)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQRNLWGYDLYGMDYWGQ
GTLVTVSS

>Lib4_9C (SEQ ID NO: 182)
EVQLQESGPGLVKPSETLSLTCTVSGFSLSDFGVSWIR
QPPGKGLEWLGLIWGSGDTYYNSPLKSRLTISKDTSKS
QVSLKLSSVTAADTAVYYCAKQRNLWGYDLYGMDYWGQ
GTLVTVSS

>Lib1_A4 (SEQ ID NO: 183)
EVQLQESGPGLVKPSETLSLTCTVSGFSLRDYGVSWIR
QPPGKGLEWLGLIWGSGDTYYNSPLKSRLTISKDNSKS
QVSLKLSSVTAADTAVYYCAKQRTLWGYDLYGMDYWGQ
GTLVTVSS

>Lib1_A3 (SEQ ID NO: 184)
EVQLQESGPGLVKPSETLSLTCTVSGFSLRDYGVSWIR
QPPGKGLEWIGLIWGSGDTYYNSPLKSRLTISKDNSKS
QVSLKLSSVTAADTAVYYCAKQRTLWGYDLYGMDYWGQ
GTLVTVSS

>Lib4_31 (SEQ ID NO: 185)
EVQLQESGPGLVKPSETLSLTCTVSGFSLSDYGVSWIR
QPPGKGLEWIGLIWGSGDTYYNSPLKSRLTISKDNSKS
QVSLKLSSVTAADTAVYYCAKQTNIWAYDLYSMDYWGQ
GTLVTVSS

>Lib2_H4 (SEQ ID NO: 186)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQTNVWGYDLYGMDYWGQ
GTLVTVSS

>Lib1_D1 (SEQ ID NO: 187)
EVQLQESGPGLVKPSETLSLTCTVSGFSLSEFGVSWIR
QPPGKGLEWIGLIWGSGDTYYNSPLKSRLTISKDNSKS
QVSLKLSSVTAADTAVYYCAKQRTLWGYDLYGMDYWGQ
GTLVTVSS

>Lib4_86 (SEQ ID NO: 188)
EVQLQESGPGLVKPSETLSLTCTVSGFSLSDFGVSWIR
QPPGKGLEWIGLIWGGGDTYYNSPLKSRLTISKDTSKS
QVSLKLSSVTAADTAVYYCAKQSNLwGyDLySmDYWGQ
GTLVTVSS

>Lib2_A6 (SEQ ID NO: 189)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQRNEwGyDLyGmDYWGQ
GTLVTVSS

>Lib4_10G (SEQ ID NO: 190)
EVQLQESGPGLVKPSETLSLTCTVSGFSLKDYGVSWIR
QPPGKGLEWIGLIWGSGDTYYNSPLKSRLTISKDNSKS
QVSLKLSSVTAADTAVYYCAKQRNIWGYDLYGMDYWGQ
GTLVTVSS

>Lib2_F1 (SEQ ID NO: 191)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCARQNNLWGYDLYGMDYWGQ
GTLVTVSS

>Lib4_7B (SEQ ID NO: 192)
EVQLQESGPGLVKPSETLSLTCTVSGFSLSNYGVSWIR
QPPGKGLEWIGLIWGGGDTYYNSPLKSRLTISKDNSKS
QVSLKLSSVTAADTAVYYCAKQRNVWGYDLYGMDYWGQ
GTLVTVSS

TABLE 3b-continued

VH/VL sequences of affinity matured H1B12.1 clones

>Lib2_D5 (SEQ ID NO: 193)
EVQLQESGPGLVKPSETLSLTCTVSGFSLSDYGVSWIR
QPPGKGLEWLGLIWGGDTYYNSPLKSRLTISKDNSKS
QVSLKLSSVTAADTAVYYCAKNRNIWGYDLYGMDYWGQ
GTLVTVSS

>Lib4_84 (SEQ ID NO: 194)
EVQLQESGPGLVKPSETLSLTCTVSGFSLMDYGVSWIR
QPPGKGLEWIGLIWGSGDTYYNSPLKSRLTISKDNSKS
QVSLKLSSVTAADTAVYYCAKQTNLWAYDLYSMDYWGQ
GTLVTVSS

>Lib1_G11 (SEQ ID NO: 195)
EVQLQESGPGLVKPSETLSLTCTVSGFSLSDYGVSWIR
QPPGKGLEWLGLIWGGDTYYNSPLKSRLTISKDTSKS
QVSLKLSSVTAADTAVYYCAKQRTLWGYDLYGMDYWGQ
GTLVTVSS

>Lib4_63 (SEQ ID NO: 196)
EVQLQESGPGLVKPSETLSLTCTVSGFSLSEYGVSWIR
QPPGKGLEWIGLIWGGDTYYNSPLKSRLTISKDNSKS
QVSLKLSSVTAADTAVYYCAKNRNLWGYDLYSMDYWGQ
GTLVTVSS

>Lib1_F9 (SEQ ID NO: 197)
EVQLQESGPGLVKPSETLSLTCTVSGFSLGEYGVSWIR
QPPGKGLEWLGLIWGGDTYYNSPLKSRLTISKDNSKS
QVSLKLSSVTAADTAVYYCAKQRTLWGYDLYGMDYWGQ
GTLVTVSS

>Lib4_6B (SEQ ID NO: 198)
EVQLQESGPGLVKPSETLSLTCTVSGFSLSEFGVSWIR
QPPGKGLEWIGLIWGSGDTYYNSPLKSRLTISKDTSKS
QVSLKLSSVTAADTAVYYCAKQRNLWGYDLYGMDYWGQ
GTLVTVSS

>Lib4_10A (SEQ ID NO: 199)
EVQLQESGPGLVKPSETLSLTCTVSGFSLRGYGVSWIR
QPPGKGLEWIGLIWGSGDTYYNSPLKSRLTISKDNSKS
QVSLKLSSVTAADTAVYYCAKQRNIWGYDLYGMDYWGQ
GTLVTVSS

>Lib4_7 (SEQ ID NO: 200)
EVQLQESGPGLVKPSETLSLTCTVSGFSLGDYGVSWIR
QPPGKGLEWLGLIWGGDTYYNSPLKSRLTISKDNSKS
QVSLKLSSVTAADTAVYYCAKQTNLWAYDLYSMDYWGQ
GTLVTVSS

>Lib4_1D (SEQ ID NO: 201)
EVQLQESGPGLVKPSETLSLTCTVSGFSLSDYGVSWIR
QPPGKGLEWLGLIWGGDTYYNSPLKSRLTISKDNSKS
QVSLKLSSVTAADTAVYYCARQRNLWAYDLYTMDYWGQ
GTLVTVSS

>Lib4_61 (SEQ ID NO: 202)
EVQLQESGPGLVKPSETLSLTCTVSGFSLRDYGVSWIR
QPPGKGLEWIGLIWGGDTYYNSPLKSRLTISKDNSKS
QVSLKLSSVTAADTAVYYCAKQTNLWAYDLYTMDYWGQ
GTLVTVSS

>Lib1_D11 (SEQ ID NO: 203)
EVQLQESGPGLVKPSETLSLTCTVSGFSLTDYGVSWIR
QPPGKGLEWIGMIWGSGDTYYNSPLKSRLTISKDNSKS
QVSLKLSSVTAADTAVYYCAKQRTLWGYDLYGMDYWGQ
GTLVTVSS

>Lib1_E4 (SEQ ID NO: 204)
EVQLQESGPGLVKPSETLSLTCTVSGFSLGEFGVSWIR
QPPGKGLEWIGLIWGGDTYYNSPLKSRLTISKDNSKS
QVSLKLSSVTAADTAVYYCAKQRTLWGYDLYGMDYWGQ
GTLVTVSS

>Lib4_3B (SEQ ID NO: 205)
EVQLQESGPGLVKPSETLSLTCTVSGFSLTEFGVSWIR
QPPGKGLEWIGLIWGSGDTYYNSPLKSRLTISKDNSKS
QVSLKLSSVTAADTAVYYCAKQTNLWAYDLYSMDYWGQ
GTLVTVSS

>Lib4_10 (SEQ ID NO: 206)
EVQLQESGPGLVKPSETLSLTCTVSGFSLSEYGVSWIR
QPPGKGLEWLGLIWGGGDTYYNSPLKSRLTISKDNSKS
QVSLKLSSVTAADTAVYYCAKQTNVWGYDLYGMDYWGQ
GTLVTVSS

>Lib1_D10 (SEQ ID NO: 207)
EVQLQESGPGLVKPSETLSLTCTVSGFSLSEYGVSWIR
QPPGKGLEWLGLIWGGGDTYYNSPLKSRLTISKDNSKS
QVSLKLSSVTAADTAVYYCAKQRTLWGYDLYGMDYWGQ
GTLVTVSS

>Lib2_H7 (SEQ ID NO: 208)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKNRNIWGVDLYGMDYWGQ
GTLVTVSS

>Lib1_D12 (SEQ ID NO: 209)
EVQLQESGPGLVKPSETLSLTCTVSGFSLTDYGVSWIR
QPPGKGLEWIGLIWGGGDTYYNSPLKSRLTISKDNSKS
QVSLKLSSVTAADTAVYYCAKQRTLWGYDLYGMDYWGQ
GTLVTVSS

>Lib2_D9 (SEQ ID NO: 210)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCARQNNVWGYDLYGMDYWGQ
GTLVTVSS

>Lib4_1F (SEQ ID NO: 211)
EVQLQESGPGLVKPSETLSLTCTVSGFSLSDYGVSWIR
QPPGKGLEWIGLIWGSGDTYYNSPLKSRLTISKDNSKS
QVSLKLSSVTAADTAVYYCAKQRNLWGYDLYGMDYWGQ
GTLVTVSS

>Lib4_57 (SEQ ID NO: 212)
EVQLQESGPGLVKPSETLSLTCTVSGFSLSDYGVSWIR
QPPGKGLEWIGLIWGGGDTYYNSPLKSRLTISKDNSKS
QVSLKLSSVTAADTAVYYCAKQNNVWGYDLYGMDYWGQ
GTLVTVSS

>Lib4_10H (SEQ ID NO: 213)
EVQLQESGPGLVKPSETLSLTCTVSGFSLSDYGVSWIR
QPPGKGLEWIGLIWGGGDTYYNSPLKSRLTISKDTSKS
QVSLKLSSVTAADTAVYYCAKQTNLWGYDLYSMDYWGQ
GTLVTVSS

>Lib2_H5 (SEQ ID NO: 214)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQTNLWGYDLYGMDYWGQ
GTLVTVSS

>Lib4_1G (SEQ ID NO: 215)
EVQLQESGPGLVKPSETLSLTCTVSGFSLSDYGVSWIR
QPPGKGLEWIGLIWGSGDTYYNSPLKSRLTISKDTSKS
QVSLKLSSVTAADTAVYYCAKQRNLWGYDLYGMDYWGQ
GTLVTVSS

>Lib1_G6 (SEQ ID NO: 216)
EVQLQESGPGLVKPSETLSLTCTVSGFSLSDYGVSWIR
QPPGKGLEWIGLIWGGGDTYYNSPLKSRLTISKDNSKS
QVSLKLSSVTAADTAVYYCAKQRTLWGYDLYGMDYWGQ
GTLVTVSS

TABLE 3b-continued

VH/VL sequences of affinity
matured H1B12.1 clones

>Lib1_F8 (SEQ ID NO: 217)
EVQLQESGPGLVKPSETLSLTCTVSGFSLKDYGVSWIR
QPPGKGLEWIGLIWGGGDTYYNSPLKSRLTISKDTSKS
QVSLKLSSVTAADTAVYYCAKQRTLWGYDLYGMDYWGQ
GTLVTVSS

>Lib4_69 (SEQ ID NO: 218)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQTNLWGYDLYGMDYWGQ
GTLVTVSS

>Lib4_4H (SEQ ID NO: 219)
EVQLQESGPGLVKPSETLSLTCTVSGFSLSDYGVSWIR
QPPGKGLEWIGLIWGSGDTYYNSPLKSRLTISKDTSKS
QVSLKLSSVTAADTAVYYCAKQTNLWAYDLYSMDYWGQ
GTLVTVSS

>Lib4_12H (SEQ ID NO: 220)
EVQLQESGPGLVKPSETLSLTCTVSGFSLTDYGVSWIR
QPPGKGLEWIGLIWGGGDTYYNSPLKSRLTISKDNSKS
QVSLKLSSVTAADTAVYYCAKQRNLWAYDLYGMDYWGQ
GTLVTVSS

>Lib4_11 (SEQ ID NO: 221)
EVQLQESGPGLVKPSETLSLTCTVSGFSLSDYGVSWIR
QPPGKGLEWIGLIWGSGDTYYNSPLKSRLTISKDNSKS
QVSLKLSSVTAADTAVYYCAKVRNVWGYDLYTMDYWGQ
GTLVTVSS

>Lib1_C8 (SEQ ID NO: 222)
EVQLQESGPGLVKPSETLSLTCTVSGFSLGDFGVSWIR
QPPGKGLEWIGLIWGGGDTYYNSPLKSRLTISKDTSKS
QVSLKLSSVTAADTAVYYCAKQRTLWGYDLYGMDYWGQ
GTLVTVSS

>Lib4_88 (SEQ ID NO: 223)
EVQLQESGPGLVKPSETLSLTCTVSGFSLSEYGVSWIR
QPPGKGLEWIGLIWGGGDTYYNSPLKSRLTISKDNSKS
QVSLKLSSVTAADTAVYYCAKQRNIWGYDLYGMDYWGQ
GTLVTVSS

>Lib2_G10 (SEQ ID NO: 224)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQNNVWGYDLYGMDYWGQ
GTLVTVSS

>Lib4_37 (SEQ ID NO: 225)
EVQLQESGPGLVKPSETLSLTCTVSGFSLSGYGVSWIR
QPPGKGLEWIGLIWGGGDTYYNSPLKSRLTISKDNSKS
QVSLKLSSVTAADTAVYYCAKQRNLWGYDLYGMDYWGQ
GTLVTVSS

>Lib4_4A (SEQ ID NO: 226)
EVQLQESGPGLVKPSETLSLTCTVSGFSLSDYGVSWIR
QPPGKGLEWIGLIWGGGDTYYNSPLKSRLTISKDNSKS
QVSLKLSSVTAADTAVYYCAKQRNLWAYDLYGMDYWGQ
GTLVTVSS

>Lib4_11G (SEQ ID NO: 227)
EVQLQESGPGLVKPSETLSLTCTVSGFSLSEFGVSWIR
QPPGKGLEWIGLIWGGGDTYYNSPLKSRLTISKDNSKS
QVSLKLSSVTAADTAVYYCAKQTNLwAyDLySMDYWGQ
GTLVTVSS

>Lib4_7C (SEQ ID NO: 228)
EVQLQESGPGLVKPSETLSLTCTVSGFSLNDYGVSWIR
QPPGKGLEWIGLIWGGGDTYYNSPLKSRLTISKDTSKS
QVSLKLSSVTAADTAVYYCAKQRNIWGyDLyGmDYWGQ
GTLVTVSS

>Lib4_12F (SEQ ID NO: 229)
EVQLQESGPGLVKPSETLSLTCTVSGFSLRDYGVSWIR
QPPGKGLEWLGLIWGSGDTYYNSPLKSRLTISKDTSKS
QVSLKLSSVTAADTAVYYCAKQRNLWGYDLYGMDYWGQ
GTLVTVSS

>Lib1_A10 (SEQ ID NO: 230)
EVQLQESGPGLVKPSETLSLTCTVSGFSLSDYGVSWIR
QPPGKGLEWIGLIWGSGDTYYNSPLKSRLTISKDTSKS
QVSLKLSSVTAADTAVYYCAKQRTLWGYDLYGMDYWGQ
GTLVTVSS

>Lib1_F3 (SEQ ID NO: 231)
EVQLQESGPGLVKPSETLSLTCTVSGFSLSEYGVSWIR
QPPGKGLEWIGLIWGGGDTYYNSPLKSRLTISKDTSKS
QVSLKLSSVTAADTAVYYCAKQRTLWGYDLYGMDYWGQ
GTLVTVSS

>Lib4_26 (SEQ ID NO: 232)
EVQLQESGPGLVKPSETLSLTCTVSGFSLSDYGVSWIR
QPPGKGLEWLGLIWGSGDTYYNSPLKSRLTISKDNSKS
QVSLKLSSVTAADTAVYYCAKQRNLWGYDLYGMDYWGQ
GTLVTVSS

>Lib2_G4 (SEQ ID NO: 233)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCARQRNLWGYDLYGMDYWGQ
GTLVTVSS

>Lib4_65 (SEQ ID NO: 234)
EVQLQESGPGLVKPSETLSLTCTVSGFSLMDYGVSWIR
QPPGKGLEWIGLIWGGGDTYYNSPLKSRLTISKDTSKS
QVSLKLSSVTAADTAVYYCAKQRNLWGYDLYGMDYWGQ
GTLVTVSS

>Lib2_F12 (SEQ ID NO: 235)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKNRNVWGYDMYAMDYWGQ
GTLVTVSS

>Lib4_66 (SEQ ID NO: 236)
EVQLQESGPGLVKPSETLSLTCTVSGFSLRDFGVSWIR
QPPGKGLEWIGLIWGGGDTYYNSPLKSRLTISKDNSKS
QVSLKLSSVTAADTAVYYCAKVRNLWGYDMYTMDYWGQ
GTLVTVSS

>Lib1_E7 (SEQ ID NO: 237)
EVQLQESGPGLVKPSETLSLTCTVSGFSLSEFGVSWIR
QPPGKGLEWIGLIWGGGDTYYNSPLKSRLTISKDNSKS
QVSLKLSSVTAADTAVYYCAKQRTLWGYDLYGMDYWGQ
GTLVTVSS

>Lib2_D7 (SEQ ID NO: 238)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQINLWGYDLYGMDYWGQ
GTLVTVSS

>Lib1_H4 (SEQ ID NO: 239)
EVQLQESGPGLVKPSETLSLTCTVSGFSLSSYGVDWIR
QPPGKGLEWIGLIWGGGDTYYNSPLKSRLTISKDTSKS
QVSLKLSSVTAADTAVYYCAKQRTLWGYDLYGMDYWGQ
GTLVTVSS

>Lib4_2A (SEQ ID NO: 240)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQRNLWGYDLYSMDYWGQ
GTLVTVSS

TABLE 3b-continued

VH/VL sequences of affinity
matured H1B12.1 clones

>Lib4_11C (SEQ ID NO: 241)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQRNLWAYDLYGMDYWGQ
GTLVTVSS

>Lib4_12 (SEQ ID NO: 242)
EVQLQESGPGLVKPSETLSLTCTVSGFSLSDFGVSWIR
QPPGKGLEWIGLIWGGGDTYYNSPLKSRLTISKDNSKS
QVSLKLSSVTAADTAVYYCAKQTNLWAYDLYSMDYWGQ
GTLVTVSS

>Lib1_G10 (SEQ ID NO: 243)
EVQLQESGPGLVKPSETLSLTCTVSGFSLSHYGVSWIR
QPPGKGLEWLGLIWGSGDTYYNSPLKSRLTISKDTSKS
QVSLKLSSVTAADTAVYYCAKQRTLWGYDLYGMDYWGQ
GTLVTVSS

>Lib4_1A (SEQ ID NO: 244)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQRNLWGYDLYGMDYWGQ
GTLVTVSS

>Lib4_2F (SEQ ID NO: 245)
EVQLQESGPGLVKPSETLSLTCTVSGFSLREYGVSWIR
QPPGKGLEWIGLIWGSGDTYYNSPLKSRLTISKDNSKS
QVSLKLSSVTAADTAVYYCAKVRNLWGYDMYTMDYWGQ
GTLVTVSS

>Lib2_E2 (SEQ ID NO: 246)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQRNLWGYDLYGMDYWXQ
GTLVTVSS

>Lib1_F5 (SEQ ID NO: 247)
EVQLQESGPGLVKPSETLSLTCTVSGFSLSEYGVSWIR
QPPGKGLEWLGLIWGGGDTYYNSPLKSRLTISKDTSKS
QVSLKLSSVTAADTAVYYCAKQRTLWGYDLYGMDYWGQ
GTLVTVSS

>Lib1_F6 (SEQ ID NO: 248)
EVQLQESGPGLVKPSETLSLTCTVSGFSLSNYGVSWIR
QPPGKGLEWIGLIWGGGDTYYNSPLKSRLTISKDNSKS
QVSLKLSSVTAADTAVYYCAKQRTLWGYDLYGMDYWGQ
GTLVTVSS

>Lib1_C9 (SEQ ID NO: 249)
EVQLQESGPGLVKPSETLSLTCTVSGFSLSDYGVSWIR
QPPGKGLEWIGLIWGSGDTYYNSPLKSRLTISKDNSKS
QVSLKLSSVTAADTAVYYCAKQRTLWGYDLYGMDYWGQ
GTLVTVSS

>Lib1_F12 (SEQ ID NO: 250)
EVQLQESGPGLVKPSETLSLTCTVSGFSLTDYGVSWIR
QPPGKGLEWIGLIWGGGDTYYNSPLKSRLTISKDTSKS
QVSLKLSSVTAADTAVYYCAKQRTLWGYDLYGMDYWGQ
GTLVTVSS

>Lib1_H12 (SEQ ID NO: 251)
EVQLQESGPGLVKPSETLSLTCTVSGFSLGDYGVSWIR
QPPGKGLEWIGLIWGSGDTYYNSPLKSRLTISKDNSKS
QVSLKLSSVTAADTAVYYCAKQRTLWGYDLYGMDYWGQ
GTLVTVSS

>Lib4_96 (SEQ ID NO: 252)
EVQLQESGPGLVKPSETLSLTCTVSGFSLSNYGVSWIR
QPPGKGLEWIGLIWGGGDTYYNSPLKSRLTISKDNSKS
QVSLKLSSVTAADTAVYYCARQRNLWAYDLYTMDYWGQ
GTLVTVSS

>Lib2_F9 (SEQ ID NO: 253)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCARQRNIWGYDLYGMDYWGQ
GTLVTVSS

>Lib4_7E (SEQ ID NO: 254)
EVQLQESGPGLVKPSETLSLTCTVSGFSLSDFGVSWIR
QPPGKGLEWLGLIWGGGDTYYNSPLKSRLTISKDNSKS
QVSLKLSSVTAADTAVYYCAKQTNIWGYDLYSMDYWGQ
GTLVTVSS

>Lib4_71 (SEQ ID NO: 255)
EVQLQESGPGLVKPSETLSLTCTVSGFSLSDFGVSWIR
QPPGKGLEWIGLIWGSGDTYYNSPLKSRLTISKDNSKS
QVSLKLSSVTAADTAVYYCAKQTNLWAYDLYSMDYWGQ
GTLVTVSS

>Lib4_95 (SEQ ID NO: 256)
EVQLQESGPGLVKPSETLSLTCTVSGFSLSDYGVSWIR
QPPGKGLEWIGLIWGGGDTYYNSPLKSRLTISKDNSKS
QVSLKLSSVTAADTAVYYCAKQSNIWAYDLYSMDYWGQ
GTLVTVSS

>Lib2_H9 (SEQ ID NO: 257)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCARQNNEWGYDLYGMDYWGQ
GTLVTVSS

>Lib2_A4 (SEQ ID NO: 258)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQRNIWGIDLYGMDYWGQ
GTLVTVSS

>Lib1_H11 (SEQ ID NO: 259)
EVQLQESGPGLVKPSETLSLTCTVSGFSLDHYGVSWIR
QPPGKGLEWIGLIWGGGDTYYNSPLKSRLTISKDTSKS
QVSLKLSSVTAADTAVYYCAKQRTLWGYDLYGMDYWGQ
GTLVTVSS

>Lib2_D1 (SEQ ID NO: 260)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQRNIWGVDMFGMDYWGQ
GTLVTVSS

>Lib4_50 (SEQ ID NO: 261)
EVQLQESGPGLVKPSETLSLTCTVSGFSLSDYGVSWIR
QPPGKGLEWIGLIWGSGDTYYNSPLKSRLTISKDTSKS
QVSLKLSSVTAADTAVYYCAKQTNLWGYDLYGMDYWGQ
GTLVTVSS

>Lib1_G5 (SEQ ID NO: 262)
EVQLQESGPGLVKPSETLSLTCTVSGFSLSKFGVSWIR
QPPGKGLEWIGLIWGGGDTYYNSPLKSRLTISKDTSKS
QVSLKLSSVTAADTAVYYCAKQRTLWGYDLYGMDYWGQ
GTLVTVSS

>Lib4_54 (SEQ ID NO: 263)
EVQLQESGPGLVKPSETLSLTCTVSGFSLRDYGVSWIR
QPPGKGLEWIGLIWGGGDTYYNSPLKSRLTISKDTSKS
QVSLKLSSVTAADTAVYYCAKQTNLWAYDLYSMDYWGQ
GTLVTVSS

>Lib1_B10 (SEQ ID NO: 264)
EVQLQESGPGLVKPSETLSLTCTVSGFSLSDYGVSWIR
QPPGKGLEWIGLIWGGGDTYYNSPLKSRLTISKDTSKS
QVSLKLSSVTAADTAVYYCAKQRTLWGYDLYGMDYWGQ
GTLVTVSS

TABLE 3b-continued

VH/VL sequences of affinity matured H1B12.1 clones

>Lib4_8D (SEQ ID NO: 265)
EVQLQESGPGLVKPSETLSLTCTVSGFSLSDYGVSWIR
QPPGKGLEWIGLIWGGDTYYNSPLKSRLTISKDNSKS
QVSLKLSSVTAADTAVYYCARQRNLWAYDLYTMDYWGQ
GTLVTVSS

>Lib1_C11 (SEQ ID NO: 266)
EVQLQESGPGLVKPSETLSLTCTVSGFSLRDYGVSWIR
QPPGKGLEWIGLIWGGDTYYNSPLKSRLTISKDTSKS
QVSLKLSSVTAADTAVYYCAKQRTLWGYDLYGMDYWGQ
GTLVTVSS

>Lib4_10F (SEQ ID NO: 267)
EVQLQESGPGLVKPSETLSLTCTVSGFSLSDYGVSWIR
QPPGKGLEWIGLIWGSGDTYYNSPLKSRLTISKDNSKS
QVSLKLSSVTAADTAVYYCAKQRNIWGYDLYGMDYWGQ
GTLVTVSS

>Lib4_59 (SEQ ID NO: 268)
EVQLQESGPGLVKPSETLSLTCTVSGFSLSDFGVSWIR
QPPGKGLEWIGLIWGSGDTYYNSPLKSRLTISKDNSKS
QVSLKLSSVTAADTAVYYCAKQRNLWGYDLYGMDYWGQ
GTLVTVSS

>Lib1_C2 (SEQ ID NO: 269)
EVQLQESGPGLVKPSETLSLTCTVSGFSLSDYGVSWIR
QPPGKGLEWIGLIWEGGDTYYNSPLKSRLTISKDTSKS
QVSLKLSSVTAADTAVYYCAKQRTLWGYDLYGMDYWGQ
GTLVTVSS

>Lib1_H5 (SEQ ID NO: 270)
EVQLQESGPGLVKPSETLSLTCTVSGFSLSECGVSWIR
QPPGKGLEWIGLIWGGGDTYYNSPLKSRLTISKDTSKS
QVSLKLSSVTAADTAVYYCAKQRTLWGYDLYGMDYWGQ
GTLVTVSS

>Lib2_F7 (SEQ ID NO: 271)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQTNVWGVDLYGMDYWGQ
GTLVTVSS

>Lib4_49 (SEQ ID NO: 272)
EVQLQESGPGLVKPSETLSLTCTVSGFSLREYGVSWIR
QPPGKGLEWIGLIWGGGDTYYNSPLKSRLTISKDNSKS
QVSLKLSSVTAADTAVYYCAKQTNIWGYDLYSMDYWGQ
GTLVTVSS

>Lib4_8E (SEQ ID NO: 273)
EVQLQESGPGLVKPSETLSLTCTVSGFSLSEFGVSWIR
QPPGKGLEWIGLIWGGGDTYYNSPLKSRLTISKDTSKS
QVSLKLSSVTAADTAVYYCAKQRNLWGYDLYGMDYWGQ
GTLVTVSS

>Lib1_E3 (SEQ ID NO: 274)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQRTLWGYDLYGMDYWGQ
GTLVTVSS

>Lib4_6 (SEQ ID NO: 275)
EVQLQESGPGLVKPSETLSLTCTVSGFSLSDYGVSWIR
QPPGKGLEWIGLIWGGGDTYYNSPLKSRLTISKDNSKS
QVSLKLSSVTAADTAVYYCAKQRNLWGYDLYGMDYWGQ
GTLVTVSS

>Lib4_12G (SEQ ID NO: 276)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQRNIWGYDLYGMDYWGQ
GTLVTVSS

>Lib1_D2 (SEQ ID NO: 277)
EVQLQESGPGLVKPSETLSLTCTVSGFSLGDYGVSWIR
QPPGKGLEWIGLIWGGGDTYYNSPLKSRLTISKDTSKS
QVSLKLSSVTAADTAVYYCAKQRTLWGYDLYGMDYWGQ
GTLVTVSS

>Lib4_9A (SEQ ID NO: 278)
EVQLQESGPGLVKPSETLSLTCTVSGFSLSDFGVSWIR
QPPGKGLEWIGLIWGSGDTYYNSPLKSRLTISKDNSKS
QVSLKLSSVTAADTAVYYCAKQRNLWGFDLYGMDYWGQ
GTLVTVSS

>Lib2_D12 (SEQ ID NO: 279)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQRNIWGYDLYGMDYWXQ
GTLVTVSS

>Lib4_77 (SEQ ID NO: 280)
EVQLQESGPGLVKPSETLSLTCTVSGFSLSEFGVSWIR
QPPGKGLEWIGLIWGGGDTYYNSPLKSRLTISKDNSKS
QVSLKLSSVTAADTAVYYCAKQRNLWAYDLYGMDYWGQ
GTLVTVSS

>Lib4_51 (SEQ ID NO: 281)
EVQLQESGPGLVKPSETLSLTCTVSGFSLKEYGVSWIR
QPPGKGLEWIGLIWGSGDTYYNSPLKSRLTISKDNSKS
QVSLKLSSVTAADTAVYYCAKQRNLWGYDLYGMDYWGQ
GTLVTVSS

>Lib4_9B (SEQ ID NO: 282)
EVQLQESGPGLVKPSETLSLTCTVSGFSLTDYGVSWIR
QPPGKGLEWIGLIWGGGDTYYNSPLKSRLTISKDNSKS
QVSLKLSSVTAADTAVYYCAKQRNLWGYDLYTMDYWGQ
GTLVTVSS

>Lib1_H9 (SEQ ID NO: 283)
EVQLQESGPGLVKPSETLSLTCTVSGFSLSHYGVSWIR
QPPGKGLEWIGLIWGGGDTYYNSPLKSRLTISKDTSKS
QVSLKLSSVTAADTAVYYCAKQRTLWGYDLYGMDYWGQ
GTLVTVSS

>Lib1_B2 (SEQ ID NO: 284)
EVQLQESGPGLVKPSETLSLTCTVSGFSLSDFGVSWIR
QPPGKGLEWIGLIWGGGDTYYNSPLKSRLTISKDNSKS
QVSLKLSSVTAADTAVYYCAKQRTLWGYDLYGMDYWGQ
GTLVTVSS

>Lib4_64 (SEQ ID NO: 285)
EVQLQESGPGLVKPSETLSLTCTVSGFSLGEHGVSWIR
QPPGKGLEWIGIIWGGGDTYYNSPLKSRLTISKDTSKS
QVSLKLSSVTAADTAVYYCAKQRNLWGYDLYGMDYWGQ
GTLVTVSS

>Lib2_C7 (SEQ ID NO: 286)
EVQLQESGPGLVKPSETLSLTCTVSGFSLSDYGVSWIR
QSPGKGLEWLGLIWGGGDTYYNSPLKSRLTISKDNSKS
QVSLKLSSVTAADTAVYYCAKQRNLWGYDLYGMDYWGQ
GTLVTVSS

>Lib4_6E (SEQ ID NO: 287)
EVQLQESGPGLVKPSETLSLTCTVSGFSLGEYGVSWIR
QPPGKGLEWLGLIWGGGDTYYNSPLKSRLTISKDTSKS
QVSLKLSSVTAADTAVYYCAKQRNIWGYDLYGMDYWGQ
GTLVTVSS

>Lib4_6F (SEQ ID NO: 288)
EVQLQESGPGLVKPSETLSLTCTVSGFSLRDYGVSWIR
QPPGKGLEWLGLIWGGGDTYYNSPLKSRLTISKDNSKS
QVSLKLSSVTAADTAVYYCAKQSNVWGYDLYSMDYWGQ
GTLVTVSS

TABLE 3b-continued

VH/VL sequences of affinity matured H1B12.1 clones

>Lib4_4 (SEQ ID NO: 289)
EVQLQESGPGLVKPSETLSLTCTVSGFSLSEYGVSWIR
QPPGKGLEWIGLIWGSGDTYYNSPLKSRLTISKDNSKS
QVSLKLSSVTAADTAVYYCAKQRNLWAYDLYGMDYWGQ
GTLVTVSS

>Lib2_B4 (SEQ ID NO: 290)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKHRNLWGFDLYGMDYWGQ
GTLVTVSS

>Lib2_G6 (SEQ ID NO: 291)
EVQLQESGPGLVKPSETLSLTCTVSGFSLSDYGVSWIR
QPPGKGLEWLGLIWGGGDTYYNSPLKSRLTISKDNSKS
QVSLKLSSVTAADTAVYYCAKQTNIWGYDLYGMDYWGQ
GTLVTVSS

>Lib1_E6 (SEQ ID NO: 292)
EVQLQESGPGLVKPSETLSLTCTVSGFSLSEYGVSWIR
QPPGKGLEWIGLIWGGGDTYYNSPLKSRLTISKDNSKS
QVSLKLSSVTAADTAVYYCAKQRTLWGYDLYGMDYWGQ
GTLVTVSS

VL SEQUENCE

>Lib4_8E (SEQ ID NO: 293)
DIQMTQSPSSLSASVGDRVTITCQASQDIDEDLNWYQ
QKPGKAPKLLISLASTLRPGVPSRFSGSGSGTDFTFT
ISSLQPEDFATYYCLQTDSFPLTFGQGTKLEIK

>Lib4_7 (SEQ ID NO: 294)
DIQMTQSPSSLSASVGDRVTITCQASTDIDDDMNWYQ
QKPGKAPKLLISLANKLRPGVPSRFSGSGSGTDFTFT
ISSLQPEDFATYYCLQSDSLPLTFGQGTKLEIK

>Lib3_C8 (SEQ ID NO: 295)
DIQMTQSPSSLSASVGDRVTITCQTSQDIDDDMNWYQ
QKPGKAPKLLISSASTLRPGVPSRFSGSGSGTDFTFT
ISSLQPEDFATYYCLQKEKLPLTFGQGTKLEIK

>Lib3_C2 (SEQ ID NO: 296)
DIQMTQSPSSLSASVGDRVTITCQASTDIDFDLNWYQ
QKPGKAPKLLISQASTLSSGVPSRFSGSGSGTDFTFT
ISSLQPEDFATYYCLQSEKLPLTFGQGTKLEIK

>Lib3_A4 (SEQ ID NO: 297)
DIQMTQSPSSLSASVGDRVTITCQTSTDIDEDLNWYQ
QKPGKAPKLLISLANNLHPGVPSRFSGSGSGTDFTFT
ISSLQPEDFATYYCLQGDRLPLTFGQGTKLEIK

>Lib3_D2 (SEQ ID NO: 298)
DIQMTQSPSSLSASVGDRVTITCQASQDIDDDLNWYQ
QKPGKAPKLLISLGSTLQPGVPSRFSGSGSGTDFTFT
ISSLQPEDFATYYCLQSDRLPLTFGQGTKLEIK

>Lib4_7E (SEQ ID NO: 299)
DIQMTQSPSSLSASVGDRVTITCQTSQDIDDDMNWYQ
QKPGKAPKLLISLGSHLRPGVPSRFSGSGSGTDFTFT
ISSLQPEDFATYYCLQSDRFPLTFGQGTKLEIK

>Lib4_12 (SEQ ID NO: 300)
DIQMTQSPSSLSASVGDRVTITCQTSQDIDEDLNWYQ
QKPGKAPKLLISLASNLRPGVPSRFSGSGSGTDFTFT
ISSLQPEDFATYYCLQSDRLPLTFGQGTKLEIK

>Lib3_G9 (SEQ ID NO: 301)
DIQMTQSPSSLSASVGDRVTITCQASQDIDVDLNWYQ
QKPGKAPKLLISQANTLRPGVPSRFSGSGSGTDFTFT
ISSLQPEDFATYYCLQSDWLPLTFGQGTKLEIK

>Lib4_9B (SEQ ID NO: 302)
DIQMTQSPSSLSASVGDRVTITCQASTDIDEDLNWYQ
QKPGKAPKLLISLASTLPPGVPSRFSGSGSGTDFTFT
ISSLQPEDFATYYCLQSDRFPLTFGQGTKLEIK

>Lib3_C3 (SEQ ID NO: 303)
DIQMTQSPSSLSASVGDRVTITCQTSQDIDEDLNWYQ
QKPGKAPKLLISQASTLRPGVPSRFSGSGSGTDFTFT
ISSLQPEDFATYYCLQVERLPLTFGQGTKLEIK

>Lib3_B3 (SEQ ID NO: 304)
DIQMTQSPSSLSASVGDRVTITCQASQDIDDDMNWYQ
QKPGKAPKLLISLASSLRPGVPSRFSGSGSGTDFTFT
ISSLQPEDFATYYCLQVDGLPLTFGQGTKLEIK

>Lib4_1D (SEQ ID NO: 305)
DIQMTQSPSSLSASVGDRVTITCQASQDIDDDLNWYQ
QKPGKAPKLLISLASTLWPGVPSRFSGSGSGTDFTFT
ISSLQPEDFATYYCLQSDSLPLTFGQGTKLEIK

>Lib3_E11 (SEQ ID NO: 306)
DIQMTQSPSSLSASVGDRVTITCQASQDIDDDLNWYQ
QKPGKAPKLLISQASTLGPGVPSRFSGSGSGTDFTFT
ISSLQPEDFATYYCLQVDRVPLTFGQGTKLEIK

>Lib3_C6 (SEQ ID NO: 307)
DIQMTQSPSSLSASVGDRVTITCQASQDIDEDMNWYQ
QKPGKAPKLLISQANKLRSGVPSRFSGSGSGTDFTFT
ISSLQPEDFATYYCLQVDRVPLTFGQGTKLEIK

>Lib4_6C (SEQ ID NO: 308)
DIQMTQSPSSLSASVGDRVTITCQASQDIDDDLNWYQ
QKPGKAPKLLISLGSTLQPGVPSRFSGSGSGTDFTFT
ISSLQPEDFATYYCLQVDSFPLTFGQGTKLEIK

>Lib4_65 (SEQ ID NO: 309)
DIQMTQSPSSLSASVGDRVTITCQTSTDIDDDMNWYQ
QKPGKAPKLLISLASTLRPGVPSRFSGSGSGTDFTFT
ISSLQPEDFATYYCLQSSWLPLTFGQGTKLEIK

>Lib4_10E (SEQ ID NO: 310)
DIQMTQSPSSLSASVGDRVTITCQASTDIDDDMNWYQ
QKPGKAPKLLISLANKLRPGVPSRFSGSGSGTDFTFT
ISSLQPEDFATYYCLQTDSFPLTFGQGTKLEIK

>Lib4_6E (SEQ ID NO: 311)
DIQMTQSPSSLSASVGDRVTITCQASQDIDDDLNWYQ
QKPGKAPKLLISLASTLWPGVPSRFSGSGSGTDFTFT
ISSLQPEDFATYYCLQSDSFPLTFGQGTKLEIK

>Lib3_E12 (SEQ ID NO: 312)
DIQMTQSPSSLSASVGDRVTITCQTSTDIDDDLNWYQ
QKPGKAPKLLISQGSTLRPGVPSRFSGSGSGTDFTFT
ISSLQPEDFATYYCLQVDRVPLTFGQGTKLEIK

>Lib4_66 (SEQ ID NO: 313)
DIQMTQSPSSLSASVGDRVTITCQASQDIDMDNWYQ
QKPGKAPKLLISLGNILRPGVPSRFSGSGSGTDFTFT
ISSLQPEDFATYYCLQSDSFPLTFGQGTKLEIK

>Lib3_B9 (SEQ ID NO: 314)
DIQMTQSPSSLSASVGDRVTITCQASQDIDVDMNWYQ
QKPGKAPKLLISLASKLRPGVPSRFSGSGSGTDFTFT
ISSLQPEDFATYYCLQVERFPLTFGQGTKLEIK

>Lib4_72 (SEQ ID NO: 315)
DIQMTQSPSSLSASVGDRVTITCQASTNIDDDMNWYQ
QKPGKAPKLLISLANMLRPGVPSRFSGSGSGTDFTFT
ISSLQPEDFATYYCLQGDRLPLTFGQGTKLEIK

>Lib3_E10 (SEQ ID NO: 316)
DIQMTQSPSSLSASVGDRVTITCQASQDIDEDLNWYQ
QKPGKAPKLLISLASTLRPGVPSRFSGSGSGTDFTFT
ISSLQPEDFATYYCLQSDNLPLTFGQGTKLEIK

>Lib4_9A (SEQ ID NO: 317)
DIQMTQSPSSLSASVGDRVTITCQASQDIDDDMNWYQ
QKPGKAPKLLISLASTLRPGVPSRFSGSGSGTDFTFT
ISSLQPEDFATYYCLQSDSLPLTFGQGTKLEIK

TABLE 3b-continued

VH/VL sequences of affinity
matured H1B12.1 clones

>Lib4_20 (SEQ ID NO: 318)
DIQMTQSPSSLSASVGDRVTITCQASQDIDEDLNWYQ
QKPGKAPKLLISLANILRPGVPSRFSGSGSGTDFTFT
ISSLQPEDFATYYCLQSDRFPLTFGQGTKLEIK

>Lib3_H10 (SEQ ID NO: 319)
DIQMTQSPSSLSASVGDRVTITCITSTDIDDDMNWYQ
QKPGKAPKLLISQASTLRPGVPSRFSGSGSGTDFTFT
ISSLQPEDFATYYCLQVDRVPLTFGQGTKLEIK

>Lib3_C7 (SEQ ID NO: 320)
DIQMTQSPSSLSASVGDRVTITCQASQDIDMDLNWYQ
QKPGKAPKLLISQGSTLWPGVPSRFSGSGSGTDFTFT
ISSLQPEDFATYYCLQVERFPLTFGQGTKLEIK

>Lib3_E9 (SEQ ID NO: 321)
DIQMTQSPSSLSASVGDRVTITCQASTDIDMDLNWYQ
QKPGKAPKLLISQANTLRPGVPSRFSGSGSGTDFTFT
ISSLQPEDFATYYCLQVDRMPLTFGQGTKLEIK

>Lib3_H5 (SEQ ID NO: 322)
DIQMTQSPSSLSASVGDRVTITCQASTDIDDDMNWYQ
QKPGKAPKLLISQANMLRPGVPSRFSGSGSGTDFTFT
ISSLQPEDFATYYCLQSDRLPLTFGQGTKLEIK

>Lib4_64 (SEQ ID NO: 323)
DIQMTQSPSSLSASVGDRVTITCQASTDIDDDLNWYQ
QKPGKAPKLLISLGSTLRPGVPSRFSGSGSGTDFTFT
ISSLQPEDFATYYCLQTDSFPLTFGQGTKLEIK

>Lib4_2B (SEQ ID NO: 324)
DIQMTQSPSSLSASVGDRVTITCQASQDIDEDLNWYQ
QKPGKAPKLLISLANILRPGVPSRFSGSGSGTDFTFT
ISSLQPEDFATYYCLQSDRLPLTFGQGTKLEIK

>Lib4_10G (SEQ ID NO: 325)
DIQMTQSPSSLSASVGDRVTITCQTSQDIDEDLNWYQ
QKPGKAPKLLISLASTLRPGVPSRFSGSGSGTDFTFT
ISSLQPEDFATYYCLQVDSFPLTFGQGTKLEIK

>Lib3_D4 (SEQ ID NO: 326)
DIQMTQSPSSLSASVGDRVTITCQASTDIDDDLNWYQ
QKPGKAPKLLISLGSTLRPGVPSRFSGSGSGTDFTFT
ISSLQPEDFATYYCLQSDRMPLTFGQGTKLEIK

>Lib3_E2 (SEQ ID NO: 327)
DIQMTQSPSSLSASVGDRVTITCQASTDIDVDMNWYQ
QKPGKAPKLLISQGSTLPPGVPSRFSGSGSGTDFTFT
ISSLQPEDFATYYCLQIDRLPLTFGQGTKVEIKR

>Lib4_8F (SEQ ID NO: 328)
DIQMTQSPSSLSASVGDRVTITCQASTDIDDDMNWYQ
QKPGKAPKLLISLANKLRPGVPSRFSGSGSGTDFTFT
ISSLQPEDFATYYCLQSDRLPLTFGQGTKLEIK

>Lib3_G7 (SEQ ID NO: 329)
DIQMTQSPSSLSASVGDRVTITCQASTDIDDDLNWYQ
QKPGKAPKLLISLGSSLWPGVPSRFSGSGSGTDFTFT
ISSLQPEDFATYYCLQGDSMPLTFGQGTKLEIK

>Lib4_6 (SEQ ID NO: 330)
DIQMTQSPSSLSASVGDRVTITCQASTDIDDDMNWYQ
QKPGKAPKLLISLANKLRPGVPSRFSGSGSGTDFTFT
ISSLQPEDFATYYCLQSDRFPLTFGQGTKLEIK

>Lib3_G11 (SEQ ID NO: 331)
DIQMTQSPSSLSASVGDRVTITCQTSTDIDVDMNWYQ
QKPGKAPKLLISLASTLRPGVPSRFSGSGSGTDFTFT
ISSLQPEDFATYYCLQSDRFPLTFGQGTKLEIK

>Lib3_D7 (SEQ ID NO: 332)
DIQMTQSPSSLSASVGDRVTITCQTSTDIDDDMNWYQ
QKPGKAPKLLISQGSLLLPGVPSRFSGSGSGTDFTFT
ISSLQPEDFATYYCQQSDRLPLTFGQGTKLEIK

>Lib3_A10 (SEQ ID NO: 333)
DIQMTQSPSSLSASVGDRVTITCQASTDIDVDMNWYQ
QKPGKAPKLLISLGNTLRPGVPSRFSGSGSGTDFTFT
ISSLQPEDFATYYCLQSDRLPLTFGQGTKLEIK

>Lib4_6A (SEQ ID NO: 334)
DIQMTQSPSSLSASVGDRVTITCQASTDIDDDMNWYQ
QKPGKAPKLLISLASTLWPGVPSRFSGSGSGTDFTFT
ISSLQPEDFATYYCLQGDSLPLTFGQGTKLEIK

>Lib4_2 (SEQ ID NO: 335)
DIQMTQSPSSLSASVGDRVTITCQASQDIDDDLNWYQ
QKPGKAPKLLISLANTLRPGVPSRFSGSGSGTDFTFT
ISSLQPEDFATYYCLQSSWLPLTFGQGTKLEIK

>Lib3_D9 (SEQ ID NO: 336)
DIQMTQSPSSLSASVGDRVTITCQTSTDIDDDLNWYQ
QKPGKAPKLLISLASTLRPGVPSRFSGSGSGTDFTFT
ISSLQPEDFATYYCLQSDRVPLTFGQGTKLEIK

>Lib4_54 (SEQ ID NO: 337)
DIQMTQSPSSLSASVGDRVTITCQASQDIDDDLNWYQ
QKPGKAPKLLISLANTLRPGVPSRFSGSGSGTDFTFT
ISSLQPEDFATYYCLQSDSLPLTFGQGTKLEIK

>Lib3_C4 (SEQ ID NO: 338)
DIQMTQSPSSLSASVGDRVTITCQASQDIDDDLNWYQ
QKPGKAPKLLISLANTLRPGVPSRFSGSGSGTDFTFT
ISSLQPEDFATYYCLQSDKMPLTFGQGTKLEIK

>Lib3_F7 (SEQ ID NO: 339)
DIQMTQSPSSLSASVGDRVTITCQTSQDIDVDMNWYQ
QKPGKAPKLLISLGSTLRPGVPSRFSGSGSGTDFTFT
ISSLQPEDFATYYCLQSDRLPLTFGQGTKLEIK

>Lib3_F4 (SEQ ID NO: 340)
DIQMTQSPSSLSASVGDRVTITCQTSTDIDFDMNWYQ
QKPGKAPKLLISQGSMLRPGVPSRFSGSGSGTDFTFT
ISSLQPEDFATYYCLQVDRVPLTFGQGTKLEIK

>Lib4_3 (SEQ ID NO: 341)
DIQMTQSPSSLSASVGDRVTITXQASQDIDDDLNWYQ
QKPGKAPKLLISLANTLRPGVPSRFSGSGSGTDFTFT
ISSLQPEDFATYYCLQSDRLPLTFGQGTKLEIK

>Lib4_23 (SEQ ID NO: 342)
DIQMTQSPSSLSASVGDRVTITCQXSQDIDDDLNWYQ
QKPGKAPKLLISLASILRPGVPSRFSGSGSGTDFTFT
ISSLQPEDFATYYCLQSDSFPLTFGQGTKLEIK

>Lib3_H6 (SEQ ID NO: 343)
DIQMTQSPSSLSASVGDRVTITCQASTDIDIDMNWYQ
QKPGKAPKLLISLGSILRPGVPSRFSGSGSGTDFTFT
ISSLQPEDFATYYCQQGDRFPLTFGQGTKLEIK

>Lib4_73 (SEQ ID NO: 344)
DIQMTQSPSSLSASVGDRVTITCQASQDIDDDLNWYQ
QKPGKAPKLLISLASILRPGVPSRFSGSGSGTDFTFT
ISSLQPEDFATYYCLQVDSFPLTFGQGTKLEIK

>Lib4_3D (SEQ ID NO: 345)
DIQMTQSPSSLSASVGDRVTITCQASQDIDDDLNWYQ
QKPGKAPKLLISLASILRHGVPSRFSGSGSGTDFTFT
ISSLQPEDFATYYCLQSDSFPLTFGQGTKLEIK

>Lib3_G4 (SEQ ID NO: 346)
DIQMTQSPSSLSASVGDRVTITCQASQDIDEDLNWYQ
QKPGKAPKLLISLANILRPGVPSRFSGSGSGTDFTFT
ISSLQPEDFATYYCLQVDMLPLTFGQGTKLEIK

>Lib3_F10 (SEQ ID NO: 347)
DIQMTQSPSSLSASVGDRVTITCQTSTDIDDDLNWYQ
QKPGKAPKLLISQASTLRPGVPSRFSGSGSGTDFTFT
ISSLQPEDFATYYCLQVDRVPLTFGQGTKLEIK

TABLE 3b-continued

VH/VL sequences of affinity matured H1B12.1 clones

>Lib4_5B (SEQ ID NO: 348)
DIQMTQSPSSLSASVGDRVTITCQASTDIDDDLNWYQ
QKPGKAPKLLISLGSTLRPGVPSRFSGSGSGTDFTFT
ISSLQPEDFATYYCLQSDRLPLTFGQGTKLEIK

>Lib3_B8 (SEQ ID NO: 349)
DIQMTQSPSSLSASVGDRVTITCQTSTDIDVDMNWYQ
QKPGKAPKLLISQASTLISGVPSRFSGSGSGTDFTFT
ISSLQPEDFATYYCLQVERLPLTFGQGTKLEIK

>Lib4_6B (SEQ ID NO: 350)
DIQMTQSPSSLSASVGDRVTITCQTSTDIDDDLNWYQ
QKPGKAPKLLISLASKLRPGVPSRFSGSGSGTDFTFT
ISSLQPEDFATYYCLQVDSFPLTFGQGTKLEIK

>Lib4_5C (SEQ ID NO: 351)
DIQMTQSPSSLSASVGDRVTITCQASTDIDEDLNWYQ
QKPGKAPKLLISLASTLRPGVPSRFSGSGSGTDFTFT
ISSLQPEDFATYYCLQTDSFPLTFGQGTKLEIK

>Lib4_12F (SEQ ID NO: 352)
DIQMTQSPSSLSASVGDRVTITCQTSTDIDEDMNWYQ
QKPGKAPKLLISLASMLRPGVPSRFSGSGSGTDFTFT
ISSLQPEDFATYYCLQGDRLPLTFGQGTKLEIK

>Lib4_11 (SEQ ID NO: 353)
DIQMTQSPSSLSASVGDRVTITCQASTDIDADLNWYQ
QKPGKAPKLLISQANTLWPGVPSRFSGSGSGTDFTFT
ISSLQPEDFATYYCLQVDRFPLTFGQGTKLEIK

>Lib3_D8 (SEQ ID NO: 354)
DIQMTQSPSSLSASVGDRVTITCQASTDIDIDMNWYQ
QKPGKAPKLLISLGSTLRPGVPSRFSGSGSGTDFTFT
ISSLQPEDFATYYCQQGDKFPLTFGQGTKLEIK

>Lib3_A8 (SEQ ID NO: 355)
DIQMTQSPSSLSASVGDRVTITCQASTDIDMDLNWYQ
QKPGKAPKLLISQASSLTPGVPSRFSGSGSGTDFTFT
ISSLQPEDFATYYCLQVEKLPLTFGQGTKLEIK

>Lib3_D11 (SEQ ID NO: 356)
DIQMTQSPSSLSASVGDRVTITCQTSQDIDADLNWYQ
QKPGKAPKLLISQASKLRPGVPSRFSGSGSGTDFTFT
ISSLQPEDFATYYCLQVESLPLTFGQGTKLEIK

>Lib4_1A (SEQ ID NO: 357)
DIQMTQSPSSLSASVGDRVTITCQASQDIDDDLNWYQ
QKPGKAPKLLISLGSTLSPGVPSRFSGSGSGTDFTFT
ISSLQPEDFATYYCLQVDWLPLTFGQGTKLEIK

>Lib3_B1 (SEQ ID NO: 358)
DIQMTQSPSSLSASVGDRVTITCQTSTDIDDDLNWYQ
QKPGKAPKLLISQASTLRPGVPSRFSGSGSGTDFTFT
ISSLQPEDFATYYCLQVDRMPLTFGQGTKLEIK

>Lib4_74 (SEQ ID NO: 359)
DIQMTQSPSSLSASVGDRVTITCQVSQDIDDDLNWYQ
QKPGKAPKLLISLASTLWPGVPSRFSGSGSGTDFTFT
ISSLQPEDFATYYCLQGDSLPLTFGQGTKLEIK

>Lib3_F6 (SEQ ID NO: 360)
DIQMTQSPSSLSASVGDRVTITCQTSTDIDVDMNWYQ
QKPGKAPKLLISQANILSSGVPSRFSGSGSGTDFTFT
ISSLQPEDFATYYCLQVEKLPLTFGQGTKLEIK

>Lib3_F8 (SEQ ID NO: 361)
DIRMTQSPSSLSASVGDRVTITCQASQDIDMDLNWYQ
QKPGKAPKLLISQASTLLPGVPSRFSGSGSGTDFTFT
ISSLQPEDFATYYCLQIDELPLTFGQGTKLEIK

>Lib4_1F (SEQ ID NO: 362)
DIQMTQSPSSLSASVGDRVTITCQASQDIDEDMNWYQ
QKPGKAPKLLISQASTLGPGVPSRFSGSGSGTDFTFT
ISSLQPEDFATYYCLQTDSFPLTFGQGTKLEIK

>Lib3_A5 (SEQ ID NO: 363)
DIQMTQSPSSLSASVGDRVTITCITSQDIDEDLNWYQ
QKPGKAPKLLISLASTLLPGVPSRFSGSGSGTDFTFT
ISSLQPEDFATYYCLQSDRLPLTFGQGTKLEIK

>Lib4_6H (SEQ ID NO: 364)
DIQMTQSPSSLSASVGDRVTITCQASTDIDDDLNWYQ
QKPGKAPKLLISLASMLGPGVPSRFSGSGSGTDFTFT
ISSLQPEDFATYYCLQTDSFPLTFGQGTKLEIK

>Lib4_10F (SEQ ID NO: 365)
DIQMTQSPSSLSASVGDRVTITCQASTDIDDDLNWYQ
QKPGKAPKLLISLGSILRPGVPSRFSGSGSGTDFTFT
ISSLQPEDFATYYCQQGDRFPLTFGQGTKLEIK

>Lib3_H7 (SEQ ID NO: 366)
DIQMTQSPSSLSASVGDRVTITCQASTDIDDDLNWYQ
QKPGKAPKLLISSANTLLPGVPSRFSGSGSGTDFTFT
ISSLQPEDFATYYCLQKEKLPLTFGQGTKLEIK

>Lib4_88 (SEQ ID NO: 367)
DIQMTQSPSSLSASVGDRVTITCQASQDIDDDLNWYQ
QKPGKAPKLLISLASTLWPGVPSRFSGSGSGTDFTFT
ISSLQPEDFATYYCLQSDRFPLTFGQGTKLEIK

>Lib4_77 (SEQ ID NO: 368)
DIQMTQSPSSLSASVGDRVTITCQTSQDIDMDLNWYQ
QKPGKAPKLLISQGSTLWPGVPSRFSGSGSGTDFTFT
ISSLQPEDFATYYCLQTDSFPLTFGQGTKLEIK

>Lib4_4D (SEQ ID NO: 369)
GIQMTQSPSSLSASVGDRVTITCQASQDIDDDMNWYQ
QKPGKAPKLLISLASMLRPGVPSRFSGSGSGTDFTFT
ISSLQPEDFATYYCLQSDSFPLTFGQGTKLEIK

>Lib4_12H (SEQ ID NO: 370)
DIQMTQSPSSLSASVGDRVTITCQASQDIDDDLNWYQ
QKPGKAPKLLISLASILPGVPSRFSGSGSGTDFTFT
ISSLQPEDFATYYCLQIDSFPLTFGQGTKLEIK

>Lib4_10H (SEQ ID NO: 371)
DIQMTQSPSSLSASVGDRVTITCQASQDIDDDLNWYQ
QKPGKAPKLLISLASNLRPGVPSRFSGSGSGTDFTFT
ISSLQPEDFATYYCLQSDSFPLTFGQGTKLEIK

>Lib3_E6 (SEQ ID NO: 372)
DIQMTQSPSSLSASVGDRVTITCQASQDIDEDLNWYQ
QKPGKAPKLLISQGSTLWSGVPSRFSGSGSGTDFTFT
ISSLQPEDFATYYCQQGDRLPLTFGQGTKLEIK

>Lib4_50 (SEQ ID NO: 373)
DIQMTQSPSSLSASVGDRVTITCQASTDIDTDLNWYQ
QKPGKAPKLLISQASTLFPGVPSRFSGSGSGTDFTFT
ISSLQPEDFATYYCLQSDWLPLTFGQGTKLEIK

>Lib4_1B (SEQ ID NO: 374)
DIQMTQSPSSLSASVGDRVTITCQASQDIDDDLNWYQ
QKPGKAPKLLISLASILRPGVPSRFSGSGSGTDFTFT
ISSLQPEDFATYYCLQSDSFPLTFGQGTKLEIK

>Lib4_76 (SEQ ID NO: 375)
DIQMTQSPSSLSASVGDRVTITCQASTDIDVDLNWYQ
QKPGKAPKLLISLGNILRPGVPSRFSGSGSGTDFTFT
ISSLQPEDFATYYCLQSDRLPLTFGQGTKLEIK

>Lib4_7F (SEQ ID NO: 376)
DIQMTQSPSSLSASVGDRVTITCQASTDIDDDLNWYQ
QKPGKAPKLLISLANTLRPGVPSRFSGSGSGTDFTFT
ISSLQPEDFATYYCLQSDRFPLTFGQGTKLEIK

>Lib4_26 (SEQ ID NO: 377)
DIQMTQSPSSLSASVGDRVTITCQASQDIDDDLNWYQ
QKPGKAPKLLISLASTLWPGVPSRFSGSGSGTDFTFT
ISSLQPEDFATYYCLQVDRFPLTFGQGTKLEIK

TABLE 3b-continued

VH/VL sequences of affinity matured H1B12.1 clones

>Lib4_69 (SEQ ID NO: 378)
DIQMTQSPSSLSASVGDRVTITCQASQDIDDDLNWYQ
QKPGKAPKLLISLASNLRPGVPSRFSGSGSGTDFTFT
ISSLQPEDFATYYCLQSDWLPLTFGQGTKLEIK

>Lib4_2H (SEQ ID NO: 379)
DIQMTQSPSSLSASVGDRVTITCQTSTDIDDDLNWYQ
QKPGKAPKLLISLASTLRPGVPSRFSGSGSGTDFTFT
ISSLQPEDFATYYCLQSDRLPLTFGQGTKLEIK

>Lib4_49 (SEQ ID NO: 380)
DIQMTQSPSSLSASVGDRVTITCQASTDIDDDLNWYQ
QKPGKAPKLLISLGSTLRPGVPSRFSGSGSGTDFTFT
ISSLQPEDFATYYCLQSDRFPLTFGQGTKLEIK

>Lib3_F9 (SEQ ID NO: 381)
DIQMTQSPSSLSASVGDRVTITCQTSTDIDVDLNWYQ
QKPGKAPKLLISQASTLHTGVPSRFSGSGSGTDFTFT
ISSLQPEDFATYYCLQVERLPLTFGQGTKLEIK

>Lib3_G8 (SEQ ID NO: 382)
DIQMTQSPSSLSASVGDRVTITCQTSQDIDDDLNWYQ
QKPGKAPKLLISQASTLFPGVPSRFSGSGSGTDFTFT
ISSLQPEDFATYYCLQQGDRLPLTFGQGTKLEIK

>Lib4_51 (SEQ ID NO: 383)
DIQMTQSPSSLSASVGDRVTITCQASTDIDDDLNWYQ
QKPGKAPKLLISLANMLHPGVPSRFSGSGSGTDFTFT
ISSLQPEDFATYYCLQSDRFPLTFGQGTKLEIK

>Lib4_10A (SEQ ID NO: 384)
DIQMTQSPSSLSASVGDRVTITCQASQDIDDDLNWYQ
QKPGKAPKLLISLASTLRPGVPSRFSGSGSGTDFTFT
ISSLQPEDFATYYCLQSDSFPLTFGQGTKLEIK

>Lib4_53 (SEQ ID NO: 385)
DIQMTQSPSSLSASVGDRVTITCQASQDIDDDLNWYQ
QKPGKAPKLLISLGSTLQPGVPSRFSGSGSGTDFTFT
ISSLQPEDFATYYCLQVDWLPLTFGQGTKLEIK

>Lib4_57 (SEQ ID NO: 386)
DIQMTQSPSSLSASVGDRVTITCQASTDIDDDLNWYQ
QKPGKAPKLLISLANTLRPGVPSRFSGSGSGTDFTFT
ISSLQPEDFATYYCLQSDSFPLTFGQGTKLEIK

>Lib4_84 (SEQ ID NO: 387)
DIQMTQSPSSLSASVGDRVTITCQTSQDIDDDMNWYQ
QKPGKAPKLLISLASMLRPGVPSRFSGSGSGTDFTFT
ISSLQPEDFATYYCLQSDRLPLTFGQGTKLEIK

>Lib3_D3 (SEQ ID NO: 388)
DIQMTQSPSSLSASVGDRVTITCQTSQDIDDDMNWYQ
QKPGKAPKLLISQGSSLLPGVPSRFSGSGSGTDFTFT
ISSLQPEDFATYYCLQVDRVPLTFGQGTKLEIK

>Lib4_3A (SEQ ID NO: 389)
DIQMTQSPSSLSASVGDRVTITCQASQDIDDDLNWYQ
QKPGKAPKLLISLASTLWPGVPSRFSGSGSGTDFTFT
ISSLQPEDFATYYCLQSDRLPLTFGQGTKLEIK

>Lib3_C10 (SEQ ID NO: 390)
DIQMTQSPSSLSASVGDRVTITCQASTDIDDDMNWYQ
QKPGKAPKLLISQASTLIPGVPSRFSGSGSGTDFTFT
ISSLQPEDFATYYCLQVDSFPLTFGQGTKLEIK

>Lib4_29 (SEQ ID NO: 391)
DIQMTQSPSSLSASVGDRVTITCQTSTDIDDDLNWYQ
QKPGKAPKLLISLASTLRPGVPSRFSGSGSGTDFTFT
ISSLQPEDFATYYCLQSDSFPLTFGQGTKLEIK

>Lib4_37 (SEQ ID NO: 392)
DIQMTQSPSSLSASVGDRVTITCQASQDIDDDLNWYQ
QKPGKAPKLLISLASTLRPGVPSRFSGSGSGTDFTFT
ISSLQPEDFATYYCLQSDRFPLTFGQGTKLEIK

>Lib4_11C (SEQ ID NO: 393)
DIQMTQSPSSLSASVGDRVTITCIASTDIDDDMNWYQ
QKPGKAPKLLISLASILRPGVPSRFSGSGSGTDFTFT
ISSLQPEDFATYYCLQSDRLPLTFGQGTKLEIK

>Lib4_95 (SEQ ID NO: 394)
DIQMTQSPSSLSASVGDRVTITCQTSTDIDVDLNWYQ
QKPGKAPKLLISLANTLRPGVPSRFSGSGSGTDFTFT
ISSLQPEDFATYYCLQSDRFPLTFGQGTKLEIK

>Lib4_4 (SEQ ID NO: 395)
DIQMTQSPSSLSASVGDRVTITCQTSQDIDDDMNWYQ
QKPGKAPKLLISLGSTLWPGVPSRFSGSGSGTDFTFT
ISSLQPEDFATYYCLQGDSLPLTFGQGTKLEIK

>Lib3_F11 (SEQ ID NO: 396)
DIQMTQSPSSLSASVGDRVTITCQASQDIDDDLNWYQ
QKPGKAPKLLISLASTLWPGVPSRFSGSGSGTDFTFT
ISSLQPEDFATYYCLQQGERFPLTFGQGTKLEIK

>Lib4_8C (SEQ ID NO: 397)
DIQMTQSPSSLSASVGDRVTITCQASQDIDDDLNWYQ
QKPGKAPKLLISLASTLWPGVPSRFSGSGSGTDFTFT
ISSLQPEDFATYYCLQGDSLPLTFGQGTKLEIK

>Lib3_F3 (SEQ ID NO: 398)
DIQMTQSPSSLSASVGDRVTITCQASTDIDEDMNWYQ
QKPGKAPKLLISSANILPRGVPSRFSGSGSGTDFTFT
ISSLQPEDFATYYCLQKERLPLTFGQGTKLEIK

>Lib3_G5 (SEQ ID NO: 399)
DIQMTQSPSSLSASVGDRVTITCQASQDIDMDMNWYQ
QKPGKAPKLLISQASTLRSGVPSRFSGSGSGTDFTFT
ISSLQPEDFATYYCLQTERFPLTFGQGTKLEIK

>Lib4_55 (SEQ ID NO: 400)
DIQMTQSPSSLSASVGDRVTITCQASTDIDADLNWYQ
QKPGKAPKLLISLGSTLRPGVSSRFSGSGSGTDFTFT
ISSLQPEDFATYYCLQVDKFPLTFGQGTKLEIK

>Lib3_D12 (SEQ ID NO: 401)
DIQMTQSPSSLSASVGDRVTITCQASQDIDVDLNWYQ
QKPGKAPKLLISLANTLHPGVPSRFSGSGSGTDFTFT
ISSLQPEDFATYYCLQVERFPLTFGQGTKLEIK

>Lib3_C11 (SEQ ID NO: 402)
DIQMTQSPSSLSASVGDRVTITCQASTDIDDDLNWYQ
QKPGKAPKLLISHGSTLQHGVPSRFSGSGSGTDFTFT
ISSLQPEDFATYYCLQVDRLPLTFGQGTKLEIK

>Lib3_B7 (SEQ ID NO: 403)
DIQMTQSPSSLSASVGDRVTITCQASTDIDDDLNWYQ
QKPGKAPKLLISLGNTLHPGVPSRFSGSGSGTDFTFT
ISSLQPEDFATYYCLQQSDRLPLTFGQGTKLEIK

>Lib4_46 (SEQ ID NO: 404)
DIQMTQSPSSLSASVGDRVTITCQASQDIDEDLNWYQ
QKPGKAPKLLISLASTLRPGVPSRFSGSGSGTDFTFT
ISSLQPEDFATYYCLQVDSFPLTFGQGTKLEIK

>Lib4_2C (SEQ ID NO: 405)
DIQMTQSPSSLSASVGDRVTITCQASQDIDDDLNWYQ
QKPGKAPKLLISLANTLRPGVPSRFSGSGSGTDFTFT
ISSLQPEDFATYYCLQSDSFPLTFGQGTKLEIK

>Lib3_C9 (SEQ ID NO: 406)
DIQMTQSPSSLSASVGDRVTITCQASTDIDEDLNWYQ
QKPGKAPKLLISLANNLRPGVPSRFSGSGSGTDFTFT
ISSLQPEDFATYYCLQIERLPLTFGQGTKLEIK

>Lib3_E8 (SEQ ID NO: 407)
DIQMTQSPSSLSASVGDRVTITCQTSTDIDDDMNWYQ
QKPGKAPKLLISLANNLRPGVPSRFSGSGSGTDFTFT
ISSLQPEDFATYYCLQCDRLPLTFGQGTKLEIK

TABLE 3b-continued

VH/VL sequences of affinity matured H1B12.1 clones

```
>Lib4_3B (SEQ ID NO: 408)
DIQMTQSPSSLSASVGDRVTITCQVSQDIDDDLNWYQ
QKPGKAPKLLISLGSTLQPGVPSRFSGSGSGTDFTFT
ISSLQPEDFATYYCLQSDRLPLTFGQGTKLEIK

>Lib4_10B (SEQ ID NO: 409)
DIQMTQSPSSLSASVGDRVTITCQASQDIDDDLNWYQ
QKPGKAPKLLISLGSKLRPGVPSRFSGSGSGTDFTFT
ISSLQPEDFATYYCLQVDSFPLTFGQGTKLEIK

>Lib4_86 (SEQ ID NO: 410)
DIQMTQSPSSLSASVGDRVTITCQASTDIDEDLNWYQ
QKPGKAPKLLISLASKLRPGVPSRFSGSGSGTDFTFT
ISSLQPEDFATYYCLQSDRFPLTFGQGTKLEIK

>Lib3_B10 (SEQ ID NO: 411)
DIQMTQSPSSLSASVGDRVTITCQASTDIDVDLNWYQ
QKPGKAPKLLISQASTLPPGVPSRFSGSGSGTDFTFT
ISSLQPEDFATYYCLQSDSLPLTFGQGTKLEIK

>Lib4_63 (SEQ ID NO: 412)
DIQMTQSPSSLSASVGDRVTITCQASTDIDDDLNWYQ
QKPGKAPKLLISLASTLRPGVPSRFSGSGSGTDFTFT
ISSLQPEDFATYYCLQSDRFPLTFGQGTKLEIK

>Lib3_E7 (SEQ ID NO: 413)
DIQMTQSPSSLSASVGDRVTITCQASTDIDDDMNWYQ
QKPGKAPKLLISLGSKLWPGVPSRFSGSGSGTDFTFT
ISSLQPEDFATYYCLQSDNLPLTFGQGTKLEIK

>Lib3_D10 (SEQ ID NO: 414)
DIQMTQSPSSLSASVGDRVTITCQASQDIDTDMNWYQ
QKPGKAPKLLIYDANTLRSGVPSRFSGSGSGTDFTFT
ISSLQPEDFATYYCLQKDRLPLTFGQGTKLEIK

>Lib4_61 (SEQ ID NO: 415)
DIQMTQSPSSLSASVGDRVTITCQASTDIDVDMNWYQ
QKPGKAPKLLISLASKLRPGVPSRFSGSGSGTDFTFT
ISSLQPEDFATYYCLQVDSFPLTFGQGTKLEIK

>Lib4_85 (SEQ ID NO: 416)
DIQMTQSPSSLSASVGDRVTITCQASQDIDADLNWYQ
QKPGKAPKLLISLASKLRPGVPSRFSGSGSGTDFTFT
ISSLQPEDFATYYCLQVDSFPLTFGQGTKLEIK

>Lib4_1G (SEQ ID NO: 417)
DIQMTQSPSSLSASVGDRVTITCQASQDIDDDMNWYQ
QKPGKAPKLLISLASTLRPGVPSRFSGSGSGTDFTFT
ISSLQPEDFATYYCLQGDSLPLTFGQGTKLEIK

>Lib4_7D (SEQ ID NO: 418)
DIQMTQSPSSLSASVGDRVTITCQASTDIDDDLNWYQ
QKPGKAPKLLISLGSTLRPGVPSRFSGSGSGTDFTFT
ISSLQPEDFATYYCLQSDSLPLTFGQGTKLEIK

>Lib4_28 (SEQ ID NO: 419)
DIQMTQSPSSLSASVGDRVTITCQASTDIDEDLNWYQ
QKPGKAPKLLISLANNLRPGVPSRFSGSGSGTDFTFT
ISSLQPEDFATYYCLQSDRFPLTFGQGTKLEIK
```

In other embodiments, the binding proteins disclosed herein contain two or more sequences with homology to two or more VH or VL sequences or fragments thereof. The binding proteins disclosed herein can contain sequences with homology to one VH and one VL sequence or fragments thereof. In one embodiment, both of the VH and/or VL sequences specifically bind to the same target protein. In other embodiments, they bind to different epitopes on the same protein.

In another embodiment, the sequences homologous to two or more VH and/or VL sequences or fragments thereof in a binding protein described herein are joined by a linker. The linker can be an amino acid sequence between 5 and 100 amino acids in length. In other embodiments, the linker moiety is between 5 and 90, 5 and 80, 5 and 70, 5 and 60, 5 and 50, 5 and 40, 5 and 30, 5 and 20 and 5 and 10 amino acids in length. In certain specific embodiments, the linker sequences are selected from TVAAP (SEQ ID NO:42) and ASTKGP (SEQ ID NO:43). Additional examples of linkers are described below. Thus, in certain embodiments, formulas for the binding proteins described herein can include VH-Linker-VH, VH-Linker-VL and VL-Linker-VL, wherein VH and VL represent sequences with homology to VH and VL domains or fragments thereof.

In certain embodiments, the binding proteins described herein contain two or more sequences with homology to two or more VH sequences or fragments thereof. In certain embodiments, each of the VH sequences specifically binds to the same proteins. In this situation, the two VH sequences can bind to different epitopes on the same protein. In other embodiments, the binding proteins described herein contain two or more sequences with homology to two or more VL sequences or fragments thereof. In certain embodiments, each of the VL sequences specifically binds to the same proteins. In this situation, the two VL sequences can bind to different epitopes on the same protein. In certain embodiments, each of the VL sequences specifically binds to different proteins. The binding proteins described herein can also be larger protein structures including three or more VH and/or VL domains. For example, the binding protein may be a DVD-Ig. Examples of these binding proteins are shown in Table 4 and include so-called "X3" sequences which are VH and VL domains from an antibody that specifically binds IL-1α and inhibits IL-1α from binding to its receptor. The X3 antibody specifically binds to IL-1α but not to IL-1β. It is also able to inhibit native human IL-1α biological activity.

TABLE 4

Binding Proteins

| Name | Sequence Identifier | Sequence 1234567890123456789012345678 90 |
|---|---|---|
| 1B12.13.SS.X3.VH | SEQ ID NO: 44 | EVQLQESGPGLVKPSETLSLTCTVSGFSLS DYGVSWIRQPPGKGLEWIGLIWGSGDTYYN SPLKSRLTISKDNSKSQVSLKLSSVTAADT AVYYCAKQTNIWAYDLYSMDYWGQGTLVTV SSASTKGPQVQLVESGGGVVQPGRSLRLSC TASGFTFSMFGVHWVRQAPGKGLEWAAVS YDGSNKYYAESVKGRFTISRDNSKNILFLQ MDSLRLEDTAVYYCARGRPKVVIPAPLAHW GQGTLVTFSS |
| 1B12.13.SS.X3.VL | SEQ ID NO: 45 | DIQMTQSPSSLSASVGDRVTITCQTSTDID DDLNWYQQKPGKAPKLLISLASTLRPGVPS RFSGSGSGTDFTFTISSLQPEDFATYYCLQ SDRLPLTFGQGTKLEIKRTVAAPDIQMTQS PSSVSASVGDRVTITCRASQGISSWLAWYQ QKPGKAPKLLIYEASNLETGVPSRFSGSGS GSDFTLTISSLQPEDFATYYCQQTSSFLLS FGGGTKVEHKR |
| 1B12.21.SS.X3.VH | SEQ ID NO: 46 | EVQLQESGPGLVKPSETLSLTCTVSGFSLS EFGVSWIRQPPGKGLEWIGLIWGGGDTYYN SPLKSRLTISKDNSKSQVSLKLSSVTAADT AVYYCAKQRNLWAYDLYGMDYWGQGTLVTV SSASTKGPQVQLVESGGGVVQPGRSLRLSC TASGFTFSMFGVHWVRQAPGKGLEWAAVS YDGSNKYYAESVKGRFTISRDNSKNILFLQ MDSLRLEDTAVYYCARGRPKVVIPAPLAHW GQGTLVTFSS |

TABLE 4-continued

Binding Proteins

| Name | Sequence Identifier | Sequence 1234567890123456789012345678901234567890 |
|---|---|---|
| 1B12.21.SS.X3.VL | SEQ ID NO: 47 | DIQMTQSPSSLSASVGDRVTITCQTSQDID MDLNWYQQKPGKAPKLLISQGSTLWPGVPS RFSGSGSGTDFTFTISSLQPEDFATYYCLQ TDSFPLTFGQGTKLEIKRTVAAPDIQMTQS PSSVSASVGDRVTITCRASQGISSWLAWYQ QKPGKAPKLLIYEASNLETGVPSRFSGSGS GSDFTLTISSLQPEDFATYYCQQTSSFLLS FGGGTKVEHKR |
| 1B12.34.SS.X3.VH | SEQ ID NO: 48 | EVQLQESGPGLVKPSETLSLTCTVSGFSLS DYGVSWIRQPPGKGLEWIGLIWGSGDTYYN SPLKSRLTISKDTSKSQVSLKLSSVTAADT AVYYCAKQTNLWAYDLYSMDYWGQGTLVTV SSASTKGPQVQLVESGGGVVQPGRSLRLSC TASGFTFSMFGVHWVRQAPGKGLEWVAAVS YDGSNKYYAESVKGRFTISRDNSKNILFLQ MDSLRLEDTAVYYCARGRPKVVIPAPLAHW GQGTLVTFSS |
| 1B12.34.SS.X3.VL | SEQ ID NO: 49 | DIQMTQSPSSLSASVGDRVTITCQASQDID DDLNWYQQKPGKAPKLLISLASILRPGVPS RFSGSGSGTDFTFTISSLQPEDFATYYCLQ SDSFPLTFGQGTKLEIKRTVAAPDIQMTQS PSSVSASVGDRVTITCRASQGISSWLAWYQ QKPGKAPKLLIYEASNLETGVPSRFSGSGS GSDFTLTISSLQPEDFATYYCQQTSSFLLS FGGGTKVEHKR |
| 1B12.A1.SS.X3.VH | SEQ ID NO: 50 | EVQLQESGPGLVKPSETLSLTCTVSGFSLR DYGVSWIRQPPGKGLEWLGLIWGSGDTYYN SPLKSRLTISKDTSKSQVSLKLSSVTAADT AVYYCAKQTNIWGYDLYGMDYWGQGTLVTV SSASTKGPQVQLVESGGGVVQPGRSLRLSC TASGFTFSMFGVHWVRQAPGKGLEWVAAVS YDGSNKYYAESVKGRFTISRDNSKNILFLQ MDSLRLEDTAVYYCARGRPKVVIPAPLAHW GQGTLVTFSS |
| 1B12.A1.SS.X3.VL | SEQ ID NO: 51 | DIQMTQSPSSLSASVGDRVTITCQASQDID MDLNWYQQKPGKAPKLLISQANTLPPGVPS RFSGSGSGTDFTFTISSLQPEDFATYYCLQ SDWLPLTFGQGTKLEIKRTVAAPDIQMTQS PSSVSASVGDRVTITCRASQGISSWLAWYQ QKPGKAPKLLIYEASNLETGVPSRFSGSGS GSDFTLTISSLQPEDFATYYCQQTSSFLLS FGGGTKVEHKR |
| 1B12.A3.SS.X3.VH | SEQ ID NO: 52 | EVQLQESGPGLVKPSETLSLTCTVSGFSLS DYGVSWIRQPPGKGLEWIGLIWGGGDTYYN SPLKSRLTISKDNSKSQVSLKLSSVTAADT AVYYCARQTNLWAYDLYSMDYWGQGTLVTV SSASTKGPQVQLVESGGGVVQPGRSLRLSC TASGFTFSMFGVHWVRQAPGKGLEWVAAVS YDGSNKYYAESVKGRFTISRDNSKNILFLQ MDSLRLEDTAVYYCARGRPKVVIPAPLAHW GQGTLVTFSS |
| 1B12.A3.SS.X3.VL | SEQ ID NO: 53 | DIQMTQSPSSLSASVGDRVTITCQASTDID DDLNWYQQKPGKAPKLLISLGSTLRPGVPS RFSGSGSGTDFTFTISSLQPEDFATYYCLQ SDRLPLTFGQGTKLEIKRTVAAPDIQMTQS PSSVSASVGDRVTITCRASQGISSWLAWYQ QKPGKAPKLLIYEASNLETGVPSRFSGSGS GSDFTLTISSLQPEDFATYYCQQTSSFLLS FGGGTKVEHKR |
| 1B12.1-SS-X3 VH | SEQ ID NO: 54 | EVQLQESGPGLVKPSETLSLTCTVSGFSLS DYGVSWIRQPPGKGLEWLGLIWGGGDTYYN SPLKSRLTISKDNSKSQVSLKLSSVTAADT AVYYCAKQRTLWGYDLYGMDYWGQGTLVTV SSASTKGPQVQLVESGGGVVQPGRSLRLSC TASGFTFSMFGVHWVRQAPGKGLEWVAAVS YDGSNKYYAESVKGRFTISRDNSKNILFLQ MDSLRLEDTAVYYCARGRPKVVIPAPLAHW GQGTLVTFSS |
| 1B12.1-SS-X3 VL | SEQ ID NO: 55 | DTQVTQSPSSLSASVGDRVTITCITSTDID VDMNWYQQKPGKPPKLLISQGNTLRPGVPS RFSSSGSGTDFTFTISSLQPEDFATYYCLQ SDNLPLTFGQGTKLEIKRTVAAPDIQMTQS PSSVSASVGDRVTITCRASQGISSWLAWYQ QKPGKAPKLLIYEASNLETGVPSRFSGSGS GSDFTLTISSLQPEDFATYYCQQTSSFLLS FGGGTKVEHKR |

"Dual variable domain" ("DVD") binding proteins of the disclosure (see, e.g., Table 4 above) comprise two or more antigen binding sites and are tetravalent or multivalent binding proteins. DVDs may be monospecific, i.e., capable of binding one antigen, or multispecific, i.e., capable of binding two or more antigens. A DVD binding protein comprising two heavy chain DVD polypeptides and two light chain DVD polypeptides is referred to as a "DVD immunoglobulin" or "DVD-Ig". Each half of a DVD-Ig comprises a heavy chain DVD polypeptide and a light chain DVD polypeptide, and two or more antigen binding sites. Each binding site comprises a heavy chain variable domain and a light chain variable domain with a total of six CDRs involved in antigen binding per antigen binding site. A description of the design, expression, and characterization of DVD-Ig molecules is provided in PCT Publication No. WO 2007/024715; U.S. Pat. No. 7,612,181; and Wu et al., Nature Biotechnol., 25: 1290-1297 (2007). A preferred example of such DVD-Ig molecules comprises a heavy chain that comprises the structural formula VD1-(X1)n-VD2-C-(X2)n, wherein VD1 is a first heavy chain variable domain, VD2 is a second heavy chain variable domain, C is a heavy chain constant domain, X1 is a linker with the proviso that it is not CH1, X2 is an Fc region, and n is 0 or 1, but preferably 1; and a light chain that comprises the structural formula VD1-(X1)n-VD2-C-(X2)n, wherein VD1 is a first light chain variable domain, VD2 is a second light chain variable domain, C is a light chain constant domain, X1 is a linker with the proviso that it is not CH1, and X2 does not comprise an Fc region; and n is 0 or 1, but preferably 1. Such a DVD-Ig may comprise two such heavy chains and two such light chains, wherein each chain comprises variable domains linked in tandem without an intervening constant region between variable regions, wherein a heavy chain and a light chain associate to form tandem functional antigen binding sites, and a pair of heavy and light chains may associate with another pair of heavy and light chains to form a tetrameric binding protein with four functional antigen binding sites. In another example, a DVD-Ig molecule may comprise heavy and light chains that each comprise three variable domains (VD1, VD2, VD3) linked in tandem without an intervening constant region between variable domains, wherein a pair of heavy and light chains may associate to form three antigen binding sites, and wherein a pair of heavy and light chains may associate with another pair of heavy and light chains to form a tetrameric binding protein with six antigen binding sites.

A DVD-Ig binding protein may bind one or more epitopes of IL-1α and/or β. A DVD-Ig binding protein may also bind an epitope of IL-1β and an epitope of a second target antigen other than an IL-1β polypeptide.

The disclosure also provides nucleic acid molecules that encode the binding proteins described herein. For example, the disclosure provides nucleic acid molecule that encode binding proteins comprising any one or more of the CDRs described above. The sequences of these CDRs include SEQ ID NOs:7, 8, 9, 10, 11, 12, 13, 14, 15, 16, 17, 18, 19, 20, 21, 22, 23, 24, 25, 26, 27, 28 and 29. The disclosure also provides nucleic acid molecules that encode any of the VH or VL domains described herein. Examples of these nucleic acid molecules are provided in Table 5, below.

TABLE 5

| Nucleic Acid Molecules Encoding VH and VL | | |
|---|---|---|
| Encodes | Sequence Identifier | Sequence 12345678901234567890123456789 |
| 1B12.9 VH (SEQ ID NO: 35) | SEQ ID NO: 56 | GAGGTACAACTTCAAGAATCTGGTCCAGGG CTTGTGAAGCCTAGTGAAACACTGTCACTG ACTTGTACCGTGTCCGGATTTAGCCTGTCC GACTACGGAGTTTCATGGATTCGACAGCCC CCCGGGAAAGGTCTGGAGTGGCTCGGGCTG ATCTGGGGTGGTGGAGACACATATTACAAT TCCCCTCTGAAATCCAGGCTTACCATCAGC AAGGATAACTCAAAAAGCCAAGTTTCATTG AAGCTGAGTTCCGTGACTGCCGCCGACACG |

TABLE 5-continued

| Nucleic Acid Molecules Encoding VH and VL | | |
|---|---|---|
| Encodes | Sequence Identifier | Sequence 12345678901234567890123456789 |
| | | GCGGTCTATTATTGTGCAAAACAGAGGACC CTGTGGGGATATGACCTCTACGGAATGGAC TATTGGGGCCAAGGCACACTTGTGACCGTG TCCAGT |
| 1B12.9 VL (SEQ ID NO: 41) | SEQ ID NO: 57 | GACACTCAAATGACACAGTCCCCATCATCT TTGTCCGCGAGTGTTGGGGACAGAGTAACT ATTACTTGCATAACCAGCACTGATATAGAC GTGGACATGAACTGGTATCAGCAGAAGCCT GGCAAGCCGCCAAAACTGCTTATCTCTCAA GGCAATACCCTGCGACCCGGCGTGCCTTCT AGATTCAGCTCTAGCGGAAGCGGAACCGAT TTTACCTTCACTATCTCAAGCCTCCAGCCC GAAGACTTCGCCACCTACTATTGTCTGCAG AGCGATAACCTCCCCTTGACTTTCGGGCAA GGTACGAAGCTTGAGATCAAGCGT |

The disclosure also provides nucleic acid molecules that encode binding proteins that include two or more VH or VL domains. Examples of these proteins are shown above in Table 4. Examples of nucleic acid molecules that encode these proteins provided in Table 6, below.

TABLE 6

| Nucleic Acid Molecules Binding Proteins | | |
|---|---|---|
| Encodes | Sequence Identifier | Sequence 12345678901234567890123456789 |
| 1B12.13.SS.X3.VH (SEQ ID NO: 44) | SEQ ID NO: 58 | GAGGTACAACTTCAAGAATCTGGTCCAGGG CTTGTGAAGCCTAGTGAAACACTGTCACTG ACTTGTACCGTGTCCGGATTTAGCCTGAGC GACTACGGAGTTTCATGGATTCGACAGCCT CCAGGGAAAGGTCTGGAGTGGATCGGGCTG ATCTGGGGCAGCGGAGATACATACTACAAT TCCCCTCTGAAATCCAGGCTTACCATCAGC AAGGATAACTCAAAAAGCCAAGTTTCATTG AAGCTGAGTTCCGTGACTGCCGCCGACACG GCGGTCTATTATTGTGCAAAACAGACGAAC ATCTGGGCGTACGACCTCTACTCCATGGAC TATTGGGGCCAAGGCACACTTGTGACCGTG TCCAGTGCTAGCACTAAAGGACCGCAGGTG CAGCTGGTGGAAAGCGGCGGCGGCGTGGTG CAGCCGGGCCGCAGCCTGCGCCTGAGCTGC ACCGCGAGCGGCTTTACCTTTAGCATGTTT GGCGTGCATTGGGTGCGCCAGGCGCCGGGC AAAGGCCTGGAATGGGTGGCGGCGGTGAGC TATGATGGCAGCAACAAATATTATGCGGAA AGCGTGAAAGGCCGCTTTACCATTAGCCGC GATAACAGCAAAAACATTCTGTTTCTGCAG ATGGATAGCCTGCGCCTGGAAGATACCGCG GTGTATTATTGCGCGCGCGCGGCCGCCCGAAA GTGGTGATTCCGGCGCCGCTGGCGCATTGG GGCCAGGGCACCCTGGTGACCTTTAGCAGC |
| 1B12.13.SS.X3.VL (SEQ ID NO: 45) | SEQ ID NO: 59 | GACATTCAAATGACACAGTCCCCATCATCT TTGTCCGCGAGTGTTGGGGACAGAGTAACT ATTACTTGCCAAACCAGTACTGATATAGAC GACGACCTGAACTGGTATCAGCAGAAGCCT GGCAAGGCGCCAAAACTGCTTATCTCTCTC GCCAGTACGCTGCGCCCGGGCGTGCCTTCT AGATTCAGCGGCAGCGGAAGCGGAACCGAT TTTACCTTCACTATCTCAAGCCTCCAGCCC GAAGACTTCGCCACCTACTATTGTCTGCAG AGTGATAGGTTGCCCTTGACTTTCGGGCAA GGTACGAAGCTTGAGATCAAGCGTACCGTC GCAGCTCCTGATATTCAGATGACCCAGAGC CCGAGCAGCGTGAGCGCGAGCGTGGGCGAT CGCGTGACCATTACCTGCCGCGCGAGCCAG GGCATTAGCAGCTGGCTGGCGTGGTATCAG CAGAAACCGGGCAAAGCGCCGAAACTGCTG ATTTATGAAGCGAGCAACCTGGAAACCGGC |

TABLE 6-continued

Nucleic Acid Molecules Binding Proteins

| Encodes | Sequence Identifier | Sequence<br>123456789012345678901234567890 |
|---|---|---|
| | | GTGCCGAGCCGCTTTAGCGGCAGCGGCAGC<br>GGCAGCGATTTTACCCTGACCATTAGCAGC<br>CTGCAGCCGGAAGATTTTGCGACCTATTAT<br>TGCCAGCAGACCAGCAGCTTTCTGCTGAGC<br>TTTGGCGGCGGCACCAAAGTGGAACATAAA<br>CGC |
| 1B12.21.SS.X3.VH<br>(SEQ ID NO: 46) | SEQ ID NO: 60 | GAGGTACAACTTCAAGAATCTGGTCCAGGG<br>CTTGTGAAGCCTAGTGAAACACTGTCACTG<br>ACTTGTACCGTGTCCGGATTAGCCTGAGC<br>GAGTTCGGAGTTTCATGGATTCGACAGCCT<br>CCAGGGAAAGGTCTGGAGTGGATCGGGCTG<br>ATCTGGGGCGGGGGAGACACATACTACAAT<br>TCCCCTCTGAAATCCAGGCTTACCATCAGC<br>AAGGATAACTCAAAAAGCCAAGTTTCATTG<br>AAGCTGAGTTCCGTGACTGCCGCCGACACG<br>GCGGTCTATTATTGTGCAAAACAGAGGAAC<br>CTGTGGGCGTACGATTTGTACGGCATGGAC<br>TATTGGGGCCAAGGCACACTTGTGACCGTG<br>TCCAGTGCTAGCACTAAAGGACCGCAGGTG<br>CAGCTGGTGGAAAGCGGCGGCGGCGTGGTG<br>CAGCCGGGCCGCAGCCTGCGCCTGAGCTGC<br>ACCGCGAGCGGCTTTACCTTTAGCATGTTT<br>GGCGTGCATTGGGTGCGCCAGGCGCCGGGC<br>AAAGGCCTGGAATGGGTGGCGGCGGTGAGC<br>TATGATGGCAGCAACAAATATTATGCGGAA<br>AGCGTGAAAGGCCGCTTTACCATTAGCCGC<br>GATAACAGCAAAAACATTCTGTTTCTGCAG<br>ATGGATAGCCTGCGCCTGGAAGATACCGCG<br>GTGTATTATTGCGCGCGCGGCCGCCCGAAA<br>GTGGTGATTCCGGCGCCGCTGGCGCATTGG<br>GGCCAGGGCACCCTGGTGACCTTTAGCAGC |
| 1B12.21.SS.X3.VL<br>(SEQ ID NO: 47) | SEQ ID NO: 61 | GACATTCAAATGACACAGTCCCCATCATCT<br>TTGTCCGCGAGTGTTGGGGACAGAGTAACT<br>ATTACTTGCCAAACCAGCCAAGATATAGAC<br>ATGGACCTGAACTGGTATCAGCAGAAGCCT<br>GGCAAGGCGCCAAAACTGCTTATCTCTCAG<br>GGCAGTACGCTGTGGCCGGGCGTGCCTTCT<br>AGATTCAGCGGCAGCGGAAGCGGAACCGAT<br>TTTACCTTCACTATCTCAAGCCTCCAGCCC<br>GAAGACTTCGCCACCTACTATTGTCTGCAG<br>ACGGATAGTTTCCCCCTTGACTTTCGGGCAA<br>GGTACGAAGCTTGAGATCAAGCGTACCGTC<br>GCAGCTCCTGATATTCAGATGACCCAGAGC<br>CCGAGCAGCGTGAGCGCGAGCGTGGGCGAT<br>CGCGTGACCATTACCTGCCGCGCGAGCCAG<br>GGCATTAGCAGCTGGCTGGCGTGGTATCAG<br>CAGAAACCGGGCAAAGCGCCGAAACTGCTG<br>ATTTATGAAGCGAGCAACCTGGAAACCGGC<br>GTGCCGAGCCGCTTTAGCGGCAGCGGCAGC<br>GGCAGCGATTTTACCCTGACCATTAGCAGC<br>CTGCAGCCGGAAGATTTTGCGACCTATTAT<br>TGCCAGCAGACCAGCAGCTTTCTGCTGAGC<br>TTTGGCGGCGGCACCAAAGTGGAACATAAA<br>CGC |
| 1B12. 34.SS.X3.VH<br>(SEQ ID NO: 48) | SEQ ID NO: 62 | GAGGTACAACTTCAAGAATCTGGTCCAGGG<br>CTTGTGAAGCCTAGTGAAACACTGTCACTG<br>ACTTGTACCGTGTCCGGATTAGCCTGAGC<br>GACTACGGAGTTTCATGGATTCGACAGCCT<br>CCAGGGAAAGGTCTGGAGTGGATCGGGCTG<br>ATCTGGGGGTCGGGAGATACATACTACAAT<br>TCCCCTCTGAAATCCAGGCTTACCATCAGC<br>AAGGATACCTCAAAAAGCCAAGTTTCATTG<br>AAGCTGAGTTCCGTGACTGCCGCCGACACG<br>GCGGTCTATTATTGTGCAAAACAGACGAAC<br>CTGTGGGCGTACGACCTCTACAGCATGGAC<br>TATTGGGGCCAAGGCACACTTGTGACCGTG<br>TCCAGTGCTAGCACTAAAGGACCGCAGGTG<br>CAGCTGGTGGAAAGCGGCGGCGGCGTGGTG<br>CAGCCGGGCCGCAGCCTGCGCCTGAGCTGC<br>ACCGCGAGCGGCTTTACCTTTAGCATGTTT<br>GGCGTGCATTGGGTGCGCCAGGCGCCGGGC<br>AAAGGCCTGGAATGGGTGGCGGCGGTGAGC |

TABLE 6-continued

Nucleic Acid Molecules Binding Proteins

| Encodes | Sequence Identifier | Sequence 123456789012345678901234567890 |
|---|---|---|
| | | TATGATGGCAGCAACAAATATTATGCGGAA<br>AGCGTGAAAGGCCGCTTTACCATTAGCCGC<br>GATAACAGCAAAAACATTCTGTTTCTGCAG<br>ATGGATAGCCTGCGCCTGGAAGATACCGCG<br>GTGTATTATTGCGCGCGCGGCCGCCCCGAAA<br>GTGGTGATTCCGGCGCCGCTGGCGCATTGG<br>GGCCAGGGCACCCTGGTGACCTTTAGCAGC |
| 1B12.34.SS.X3.VL<br>(SEQ ID NO: 49) | SEQ ID NO: 63 | GACATTCAAATGACACAGTCCCCATCATCT<br>TTGTCCGCGAGTGTTGGGGACAGAGTAACT<br>ATTACTTGCCAAGCCAGCCAAGATATAGAC<br>GACGACCTGAACTGGTATCAGCAGAAGCCT<br>GGCAAGGCGCCAAAACTGCTTATCTCTCTG<br>GCCAGTATCCTGCGCCCGGGCGTGCCTTCT<br>AGATTCAGCGGCAGCGGAAGCGGAACCGAT<br>TTTACCTTCACTATCTCAAGCCTCCAGCCC<br>GAAGACTTCGCCACCTACTATTGTCTGCAG<br>AGTGACAGTTTCCCCTTGACTTTCGGGCAA<br>GGTACGAAGCTTGAGATCAAGCGTACCGTC<br>GCAGCTCCTGATATTCAGATGACCCAGAGC<br>CCGAGCAGCGTGAGCGCGAGCGTGGGCGAT<br>CGCGTGACCATTACCTGCCGCGCGAGCCAG<br>GGCATTAGCAGCTGGCTGGCGTGGTATCAG<br>CAGAAACCGGGCAAAGCGCCGAAACTGCTG<br>ATTTATGAAGCGAGCAACCTGGAAACCGGC<br>GTGCCGAGCCGCTTTAGCGGCAGCGGCAGC<br>GGCAGCGATTTTACCCTGACCATTAGCAGC<br>CTGCAGCCGGAAGATTTTGCGACCTATTAT<br>TGCCAGCAGACCAGCAGCTTTCTGCTGAGC<br>TTTGGCGGCGGCACCAAAGTGGAACATAAA<br>CGC |
| 1B12.A1.SS.X3.VH<br>(SEQ ID NO: 50) | SEQ ID NO: 64 | GAGGTACAACTTCAAGAATCTGGTCCAGGG<br>CTTGTGAAGCCTAGTGAAACACTGTCACTG<br>ACTTGTACCGTGTCCGGATTAGCCTGAGG<br>GACTACGGAGTTTCATGGATTCGACAGCCT<br>CCAGGGAAAGGTCTGGAGTGGCTCGGGCTG<br>ATCTGGGGGAGCGGAGACACATACTACAAT<br>TCCCCTCTGAAATCCAGGCTTACCATCAGC<br>AAGGATACCTCAAAAAGCCAAGTTTCATTG<br>AAGCTGAGTTCCGTGACTGCCGCCGACACG<br>GCGGTCTATTATTGTGCAAAACAGACGAAC<br>ATCTGGGGCTACGATCTCTACGGCATGGAC<br>TATTGGGGCCAAGGCACACTTGTGACCGTG<br>TCCAGTGCTAGCACTAAAGGACCGCAGGTG<br>CAGCTGGTGGAAAGCGGCGGCGGCGTGGTG<br>CAGCCGGGCCGCAGCCTGCGCCTGAGCTGC<br>ACCGCGAGCGGCTTTACCTTTAGCATGTTT<br>GGCGTGCATTGGGTGCGCCAGGCGCCGGGC<br>AAAGGCCTGGAATGGGTGGCGGCGGTGAGC<br>TATGATGGCAGCAACAAATATTATGCGGAA<br>AGCGTGAAAGGCCGCTTTACCATTAGCCGC<br>GATAACAGCAAAAACATTCTGTTTCTGCAG<br>ATGGATAGCCTGCGCCTGGAAGATACCGCG<br>GTGTATTATTGCGCGCGCGGCCGCCCCGAAA<br>GTGGTGATTCCGGCGCCGCTGGCGCATTGG<br>GGCCAGGGCACCCTGGTGACCTTTAGCAGC |
| 1B12.A1.SS.X3.VL<br>(SEQ ID NO: 51) | SEQ ID NO: 65 | GACATTCAAATGACACAGTCCCCATCATCT<br>TTGTCCGCGAGTGTTGGGGACAGAGTAACT<br>ATTACTTGCCAAGCCAGCCAAGATATAGAC<br>ATGGACCTGAACTGGTATCAGCAGAAGCCT<br>GGCAAGGCGCCAAAACTGCTTATCTCTCAG<br>GCCAATACGCTGCCCCCGGGCGTGCCTTCT<br>AGATTCAGCGGCAGCGGAAGCGGAACCGAT<br>TTTACCTTCACTATCTCAAGCCTCCAGCCC<br>GAAGACTTCGCCACCTACTATTGTCTGCAG<br>AGTGATTGGTTGCCCTTGACTTTCGGGCAA<br>GGTACGAAGCTTGAGATCAAGCGTACCGTC<br>GCAGCTCCTGATATTCAGATGACCCAGAGC<br>CCGAGCAGCGTGAGCGCGAGCGTGGGCGAT<br>CGCGTGACCATTACCTGCCGCGCGAGCCAG<br>GGCATTAGCAGCTGGCTGGCGTGGTATCAG<br>CAGAAACCGGGCAAAGCGCCGAAACTGCTG<br>ATTTATGAAGCGAGCAACCTGGAAACCGGC |

TABLE 6-continued

Nucleic Acid Molecules Binding Proteins

| Encodes | Sequence Identifier | Sequence 12345678901234567890123456789 0 |
|---|---|---|
|  |  | GTGCCGAGCCGCTTTAGCGGCAGCGGCAGC GGCAGCGATTTTACCCTGACCATTAGCAGC CTGCAGCCGGAAGATTTTGCGACCTATTAT TGCCAGCAGACCAGCAGCTTTCTGCTGAGC TTTGGCGGCGGCACCAAAGTGGAACATAAA CGC |
| 1B12.A3.SS.X3.VH (SEQ ID NO: 52) | SEQ ID NO: 66 | GAGGTACAACTTCAAGAATCTGGTCCAGGG CTTGTGAAGCCTAGTGAAACACTGTCACTG ACTTGTACCGTGTCCGGATTAGCCTGAGC GACTACGGAGTTTCATGGATTCGACAGCCT CCAGGGAAAGGTCTGGAGTGGATCGGGCTC ATCTGGGGCGGGGGAGATACATACTACAAT TCCCCTCTGAAATCCAGGCTTACCATCAGC AAGGATAACTCAAAAAGCCAAGTTTCATTG AAGCTGAGTTCCGTGACTGCCGCCGACACG GCGGTCTATTATTGTGCAAGACAGACGAAC CTGTGGGCGTACGACTTGTACAGCATGGAC TATTGGGGCCAAGGCACACTTGTGACCGTG TCCAGTGCTAGCACTAAAGGACCGCAGGTG CAGCTGGTGGAAAGCGGCGGCGGCGTGGTG CAGCCGGGCCGCAGCCTGCGCCTGAGCTGC ACCGCGAGCGGCTTTACCTTTAGCATGTTT GGCGTGCATTGGGTGCGCCAGGCGCCGGGC AAAGGCCTGGAATGGGTGGCGGCGGTGAGC TATGATGGCAGCAACAAATATTATGCGGAA AGCGTGAAAGGCCGCTTTACCATTAGCCGC GATAACAGCAAAAACATTCTGTTTCTGCAG ATGGATAGCCTGCGCCTGGAAGATACCGCG GTGTATTATTGCGCGCGCGGCCGCCCCGAAA GTGGTGATTCCGGCGCCGCTGGCGCATTGG GGCCAGGGCACCCTGGTGACCTTTAGCAGC |
| 1B12.A3.SS.X3.VL (SEQ ID NO: 53) | SEQ ID NO: 67 | GACATTCAAATGACACAGTCCCCATCATCT TTGTCCGCGAGTGTTGGGGACAGAGTAACT ATTACTTGCCAAGCCAGCACTGATATAGAC GACGACCTGAACTGGTATCAGCAGAAGCCT GGCAAGGCGCCAAAACTGCTTATCTCTCTG GGCAGTACCCTGCGGCCCGGCGTGCCTTCT AGATTCAGCGGCAGCGGAAGCGGAACCGAT TTTACCTTCACTATCTCAAGCCTCCAGCCC GAAGACTTCGCCACCTACTATTGTCTGCAG AGTGATAGGTTGCCCTTGACTTTCGGGCAA GGTACGAAGCTTGAGATCAAGCGTACCGTC GCAGCTCCTGATATTCAGATGACCCAGAGC CCGAGCAGCGTGAGCGCGAGCGTGGGCGAT CGCGTGACCATTACCTGCCGCGCGAGCCAG GGCATTAGCAGCTGGCTGGCGTGGTATCAG CAGAAACCGGGCAAAGCGCCGAAACTGCTG ATTTATGAAGCGAGCAACCTGGAAACCGGC GTGCCGAGCCGCTTTAGCGGCAGCGGCAGC GGCAGCGATTTTACCCTGACCATTAGCAGC CTGCAGCCGGAAGATTTTGCGACCTATTAT TGCCAGCAGACCAGCAGCTTTCTGCTGAGC TTTGGCGGCGGCACCAAAGTGGAACATAAA CGC |
| 1B12.1-SS-X3 VH (SEQ ID NO: 54) | SEQ ID NO: 68 | GAGGTACAACTTCAAGAATCTGGTCCAGGG CTTGTGAAGCCTAGTGAAACACTGTCACTG ACTTGTACCGTGTCCGGATTAGCCTGTCC GACTACGGAGTTTCATGGATTCGACAGCCC CCCGGGAAAGGTCTGGAGTGGCTCGGGCTG ATCTGGGGTGGTGGAGACACATATTACAAT TCCCCTCTGAAATCCAGGCTTACCATCAGC AAGGATAACTCAAAAAGCCAAGTTTCATTG AAGCTGAGTTCCGTGACTGCCGCCGACACG GCGGTCTATTATTGTGCAAAACAGAGGACC CTGTGGGGATATGACCTCTACGGAATGGAC TATTGGGGCCAAGGCACACTTGTGACCGTG TCCAGTGCCTCAACAAAAGGGCCTCAGGTG CAGCTGGTGGAAAGCGGCGGCGGCGTGGTG CAGCCGGGCCGCAGCCTGCGCCTGAGCTGC ACCGCGAGCGGCTTTACCTTTAGCATGTTT GGCGTGCATTGGGTGCGCCAGGCGCCGGGC AAAGGCCTGGAATGGGTGGCGGCGGTGAGC |

TABLE 6-continued

Nucleic Acid Molecules Binding Proteins

| Encodes | Sequence Identifier | Sequence 123456789012345678901234567890 |
|---|---|---|
| | | TATGATGGCAGCAACAAATATTATGCGGAA<br>AGCGTGAAAGGCCGCTTTACCATTAGCCGC<br>GATAACAGCAAAAACATTCTGTTTCTGCAG<br>ATGGATAGCCTGCGCCTGGAAGATACCGCG<br>GTGTATTATTGCGCGCGCGGCCGCCCGAAA<br>GTGGTGATTCCGGCGCCGCTGGCGCATTGG<br>GGCCAGGGCACCCTGGTGACCTTTAGCAGC |
| 1B12.1-SS-X3 VL (SEQ ID NO: 55) | SEQ ID NO: 69 | GACACTCAAGTGACACAGTCCCCATCATCT<br>TTGTCCGCGAGTGTTGGGGACAGAGTAACT<br>ATTACTTGCATAACCAGCACTGATATAGAC<br>GTGGACATGAACTGGTATCAGCAGAAGCCT<br>GGCAAGCCGCCAAAACTGCTTATCTCTCAA<br>GGCAATACCCTGCGACCCGGCGTGCCTTCT<br>AGATTCAGCTCTAGCGGAAGCGGAACCGAT<br>TTTACCTTCACTATCTCAAGCCTCCAGCCC<br>GAAGACTTCGCCACCTACTATTGTCTGCAG<br>AGCGATAACCTCCCCTTGACTTTCGGGCAA<br>GGTACGAAGCTTGAGATCAAGCGTACGGTG<br>GCTGCACCAGATATTCAGATGACCCAGAGC<br>CCGAGCAGCGTGAGCGCGAGCGTGGGCGAT<br>CGCGTGACCATTACCTGCCGCGCGAGCCAG<br>GGCATTAGCAGCTGGCTGGCGTGGTATCAG<br>CAGAAACGGGCAAAGCGCCGAAACTGCTG<br>ATTTATGAAGCGAGCAACCTGGAAACCGGC<br>GTGCCGAGCCGCTTTAGCGGCAGCGGCAGC<br>GGCAGCGATTTTACCCTGACCATTAGCAGC<br>CTGCAGCCGGAAGATTTTGCGACCTATTAT<br>TGCCAGCAGACCAGCAGCTTTCTGCTGAGC<br>TTTGGCGGCGGCACCAAAGTGGAACATAAA<br>CGC |

The disclosure also provides nucleic acid molecules that are 70, 75, 80, 85, 90, 91, 92, 93, 94, 95, 96, 97, 98, 99 or 100% identical to a nucleic acid molecule that can encode any of the CDRs, VH, VL or any other binding protein described herein. The disclosure also provides fragments of these nucleic acid molecules. In certain embodiments, fragments can have 363 nucleic acids or fewer. In other embodiments, fragments can have 321 nucleic acids or fewer. In other embodiments, fragments can have 15, 30, 45, 60, 75, 90, 105, 120, 135, 150, 165, 180, 195, 210, 225, 240, 255, 270, 285, 300, 315 or fewer nucleic acids.

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of the term "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Abbreviations used herein include Ag, meaning antigen; DNA, meaning deoxyribonucleic acid; FACS, meaning fluorescence-activated cell sorting; IgG, meaning immunoglobulin G; PCR, meaning polymerase chain reaction; PE, meaning R-Phycoerythrin; ScFv, meaning single chain variable fragment; CDR, meaning complementarity determining region; Cyno, meaning cynomolgus; MACS, meaning magnetic activated cell sorting; VH, meaning variable heavy and Vk, meaning variable kappa.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present disclosure are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the present disclosure may be more readily understood, select terms are defined below.

The term "polypeptide" refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric. The term "polypeptide" encompasses fragments and variants (including fragments of variants) thereof, unless otherwise contradicted by context. For an antigenic polypeptide, a fragment of polypeptide optionally contains at least one contiguous or non-linear epitope of polypeptide. The precise boundaries of the at least one epitope fragment can be confirmed using ordinary skill in the art. The fragment comprises at least about 5 contiguous amino acids, such as at least about 10 contiguous amino acids, at least about 15 contiguous amino acids, or at least about 20 contiguous amino acids. A variant of polypeptide is as described herein.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" refers to the process of rendering a chemical species such as a polypeptide substantially free of naturally associated components by isolation, e.g., using protein purification techniques well known in the art.

The term "human IL-1α" (abbreviated herein as hIL-1α, or IL-1 α) includes a pleiotropic cytokine involved in various immune responses, inflammatory processes, and hematopoiesis. For example, IL-1α includes the human cytokine produced by activated macrophages; it stimulates thymocyte proliferation by inducing IL-2 release, B-cell maturation and proliferation, and fibroblast growth factor activity. The term human IL-1α is intended to include recombinant human IL-1α (rh IL-1α) that can be prepared by standard recombinant expression methods.

The term "human IL-1β" (abbreviated herein as hIL-1β, or IL-1β) includes a pleiotropic cytokine involved in various immune responses, inflammatory processes, and hematopoiesis. The term human IL-1β includes recombinant human IL-1β (rh IL-1β) that can be prepared by standard recombinant expression methods.

The amino acid sequences of human IL-1α and IL-1β are shown in Table 7.

TABLE 7

Sequence of Human IL-1α and Human IL-1β

| Protein | Sequence Identifier | Sequence 12345678901234567890123456789 0 |
|---|---|---|
| Mature human IL-1α | SEQ ID NO: 70 | SAPFSFLSNVKYNFMRIIKYEFILNDALNQ SIIRANDQYLTAAALHNLDEAVKFDMGAYK SSKDDAKITVILRISKTQLYVTAQDEDQPV LLKEMPEIPKTITGSETNLLFFWETHGTKN YFTSVAHPNLFIATKQDYWVCLAGGPPSIT DFQILENQA |
| Mature human IL-1β | SEQ ID NO: 71 | APVRSLNCTLRDSQQKSLVMSGPYELKALH LQGQDMEQQVVFSMSFVQGEESNDKIPVAL GLKEKNLYLSCVLKDDKPTLQLESVDPKNY PKKKMEKRFVFNKIEINNKLEFESAQFPNW YISTSQAENMPVFLGGTKGGQDITDFTMQF VSS |

The term "biological activity" refers to all inherent biological properties of the IL-1 cytokine, e.g., IL-1α and/or IL-1β. Biological properties of IL-1α and IL-1β include, but are not limited to, binding to an IL-1 receptor.

The terms "specific binding" or "specifically binding" in reference to the interaction of an antibody, a binding protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody. In certain embodiments, a binding protein that specifically binds to an antigen binds to that antigen with a $K_D$ greater than $10^{-6}$, $10^{-7}$, $10^{-8}$, $10^{-9}$, $10^{-10}$, $10^{-11}$, $10^{-12}$, $10^{-13}$ or $10^{-14}$ M. In other embodiments, a binding protein that specifically binds to an antigen binds to that antigen with a $K_D$ of between $10^{-6}$ and $10^{-7}$, $10^{-6}$ and $10^{-8}$, $10^{-6}$ and $10^{-9}$, $10^{-6}$ and $10^{-10}$, $10^{-6}$ and $10^{-11}$, $10^{-6}$ and $10^{-12}$, $10^{-6}$ and $10^{-13}$, $10^{-6}$ and $10^{-14}$, $10^{-9}$ and $10^{-10}$, $10^{-9}$ and $10^{-11}$, $10^{-9}$ and $10^{-12}$, $10^{-9}$ and $10^{-13}$ or $10^{-9}$ and $10^{-14}$M.

The term "antibody" broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below.

In a full-length antibody, each heavy chain is comprised of a heavy chain variable region (abbreviated herein as HCVR or VH) and a heavy chain constant region. The heavy chain constant region is comprised of three domains: CH1, CH2, and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain, and a CH3 domain, and optionally comprises a CH4 domain. Replacements of amino acid residues in the Fc portion to alter antibody effector function are known in the art (Winter et al., U.S. Pat. Nos. 5,648,260 and 5,624,821). The Fc portion of an antibody mediates several important effector functions, for example, cytokine induction, ADCC, phagocytosis, complement dependent cytotoxicity (CDC), and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered. The dimerization of two identical heavy chains of an immunoglobulin is mediated by the dimerization of CH3 domains and is stabilized by the disulfide bonds within the hinge region (Huber et al., Nature, 264: 415-420 (1976); Thies et al., J. Mol. Biol., 293: 67-79 (1999)). Mutation of cysteine residues within the hinge regions to prevent heavy chain-heavy chain disulfide bonds will destabilize dimerization of CH3 domains. In certain embodiments, residues 234 and 235 of the IgG1 Fc region are mutated from LL to AA (Alegre M L, Peterson, L J, Xu, D., et al. Transplantation 1994; 57:1537; Armour, K L., van de Winkel, J. G. J., et al. 2003; Molecular Immunology; 40:585.) Other residues responsible for CH3 dimerization have been identified (Dall'Acqua et al., Biochemistry, 37: 9266-9273 (1998)). Therefore, it is possible to generate a monovalent half-Ig. Interestingly, these monovalent half Ig molecules have been found in nature for both IgG and IgA subclasses (Seligmann et al., Ann. Immunol., 129 C: 855-870 (1978); Biewenga et al., Clin. Exp. Immunol., 51: 395-400 (1983)). The stoichiometry of FcRn: Ig Fc region has been determined to be 2:1 (West et al., Biochemistry, 39: 9698-9708 (2000)), and half Fc is sufficient for mediating FcRn binding (Kim et al., Eur. J. Immunol., 24: 542-548 (1994)). Mutations to disrupt the dimerization of CH3 domain may not have greater adverse effect on its FcRn binding as the residues important for CH3 dimerization are located on the inner interface of CH3 b sheet structure, whereas the region responsible for FcRn binding is located on the outside interface of CH2-CH3 domains. However, the half Ig molecule may have certain advantage in tissue penetration due to its smaller size than that of a regular antibody. In one embodiment, at least one amino acid residue is replaced in the constant region of the binding protein of the disclosure, for example the Fc region, such that the dimerization of the heavy chains is disrupted, resulting in half DVD Ig molecules. The anti-inflammatory activity of IgG is completely dependent on sialylation of the N-linked glycan of the IgG Fc fragment. The precise glycan requirements for anti-inflammatory activity has been determined, such that an appropriate IgG1 Fc fragment can be created, thereby generating a fully recombinant, sialylated IgG1 Fc with greatly enhanced potency (Anthony et al., Science, 320:373-376 (2008)).

The term "antigen-binding portion" of an antibody refers to one or more fragments of an antibody that retain the ability to specifically bind to an antigen (e.g., hIL-1α or hIL-1β). It has been shown that the antigen-binding function of an antibody can be performed by fragments of a full-length antibody. Such antibody embodiments may also be bispecific, dual specific, or multispecific formats; specifically binding to two or more different antigens (e.g., hIL-1β and a different antigen molecule, such as hIL-1α). Examples of binding fragments encompassed within the term "antigen-binding portion" of an antibody include (i) a Fab fragment, a monovalent fragment consisting of the VL, VH, CL, and CH1 domains; (ii) a F(ab')₂ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., Nature, 341: 544-546 (1989); PCT Publication No. WO 90/05144), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, for example, Bird et al., Science, 242: 423-426 (1988); and Huston et al., Proc. Natl. Acad. Sci. USA, 85: 5879-5883 (1988)). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., Proc. Natl. Acad. Sci. USA, 90: 6444-6448 (1993); Poljak, R. J., Structure, 2: 1121-1123 (1994)). Such antibody binding portions are known in the art (Kontermann and Dubel eds., Antibody Engineering (Springer-Verlag, New York, 2001), p. 790 (ISBN 3-540-41354-5)). In addition single chain antibodies also include "linear antibodies" comprising a pair of tandem Fv segments (VH-CH1-VH-CH1) which, together with complementary light chain polypeptides, form a pair of antigen binding regions (Zapata et al., Protein Eng., 8(10): 1057-1062 (1995); and U.S. Pat. No. 5,641,870)).

An immunoglobulin constant (C) domain refers to a heavy (CH) or light (CL) chain constant domain. Murine and human IgG heavy chain and light chain constant domain amino acid sequences are known in the art.

The term "IL-1α or β binding protein construct" (or "binding protein construct") refers to a polypeptide comprising one or more of the antigen binding portions of the disclosure linked to a linker or an immunoglobulin constant domain. A "linker polypeptide" comprises two or more amino acid residues joined by peptide bonds and are used to link one or more antigen binding portions. Such linker polypeptides are well known in the art (see e.g., Holliger et al., Proc. Natl. Acad. Sci. USA, 90: 6444-6448 (1993); Poljak, R. J., Structure, 2: 1121-1123 (1994)). An immunoglobulin constant domain refers to a heavy or light chain constant domain. Human IgG heavy chain and light chain constant domain amino acid sequences are known in the art and represented in Table 8.

TABLE 8

Sequence of Human IgG Heavy Chain Constant Domain and Light Chain Constant Domain

| Protein | Sequence Identifier | Sequence 12345678901234567890123456789 |
|---|---|---|
| Ig gamma-1 constant region | SEQ ID NO: 72 | ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK |

TABLE 8-continued

Sequence of Human IgG Heavy Chain Constant Domain
and Light Chain Constant Domain

| Protein | Sequence Identifier | Sequence<br>123456789012345678901234567890 |
|---|---|---|
| Ig gamma-1 constant region 234, 235 mutant | SEQ ID NO: 73 | ASTKGPSVFPLAPSSKSTSGGTAALGCLVK<br>DYFPEPVTVSWNSGALTSGVHTFPAVLQSS<br>GLYSLSSVVTVPSSSLGTQTYICNVNHKPS<br>NTKVDKKVEPKSCDKTHTCPPCPAPEAAGG<br>PSVFLFPPKPKDTLMISRTPEVTCVVVDVS<br>HEDPEVKFNWYVDGVEVHNAKTKPREEQYN<br>STYRVVSVLTVLHQDWLNGKEYKCKVSNKA<br>LPAPIEKTISKAKGQPREPQVYTLPPSREE<br>MTKNQVSLTCLVKGFYPSDIAVEWESNGQP<br>ENNYKTTPPVLDSDGSFFLYSKLTVDKSRW<br>QQGNVFSCSVMHEALHNHYTQKSLSLSPGK |
| Ig Kappa constant region | SEQ ID NO: 74 | TVAAPSVFIFPPSDEQLKSGTASVVCLLNN<br>FYPREAKVQWKVDNALQSGNSQESVTEQDS<br>KDSTYSLSSTLTLSKADYEKHKVYACEVTH<br>QGLSSPVTKSFNRGEC |
| Ig Lambda constant region | SEQ ID NO: 75 | QPKAAPSVTLFPPSSEELQANKATLVCLIS<br>DFYPGAVTVAWKADSSPVKAGVETTTPSKQ<br>SNNKYAASSYLSLTPEQWKSHRSYSCQVTH<br>EGSTVEKTVAPTECS |

Still further, an IL-1α or β binding protein, an antibody antigen-binding portion thereof, may be part of a larger immunoadhesion molecule, formed by covalent or noncovalent association of the antibody antigen-binding portion with one or more other proteins or peptides. Examples of such immunoadhesion molecules include use of the streptavidin core region to make a tetrameric scFv molecule (Kipriyanov et al., Human Antibod. Hybridomas, 6: 93-101 (1995)) and use of a cysteine residue, a marker peptide and a C-terminal polyhistidine tag to make bivalent and biotinylated scFv molecules (Kipriyanov et al., Mol. Immunol., 31: 1047-1058 (1994)). Antibody portions, such as Fab and F(ab')$_2$ fragments, can be prepared from whole antibodies using conventional techniques, such as papain or pepsin digestion, respectively, of whole antibodies. Moreover, antibodies, antigen-binding portions thereof, and immunoadhesion molecules can be obtained using standard recombinant DNA techniques. An IL-1α or β binding protein, such as an antigen-binding portion of an antibody may also be part of a DVD-Ig™.

An "isolated antibody" is intended to refer to an antibody that is substantially free of other antibodies having different antigenic specificities (e.g., an isolated antibody that specifically binds hIL-1α or hIL-1β is substantially free of antibodies that specifically bind antigens other than hIL-1α or hIL-1β). An isolated antibody that specifically binds hIL-1α or hIL-1β may, however, have cross-reactivity to other antigens, such as hIL-1α or IL-1β molecules from other species. Moreover, an isolated antibody may be substantially free of other cellular material and/or chemicals.

The term "monoclonal antibody" or "mAb" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each mAb is directed against a single determinant on the antigen. The modifier "monoclonal" is not to be construed as requiring production of the antibody by any particular method.

The term "human antibody" includes antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody" does not include antibodies in which CDR sequences derived from the germline of another mammalian species, such as a mouse, have been grafted onto human framework sequences.

The term "recombinant human antibody" includes all human antibodies that are prepared, expressed, created or isolated by recombinant means, such as antibodies expressed using a recombinant expression vector transfected into a host cell (described further in Section II C, below), antibodies isolated from a recombinant, combinatorial human antibody library (Hoogenboom, H. R., Trends Biotechnol., 15: 62-70 (1997); Azzazy and Highsmith, Clin. Biochem., 35: 425-445 (2002); Gavilondo and Larrick, BioTechniques, 29: 128-145 (2000); Hoogenboom and Chames, Immunol. Today, 21: 371-378 (2000)), antibodies isolated from an animal (e.g., a mouse) that is transgenic for human immunoglobulin genes (see, e.g., Taylor et al., Nucl. Acids Res., 20: 6287-6295 (1992); Kellermann and Green, Curr. Opin. Biotechnol., 13: 593-597 (2002); Little et al., Immunol. Today, 21: 364-370 (2000)); or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "chimeric antibody" refers to antibodies that comprise heavy and light chain variable region sequences from one species and constant region sequences from another species, such as antibodies having murine heavy and light chain variable regions linked to human constant regions.

The term "CDR-grafted antibody" refers to antibodies that comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia and Lesk, J. Mol. Biol., 196: 901-917 (1987); and Chothia et al., Nature, 342: 877-883 (1989)) found that certain sub-portions within Kabat CDRs adopt nearly identical peptide backbone conformations, despite having great diversity at the level of amino acid sequence. These sub-portions were designated as L1, L2, and L3 or H1, H2, and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan et al. (FASEB J., 9: 133-139 (1995)) and MacCallum et al. (J. Mol. Biol., 262(5): 732-745 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although exemplary embodiments use Kabat or Chothia defined CDRs.

The terms "Kabat numbering", "Kabat definitions", and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al., Ann. NY Acad. Sci., 190: 382-391 (1971); and Kabat et al., Sequences of Proteins of Immunological Interest, Fifth Edition, U.S. Department of Health and Human Services, NIH Publication No. 91-3242 (1991)). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

The growth and analysis of extensive public databases of amino acid sequences of variable heavy and light regions over the past twenty years have led to the understanding of the typical boundaries between framework regions (FR) and CDR sequences within variable region sequences and enabled persons skilled in this art to accurately determine the CDRs according to Kabat numbering, Chothia numbering, or other systems. See, e.g., Martin, "Protein Sequence and Structure Analysis of Antibody Variable Domains," Chapter 31, In Antibody Engineering, (Kontermann and Dubel, eds.) (Springer-Verlag, Berlin, 2001), especially pages 432-433. A useful method of determining the amino acid sequences of Kabat CDRs within the amino acid sequences of variable heavy (VH) and variable light (VL) regions is provided below:

To identify a CDR-L1 amino acid sequence: Starts approximately 24 amino acid residues from the amino terminus of the VL region; Residue before the CDR-L1 sequence is always cysteine (C); Residue after the CDR-L1 sequence is always a tryptophan (W) residue, typically Trp-Tyr-Gln (W-Y-Q), but also Trp-Leu-Gln (W-L-Q), Trp-Phe-Gln (W-F-Q), and Trp-Tyr-Leu (W-Y-L); Length is typically 10 to 17 amino acid residues.

To identify a CDR-L2 amino acid sequence: Starts always 16 residues after the end of CDR-L1; Residues before the CDR-L2 sequence are generally Ile-Tyr (I-Y), but also Val-Tyr (V-Y), Ile-Lys (I-K), and Ile-Phe (I-F); Length is always 7 amino acid residues.

To identify a CDR-L3 amino acid sequence: Starts always 33 amino acids after the end of CDR-L2; Residue before the CDR-L3 amino acid sequence is always a cysteine (C); Residues after the CDR-L3 sequence are always Phe-Gly-X-Gly (F-G-X-G) (SEQ ID NO:76), where X is any amino acid; Length is typically 7 to 11 amino acid residues.

To identify a CDR-H1 amino acid sequence: Starts approximately 31 amino acid residues from amino terminus of VH region and always 9 residues after a cysteine (C); Residues before the CDR-H1 sequence are always Cys-X-X-X-X-X-X-X-X (SEQ ID NO: 430), where X is any amino acid; Residue after CDR-H1 sequence is always a Trp (W), typically Trp-Val (W-V), but also Trp-Ile (W-I), and Trp-Ala (W-A); Length is typically 5 to 7 amino acid residues.

To identify a CDR-H2 amino acid sequence: Starts always 15 amino acid residues after the end of CDR-H1; Residues before CDR-H2 sequence are typically Leu-Glu-Trp-Ile-Gly (L-E-W-I-G) (SEQ ID NO:77), but other variations also; Residues after CDR-H2 sequence are Lys/Arg-Leu/Ile/Val/Phe/Thr/Ala-Thr/Ser/Ile/Ala (K/R-L/I/V/F/T/A-T/S/I/A); Length is typically 16 to 19 amino acid residues.

To identify a CDR-H3 amino acid sequence: Starts always 33 amino acid residues after the end of CDR-H2 and always 3 after a cysteine (C)' Residues before the CDR-H3 sequence are always Cys-X-X (C-X-X), where X is any amino acid, typically Cys-Ala-Arg (C-A-R); Residues after the CDR-H3 sequence are always Trp-Gly-X-Gly (W-G-X-G) (SEQ ID NO:78), where X is any amino acid; Length is typically 3 to 25 amino acid residues.

As used herein, the term "canonical" residue refers to a residue in a CDR or framework that defines a particular canonical CDR structure as defined by Chothia et al. (J. Mol. Biol., 196: 901-917 (1987)); and Chothia et al. (J. Mol. Biol., 227: 799-817 (1992)), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

An "affinity matured" antibody is an antibody with one or more alterations in one or more CDRs thereof which result in an improvement in the affinity of the antibody for a target antigen, compared to a parent antibody which does not possess the alteration(s). Exemplary affinity matured antibodies will have nanomolar or even picomolar affinities for the target antigen. A variety of procedures for producing affinity matured antibodies are known in the art. For example, Marks et al., BioTechnology, 10: 779-783 (1992) describes affinity maturation by VH and VL domain shuffling. Random mutagenesis of CDR and/or framework residues is described by Barbas et al., Proc. Nat. Acad. Sci. USA, 91: 3809-3813 (1994); Schier et al., Gene, 169: 147-155 (1995); Yelton et al., J. Immunol., 155: 1994-2004 (1995); Jackson et al., J. Immunol., 154(7): 3310-3319 (1995); Hawkins et al., J. Mol. Biol., 226: 889-896 (1992). Selective mutation at selective mutagenesis positions and at contact or hypermutation positions with an activity enhancing amino acid residue is described in U.S. Pat. No. 6,914, 128 B1.

The term "multivalent binding protein" denotes a binding protein comprising two or more antigen binding sites. A multivalent binding protein is preferably engineered to have three or more antigen binding sites, and is generally not a naturally occurring antibody. The term "multispecific binding protein" refers to a binding protein capable of binding two or more related or unrelated targets.

The term "bispecific antibody", as used herein, refers to full-length antibodies that are generated by quadroma technology (see Milstein and Cuello, Nature, 305: 537-540 (1983)), by chemical conjugation of two different monoclonal antibodies (see Staerz et al., Nature, 314: 628-631 (1985)), or by knob-into-hole or similar approaches which introduces mutations in the Fc region (see Holliger et al., Proc. Natl. Acad. Sci. USA, 90(14): 6444-6448 (1993)), resulting in multiple different immunoglobulin species of which only one is the functional bispecific antibody. By molecular function, a bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen binding arms (in both specificity and CDR sequences), and is monovalent for each antigen it binds.

The term "dual-specific antibody", as used herein, refers to full-length antibodies that can bind two different antigens (or epitopes) in each of its two binding arms (a pair of HC/LC) (see PCT Publication No. WO 02/02773). Accordingly a dual-specific binding protein has two identical antigen binding arms, with identical specificity and identical CDR sequences, and is bivalent for each antigen to which it binds.

A "functional antigen binding site" of a binding protein is one that is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same.

As used herein, the terms "donor" and "donor antibody" refer to an antibody providing one or more CDRs. In an exemplary embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, —H2, and —H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

As used herein, the terms "acceptor" and "acceptor antibody" refer to the antibody providing or nucleic acid sequence encoding at least 80%, at least 85%, at least 90%, at least 95%, at least 98%, or 100% of the amino acid sequences of one or more of the framework regions. In some embodiments, the term "acceptor" refers to the antibody amino acid providing or nucleic acid sequence encoding the constant region(s). In yet another embodiment, the term "acceptor" refers to the antibody amino acid providing or nucleic acid sequence encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well known in the art, antibodies in development, or antibodies commercially available).

Human heavy chain and light chain acceptor sequences are known in the art. In one embodiment of the disclosure the human heavy chain and light chain acceptor sequences are selected from the sequences listed from V-base (vbase.mrc-cpe.cam.ac.uk/) or from IMGT®, the international ImMunoGeneTics Information System® (imgt.cines.fr/textes/IMGTrepertoire/LocusGenes/). In another embodiment of the disclosure the human heavy chain and light chain acceptor sequences are selected from the sequences described in Table 3 and Table 4 of U.S. Patent Publication No. 2011/0280800, incorporated by reference herein in their entireties.

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., Crit. Rev. Immunol., 22(3): 183-200 (2002); Marchalonis et al., Adv. Exp. Med. Biol., 484: 13-30 (2001)). One of the advantages provided by various embodiments of the present disclosure stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR/and the Kabat definition of the first heavy chain framework.

The term "humanized antibody" refers to antibodies that comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. Also "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(aN)$_2$, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

A humanized antibody may be selected from any class of immunoglobulins, including IgM, IgG, IgD, IgA and IgE, and any isotype including without limitation IgG1, IgG2, IgG3, and IgG4. The humanized antibody may comprise sequences from more than one class or isotype, and particular constant domains may be selected to optimize desired effector functions using techniques well known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In an exemplary embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, e.g., Winnaker, From Genes to Clones (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

With respect to constructing DVD-Ig or other binding protein molecules, a "linker" is used to denote a single amino acid or a polypeptide ("linker polypeptide") comprising two or more amino acid residues joined by peptide bonds and used to link one or more antigen binding portions. Such linker polypeptides are well known in the art (see, e.g., Holliger et al., Proc. Natl. Acad. Sci. USA, 90: 6444-6448 (1993); Poljak, R. J., Structure, 2: 1121-1123 (1994)). Exemplary linkers include, but are not limited to, SEQ ID NOs: 42 and 43; GGGGSG (SEQ ID NO:79), GGSGG (SEQ ID NO:80), GGGGSGGGGS (SEQ ID NO:81), GGSGGGGSG (SEQ ID NO:82), GGSGGGGSGS (SEQ ID NO:83), GGSGGGGSGGGS (SEQ ID NO:84), GGGGSGGGGSGGGG (SEQ ID NO:85), GGGGSGGGGSGGGGS (SEQ ID NO:86), ASTKGPSVF-PLAP (SEQ ID NO:87), RTVAAP (SEQ ID NO:88), TVAAPSVFIFPP (SEQ ID NO:89), RTVAAPSVFIFPP (SEQ ID NO:90), AKTTPKLEEGEFSEAR (SEQ ID NO:91), AKTTPKLEEGEFSEARV (SEQ ID NO:92), AKTTPKLGG (SEQ ID NO:93), SAKTTPKLGG (SEQ ID NO:94), SAKTTP (SEQ ID NO:95), RADAAP (SEQ ID NO:96), RADAAPTVS (SEQ ID NO:97), RADAAAAGG-PGS (SEQ ID NO:98), RADAAAAGGGGSGGGGSGGGGSGGGS (SEQ ID NO:99), SAKTTPKLEEGEFSEARV (SEQ ID NO:100), ADAAP (SEQ ID NO:101), ADAAPTVSIFPP (SEQ ID NO:102), QPKAAP (SEQ ID NO:103), QPKAAPS-VTLFPP (SEQ ID NO:104), AKTTPP (SEQ ID NO:105), AKTTPPSVTPLAP (SEQ ID NO:106), AKTTAP (SEQ ID NO:107), AKTTAPSVYPLAP (SEQ ID NO:108), GENK-VEYAPALMALS (SEQ ID NO:109), GPAKELT-PLKEAKVS (SEQ ID NO:110), and GHEAAAVMQVQY-PAS (SEQ ID NO:111).

As used herein, "Vernier" zone refers to a subset of framework residues that may adjust CDR structure and fine-tune the fit to antigen as described by Foote and Winter, J. Mol. Biol., 224:487-499 (1992), which is incorporated herein by reference). Vernier zone residues form a layer underlying the CDRs and may impact on the structure of CDRs and the affinity of the antibody.

As used herein, the term "neutralizing" refers to neutralization of the biological activity of an antigen (e.g., the cytokines hIL-1α or IL-1β) when a binding protein specifically binds the antigen. Preferably, a neutralizing binding protein described herein binds to hIL-1α or hIL-1β resulting in the inhibition of a biological activity of hIL-1α or hIL-1β. Preferably, the neutralizing binding protein binds hIL-1β and reduces a biologically activity of hIL-1α or hIL-1β by at least about 20%, 40%, 60%, 80%, 85%, or more. Inhibition of a biological activity of hIL-1α or hIL-1β by a neutralizing binding protein can be assessed by measuring one or more indicators of hIL-1α or hIL-1β biological activity well known in the art. For example inhibition inhibition of human IL-8 secretion MRC-5 cells.

The term "activity" includes activities such as the binding specificity/affinity of an binding protein for an antigen, for example, an binding protein that specifically binds to an IL-1α antigen and IL-1β antigen and/or the neutralizing potency of an binding protein, for example, an anti-IL-1α/β binding protein whose binding to h IL-1α and β inhibits the biological activity of h IL-1α and β, for example, inhibition of human IL-8 secretion MRC-5 cells.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by a binding protein. In certain embodiments, a binding protein is said to specifically bind an antigen when it preferentially recognizes its target antigen in a complex mixture of proteins and/or macromolecules. Binding proteins are said to "bind to the same epitope" if the binding proteins cross-compete (one prevents the binding or modulating effect of the other). In addition, structural definitions of epitopes (overlapping, similar, identical) are informative, but functional definitions are often more relevant as they encompass structural (binding) and functional (modulation, competition) parameters.

The term "surface plasmon resonance", as used herein, refers to an optical phenomenon that allows for the analysis of real-time b10 specific interactions by detection of alterations in protein concentrations within a biosensor matrix, for example using the BIAcore system (Pharmacia Biosensor AB, Uppsala, Sweden and Piscataway, N.J.). For further descriptions, see Jonsson et al., Ann. Biol. Clin., 51: 19-26 (1993); Jonsson et al., BioTechniques, 11: 620-627 (1991); Johnsson et al., J. Mol. Recognit., 8: 125-131 (1995); and Johnsson et al., Anal. Biochem., 198: 268-277 (1991).

The term "$K_{on}$" (also "Kon", "kon"), as used herein, is intended to refer to the on rate constant for association of a binding protein (e.g., a DVD-Ig) to an antigen to form an association complex, e.g., binding protein/antigen complex, as is known in the art. The "$K_{on}$" also is known by the terms "association rate constant", or "ka", as used interchangeably herein. This value indicates the binding rate of a binding protein to its target antigen or the rate of complex formation between an antibody and antigen as is shown by the equation below:

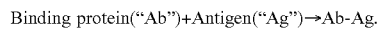

Binding protein("Ab")+Antigen("Ag")→Ab-Ag.

The term "$K_{off}$" (also "Koff", "koff"), as used herein, is intended to refer to the off rate constant for dissociation, or "dissociation rate constant", of a binding protein (e.g., an DVD-Ig) from an association complex (e.g., a binding protein/antigen complex) as is known in the art. This value indicates the dissociation rate of an antibody from its target antigen or separation of Ab-Ag complex over time into free binding protein and antigen as shown by the equation below:

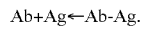

Ab+Ag←Ab-Ag.

The term "$K_D$" (also "$K_d$"), as used herein, is intended to refer to the "equilibrium dissociation constant", and refers to the value obtained in a titration measurement at equilibrium, or by dividing the dissociation rate constant (Koff) by the association rate constant (Kon). The association rate constant (Kon), the dissociation rate constant (Koff), and the equilibrium dissociation constant (K are used to represent the binding affinity of a binding protein to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) can also be used.

The terms "label" and "detectable label" mean a moiety attached to a specific binding partner, such as a binding protein or an analyte, e.g., to render the reaction between members of a specific binding pair, such as a binding protein and an analyte, detectable. The specific binding partner, e.g., binding protein or analyte, so labeled is referred to as "detectably labeled". Thus, the term "labeled binding protein" as used herein, refers to a protein with a label incorporated that provides for the identification of the binding protein. In an embodiment, the label is a detectable marker that can produce a signal that is detectable by visual or instrumental means, e.g., incorporation of a radiolabeled amino acid or attachment to a polypeptide of biotinyl moieties that can be detected by marked avidin or streptavidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^3$H $^{14}$C, $^{35}$S, $^{90}$Y, $^{99}$Tc, $^{111}$In, $^{125}$I, $^{131}$I, $^{177}$Lu, $^{166}$Ho, or $^{153}$Sm), chromogens, fluorescent labels (e.g., FITC, rhodamine, lanthanide phosphors), enzymatic labels (e.g., horseradish peroxidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), and magnetic agents (e.g., gadolinium chelates). Representative examples of labels commonly employed for immunoassays include moieties that produce light, e.g., acridinium compounds, and moieties that produce fluorescence, e.g., fluorescein. Other labels are described herein. In this regard, the moiety itself may not be detectably labeled but may become detectable upon reaction with yet another moiety. Use of the term "detectably labeled" is intended to encompass the latter type of detectable labeling.

The term "binding protein conjugate" refers to a binding protein described herein chemically linked to a second chemical moiety, such as a therapeutic or cytotoxic agent. The term "agent" is used herein to denote a chemical compound, a mixture of chemical compounds, a biological macromolecule, or an extract made from biological materials. Preferably the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. When employed in the context of an immunoassay, a binding protein conjugate may be a detectably labeled antibody, which is used as the detection antibody.

The terms "crystal" and "crystallized" as used herein, refer to a binding protein (e.g., a DVD-Ig), or antigen binding portion thereof, that exists in the form of a crystal. Crystals are one form of the solid state of matter that is distinct from other forms such as the amorphous solid state or the liquid crystalline state. Crystals are composed of regular, repeating, three-dimensional arrays of atoms, ions, molecules (e.g., proteins such as DVD-Igs), or molecular assemblies (e.g., antigen/binding protein complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege et al., Chapter 1, In Crystallization of Nucleic Acids and Proteins, a Practical Approach, 2nd ed., (Ducruix and Giege, eds.) (Oxford University Press, New York, 1999) pp. 1-16.

The term "polynucleotide" means a polymeric form of two or more nucleotides, either ribonucleotides or deoxynucleotides or a modified form of either type of nucleotide. The term includes single and double stranded forms of DNA.

The term "isolated polynucleotide" shall mean a polynucleotide (e.g., of genomic, cDNA, or synthetic origin, or some combination thereof) that, by virtue of its origin, the "isolated polynucleotide" is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences.

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), is intended to refer to a cell into which exogenous DNA has been introduced. In an embodiment, the host cell comprises two or more (e.g., multiple) nucleic acids encoding antibodies, such as the host cells described in U.S. Pat. No. 7,262,028, for example. Such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. In an embodiment, host cells include prokaryotic and eukaryotic cells selected from any of the Kingdoms of life. In another embodiment, eukaryotic cells include protist, fungal, plant and animal cells. In another embodiment, host cells include but are not limited to the prokaryotic cell line *Escherichia coli*; mammalian cell lines CHO, HEK 293, COS, NSO, SP2 and PER.C6; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., Molecular Cloning: A Laboratory Manual, 2nd ed. (Cold Spring Harbor Laboratory Press, Cold Spring Harbor, N.Y., 1989).

"Transgenic organism", as known in the art, refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

The terms "regulate" and "modulate" are used interchangeably, and, as used herein, refers to a change or an alteration in the activity of a molecule of interest (e.g., the biological activity of h IL-1α and β). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," as used herein, is a compound capable of changing or altering an activity or function of a molecule of interest (e.g., the biological activity of hIL-1α and β). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in PCT Publication No. WO 01/83525.

The term "agonist", as used herein, refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, IL-1α and/or β polypeptides, nucleic acids, carbohydrates, or any other molecule that binds to hIL-1α or β.

The terms "antagonist" and "inhibitor", as used herein, refer to a modulator that, when contacted with a molecule of interest causes a decrease in the magnitude of a certain activity or function of the molecule compared to the magnitude of the activity or function observed in the absence of the antagonist. Particular antagonists of interest include those that block or modulate the biological or immunological activity of human IL-1α or β. Antagonists and inhibitors of human IL-1α or β may include, but are not limited to, proteins, nucleic acids, carbohydrates, or any other molecules, which bind to human IL-1α or β.

As used herein, the term "effective amount" refers to the amount of a therapy that is sufficient to reduce or ameliorate the severity and/or duration of a disorder or one or more symptoms thereof; prevent the advancement of a disorder; cause regression of a disorder; prevent the recurrence, development, onset, or progression of one or more symptoms associated with a disorder; detect a disorder; or enhance or improve the prophylactic or therapeutic effect(s) of another therapy (e.g., prophylactic or therapeutic agent).

"Patient" and "subject" may be used interchangeably herein to refer to an animal, such as a mammal, including a primate (for example, a human, a monkey, and a chimpanzee), a non-primate (for example, a cow, a pig, a camel, a llama, a horse, a goat, a rabbit, a sheep, a hamster, a guinea pig, a cat, a dog, a rat, a mouse or a whale), a bird (e.g., a duck or a goose), and a fish (e.g. zebrafish or a shark). Preferably, a patient or subject is a human, such as a human being treated or assessed for a disease, disorder or condition, a human at risk for a disease, disorder or condition, a human having a disease, disorder or condition, and/or human being treated for a disease, disorder or condition.

The term "sample", as used herein, is used in its broadest sense. A "biological sample", as used herein, includes, but is not limited to, any quantity of a substance from a living thing or formerly living thing. Such living things include, but are not limited to, humans, non-human primates, mice, rats, monkeys, dogs, rabbits and other animals. Such substances include, but are not limited to, blood (e.g., whole blood), plasma, serum, urine, amniotic fluid, synovial fluid, endothelial cells, leukocytes, monocytes, other cells, organs, tissues, bone marrow, lymph nodes and spleen.

"Component", "components," and "at least one component," refer generally to a capture antibody, a detection or conjugate antibody, a control, a calibrator, a series of calibrators, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, serum or plasma sample, in accordance with the methods described herein and other methods known in the art. Thus, in the context of the present disclosure, "at least one component," "component," and "components" can include a polypeptide or other analyte as above, such as a composition comprising an analyte such as polypeptide, which is optionally immobilized on a solid support, such as by binding to an anti-analyte (e.g., anti-polypeptide) binding protein. Some components can be in solution or lyophilized for reconstitution for use in an assay.

"Control" refers to a composition known to not analyte ("negative control") or to contain analyte ("positive control"). A positive control can comprise a known concentration of analyte. "Control," "positive control," and "calibrator" may be used interchangeably herein to refer to a composition comprising a known concentration of analyte. A "positive control" can be used to establish assay performance characteristics and is a useful indicator of the integrity of reagents (e.g., analytes).

"Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.). While the present disclosure may provide exemplary predetermined levels, it is well-known that cutoff values may vary depending on the nature of the immunoassay (e.g., antibodies employed, etc.). It further is well within the ordinary skill of one in the art to adapt the disclosure herein for other immunoassays to obtain immunoassay-specific cutoff values for those other immunoassays based on this disclosure. Whereas the precise value of the predetermined cutoff/level may vary between assays, correlations as described herein (if any) should be generally applicable.

"Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. Among other things, solubilizing the analyte (e.g., polypeptide of interest) may entail release of the analyte from any endogenous binding proteins present in the sample. A pretreatment reagent may be homogeneous (not requiring a separation step) or heterogeneous (requiring a separation step). With use of a heterogeneous pretreatment reagent there is removal of any precipitated analyte binding proteins from the test sample prior to proceeding to the next step of the assay.

"Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction so as to comprise a "sensitivity panel."

"Risk" refers to the possibility or probability of a particular event occurring either presently or at some point in the future. "Risk stratification" refers to an array of known clinical risk factors that allows physicians to classify patients into a low, moderate, high or highest risk of developing a particular disease, disorder or condition.

"Specific" and "specificity" in the context of an interaction between members of a specific binding pair (e.g., an antigen (or fragment thereof) and a binding protein (or antigenically reactive fragment thereof)) refer to the selective reactivity of the interaction. The phrase "specifically binds to" and analogous phrases refer to the ability of binding proteins to bind specifically to analyte (or a fragment thereof) and not bind specifically to other entities.

"Specific binding partner" is a member of a specific binding pair. A specific binding pair comprises two different molecules, which specifically bind to each other through chemical or physical means. Therefore, in addition to antigen and binding protein specific binding pairs of common immunoassays, other specific binding pairs can include biotin and avidin (or streptavidin), carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes, fragments, and variants (including fragments of variants) thereof, whether isolated or recombinantly produced.

"Variant" as used herein means a polypeptide that differs from a given polypeptide (e.g., binding proteins or IL-1α or β polypeptide) in amino acid sequence by the addition (e.g., insertion), deletion, or conservative substitution of amino acids, but that retains the biological activity of the given polypeptide (e.g., a variant IL-1β can compete with anti-IL-1β binding protein for binding to IL-1β.) A conservative substitution of an amino acid, i.e., replacing an amino acid with a different amino acid of similar properties (e.g., hydrophilicity and degree and distribution of charged regions) is recognized in the art as typically involving a minor change. These minor changes can be identified, in part, by considering the hydropathic index of amino acids, as understood in the art (see, e.g., Kyte et al., J. Mol. Biol., 157: 105-132 (1982)). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids also can be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554,101). Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Variant" also can be used to describe a polypeptide or fragment thereof that has been differentially processed, such as by proteolysis, phosphorylation, or other post-translational modification, yet retains its biological activity or antigen reactivity, e.g., the ability to bind to IL-1β. Use of "variant" herein is intended to encompass fragments of a variant unless otherwise contradicted by context.

Alternatively or additionally, a "variant" is to be understood as a polynucleotide or protein which differs in comparison to the polynucleotide or protein from which it is derived by one or more changes in its length or sequence. The polypeptide or polynucleotide from which a protein or nucleic acid variant is derived is also known as the parent polypeptide or polynucleotide. The term "variant" comprises "fragments" or "derivatives" of the parent molecule. Typically, "fragments" are smaller in length or size than the parent molecule, whilst "derivatives" exhibit one or more differences in their sequence in comparison to the parent molecule. Also encompassed modified molecules such as but not limited to post-translationally modified proteins (e.g. glycosylated, biotinylated, phosphorylated, ubiquitinated, palmitoylated, or proteolytically cleaved proteins) and modified nucleic acids such as methylated DNA. Also mixtures of different molecules such as but not limited to RNA-DNA hybrids, are encompassed by the term "variant". Typically, a variant is constructed artificially, preferably by gene-technological means whilst the parent polypeptide or polynucleotide is a wild-type protein or polynucleotide. However, also naturally occurring variants are to be understood to be encompassed by the term "variant" as used herein. Further, the variants usable in the present disclosure may also be derived from homologs, orthologs, or paralogs of the parent molecule or from artificially constructed variant, provided that the variant exhibits at least one biological activity of the parent molecule, i.e. is functionally active.

Alternatively or additionally, a "variant" as used herein, can be characterized by a certain degree of sequence identity to the parent polypeptide or parent polynucleotide from which it is derived. More precisely, a protein variant in the context of the present disclosure exhibits at least 80% sequence identity to its parent polypeptide. A polynucleotide variant in the context of the present disclosure exhibits at least 80% sequence identity to its parent polynucleotide. The term "at least 80% sequence identity" is used throughout the specification with regard to polypeptide and polynucleotide sequence comparisons. This expression preferably refers to a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide.

The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90: 5873-5877), with hmmalign (HMMER package, hmmer.wustl.edu/) or with the CLUSTAL algorithm (Thompson, J. D., Higgins, D. G. & Gibson, T. J. (1994) Nucleic Acids Res. 22, 4673-80) available e.g. on www.ebi.ac.uk/Tools/clustalw/or on www.ebi.ac.uk/Tools/clustalw2/index.html or on npsa-pbil.ibcp.fr/cgi-bin/npsa_automat.pl?page=/NPSA/npsa_clustalw.html. Preferred parameters used are the default parameters as they are set on www.ebi.ac.uk/Tools/clustalw/or www.ebi.ac.uk/Tools/clustalw2/index.html. The grade of sequence identity (sequence matching) may be calculated using e.g. BLAST, BLAT or BlastZ (or BlastX). A similar algorithm is incorporated into the BLASTN and BLASTP programs of Altschul et al. (1990) J. Mol. Biol. 215: 403-410. BLAST polynucleotide searches are performed with the BLASTN program, score=100, word length=12, to obtain polynucleotide sequences that are homologous to those nucleic acids which encode mir-146a. BLAST protein searches are performed with the BLASTP program, score=50, word length=3, to obtain amino acid sequences homologous to mir-146a. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields. When percentages of sequence identity are referred to in the present application, these percentages are calculated in relation to the full length of the longer sequence, if not specifically indicated otherwise.

I. Method of Making Anti-IL-1α or β Antibodies

Anti-IL-1α or β antibodies of the present disclosure may be made by any of a number of techniques known in the art. In particular, methods of making anti-IL-1β antibodies are described in U.S. Patent Publication No. 2011/0280800, incorporated by reference, herein, in its entirety.

B. Anti IL-1α/β DVD-Ig™ Binding Proteins

Provided herein are dual variable domain immunoglobulin binding proteins (DVD-Igs) that bind one or more epitopes of IL-1α and/or β. A DVD-Ig binding protein may also bind an epitope of IL-1α or β and an epitope of a second target antigen other than an IL-1α or β polypeptide. An exemplary embodiment of such DVD-Ig molecules comprises a heavy chain that comprises the structural formula VD1-(X1)n-VD2-C-(X2)n, wherein VD1 is a first heavy chain variable domain, VD2 is a second heavy chain variable domain, C is a heavy chain constant domain, X1 is a linker with the proviso that it is not CH1, X2 is an Fc region, and n is 0 or 1, and preferably 1; and a light chain that comprises the structural formula VD1-(X1)n-VD2-C-(X2)n, wherein VD1 is a first light chain variable domain, VD2 is a second light chain variable domain, C is a light chain constant domain, X1 is a linker with the proviso that it is not CH1, and X2 does not comprise an Fc region; and n is 0 or 1, and preferably 1. Such a DVD-Ig may comprise two such heavy chains and two such light chains, wherein each chain comprises variable domains linked in tandem without an intervening constant region between variable regions, wherein a heavy chain and a light chain associate to form two tandem antigen binding sites, and a pair of heavy and light chains may associate with another pair of heavy and light chains to form a tetrameric binding protein with four antigen binding sites. In another embodiment, a DVD-Ig molecule may comprise heavy and light chains that each comprise three variable domains, e.g., VD1, VD2, VD3, linked in tandem without an intervening constant region between variable domains, wherein a pair of heavy and light chains may associate to form three antigen binding sites, and wherein a pair of heavy and light chains may associate with another pair of heavy and light chains to form a tetrameric binding protein with six antigen binding sites.

Each variable domain (VD) in a DVD-Ig may be obtained from one or more "parent" monoclonal antibodies that bind one or more desired antigens or epitopes, such as IL-1β and/or IL-1α antigens or epitopes. General methods of making DVD-Ig and properties associated with DVD-Igs are described in U.S. Patent Publication No. 2011/0280800, incorporated by reference, herein, in its entirety. Specific methods used with the DVD-Ig specifically presented herein are provided below.

III. Use of DVD-Igs in Various Diseases

DVD-Ig molecules of the disclosure are also useful as therapeutic molecules to treat various diseases. Such DVD molecules may bind one or more targets involved in a specific disease. Examples of such targets in various diseases are described below.

IL-1 family members (IL-1β and IL-1α) play a critical role in the pathology associated with a variety of disorders involving immune and inflammatory elements. An IL-1 binding protein described herein may be administered to an individual to treat such disorders. In an embodiment, a disorder that may be treated by a method of the disclosure comprising administering to a subject an IL-1 binding protein described herein includes, but is not limited to, diabetes; uveitis; neuropathic pain; osteoarthritic pain; inflammatory pain; rheumatoid arthritis; osteoarthritis; juvenile chronic arthritis; septic arthritis; Lyme arthritis; psoriatic arthritis; reactive arthritis; spondyloarthropathy; systemic lupus erythematosus (SLE); Crohn's disease; ulcerative colitis; inflammatory bowel disease; autoimmune diabetes; insulin dependent diabetes mellitus; thyroiditis; asthma; allergic diseases; psoriasis; dermatitis; scleroderma; graft versus host disease; organ transplant rejection; acute immune disease associated with organ transplantation; chronic immune disease associated with organ transplantation; sarcoidosis; atherosclerosis; disseminated intravascular coagulation (DIC); Kawasaki's disease; Grave's disease; nephrotic syndrome; chronic fatigue syndrome; Wegener's granulomatosis; Henoch-Schoenlein purpurea; microscopic vasculitis of the kidneys; chronic active hepatitis; autoimmune uveitis; septic shock; toxic shock syndrome; sepsis syndrome; cachexia; infectious diseases; parasitic diseases; acute transverse myelitis; Huntington's chorea; Parkinson's disease; Alzheimer's disease; stroke; primary biliary cirrhosis; hemolytic anemia; malignancies; heart failure; myocardial infarction; Addison's disease; sporadic polyglandular deficiency type I; polyglandular deficiency type II (Schmidt's syndrome); acute respiratory distress syndrome (ARDS); alopecia; alopecia greata; seronegative arthropathy; arthropathy; Reiter's disease; psoriatic arthropathy; ulcerative colitic arthropathy; enteropathic synovitis; chlamydia; *Yersinia* and *Salmonella* associated arthropathy; spondyloarthropathy; atheromatous disease/arteriosclerosis; atopic allergy; autoimmune bullous disease; pemphigus vulgaris; pemphigus foliaceus; pemphigoid; linear IgA disease; autoimmune haemolytic anemia; Coombs positive haemolytic anemia; acquired pernicious anemia; juvenile pernicious anemia; myalgic encephalitis/Royal Free disease; chronic mucocutaneous candidiasis; giant cell arteritis (GCA); primary sclerosing hepatitis; cryptogenic autoimmune hepatitis; acquired immunodeficiency syndrome (AIDS); acquired immunodeficiency related diseases; hepatitis B; hepatitis C; common varied immunodeficiency (common variable hypogammaglobulinaemia); dilated cardiomyopathy; female infertility; ovarian failure; premature ovarian failure; fibrotic lung disease; cryptogenic fibrosing alveolitis; post-inflammatory interstitial lung disease; interstitial pneumonitis; connective tissue disease associated interstitial lung disease; mixed connective tissue disease associated lung disease; systemic sclerosis associated interstitial lung disease; rheumatoid arthritis associated interstitial lung disease; systemic lupus erythematosus associated lung disease; dermatomyositis/polymyositis associated lung disease; Sjorgren's disease associated lung disease; ankylosing spondylitis associated lung disease; vasculitic diffuse lung disease; haemosiderosis associated lung disease; drug-induced interstitial lung disease; fibrosis; radiation fibrosis; bronchiolitis obliterans; chronic eosinophilic pneumonia; lymphocytic infiltrative lung disease; postinfectious interstitial lung disease; gouty arthritis; autoimmune hepatitis; type-1 autoimmune hepatitis (classical autoimmune or lupoid hepatitis); type-2 autoimmune hepatitis (anti-LKM antibody hepatitis); autoimmune mediated hypoglycemia; type B insulin resistance with acanthosis nigricans; hypoparathyroidism; osteoarthritis; primary sclerosing cholangitis; psoriasis type 1; psoriasis type 2; idiopathic leucopenia; autoimmune neutropaenia; renal disease NOS; glomerulonephritides; microscopic vasculitis of the kidneys; Lyme disease; discoid lupus erythematosus; idiopathic male infertility; nitric oxide-associated male infertility; sperm autoimmunity; multiple sclerosis (all subtypes, including primary progressive, secondary progressive, relapsing remitting); sympathetic ophthalmia; pulmonary hypertension secondary to connective tissue disease; Goodpasture's syndrome; pulmonary manifestation of polyarteritis nodosa; acute rheumatic fever; rheumatoid spondylitis; Still's disease; systemic sclerosis; Sjorgren's syndrome; Takayasu's disease/arteritis; autoimmune thrombocytopenia (AITP); idiopathic thrombocytopenia; autoimmune thyroid disease; hyperthyroidism; goitrous autoimmune hypothyroidism (Hashimoto's disease); atrophic autoimmune hypothyroidism; primary myxoedema; phacogenic uveitis; primary vasculitis; vitiligo; acute liver disease; chronic liver disease; alcoholic cirrhosis; alcohol-induced liver injury; cholestasis; hypercholesterolemia; idiosyncratic liver disease; drug-induced hepatitis; non-alcoholic steatohepatitis; allergy; group B Streptococci (GBS) infection; mental disorders (e.g., depression and schizophrenia); Th2 Type and Th1 Type mediated diseases; acute and chronic pain (different forms of pain); cancer (such as lung, breast, stomach, bladder, colon, pancreas, ovarian, prostate, and rectal cancer); hematopoietic malignancies; leukemia; lymphoma; abetalipoproteinemia; acrocyanosis; acute and chronic parasitic or infectious processes; acute leukemia; acute lymphoblastic leukemia (ALL); T-cell ALL; FAB ALL; acute myeloid leukemia (AML); acute or chronic bacterial infection; acute pancreatitis; acute renal failure; adenocarcinomas; atrial ectopic beats; AIDS dementia complex; alcohol-induced hepatitis; allergic conjunctivitis; allergic contact dermatitis; allergic rhinitis; allograft rejection; alpha-1-antitrypsin deficiency; amyotrophic lateral sclerosis; anemia; angina pectoris; anterior horn cell degeneration; anti-CD3 therapy; antiphospholipid syndrome; anti-receptor hypersensitivity reactions; aortic and peripheral aneurysms; aortic dissection; arterial hypertension; arteriosclerosis; arteriovenous fistula; ataxia; atrial fibrillation (sustained or paroxysmal); atrial flutter; atrioventricular block; B cell lymphoma; bone graft rejection; bone marrow transplant (BMT) rejection; bundle branch block; Burkitt's lymphoma; burns; cardiac arrhythmias; cardiac stun syndrome; cardiac tumors; cardiomyopathy; cardiopulmonary bypass inflammation response; cartilage transplant rejection; cerebellar cortical degenerations; cerebellar disorders; chaotic or multifocal atrial tachycardia; chemotherapy associated disorders; chronic myelocytic leukemia (CML); chronic alcoholism; chronic inflammatory pathologies; chronic lymphocytic leukemia (CLL); chronic obstructive pulmonary disease (COPD); chronic salicylate intoxication; colorectal carcinoma; congestive heart failure; conjunctivitis; contact dermatitis; cor pulmonale; coronary artery disease; Creutzfeldt-Jakob disease; culture negative sepsis; cystic fibrosis; cytokine therapy associated disorders; dementia pugilistica; demyelinating diseases; dengue hemorrhagic fever; dermatitis; dermatologic conditions; diabetes mellitus; diabetic arteriosclerotic disease; diffuse Lewy body disease; dilated congestive cardiomyopathy; disorders of the basal ganglia; Down's syndrome in middle age; drug-induced movement disorders induced by drugs which block CNS dopamine receptors; drug sensitivity; eczema; encephalomyelitis; endocarditis; endocrinopathy; epiglottitis; Epstein-Barr virus infection; erythromelalgia; extrapyramidal and cerebellar disorders; familial hemophagocytic lymphohistiocytosis; fetal thymus implant rejection; Friedreich's ataxia; functional peripheral arterial disorders; fungal sepsis; gas gangrene; gastric ulcer; glomerular nephritis; graft rejection of any organ or tissue; gram negative sepsis; gram positive sepsis; granulomas due to intracellular organisms; hairy cell leukemia; Hallervorden-Spatz disease; Hashimoto's thyroiditis; hay fever; heart transplant rejection; hemochromatosis; hemodialysis; hemolytic uremic syndrome/thrombolytic thrombocytopenic purpura; hemorrhage; hepatitis A; His bundle arrhythmias; HIV infection/HIV neuropathy; Hodgkin's disease; hyperkinetic movement disorders; hypersensitivity reactions; hypersensitivity pneumonitis; hypertension; hypokinetic movement disorders; hypothalamic-pituitary-adrenal axis evaluation; idiopathic Addison's disease; idiopathic pulmonary fibrosis (IPF); antibody mediated cytotoxicity; asthenia; infantile spinal muscular atrophy; inflammation of the aorta; influenza a; ionizing radiation exposure; iridocyclitis/uveitis/optic neuritis; ischemia-reperfusion injury; ischemic stroke; juvenile rheumatoid arthritis; juvenile spinal muscular atrophy; Kaposi's sarcoma; kidney transplant rejection; legionella; leishmaniasis; leprosy; lesions of the corticospinal system; lipedema; liver transplant rejection; lymphedema; malaria; malignant lymphoma; malignant histiocytosis; malignant melanoma; meningitis; meningococcemia; metabolic syndrome migraine headache; idiopathic migraine headache; mitochondrial multisystem disorder; mixed connective tissue disease; monoclonal gammopathy; multiple myeloma; multiple systems degenerations (Menzel; Dejerine-Thomas; Shy-Drager; and Machado-Joseph); myasthenia gravis; *mycobacterium avium* intracellulare; *mycobacterium tuberculosis*; myelodysplastic syndrome; myocardial infarction; myocardial ischemic disorders; nasopharyngeal carcinoma; neonatal chronic lung disease; nephritis; nephrosis; neurodegenerative diseases; neurogenic I muscular atrophies; neutropenic fever; non-Hodgkin's lymphoma; occlusion of the abdominal aorta and its branches; occlusive arterial disorders; OKT3® therapy; orchitis/epididymitis; orchitis/vasectomy reversal procedures; organomegaly;

osteoporosis; pancreas transplant rejection; pancreatic carcinoma; paraneoplastic syndrome/hypercalcemia of malignancy; parathyroid transplant rejection; pelvic inflammatory disease; perennial rhinitis; pericardial disease; peripheral atherosclerotic disease; peripheral vascular disorders; peritonitis; pernicious anemia; *pneumocystis carinii* pneumonia; pneumonia; POEMS syndrome (polyneuropathy, organomegaly, endocrinopathy, monoclonal gammopathy, and skin changes syndrome); post perfusion syndrome; post pump syndrome; post-MI cardiotomy syndrome; preeclampsia; progressive supra nucleo palsy; primary pulmonary hypertension; radiation therapy; Raynaud's phenomenon; Raynaud's disease; Refsum's disease; regular narrow QRS tachycardia; renovascular hypertension; reperfusion injury; restrictive cardiomyopathy; sarcomas; senile chorea; senile dementia of Lewy body type; seronegative arthropathies; shock; sickle cell anemia; skin allograft rejection; skin changes syndrome; small bowel transplant rejection; solid tumors; specific arrhythmias; spinal ataxia; spinocerebellar degenerations; streptococcal myositis; structural lesions of the cerebellum; subacute sclerosing panencephalitis; syncope; syphilis of the cardiovascular system; systemic anaphylaxis; systemic inflammatory response syndrome; systemic onset juvenile rheumatoid arthritis; telangiectasia; thromboangitis obliterans; thrombocytopenia; toxicity; transplants; trauma/hemorrhage; type III hypersensitivity reactions; type IV hypersensitivity; unstable angina; uremia; urosepsis; urticaria; valvular heart diseases; varicose veins; vasculitis; venous diseases; venous thrombosis; ventricular fibrillation; viral and fungal infections; viral encephalitis/aseptic meningitis; viral-associated hemophagocytic syndrome; Wernicke-Korsakoff syndrome; Wilson's disease; xenograft rejection of any organ or tissue; acute coronary syndromes; acute idiopathic polyneuritis; acute inflammatory demyelinating polyradiculoneuropathy; acute ischemia; adult Still's disease; alopecia greata; anaphylaxis; antiphospholipid antibody syndrome; aplastic anemia; arteriosclerosis; atopic eczema; atopic dermatitis; autoimmune dermatitis; autoimmune disorder associated with *Streptococcus* infection; autoimmune enteropathy; autoimmune hearing loss; autoimmune lymphoproliferative syndrome (ALPS); autoimmune myocarditis; autoimmune premature ovarian failure; blepharitis; bronchiectasis; bullous pemphigoid; cardiovascular disease; catastrophic antiphospholipid syndrome; celiac disease; cervical spondylosis; chronic ischemia; cicatricial pemphigoid; clinically isolated syndrome (CIS) with risk for multiple sclerosis; conjunctivitis; childhood onset psychiatric disorder; dacryocystitis; dermatomyositis; diabetic retinopathy; disk herniation; disk prolapse; drug induced immune hemolytic anemia; endocarditis; endometriosis; endophthalmitis; episcleritis; erythema multiforme; erythema multiforme major; gestational pemphigoid; Guillain-Barre syndrome (GBS); hay fever; Hughes syndrome; idiopathic Parkinson's disease; idiopathic interstitial pneumonia; IgE-mediated allergy; immune hemolytic anemia; inclusion body myositis; infectious ocular inflammatory disease; inflammatory demyelinating disease; inflammatory heart disease; inflammatory kidney disease; iritis; keratitis; keratojunctivitis sicca; Kussmaul disease or Kussmaul-Meier disease; Landry's paralysis; Langerhan's cell histiocytosis; livedo reticularis; macular degeneration; microscopic polyangiitis; Morbus Bechterev; motor neuron disorders; mucous membrane pemphigoid; multiple organ failure; myasthenia gravis; myelodysplastic syndrome; myocarditis; nerve root disorders; neuropathy; non-A non-B hepatitis; optic neuritis; osteolysis; pauciarticular JRA; peripheral artery occlusive disease (PAOD); peripheral vascular disease (PVD); peripheral artery; disease (PAD); phlebitis; polyarteritis nodosa (or periarteritis nodosa); polychondritis; polymyalgia rheumatica; poliosis; polyarticular JRA; polyendocrine deficiency syndrome; polymyositis; polymyalgia rheumatica (PMR); post-pump syndrome; primary Parkinsonism; secondary Parkinsonism; prostatitis; pure red cell aplasia; primary adrenal insufficiency; recurrent neuromyelitis optica; restenosis; rheumatic heart disease; SAPHO (synovitis, acne, pustulosis, hyperostosis, and osteitis); secondary amyloidosis; shock lung; scleritis; sciatica; secondary adrenal insufficiency; silicone associated connective tissue disease; Sneddon-Wilkinson dermatosis; spondylitis ankylosans; Stevens-Johnson syndrome (SJS); systemic inflammatory response syndrome; temporal arteritis; toxoplasmic retinitis; toxic epidermal necrolysis; transverse myelitis; TRAPS (tumor necrosis factor receptor type 1 (TNFR)-associated periodic syndrome); type B insulin resistance with acanthosis nigricans; type 1 allergic reaction; type II diabetes; urticaria; usual interstitial pneumonia (UIP); vernal conjunctivitis; viral retinitis; Vogt-Koyanagi-Harada syndrome (VKH syndrome); wet macular degeneration; wound healing; and *Yersinia* and *Salmonella* associated arthropathy.

The binding proteins of the disclosure can be used to treat humans suffering from autoimmune diseases, in particular those associated with inflammation, rheumatoid arthritis (RA), osteoarthritis, psoriasis, multiple sclerosis (MS), and other autoimmune diseases.

Allergic asthma is characterized by the presence of eosinophilia, goblet cell metaplasia, epithelial cell alterations, airway hyperreactivity (AHR), and Th2 and Th1 cytokine expression, as well as elevated serum IgE levels. It is now widely accepted that airway inflammation is the key factor underlying the pathogenesis of asthma, involving a complex interplay of inflammatory cells such as T cells, B cells, eosinophils, mast cells and macrophages, and of their secreted mediators including cytokines and chemokines. Corticosteroids are the most important anti-inflammatory treatment for asthma today, however their mechanism of action is non-specific and safety concerns exist, especially in the juvenile patient population. The development of more specific and targeted therapies is therefore warranted.

Animal models such as OVA-induced asthma mouse model, where both inflammation and AHR can be assessed, are known in the art and may be used to determine the ability of various DVD-Ig molecules to treat asthma. Animal models for studying asthma are disclosed in Coffman et al., J. Exp. Med., 201(12): 1875-1879 (2005); Lloyd et al., Adv. Immunol., 77: 263-295 (2001); Boyce et al., J. Exp. Med., 201(12): 1869-1873 (2005); and Snibson et al., Clin. Exp. Allergy, 35(2): 146-152 (2005). In addition to routine safety assessments of these target pairs specific tests for the degree of immunosuppression may be warranted and helpful in selecting the best target pairs (see Luster et al., Toxicology, 92(1-3): 229-243 (1994); Descotes, J., Develop. Biol. Standard., 77: 99-102 (1992); Hart et al., J. Allergy Clin. Immunol., 108(2): 250-257 (2001)).

One aspect of the disclosure includes a dual-specific anti-IL-1β/IL-1α DVD-Ig as a therapeutic agent beneficial for the treatment of asthma.

Osteoarthritis

The articular cartilage, or "hyaline cartilage", of healthy vertebrates (including humans and other mammals) is a semi-transparent, opalescent connective tissue characterized by a columnar growth pattern of chondrocytes in an extracellular matrix (ECM) composed predominantly of proteoglycans, type II collagen, and water. Articular cartilage provides an effective weight-bearing cushion to prevent contact between opposing bones in a joint and thus is critical to the normal function of the joint. Articular cartilage is not only susceptible to damage by joint trauma, but also to a gradual process of erosion. Initially, such an erosion may be simply an asymptomatic "partial thickness defect" in which an area of reduced hyaline cartilage does not penetrate completely to the subchondral bone. Such partial thickness defects are usually not painful and typically are only detected during arthroscopic examination. However, if the erosive process is not treated, the base of a partial thickness defect may continue to wear away and the diameter of the defect may increase such that the defect eventually progresses to a "full thickness defect" that penetrates the underlying bone. Such full thickness defects may become sufficiently large that surfaces of opposing bones of the joint make contact and begin to erode one another, leading to inflammation, pain, and other degenerative changes, i.e., the classic symptoms of osteoarthritis (OA). Osteoarthritis is thus a degenerative, progressive, and crippling disease that results in joint deformity, instability, impairment, and pain. Eventually, joint replacement surgery may be the only practical recourse for restoring, at least in part, some level of mobility to an individual.

One aspect of the disclosure includes a dual-specific anti-IL-1β/IL-1α DVD-Ig as a therapeutic agent beneficial for the treatment of asthma.

Pain

The invention also provides a method of treating pain in an individual (human or other mammal) comprising the step of administering to the individual a protein that binds IL-1α and another protein that binds IL-1β. In an embodiment, the binding proteins are administered in combination, for example, in a mixture, by successive administration, or by concurrent administration. Binding proteins useful in a method of treating pain according to the invention include, but are not limited to, antibodies that bind IL-1α and antibodies that bind IL-1β.

In another aspect of the invention, a method of treating pain in an individual comprises the step of administering to the individual a dual variable domain immunoglobulin binding protein (also referred herein as "DVD-Ig™" or "DVD-Ig" binding protein or molecule) that comprises at least one antigen binding site that binds IL-1α and at least one antigen binding site that binds IL-1β.

In an embodiment, the invention provides a method of treating pain in an individual suffering from a disease or disorder associated with IL-1 accumulation. Such IL-1 accumulation in the individual can be the result of reduced IL-1 expression or reduced metabolism of IL-1. Accumulation of IL-1 may be in plasma or local tissue of the individual.

In an embodiment, the invention provides a method for treating an individual for pain wherein the individual is suffering from a disease or disorder associated with IL-1 accumulation.

In an embodiment, the compositions and methods described herein can be used to treat pain in an individual suffering from a disease or disorder selected from the group comprising osteoarthritis, rheumatoid arthritis, juvenile chronic arthritis, septic arthritis, Lyme arthritis, psoriatic arthritis, reactive arthritis, spondyloarthropathy, systemic lupus erythemato sus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, *yersinia* and *salmonella* associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjorgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, cholestasis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitryp sin deficiency, amyotrophic lateral sclerosis, anemia, angina pectoris, anterior horn cell degeneration, anti cd3 therapy, antiphospholipid syndrome, anti-receptor hypersensitivity reactions, aortic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chronic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic ateriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallerrorden-Spatz disease, hashimoto's thyroiditis, hay fever, heart transplant rejection, hemachromatosis, hemodialysis, hemolytic uremic syndrome/thrombolytic thrombocytopenic purpura, hemorrhage, hepatitis (A), His bundle arrythmias, HIV infection/HIV neuropathy, Hodgkin's disease, hyperkinetic movement disorders, hypersensitity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, legionella, leishmaniasis, leprosy, lesions of the corticospinal system, lipedema, liver transplant rejection, lymphederma, malaria, malignamt Lymphoma, malignant histiocytosis, malignant melanoma, meningitis, meningococcemia, metabolic/idiopathic diseases, migraine headache, mitochondrial multi.system disorder, mixed connective tissue disease, monoclonal gammopathy, multiple myeloma, multiple systems degenerations (Mencel Dejerine-Thomas Shi-Drager and Machado-Joseph), myasthenia gravis, *mycobacterium avium* intracellulare, *mycobacterium tuberculosis*, myelodyplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-hodgkins lymphoma, occlusion of the abdominal aorta and its branches, occlusive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranucleo Palsy, primary pulmonary hypertension, radiation therapy, Raynaud's phenomenon and disease, Raynoud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, acute coronary syndromes, acute idiopathic polyneuritis, acute inflammatory demyelinating polyradiculoneuropathy, acute ischemia, adult Still's disease, alopecia greata, anaphylaxis, anti-phospholipid antibody syndrome, aplastic anemia, arteriosclerosis, atopic eczema, atopic dermatitis, autoimmune dermatitis, autoimmune disorder associated with *streptococcus* infection, autoimmune enteropathy, autoimmune hearing loss, autoimmune lymphoproliferative syndrome (ALPS), autoimmune myocarditis, autoimmune premature ovarian failure, blepharitis, bronchiectasis, bullous pemphigoid, cardiovascular disease, catastrophic antiphospholipid syndrome, celiac disease, cervical spondylosis, chronic ischemia, cicatricial pemphigoid, clinically isolated syndrome (CIS) with risk for multiple sclerosis, conjunctivitis, childhood onset psychiatric disorder, chronic obstructive pulmonary disease (COPD), dacryocystitis, dermatomyositis, diabetic retinopathy, diabetes mellitus, disk herniation, disk prolaps, drug induced immune hemolytic anemia, endocarditis, endometriosis, endophthalmitis, episcleritis, erythema multiforme, erythema multiforme major, gestational pemphigoid, Guillain-Barré syndrome (GBS), hay fever, Hughes syndrome, idiopathic Parkinson's disease, idiopathic interstitial pneumonia, IgE-mediated allergy, immune hemolytic anemia, inclusion body myositis, infectious ocular inflammatory disease, inflammatory demyelinating disease, inflammatory heart disease, inflammatory kidney disease, IPF/UIP, iritis, keratitis, keratojuntivitis sicca, Kussmaul disease or Kussmaul-Meier disease, Landry's paralysis, Langerhan's cell histiocytosis, livedo reticularis, macular degeneration, microscopic polyangiitis, morbus bechterev, motor neuron disorders, mucous membrane pemphigoid, multiple organ failure, myasthenia gravis, myelodysplastic syndrome, myocarditis, nerve root disorders, neuropathy, non-A non-B hepatitis, optic neuritis, osteolysis, ovarian cancer, pauciarticular JRA, peripheral artery occlusive disease (PAOD), peripheral vascular disease (PVD), peripheral artery, disease (PAD), phlebitis, polyarteritis nodosa (or periarteritis nodosa), polychondritis, polymyalgia rheumatica, polio sis, polyarticular JRA, polyendocrine deficiency syndrome, polymyositis, polymyalgia rheumatica (PMR), post-pump syndrome, primary Parkinsonism, prostate and rectal cancer and hematopoietic malignancies (leukemia and lymphoma), prostatitis, pure red cell aplasia, primary adrenal insufficiency, recurrent neuromyelitis optica, restenosis, rheumatic heart disease, sapho (synovitis, acne, pustulosis, hyperostosis, and osteitis), scleroderma, secondary amyloidosis, shock lung, scleritis, sciatica, secondary adrenal insufficiency, silicone associated connective tissue disease, sneddon-wilkinson dermatosis, spondilitis ankylosans, Stevens-Johnson syndrome (SJS), systemic inflammatory response syndrome, temporal arteritis, toxoplasmic retinitis, toxic epidermal necrolysis, transverse myelitis, TRAPS (tumor necrosis factor receptor, type 1 allergic reaction, type II diabetes, urticaria, usual interstitial pneumonia (UIP), vasculitis, vernal conjunctivitis, viral retinitis, Vogt-Koyanagi-Harada syndrome (VKH syndrome), wet macular degeneration (wet AMD), dry macular degeneration (dry AMD) and other inflammatory disorders of the eye (e.g., uveitis, retinitis, choroiditis, sclerosis, dry eye syndrome (DES) and the like), wound healing, *yersinia* and *salmonella* associated arthropathy.

In an embodiment, the compositions and methods described herein can be used to treat pain in an individual suffering from a disease selected from the group consisting of primary and metastatic cancers, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), solid tumors arising from hematopoietic malignancies such as leukemias, and lymphomas (both Hodgkin's and non-Hodgkin's lymphomas).

IV. Pharmaceutical Compositions

The disclosure also provides pharmaceutical compositions comprising binding proteins (including DVD-Igs described herein), of the disclosure and a pharmaceutically acceptable carrier. The pharmaceutical compositions comprising antibodies of the disclosure are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies of the disclosure. In another embodiment, the pharmaceutical composition comprises one or more antibodies of the disclosure and one or more prophylactic or therapeutic agents other than antibodies of the disclosure for treating a disorder in which IL-1α and or β activity is detrimental. In an embodiment, the prophylactic or therapeutic agents are known to be useful for or having been or currently being used in the prevention, treatment, management, or amelioration of a disorder or one or more symptoms thereof. In accordance with these embodiments, the composition may further comprise of a carrier, diluent or excipient.

The binding proteins of the disclosure can be incorporated into pharmaceutical compositions suitable for administration to a subject. Typically, the pharmaceutical composition comprises a binding protein of the disclosure and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the binding protein.

Various delivery systems are known and can be used to administer one or more antibodies of the disclosure or the combination of one or more antibodies of the disclosure and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the binding protein, receptor-mediated endocytosis (see, e.g., Wu and Wu, J. Biol. Chem., 262: 4429-4432 (1987)), construction of a nucleic acid as part of a retroviral or other vector. Methods of administering a prophylactic or therapeutic agent of the disclosure include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913 and 5,290,540; and PCT Publication Nos. WO 92/19244, WO 97/32572, WO 97/44013, WO 98/31346, and WO 99/66903, each of which is incorporated herein by reference their entireties. In one embodiment, a binding protein of the disclosure, combination therapy, or a composition of the disclosure is administered using Alkermes AIR® pulmonary drug delivery technology (Alkermes, Inc., Cambridge, Mass.). In a specific embodiment, prophylactic or therapeutic agents of the disclosure are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal, and intestinal mucosa, etc.) and may be administered together with other biologically active agents. Administration can be systemic or local.

In an embodiment, specific binding of antibody-coupled carbon nanotubes (CNTs) to tumor cells in vitro, followed by their highly specific ablation with near-infrared (NIR) light can be used to target tumor cells. For example, biotinylated polar lipids can be used to prepare stable, biocompatible, noncytotoxic CNT dispersions that are then attached to one or two different neutralite avidin-derivatized DVD-Igs directed against one or more tumor antigens (e.g., CD22) (Chakravarty et al., Proc. Natl. Acad. Sci. USA, 105: 8697-8702 (2008)).

In a specific embodiment, it may be desirable to administer the prophylactic or therapeutic agents of the disclosure locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies of the disclosure antagonists is administered locally to the affected area to a subject to prevent, treat, manage, and/or ameliorate a disorder or a symptom thereof. In another embodiment, an effective amount of one or more antibodies of the disclosure is administered locally to the affected area in combination with an effective amount of one or more therapies (e.g., one or more prophylactic or therapeutic agents) other than a binding protein of the disclosure of a subject to prevent, treat, manage, and/or ameliorate a disorder or one or more symptoms thereof.

In another embodiment, the prophylactic or therapeutic agent can be delivered in a controlled release or sustained release system. In one embodiment, a pump may be used to achieve controlled or sustained release (see Langer, supra; Sefton, M. V., CRC Crit. Rev. Biomed. Eng., 14: 201-240 (1987); Buchwald et al., Surgery, 88: 507-516 (1980); Saudek et al., N. Engl. J. Med., 321: 574-579 (1989)). In another embodiment, polymeric materials can be used to achieve controlled or sustained release of the therapies of the disclosure (see, e.g., Goodson, J. M., Chapter 6, In Medical Applications of Controlled Release, Vol. II, Applications and Evaluation, (Langer and Wise, eds.) (CRC Press, Inc., Boca Raton, 1984) pp. 115-138; Langer and Peppas, J. Macromol. Sci. Rev. Macromol. Chem. Phys., C23(1): 61-126 (1983); see also Levy et al., Science, 228:190-192 (1985); During et al., Ann. Neurol., 25:351-356 (1989); Howard et al., J. Neurosurg., 71:105-112 (1989)); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In an exemplary embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (Science, 249:1527-1533 (1990)). Any technique known to one of skill in the art can be used to produce sustained release formulations comprising one or more therapeutic agents of the disclosure. See, e.g., U.S. Pat. No. 4,526,938, PCT Publication No. WO 91/05548, PCT Publication No. WO 96/20698; Ning et al., "Intratumoral radioimmunotherapy of a human colon cancer xenograft using a sustained-release gel," Radiotherapy Oncol., 39: 179-189 (1996); Song et al., "Antibody Mediated Lung Targeting of Long-Circulating Emulsions," PDA J. Pharm. Sci. Technol., 50: 372-377 (1996); Cleek et al., "Biodegradable Polymeric Carriers for a bFGF Antibody for Cardiovascular Application," Proceed. Int'l. Symp. Control. Rel. Bioact. Mater., 24: 853-854 (1997); and Lam et al., "Microencapsulation of Recombinant Humanized Monoclonal Antibody for Local Delivery," Proceed. Int'l. Symp. Control Rel. Bioact. Mater., 24: 759-760 (1997), each of which is incorporated herein by reference in their entireties.

In a specific embodiment, where the composition of the disclosure is a nucleic acid encoding a prophylactic or therapeutic agent, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic®, DuPont), or coating with lipids or cell-surface receptors or transfecting agents, or by administering it in linkage to a homeobox-like peptide which is known to enter the nucleus (see, e.g., Joliot et al., Proc. Natl. Acad. Sci. USA, 88: 1864-1868 (1991)). Alternatively, a nucleic acid can be introduced intracellularly and incorporated within host cell DNA for expression by homologous recombination.

A pharmaceutical composition of the disclosure is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic, such as lignocaine, to ease pain at the site of the injection.

If the compositions of the disclosure are to be administered topically, the compositions can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semisolid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as FREON®) or in a squeeze bottle. Moisturizers or humectants can also be added to pharmaceutical compositions and dosage forms if desired. Examples of such additional ingredients are well known in the art.

If the method of the disclosure comprises intranasal administration of a composition, the composition can be formulated in an aerosol form, spray, mist or in the form of drops. In particular, prophylactic or therapeutic agents for use according to the present disclosure can be conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the disclosure comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulfate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the disclosure may comprise pulmonary administration, e.g., by use of an inhaler or nebulizer, of a composition formulated with an aerosolizing agent. See, e.g., U.S. Pat. Nos. 6,019,968; 5,985,320; 5,985,309; 5,934, 272; 5,874,064; 5,855,913; and 5,290,540; and PCT Publication Nos. WO 92/19244, WO 97/32572, WO 97/44013, WO 98/31346, and WO 99/66903, each of which is incorporated herein by reference their entireties. In a specific embodiment, a binding protein of the disclosure, combination therapy, and/or composition of the disclosure is administered using Alkermes AIR® pulmonary drug delivery technology (Alkermes, Inc., Cambridge, Mass.).

The method of the disclosure may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

The methods of the disclosure may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the disclosure encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachet indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the disclosure also provides that one or more of the prophylactic or therapeutic agents, or pharmaceutical compositions of the disclosure is packaged in a hermetically sealed container such as an ampoule or sachette indicating the quantity of the agent. In one embodiment, one or more of the prophylactic or therapeutic agents, or pharmaceutical compositions of the disclosure is supplied as a dry sterilized lyophilized powder or water free concentrate in a hermetically sealed container and can be reconstituted (e.g., with water or saline) to the appropriate concentration for administration to a subject. Preferably, one or more of the prophylactic or therapeutic agents or pharmaceutical compositions of the disclosure is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, at least 100 mg or at least 200 mg/mL. The lyophilized prophylactic or therapeutic agents or pharmaceutical compositions of the disclosure should be stored at between 2° C. and 8° C. in its original container and the prophylactic or therapeutic agents, or pharmaceutical compositions of the disclosure should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the disclosure is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml, at least 100 mg/ml or at least 200 mg/mL. The liquid form should be stored at between 2° C. and 8° C. in its original container.

The binding protein of the disclosure can be incorporated into a pharmaceutical composition suitable for parenteral administration. Preferably, the binding protein will be prepared as an injectable solution containing 0.1-250 mg/ml binding protein. The injectable solution can be composed of either a liquid or lyophilized dosage form in a flint or amber vial, ampoule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising a binding protein of the disclosure prepared as an injectable solution for parenteral administration, can further comprise an agent useful as an adjuvant, such as those used to increase the absorption, or dispersion of a therapeutic protein (e.g., DVD-Ig). A particularly useful adjuvant is hyaluronidase (such as Hylenex® recombinant human hyaluronidase). Addition of hyaluronidase in the injectable solution improves human bioavailability following parenteral administration, particularly subcutaneous administration. It also allows for greater injection site volumes (i.e., greater than 1 ml) with less pain and discomfort, and minimum incidence of injection site reactions (see, PCT Publication No. WO 2004/078140 and US Publication No. 2006/104968).

The compositions provided in this disclosure may be in a variety of forms. These include, for example, liquid, semisolid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In an exemplary embodiment, the binding protein is administered by intravenous infusion or injection. In another preferred embodiment, the binding protein is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., binding protein) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The binding proteins of the present disclosure can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, (J. R. Robinson, ed.) (Marcel Dekker, Inc., New York, 1978).

In certain embodiments, a binding protein of the disclosure may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the disclosure by other than parenteral administration, it may be necessary to coat the compound with, or co-administer the compound with, a material to prevent its inactivation.

Supplementary active compounds can also be incorporated into the compositions. In certain embodiments, a binding protein of the disclosure is coformulated with and/or coadministered with one or more additional therapeutic agents that are useful for treating disorders in which IL-1α and/or β activity is detrimental. For example, an anti-human IL-1α or β binding protein of the disclosure may be coformulated and/or coadministered with one or more additional antibodies that bind other targets (e.g., antibodies that bind other cytokines or that bind cell surface molecules). Furthermore, one or more antibodies of the disclosure may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, a binding protein to IL-1α or β or fragment thereof is linked to a half-life extending vehicle known in the art. Such vehicles include, but are not limited to, the Fc domain, polyethylene glycol, and dextran. Such vehicles are described, e.g., in U.S. Ser. No. 09/428,082 (now U.S. Pat. No. 6,660,843) which is hereby incorporated by reference for any purpose.

In a specific embodiment, nucleic acid sequences comprising nucleotide sequences encoding a binding protein of the disclosure or another prophylactic or therapeutic agent of the disclosure are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the disclosure, the nucleic acids produce their encoded binding protein or prophylactic or therapeutic agent of the disclosure that mediates a prophylactic or therapeutic effect.

Any of the methods for gene therapy available in the art can be used according to the present disclosure. For general reviews of the methods of gene therapy, see Goldspiel et al., Clinical Pharm., 12: 488-505 (1993); Wu et al., "Delivery systems for gene therapy," Biotherapy, 3: 87-95 (1991); Tolstoshev, P., Ann. Rev. Pharmacol. Toxicol., 32: 573-596 (1993); Mulligan, R. C., Science, 260: 926-932 (1993); and Morgan and Anderson, "Human Gene Therapy," Ann. Rev. Biochem., 62:191-217 (1993); Robinson, C., Trends Biotechnol., 11:155 (1993). Methods commonly known in the art of recombinant DNA technology which can be used are described in Ausubel et al. (eds.), Current Protocols in Molecular Biology, John Wiley & Sons, New York (1993); and Kriegler, Gene Transfer and Expression, A Laboratory Manual, Stockton Press, New York (1990). Detailed description of various methods of gene therapy are disclosed in US Publication No. 2005/0042664 A1, which is incorporated herein by reference.

A binding protein of the disclosure also can be administered with one or more additional therapeutic agents useful in the treatment of various diseases. Binding proteins of the disclosure, can be used alone or in combination to treat such diseases. It should be understood that the binding proteins of the disclosure can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the binding protein of the present disclosure. The additional agent also can be an agent that imparts a beneficial attribute to the therapeutic composition, e.g., an agent that affects the viscosity of the composition.

It should further be understood that the combinations which are to be included within this disclosure are those combinations useful for their intended purpose. The agents set forth below are illustrative for purposes and not intended to be limited. The combinations, which are part of this disclosure, can be the antibodies of the present disclosure and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the anti-IL-1α and β binding proteins of this disclosure. Non-limiting examples of therapeutic agents for rheumatoid arthritis with which a binding protein can be combined include, but are not limited to, the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-15, IL-16, IL-18, IL-21, interferons, EMAP-II, GM-CSF, FGF, and PDGF. Antibodies of the disclosure, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7, (PCT Publication No. WO 97/29131), CA2 (REMICADE®), CDP 571, and soluble p55 or p75 TNF receptors, derivatives, thereof, (p75TNFR1gG (ENBREL®) or p55TNFR1gG (LENERCEPT®), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet another preferred combination are other key players of the autoimmune response which may act parallel to, dependent on or in concert with IL-1α or β function. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

The binding proteins of the disclosure may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, colchicine, cortico steroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as TNF-α or IL-1 (e.g., IRAK, NIK, IKK, p38, or MAP kinase inhibitors), IL-1β converting enzyme inhibitors, TNFα converting enzyme (TACE) inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors and the derivatives p75TNFRIgG (ENBREL® and p55TNFRIgG (LENERCEPT®)), sIL-1RI, sIL-1RII, sIL-6R), anti-inflammatory cytokines (e.g., IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, human recombinant, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl, misoprostol, naproxen sodium, omeprazole, cyclophosphamide, rituximab, IL-1 TRAP, MRA, CTLA4-IG, IL-18 BP, anti-IL-18, anti-IL15, BIRB-796, SCIO-469, VX-702, AMG-548, VX-740, Roflumilast, IC-485, CDC-801, and Mesopram. Preferred combinations include methotrexate or leflunomide and in moderate or severe rheumatoid arthritis cases, cyclosporine.

Non-limiting additional agents which can also be used in combination with a binding protein to treat rheumatoid arthritis (RA) include, but are not limited to, the following: non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex; see e.g., Moreland et al. (Abstract No. 813), Arthritis Rheum., 37: 5295 (1994); Baumgartner et al., J. Invest. Med., 44(3): 235A (March 1996); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline; see e.g., Kaine et al. (Abstract No. 195), Arthritis Rheum., 38: 5185 (1995)); DAB 486-IL-2 and/or DAB 389-IL-2 (IL-2 fusion proteins; Seragen; see e.g., Sewell et al., Arthritis Rheum., 36(9): 1223-1233 (September 1993)); Anti-Tac (humanized anti-IL-2Rα; Protein Design Labs/ Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein; see e.g., Evans et al. (Abstract No. 1540), Arthritis Rheum., 39(9) (supplement): 5284 (1996)); Kapadia et al., Amer. J. Physiol.—Heart and Circulatory Physiology, 268: H517-H525 (1995)); RP73401 (phosphodiesterase Type IV inhibitor; see e.g., Chikanza et al. (Abstract No. 1527), Arthritis Rheum., 39(9)(supplement): 5282 (1996)); MK-966 (COX-2 Inhibitor; see e.g., Erich et al. (Abstract Nos. 328 and 329), Arthritis Rheum., 39(9)(supplement): S81 (1996)); Iloprost (see e.g., Scholz, P. (Abstract No. 336), Arthritis Rheum., 39(9)(supplement): S82 (1996)); methotrexate; thalidomide (see e.g., Lee et al. (Abstract No. 1524), Arthritis Rheum., 39(9)(supplement): 5282 (1996)) and thalidomide-related drugs (e.g., Celgen); leflunomide (anti-inflammatory and cytokine inhibitor; see e.g., Finnegan et al. (Abstract No. 627), Arthritis Rheum., 39(9)(supplement): S131 (1996)); Thoss et al., Inflamm. Res., 45: 103-107 (1996)); tranexamic acid (inhibitor of plasminogen activation; see e.g., Ronday et al. (Abstract No. 1541), Arthritis Rheum., 39(9)(supplement): 5284 (1996)); T-614 (cytokine inhibitor; see e.g., Hara et al. (Abstract No. 1526), Arthritis Rheum., 39(9) (supplement): 5282 (1996)); prostaglandin E1 (see e.g., Moriuchi et al. (Abstract No. 1528), Arthritis Rheum., 39(9)(supplement): 5282 (1996)); Tenidap (non-steroidal anti-inflammatory drug; see e.g., Guttadauria, M. (Abstract No. 1516), Arthritis Rheum., 39(9)(supplement): 5280 (1996)); Naproxen (non-steroidal anti-inflammatory drug; see e.g., Fiebich et al., Neuro Report, 7: 1209-1213 (1996)); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine (see e.g., Farr et al. (Abstract No. 1519), Arthritis Rheum., 39(9)(supplement): S281 (1996)); Azathioprine (see e.g., Hickey et al. (Abstract No. 1521), Arthritis Rheum., 39(9)(supplement): S281 (1996)); ICE inhibitor (inhibitor of the enzyme interleukin-1β converting enzyme); zap-70 and/or lck inhibitor (inhibitor of the tyrosine kinase zap-70 or lck); VEGF inhibitor and/or VEGF-R inhibitor (inhibitors of vascular endothelial cell growth factor or vascular endothelial cell growth factor receptor; inhibitors of angiogenesis); cortico steroid anti-inflammatory drugs (e.g., SB203580); TNF-convertase inhibitors; anti-IL-12 antibodies; anti-IL-18 antibodies; interleukin-11 (see e.g., Keith Jr. et al. (Abstract No. 1613), Arthritis Rheum., 39(9)(supplement): S296 (1996)); interleukin-13 (see e.g., Bessis et al. (Abstract No. 1681), Arthritis Rheum., 39(9)(supplement): 5308 (1996)); interleukin-17 inhibitors (see e.g., Lotz et al. (Abstract No. 559), Arthritis Rheum., 39(9)(supplement): 5120 (1996)); gold; penicillamine; chloroquine; chlorambucil; hydroxychloroquine; cyclosporine; cyclophosphamide; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 anti-sense phosphorothioate oligo-deoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; see e.g., DeLuca et al., Rheum. Dis. Clin. North Am., 21: 759-777 (1995)); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine); methotrexate; bcl-2 inhibitors (see Bruncko et al., J. Med. Chem., 50(4), 641-662 (2007)); antivirals and immune modulating agents.

In one embodiment, the binding protein described herein is administered in combination with one of the following agents for the treatment of rheumatoid arthritis (RA): small molecule inhibitor of KDR, small molecule inhibitor of Tie-2; methotrexate; prednisone; celecoxib; folic acid; hydroxychloroquine sulfate; rofecoxib; etanercept; infliximab; leflunomide; naproxen; valdecoxib; sulfasalazine; methylprednisolone; ibuprofen; meloxicam; methylprednisolone acetate; gold sodium thiomalate; aspirin; azathioprine; triamcinolone acetonide; propoxyphene napsylate/ apap; folate; nabumetone; diclofenac; piroxicam; etodolac; diclofenac sodium; oxaprozin; oxycodone HCl; hydrocodone bitartrate/apap; diclofenac sodium/misoprostol; fentanyl; anakinra, human recombinant; tramadol HCl; salsalate; sulindac; cyanocobalamin/fa/pyridoxine; acetaminophen; alendronate sodium; prednisolone; morphine sulfate; lidocaine hydrochloride; indomethacin; glucosamine sulfate/chondroitin; cyclosporine; amitriptyline HCl; sulfadiazine; oxycodone HCl/acetaminophen; olopatadine HCl; misoprostol; naproxen sodium; omeprazole; mycophenolate mofetil; cyclophosphamide; rituximab; IL-1 TRAP; MRA; CTLA4-IG; IL-18 BP; IL-12/23; anti-IL 18; anti-IL 15; BIRB-796; SCIO-469; VX-702; AMG-548; VX-740; Roflumilast; IC-485; CDC-801; and mesopram.

Non-limiting examples of therapeutic agents for inflammatory bowel disease with which a binding protein of the disclosure can be combined include the following: budenoside; epidermal growth factor; corticosteroids; cyclosporin, sulfasalazine; amino salicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β mAbs; anti-IL-6 mAbs; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-15, IL-16, IL-17, IL-18, EMAP-II, GM-CSF, FGF, and PDGF. Antibodies of the disclosure, or antigen binding portions thereof, can be combined with antibodies to cell surface molecules such as CD2, CD3, CD4, CD8, CD25, CD28, CD30, CD40, CD45, CD69, CD90 or their ligands. The binding proteins of the disclosure may also be combined with agents, such as methotrexate, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signaling by proinflammatory cytokines such as TNFα or IL-1 (e.g., IRAK, NIK, IKK, p38 or MAP kinase inhibitors), IL-1β converting enzyme inhibitors, TNFα converting enzyme inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors, sIL-1RI, sIL-1RII, sIL-6R) and anti-inflammatory cytokines (e.g., IL-4, IL-10, IL-11, IL-13 and TGFβ) and bcl-2 inhibitors.

Non-limiting examples of therapeutic agents for multiple sclerosis (MS) with which binding proteins of the disclosure can be combined include the following: corticosteroids; prednisolone; methylprednisolone; azathioprine; cyclophosphamide; cyclosporine; methotrexate; 4-aminopyridine; tizanidine; interferon-β1a (AVONEX; Biogen); interferon-β1b (BETASERON; Chiron/Berlex); interferon α-n3) (Interferon Sciences/Fujimoto), interferon-α1b (Alfa Wassermann/J&J), interferon β1A-IF (Serono/Inhale Therapeutics), Peginterferon α 2b (Enzon/Schering-Plough), Copolymer 1 (Cop-1; COPAXONE; Teva Pharmaceutical Industries, Inc.); hyperbaric oxygen; intravenous immunoglobulin; clabribine; antibodies to or antagonists of other human cytokines or growth factors and their receptors, for example, TNF, LT, IL-1, IL-2, IL-6, IL-7, IL-8, IL-23, IL-15, IL-16, IL-18, EMAP-II, GM-CSF, FGF, and PDGF. Binding proteins of the disclosure can be combined with antibodies to cell surface molecules such as CD2, CD3, CD4, CD8, CD19, CD20, CD25, CD28, CD30, CD40, CD45, CD69, CD80, CD86, CD90 or their ligands. Binding proteins of the disclosure, may also be combined with agents, such as methotrexate, cyclosporine, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as TNFα or IL-1 (e.g., IRAK, NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors, sIL-1RI, sIL-1RII, sIL-6R), anti-inflammatory cytokines (e.g., IL-4, IL-1β, IL-13 and TGFβ) and bcl-2 inhibitors.

Examples of therapeutic agents for multiple sclerosis with which binding proteins of the disclosure can be combined include interferon-β, for example, IFNβ1a and IFNβ1b; copaxone; corticosteroids; caspase inhibitors, for example inhibitors of caspase-1; IL-1 inhibitors; TNF inhibitors; and antibodies to CD40 ligand and CD80.

The binding proteins of the disclosure, may also be combined with agents, such as alemtuzumab, dronabinol, Unimed, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist) MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists, IL-4 agonists.

Non-limiting examples of therapeutic agents for angina with which binding proteins of the disclosure can be combined include the following: aspirin, nitroglycerin, isosorbide mononitrate, metoprolol succinate, atenolol, metoprolol tartrate, amlodipine besylate, diltiazem hydrochloride, isosorbide dinitrate, clopidogrel bisulfate, nifedipine, atorvastatin calcium, potassium chloride, furosemide, simvastatin, verapamil HCl, digoxin, propranolol hydrochloride, carvedilol, lisinopril, spironolactone, hydrochlorothiazide, enalapril maleate, nadolol, ramipril, enoxaparin sodium, heparin sodium, valsartan, sotalol hydrochloride, fenofibrate, ezetimibe, bumetanide, losartan potassium, lisinopril/hydrochlorothiazide, felodipine, captopril, bisoprolol fumarate.

Non-limiting examples of therapeutic agents for ankylosing spondylitis with which binding proteins of the disclosure can be combined include the following: ibuprofen, diclofenac and misoprostol, naproxen, meloxicam, indomethacin, diclofenac, celecoxib, rofecoxib, sulfasalazine, methotrexate, azathioprine, minocyclin, prednisone, etanercept, infliximab.

Non-limiting examples of therapeutic agents for asthma with which binding proteins of the disclosure can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, methylprednisolone, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, metaproterenol sulfate.

Non-limiting examples of therapeutic agents for COPD with which binding proteins of the disclosure can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, Cilomilast, Roflumilast.

Non-limiting examples of therapeutic agents for HCV with which binding proteins of the disclosure can be combined include the following: Interferon-alpha-2a, Interferon-alpha-2b, Interferon-alpha con1, Interferon-alpha-n1, PEGylated interferon-alpha-2a, PEGylated interferon-alpha-2b, ribavirin, Peginterferon alfa-2b+ribavirin, Ursodeoxycholic Acid, Glycyrrhizic Acid, Thymalfasin, Maxamine, VX-497 and any compounds that are used to treat HCV through intervention with the following targets: HCV polymerase, HCV protease, HCV helicase, HCV IRES (internal ribosome entry site).

Non-limiting examples of therapeutic agents for idiopathic pulmonary fibrosis with which binding proteins of the disclosure can be combined include the following: prednisone, azathioprine, albuterol, colchicine, albuterol sulfate, digoxin, gamma interferon, methylprednisolone sod succ, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone hcl, potassium chloride, triamcinolone acetonide, tacrolimus anhydrous, calcium, interferon-alpha, methotrexate, mycophenolate mofetil, Interferon-gamma-1β.

Non-limiting examples of therapeutic agents for myocardial infarction with which binding proteins of the disclosure can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril HCl/mag carb, bumetanide, alteplase, enalaprilat, amiodarone hydrochloride, tirofiban HCl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, cariporide.

Non-limiting examples of therapeutic agents for psoriasis with which binding proteins of the disclosure can be combined include the following: small molecule inhibitor of KDR, small molecule inhibitor of Tie-2, calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine.

Non-limiting examples of therapeutic agents for psoriatic arthritis with which binding proteins of the disclosure can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, efalizumab and bcl-2 inhibitors.

Non-limiting examples of therapeutic agents for restenosis with which binding proteins of the disclosure can be combined include the following: sirolimus, paclitaxel, everolimus, tacrolimus, Zotarolimus, acetaminophen.

Non-limiting examples of therapeutic agents for sciatica with which binding proteins of the disclosure can be combined include the following: hydrocodone bitartrate/apap, rofecoxib, cyclobenzaprine HCl, methylprednisolone, naproxen, ibuprofen, oxycodone HCl/acetaminophen, celecoxib, valdecoxib, methylprednisolone acetate, prednisone, codeine phosphate/apap, tramadol HCl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone HCl, tizanidine HCl, diclofenac sodium/misoprostol, propoxyphene napsylate/apap, asa/oxycod/oxycodone ter, ibuprofen/hydrocodone bit, tramadol HCl, etodolac, propoxyphene HCl, amitriptyline HCl, carisoprodol/codeine phos/asa, morphine sulfate, multivitamins, naproxen sodium, orphenadrine citrate, temazepam.

Examples of therapeutic agents for SLE (lupus) with which binding proteins of the disclosure can be combined include the following: NSAIDS, for example, diclofenac, naproxen, ibuprofen, piroxicam, indomethacin; COX2 inhibitors, for example, Celecoxib, rofecoxib, valdecoxib; anti-malarials, for example, hydroxychloroquine; Steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept. Binding proteins of the disclosure, may also be combined with agents such as sulfasalazine, 5-amino salicylic acid, olsalazine, Imuran and agents which interfere with synthesis, production or action of proinflammatory cytokines such as IL-1, for example, caspase inhibitors like IL-1β converting enzyme inhibitors and IL-1ra. Binding proteins of the disclosure may also be used with T cell signaling inhibitors, for example, tyrosine kinase inhibitors; or molecules that target T cell activation molecules, for example, CTLA-4-IgG or anti-B7 family antibodies, anti-PD-1 family antibodies. Binding proteins of the disclosure, can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. Antibodies of the disclosure or antigen binding portion thereof may also be used with LJP 394 (abetimus), agents that deplete or inactivate B-cells, for example, RITUXIMAB™ (anti-CD20 antibody), lymphostat-B (anti-BlyS antibody), TNF antagonists, for example, anti-TNF antibodies, Adalimumab (PCT Publication No. WO 97/29131; HUMIRA®), CA2 (REMICADE®), CDP 571, TNFR-Ig constructs, (p75TNFRIgG (ENBREL®) and p55TNFRIgG (LENERCEPT®)) and bcl-2 inhibitors, because bcl-2 overexpression in transgenic mice has been demonstrated to cause a lupus like phenotype (see Marquina et al., J. Immunol., 172(11): 7177-7185 (2004)), therefore inhibition is expected to have therapeutic effects.

The pharmaceutical compositions of the disclosure may include a "therapeutically effective amount" or a "prophylactically effective amount" of a binding protein of the disclosure. A "therapeutically effective amount" refers to an amount effective, at dosages and for periods of time necessary, to achieve the desired therapeutic result. A therapeutically effective amount of the binding protein may be determined by a person skilled in the art and may vary according to factors such as the disease state, age, sex, and weight of the individual, and the ability of the binding protein to elicit a desired response in the individual. A therapeutically effective amount is also one in which any toxic or detrimental effects of the binding protein, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

V. Diagnostics

The disclosure herein also provides diagnostic applications. This is further elucidated below. Binding proteins that bind IL-1α and/or β of the disclosure may be employed in any of a variety of formats to detect IL-1α and/or β in vivo, in vitro, or ex vivo (i.e., in cells or tissues that have been obtained from a living individual, subjected to a procedure, then returned to the individual). DVD-Igs of the disclosure offer the further advantage of being capable of binding to an epitope of IL-1α or β as well as other antigens or epitopes in various diagnostic and detection assay formats. In particular, methods of using IL-1α and β binding proteins as diagnostics are described in U.S. Patent Publication No. 2011/0280800, incorporated by reference, herein, in its entirety.

VI. Kits

A kit for assaying a test sample for the presence, amount or concentration of an analyte (or a fragment thereof) in a test sample is also provided. The kit comprises at least one component for assaying the test sample for IL-1α or β (or fragments thereof) and instructions for assaying the test sample for the analyte (or a fragment thereof). The at least one component for assaying the test sample for the analyte (or a fragment thereof) can include a composition comprising an anti-IL-1α and/or β binding protein, such as a DVD-Ig (or a fragment, a variant, or a fragment of a variant thereof), as described herein and which is optionally immobilized on a solid phase. In particular, kits using IL-1α and β binding proteins and methods of using them are described in U.S. Patent Publication No. 2011/0280800, incorporated by reference, herein, in its entirety.

It will be readily apparent to those skilled in the art that other suitable modifications and adaptations of the methods of the disclosure described herein are obvious and may be made using suitable equivalents without departing from the scope of the disclosure or the embodiments disclosed herein.

Having now described the binding proteins and methods of making and using them of the disclosure in detail, the same will be more clearly understood by reference to the following examples, which are included for purposes of illustration only and are not intended to be limiting of the disclosure.

EXAMPLES

Materials and Methods

Materials
1B12.13-SS-X3, human anti-IL-1α/β DVD IgG1/k mut (234,235); PR-1358316
1B12.21-SS-X3, human anti-IL-1α/β DVD IgG1/k mut (234,235); PR-1358317

1B12.34-SS-X3, human anti-IL-1α/β DVD IgG1/k mut (234,235); PR-1358318
1B12.A1-SS-X3, human anti-IL-1α/β DVD IgG1/k mut (234,235); PR-1358319
1B12.A3-SS-X3, human anti-IL-1α/β DVD IgG1/k mut (234,235); PR-1358321
1B12.9, human anti-IL-1β IgG1/k mut (234,235); PR-1317335
Human IL-8 Tissue Culture Kit (K111AN), Meso Scale Discovery MA6000

Methods

MRC-5 Bioassay

MRC-5 cells were grown and cultured in cMEM containing 10% FBS in a 37° C., 5% $CO_2$ incubator. One day prior to assay, 100 µL of MRC-5 cells were plated well into a 96 well flat bottom plate (Costar#3599) at a density of $1 \times 10^4$ cells per well and incubated overnight at 37° C., 5% $CO_2$. On the day of the assay, Igs and IL-1α, and IL-1β antigens were prepared at a 4× stock concentration in cMEM. An eight point serial dilution of Igs was prepared at a 4× range of 25,000-0.096 pM in cMEM. Sixty-five µL of diluted Igs was transferred in quadruplicate to a 96 well v-bottom plate (Costar#3894) then 65 µL of a 4× stock of approximately 11 µM of recombinant human IL-1α or recombinant human IL-1β, cyno IL-1β or purified native IL-1β was added to wells containing Igs. For assays using native human IL-1α present in crude supernatants, supernatants were diluted in cMEM to contain approximately 11 pM of native human IL-1α. Antigen control wells received 65 µL of antigen and 65 µL of cMEM media. Cell alone control wells received 130 µL of cMEM media.

Following an hour pre-incubation, 100 µL of IL-1 and Ig complexes was added to the MRC-5 cells. Final well volumes equaled 200 µL and all reagents were at a 1× final concentration. After an overnight incubation (16-24 hour), 150 µL of supernatant was transferred to a 96-well round bottom plate (Costar#3799) and the plates were placed in a –20° C. freezer. The supernatants were tested for human IL-8 levels using a MSD chemiluminescent kit. The neutralization potency of each Ig was determined by calculating percent inhibition relative to the IL-1α or IL-1β control values (in the absence of Ig). $IC_{50}$ values were calculated using Graph Pad Prism analysis software.

Affinity measurements by Biacore

Goat IgGs specific to human IgG Fc were covalently linked to the carboxy methyl dextran matrix on the CM5 biosensor chip via free amine groups using an amine coupling kit and the immobilization wizard option in the Biacore instruments controlling software. Specifically, carboxyl groups of the dextran matrix on the chip were activated with NHS and EDC. Goat anti-human IgG Fc antibodies (25 µg/mL), diluted in 10 mM sodium acetate, pH 4.5, were injected across the activated surface. Once the level of binding response reached the desired value, unreacted groups were deactivated by injection of 1M ethanolamine. For binding of IL-1α & IL-1β to captured Ig, a 1 µg/mL concentration of Ig in HBS-EP+ was injected over the goat anti-human IgG Fc surface at a flow rate of 10 µL/min for 1 minute. The net difference in the baseline signal and the signal after the completion of the Ig injection was taken to represent the amount of bound Ig.

Preformulation Studies

Assays included high concentration drug-like property characterization, accelerated stability at 50 mg/ml (for degradation kinetics), freeze-thaw stability at 50 mg/ml, viscosity at 80 mg/ml, serum stability under crowded conditions, low concentration drug-like property characterization, accelerated stability at 1 mg/ml (for pH optimum determination), freeze-thaw stability at 1 mg/ml (for better resolution of freeze-thaw degradation), biophysical and structural characterization, differential scanning calorimetry (for conformational stability), and FTIR (for secondary structure analysis).

Example 1. Generation of Anti-Human IL-1β mAb 1B12.9

A new version of h1B12.1 (US 2011/0142761 A1) was generated to allow the characterization of a single amino acid substitution at the N-terminus of the light chain—this new version was called 1B12.9. Humanized monoclonal antibody 1B12.1 (also referred to as h1B12.1) is composed of the heavy chain variable domain 1B12 VH1a and the light chain variable domain VL1a, and was derived from mouse monoclonal 1B12.4H4. 1B12.9 contains the identical heavy chain as 1B12.1, but the light chain variable domain has a single amino acid change at amino acid position 4 in the variable light domain. The valine at position 4 was substituted to a methionine using site-directed mutagenesis, and the resulting light chain plasmid was named h1B12 VL1c.

The V4M mutation was introduced into plasmid pHybE-1B12 VL1a using mutagenic primers (Table 9) and the QUIKCHANGE® II Site-Directed Mutagenesis kit (Stratagene, cat #200524-5) following the manufacturer's instructions. The pHybE series of expression vectors are described in U.S. Pat. No. 8,187,836 and International PCT Publication No. WO 2009/091912, which are specifically incorporated by reference herein in their entirety. Clones containing the correct sequence were identified by colony sequencing. The DNA of a single clone containing the correct sequence was scaled-up using QIAGEN® Maxi kit. 1B12.9 was expressed as a human IgG1 mutant (234,235)/k by co-transfection of the heavy chain plasmid (pHybE-1B12 VL1a) and light chain plasmid (pHybeE-1B12 VL1c). Expression of mAb 1B12.9 was performed using small-scale (500 mL) 293 FreeStyle expression system. Light chain, 1B12VH1, and heavy chain, 1B12VL1C, DNA was PEI transfected at a 1:1.5 (heavy chain plasmid to light chain plasmid) ratio. Cell supernatants were purified by protein A chromatography.

TABLE 9

Primers used to construct h1B12 VL1c

| Primer Name | Nucleotide sequence | SEQ ID NO: |
|---|---|---|
| V4M-F | GCGATGCGACACTCAAATGACACAGTCCCCATC | 130 |
| V4M-R | GATGGGGACTGTGTCATTTGAGTGTCGCATCGC | 131 |

Example 2. Construction of 1B12.1-SS-X3 DVD-Ig

The variable heavy and light chain domains of h1B12.1 were PCR amplified from DNA templates pHybE-h1B12 VH1a and pHybE-h1B12 VL1a, respectively, using primers containing linker sequences. The variable heavy and light chain domains of $X_3$ were PCR amplified from DNA templates pHybE-X3 VH and pHybE-X3 (1R) VL, respectively, using primers containing linker sequences (Table 10). h1B12.1 VH and X3 VH with the intervening HC-short linker sequence were combined and sub-cloned into pHybE-hCg1mut (234,235) at the FspAI and SalI sites via homologous recombination in DH5α chemically competent cells. Likewise, h1B12.1VL and X3 VL with the intervening LC-short linker sequence were sub-cloned into pHybE-hCk at the FspAI and NotI sites. Clones containing the correct sequences were identified by colony sequencing. Expression plasmids were scaled-up using Qiagen Maxi kit.

TABLE 10

Primers used to construct 1B12.1-SS-X3 DVD-Ig

| Primer Name | Nucleotide Sequence | SEQ ID NO: |
|---|---|---|
| 1B12.1-X3-VH-F | ACCGTGTCCAGTGCCTCAACAAAAGGGCCT CAGGTGCAGCTGGTGGAAAG | 112 |
| 1B12.1-X3-VH-R | CAGCTGCACCTGAGGCCCTTTTGTTGAGGCA CTGGACACGGTCACAAGTG | 113 |
| 1B12.1-X3-VL-F | CTTGAGATCAAGCGTACGGTGGCTGCACCA GATATTCAGATGACCCAGAG | 114 |
| 1B12.1-X3-VL-R | GGTCATCTGAATATCTGGTGCAGCCACCGTA CGCTTGATCTCAAGCTTCG | 115 |
| 1B12-VH1a-F | CTGGCTTTTTCTTGTCGCGATTTTAAAAGGT GTCCAGTGCGAGGTACAACTTCAAGAATC | 116 |
| 1B12-VL1a-F | GCTGGGCCTGCTGCTGCTGTGGTTCCCCGGC TCGCGATGCGACACTCAAGTGACACAGTC | 117 |
| VHRO hCg1 5' Rev | AGGGTGCCAGGGGGAAGACCGATGGGCCCT TGGTCGACGC | 118 |
| 7416 | CCTTTATTAGCCAGAGGTCGAGGTC | 119 |

For DVD-Ig protein expression, the 1B12.1-SS-X3 DVD-Ig heavy chain pHybE expression vector and 1B12.1-SS-X3 DVD-Ig light chain pHybE expression vector were co-transfected into 293-6E HEK cells in a small-scale expression (500 mL) 293 FreeStyle expression system. The expression level of DVD-Ig was measured by human Ig ELISA and determined to be approximately 45 ug/ml.

Example 3. Humanized IL-1β h1B12.1 Affinity Maturation Design

Sequence alignment shows that the IL-1β antibody h1B12.1 shares the highest identity to human germlines VH4-59/JH4 and IGKV1-39/Jk2. To improve the affinity of h1B12.1 to IL-1β, hypermutated CDR residues were identified from other human antibody sequences in the IgBLAST database that also shared high identity to germlines VH34-59 and IGKV1-39. The corresponding h1B12.1 CDR residues were then subjected to limited mutagenesis by PCR with primers having low degeneracy at these positions to create three antibody libraries in the scFv format suitable for yeast surface display. The first library (H1+H2) contained mutations in HCDR1 and HCDR2. The second library (H3) contained mutations in HCDR3 and the third library (LC) contained mutations in all LCDRs. To further increase the identity of h1B12.1 to the human germline framework sequences, a binary degeneracy at certain positions were introduced into the libraries. The library designs are indicated below:
CDRs H1 and H2: Introduce limited mutagenesis at nine amino acid positions (30, 31, 32, 51, 52, 53, 54, 56, and 58) and in VH.1a and germline (F27G, L48I, K71V, N73T)
CDR H3: Introduce limited mutagenesis at eleven amino acid positions (95-100, 100a-100e) and toggle between VH.1a and germline: K94R
CDRs L1, L2 and L3: Introduce limited mutagenesis at eleven amino acid positions (30, 31, 32, 50, 53, 55, 56, and 91-94) at 79-7-7-7 ratio and in VL.1d and germline (T21, 124Q, T25A, T27Q, M33L, S49Y, G51A, N52S, S64G, L89Q)
These h1B12.1 libraries were transformed into yeast cells and displayed on cell surfaces to be selected against a low concentration of biotinylated human and/or cynoIL-1β by magnetic then fluorescence activated cell sorting.

Example 4. h1B12 scFv Expression and Binding Analysis on the Surface of Yeast h1B12.1 was expressed as scFv on the surface of yeast using the pYD1 yeast display vector (Invitrogen). The scFv-expressing yeast were exposed to different biotinylated antigen concentrations under different time and temperature conditions. ScFv expression was monitored by tag-specific antibodies. Fluorochrome labeled donkey anti-mouse (PerCP), goat (PE) or rabbit (DyLight488) antibodies from Jackson Immunoresearch were used as detection reagents. Antigen binding was monitored by APC conjugated streptavidin or Dylight633 conjugated neutravidin. All samples were analyzed by flow cytometry using a FACS Canto II cytometer and FACS Diva software version 4.3. Tag specific antibodies are described in Table 11.

The best Ag binding conditions for library selections were first identified by scouting experiments. We looked for conditions that best discriminate library populations with different binding affinities towards IL-1β. These conditions allowed detection of bound Ag and library-specific tags to normalize the antigen-binding signal for expression. The next step was to sort and collect library for further analysis. The cells were run in a FACSAria II cell sorter and the clones to select were gated according to their binding and expression. In each round of selection (see Table 12 for details) clones with the best affinity and expression were collected.

Selection for improved on-rate, off-rate, or both were carried out and antibody protein sequences of affinity-modulated h1B12.1 variants (see below) were recovered from yeast cells for converting back to IgG format for further characterization.

TABLE 11

Commercially available anti-peptide tagged antibodies used to monitor ScFv antibody expression on yeast

| Tag | Ab Source | Clone | Company | Cat # |
|---|---|---|---|---|
| S | Mouse | SBSTAGa | Abcam | ab24838 |
| S | Rabbit | Polyclonal | S tag antibody [SBSTAGa] | ab18588 |
| AcV5 | Mouse | AcV5 | Abcam. Rabbit S tag antibody | ab49581 |
| E2 | Mouse | 5E11 | Abcam. AcV5 tag antibody [AcV5] | ab977 |
| E | Rabbit | Polyclonal | T7 tag ® antibody [T7 Tag] | ab3397 |
| E | Goat | Polyclonal | Abcam | ab95868 |
| E | Chicken | Polyclonal | KT3 tag antibody [KT3] | ab18695 |
| StrepII | Mouse | Strep-tag | Abcam. E tag antibody | MCA2489 |
| StrepII | Rabbit | Polyclonal | Abcam. E tag antibody | A00626 |
| HA | Mouse | HA-7 | Sigma | H9658 |
| HA | Goat | Polyclonal | Abcam | ab9134 |
| HA | Rat (IgG1) | 3F10 | Roche | 11 867 423 |
| c-myc | Mouse | 9E10 | Sigma | M4439 |
| c-myc | Rabbit | Polyclonal | Sigma | C3956 |
| Flag | Mouse | M2 | Sigma | F3165 |

TABLE 11-continued

Commercially available anti-peptide tagged antibodies used to monitor ScFv antibody expression on yeast

| Tag | Ab Source | Clone | Company | Cat # |
|---|---|---|---|---|
| Flag | Rabbit | Polyclonal | Sigma | F7425 |
| HSV | Rabbit | Polyclonal | Sigma | H6030 |

TABLE 12

Commercially available secondary reagents used to monitor scFv antibody expression and binding on the surface of yeast

| Secondary reagent | Fluorocrome | Company | Cat # |
|---|---|---|---|
| F(ab')2 Frag. Donkey Anti-Rat IgG (H + L) | PerCp | Jackson ImmunoResearch | |
| F(ab')2 Frag. Donkey Anti-Goat IgG (H + L) | R-PE | Jackson ImmunoResearch | |
| F(ab')2 Frag. Donkey Anti-Rabbit IgG (H + L) | DyLight-488 | Jackson ImmunoResearch | |
| F(ab')2 Frag. Goat Anti-Rabbit IgG (H + L) | R-PE | Jackson ImmunoResearch | |
| F(ab')2 Frag. Goat Anti-Rabbit IgG (H + L) | Alexafluor | Invitrogen | |
| Chicken anti mouse IgG (H + L) | PerCP | Jackson ImmunoResearch | |
| F(ab')2 Frag Donkey Anti-Mouse IgG(H + L) | Alexafluor | ThermoScientific | |
| Streptavidin | APC | | |
| Streptavidin | PE | | |
| Neutravidin | PE | | |
| Neutravidin | DyLight-633 | | |

Example 5. Generation of Affinity-Matured h1B12.1 IgG1/k (Mut (234,235) mAbs Five h1B12 affinity matured antibodies named h1b12-AM1-5 were produced in HEK-293-6E cells. All mAbs were generated as human IgG1/k mut (234,235) constructs. They were produced via small-scale transfections with a 200 mL transfection volume. The supernatants were harvested on day 6 post transfection. The titer of an aliquot of the supernatant was determined by human Ig ELISA in the assay lab. MabSelect SuRe resin (GE Healthcare) was used for affinity purification. Following elution, the antibodies were dialyzed against 15 mM histidine pH 6 overnight. The solutions were sterile filtered and analyzed by mass spectrometry and SEC for identity and purity confirmation.

Example 6. Indirect IL-1β Binding ELISA

An indirect ELISA was performed to assess the relative affinity of the affinity matured h1B12.1 mAbs to a human chimeric version of the murine 1B12 mAb. An ELISA plate was coated with goat anti-human IgG (Jackson Immunoresearch cat#109-005-098) at 0.5 ug/mL overnight. The plate was blocked with 5% milk for 1 hour and washed three times with TPBS. Affinity-matured h1B12.1 antibodies and human IgG control (Sigma cat#12511) were incubated on the plate for 30 min at 0.2 µg/mL and then the plates were washed three times. A titration of biotinylated human IL-1β or biotinylated cyno IL-1β was added to the plate, starting at 10 nM and decreasing in concentration following a series of 1:3 dilutions. Binding of biotinylated IL-1β was detected with a 1:10000 dilution of peroxidase-conjugated streptavidin (Jackson Immunoresearch cat#016-030-084) and TMB substrate (Invitrogen). The data were fit in Graphpad prism to determine the $EC_{50}$ values.

Example 7. Expression of 5 New DVD-Igs from Affinity-Matured h1B12.1 Variable Domains Five DVD-Ig molecules were generated with the affinity-matured h1B12 variable domains and the X3 variable domain with the light chain short linker sequence TVAAP (SEQ ID NO:42) and the heavy chain short linker sequence ASTKGP (SEQ ID NO:43). These are referred to as DVD1-h1B12.13-SS-X3 (PR-1358316), DVD2-h1B12.21-SS-X3 (PR-1358317), DVD3-h1B12.34-SS-X3 (PR-1358318), DVD4-h1B12.A1-SS-X3 (PR-1358319), DVD5-h1B12.A3-SS-X3 (PR-1358321). The affinity-matured heavy chain and light chain 1B12 variable regions were PCR'd out using overlapping primers from the monoclonal heavy chain and light chain constructs (Tables 13 and 14). The X3 VH and VL (including the short-short linker with overlapping primers) were also PCR'd out using the 1B12.1.5S.X3 VH and VL DVD constructs as templates. The two VH and VL with the linker were then combined with overlapping PCR. Using homologous recombination these constructs were cloned into the linearized vector pHybE hCG1 mut (234,235) digested with FSPA1 and SaiI for heavy chain and pHybE hCk digested with FSPAI and BSWiI for light chain followed by transformation into DH5a chemically competent cells. Correct clones identified by colony sequencing were scaled up. The Fc region of these five DVD-Ig molecules is IgG1 mutant 234,235. Table 15 lists the heavy chain and light chain constructs used to express each IL-1α/β back up DVD-Ig. For protein expression, a heavy chain pHybE expression vector and light chain pHybE expression vector were co-transfected into 293 cells, followed by purification using Protein A chromatography. In a small-scale expression (500 mL) in 293 freestyle expression system, the expression levels of DVD-Ig molecules were determined by human Ig ELISA.

TABLE 13

Heavy chain primer sequences

| Heavy chain primer name | Nucleotide sequence | SEQ NO: |
|---|---|---|
| VH1B12.13.ss.X3.F1 | TGGCTTTTTCTTGTCGCGATTTTAAAAGG TGTCCAGTGCGAGGTACAACTTCAAGAA TCTGGTCCAGGG | 120 |
| VH1B12.13.ss.X3.R1 | GCTTTCCACCAGCTGCACCTGCGGTCCTT TAGTGCTAGCACTGGACACGGTCACAAG TGTGCCTTGGCC | 121 |
| VH1B12.13.ss.X3.F2 | ACACTTGTGACCGTGTCCAGTGCTAGCA CTAAAGGACCGCAGGTGCAGCTGGTGGA AAGCGGCGGCGGCGTG | 122 |
| VH1B12.13.ss.X3.R2 | GGGTGCCAGGGGGAAGACCGATGGGCCC TTGGTCGACGCGCTGCTAAAGGTCACCA GGGTGCCCTGGCCCCA | 123 |

TABLE 14

Light chain primer sequences

| Light chain primer name | Nucleotide sequence | SEQ NO: |
|---|---|---|
| VL1B12.13.ss.X3.F1 | CTGGGCCTGCTGCTGCTGTGGTTCCCCGG CTCGCGATGCGACATTCAAATGACACAG TCCCCATCATCTTTG | 124 |

TABLE 14-continued

Light chain primer sequences

| Light chain primer name | Nucleotide sequence | SEQ NO: |
|---|---|---|
| VL1B12.13.ss.X3.R1 | GCTCTGGGTCATCTGAATATCAGGAGCT GCGACGGTACGCTTGATCTCAAGCTTCGT ACCTTGCCCGAAAGT | 125 |
| VL1B12.13.ss.X3.F2 | CAAGGTACGAAGCTTGAGATCAAGCGTA CCGTCGCAGCTCCTGATATTCAGATGACC CAGAGCCCGAGCAGCGTGAGC | 126 |
| VL1B12.6.13.ss.X3.R2 | GAAGATGAAGACAGATGGTGCAGCCACC GTGCGTTTATGTTCCACTTTGGTGCCGCC GCCAAAGCTCAG | 127 |

TABLE 15 pHybE Expression plasmids to generate IL-1 α/β back up DVD-Igs

| DVD-Ig | Heavy chain plasmid | Light chain plasmid |
|---|---|---|
| h1B12.13.SS.X3 | pHybE-hCg1, mut(234,235), h1B12.13-SS-X3 VH | pHybE hCk h1B12.13.SS.X3 VL |
| h1B12.21.SS.X3 | pHybE-hCg1, mut(234,235), h1B12.21-SS-X3 VH | pHybE hCk h1B12.21.SS.X3 VL |
| h1B12.34.SS.X3 | pHybE-hCg1, mut(234,235), h1B12.34-SS-X3 VH | pHybE hCk h1B12.34.SS.X3 VL |
| h1B12.A1.SS.X3 | pHybE-hCg1, mut(234,235), h1B12.A1-SS-X3 VH | pHybE hCk h1B12.A1.SS.X3 VL |
| h1B12.A3.SS.X3 | pHybE-hCg1, mut(234,235), h1B12.A3-SS-X3 VH | pHybE hCk h1B12.A3.SS.X3 VL |

Example 8. Characterization of 1B12.1-SS-X3 DVD-Ig and Anti-Human IL-1β mAb 1B12.9

The 1B12.1-SS-X3 DVD-Ig IgG1/k mut (234,235) DVD contains the light chain short linker sequence TVAAP (SEQ ID NO: 42) and the heavy chain short linker sequence ASTKGP (SEQ ID NO: 43). Anti-human IL-1β mAb 1B12.9 was generated as described above. Characterization data for both molecules is shown in Tables 16, 17, 18a, and 18b.

TABLE 16

Expression data on Igs 1B12.1-SS-X3 and 1B12.9 purified from 500 mL HEK293 cell supernatant

| mAb/DVD Name | Concentration of Purified mAb/DVD (mg/mL) | Total Yield (mg) |
|---|---|---|
| 1B12.9 | 2.3 | 33 |
| 1B12.1-SS-X3 | 2.1 | 10.5 |

TABLE 17

Characterization of 1B12.1-SS-X3 DVD-Ig and 1B12.9 by SEC

| Ig Name | % Monomer |
|---|---|
| 1B12.9 | 92 |
| 1B12.1-SS-X3 | 87 |

TABLE 18a

Characterization of 1B12.1-SS-X3 DVD-Ig by Biacore

| | Human IL-1β | Human IL-1α | Cyno IL-1β | Cyno IL-1α |
|---|---|---|---|---|
| $K_{on}$ (1/Ms) | >1.0E+06 | 2.1E+05 | 7.3E+06 | 7.4E+04 |
| $K_{off}$ (1/s) | 8.2E-04 | 2.4E-05 | 8.0E-04 | 2.6E-04 |
| $K_D$ | <8.2E-10 | 1.2E-10 | 1.1E-10 | 3.5E-09 |

TABLE 18b

Characterization of 1B12.1-SS-X3 DVD-Ig by Biacore

1B12.9 hu IgG1/k mut (234,235), PR-1317335, Lot# 1808846

| Antigens | | $k_a$ (1/Ms) | $k_d$ (1/s) | $K_D$ (M) |
|---|---|---|---|---|
| Human IL-1β | Expt 1 | 5.5E+06 | 7.6E-04 | 1.4E-10 |
| PR-1317335 | Expt 2 | 5.8E+06 | 7.7E-04 | 1.3E-10 |
| lot 1808846 | Average | 5.7E+06 | 7.7E-04 | 1.4E-10 |
| Cyno IL-1β | Expt 1 | 2.0E+06 | 9.8E-04 | 4.9E-10 |
| A-1198637 | Expt 2 | 1.4E+06 | 8.5E-04 | 6.0E-10 |
| lot 1667136 | Average | 1.7E+06 | 9.2E-04 | 5.5E-10 |

Example 9. Potency of IgGs

The neutralization potency of 1B12.9 and 1B12.1-SS-X3 DVD-Ig on human and cynomolgus IL-1β and native human IL-1β was assessed by the MRC-5 cell-based bioassay. 1B12.1 was used as a positive control comparator in the assay. In addition, the potency of 1B12.1-SS-X3 DVD-Ig on human and cynomolgus IL-1α and native human IL-1α was also assessed (Table 19).

TABLE 19

Neutralization potency determined by MRC-5 bioassay.

| | Potency IC50 (pM) | | | | | |
|---|---|---|---|---|---|---|
| | Human | | Cynomolgus | | Native | |
| mAb/DVD-Ig | IL-1a | IL-1b | IL-1a | IL-1b | IL-1a | IL-1b |
| 1B12.9 PR-1317335 | | 691 | | 352 | | 214 |
| 1B12.1 PR-1262922 | | 913 | | 410 | | 329 |
| 1B12.1.SS.X3 PR-1308565 | 27 | 26 | 2508 | 461 | 79 | 156 |

Example 10. h1B12.1 Libraries Binding and Selection Using Human and Cyno IL-1β

The h1B12.1 scFv clone was able to bind human and cyno IL-1β with affinities in the 10 to 30 nM range. Both the on-rates and off-rates were targeted for improvement following the rounds of selection described in Table 20.

TABLE 20

H1 + H2, H3 and LC Libraries selection conditions

| Selection round | Library | Ag [Ag] | Time | Temp. | Off rate competition w/ unlabeled IL-1β at 37° C. |
|---|---|---|---|---|---|
| M1 | All | 30 nM huIL-1b | 30 min | 37° C. | |
| M2 | h1B12 H1 + H2 h1B12 H3 | 1 nM cynoIL-1b | 3 min | Ice | |
| M2 | h1B12 LC | 1 nM cynoIL-1b | 5 min | Ice | |
| M2S1 | h1B12 H1 + H2 h1B12 H3 | 0.3 nM huIL-1b | 3 min | Ice | |
| M2S1 | h1B12 LC | 0.3 nM huIL-1b | 5 min | Ice | |
| M2S2-2 | h1B12 H1 + H2 | 0.3 nM huIL-1b | 2 min | Ice | |
| M2S2-2 | h1B12 H3 h1B12 LC | 0.1 nM huIL-1b | 2 min | Ice | |
| M2S3-2 | h1B12 LC | 1 nM huIL-1b | 2 min | ice | |

H1+H2, H3 and LC libraries displayed at least 10 fold improved binding to IL-1β compared to parental h1B12 scFv. However, improvement of 100 fold was highly desirable. To achieve affinity improvements >10-fold, a new h1B12 scFv library recombining the improved sequences from all 3 selected libraries was then generated and again selected for clones with improved human and cyno IL-1β binding following the rounds of selection on Table 21.

TABLE 21

Recombined h1B12 (rHC + LC) library selection conditions

| Selection round | Library | Ag [Ag] | Time | Temp. | Off rate competition w/ unlabeled IL-1β at 37° C. |
|---|---|---|---|---|---|
| M1 | h1B12 rHC + LC | 1 nM huIL-1b | 2 min | Ice | 2 hour |
| M1S1 | h1B12 rHC + LC | 0.04 nM huIL-1b | 1 min | Ice | |
| M1S2 | h1B12 rHC + LC | 1 nM huIL-1b | 2 min | ice | 6 hour |
| M1S3-2 | h1B12 rHC + LC | 1 nM huIL-1b | 2 min | ice | 24 hour |
| M1S4 | h1B12 rHC + LC | 0.03 nM huIL-1b | 30 min | RT | |

Example 11. Affinity of the h1B12.1 rHC+LC Library is More than 150 Fold Improved Compared to Parental h1B12.1 scFv A binding analysis comparison of the h1B12.1 scFv and the final M1S3-2 library output was generated in order to show the relative improvement in affinity of the library output. H1B12 and rHC+LC M1S3-2 were exposed to different concentrations of human and cyno IL-1β. The analysis shows a comparable binding to human or cyno IL-1β and at least 150 fold improvement in the binding of M1S3-2 output over h1B12 parental scFv (FIG. 1).

Figure 3:
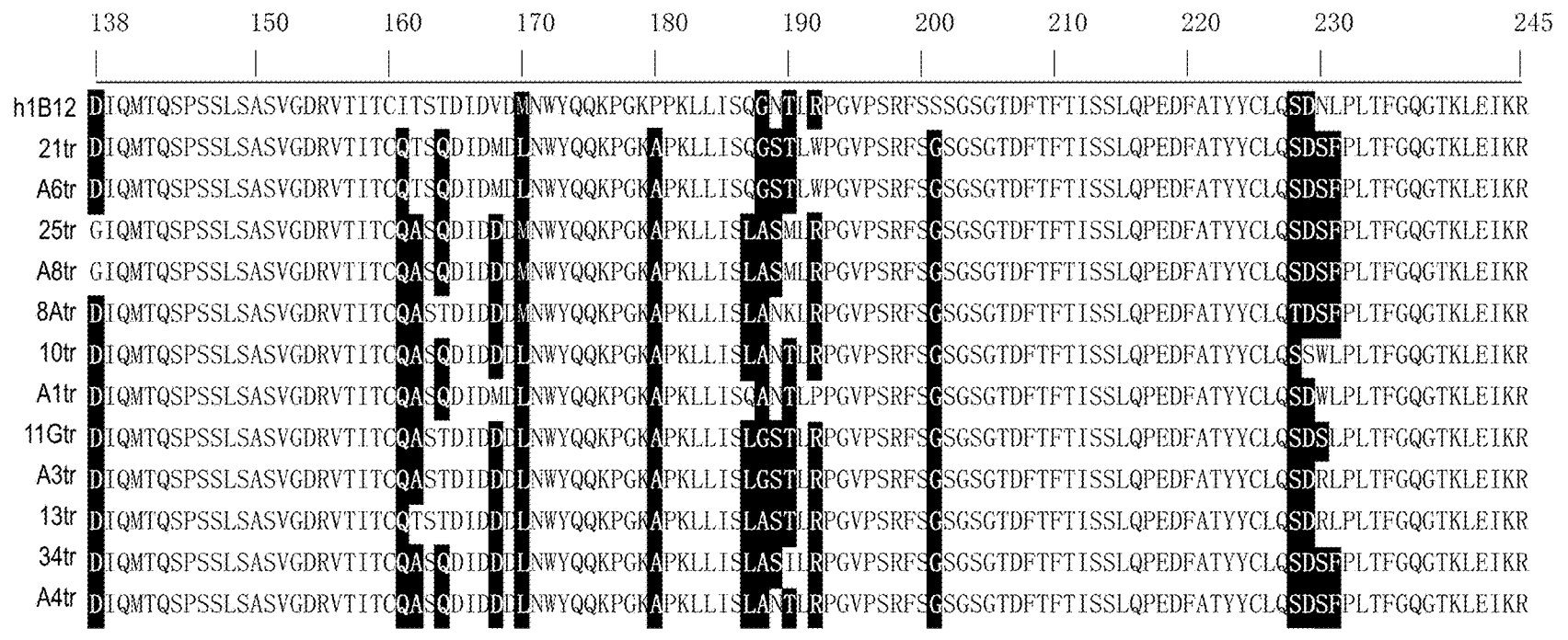

The sequences of 12 variable heavy chain domains (FIG. 2) and 12 variable light chain domains (FIG. 3) were aligned with h1B12.1 to show the sequence changes resulting in affinity improvements. Within these 12 sequences, there are 2 duplications in each of the heavy chain and light chain sequences, so a final total of 10 different clones were identified with improved binding to human and cyno IL-1β were identified from M1S3-2 output (off-rate selection) and M1S4 selection (equilibrium binding).

Example 12. Protein Sequence Liability Screening of h1B12.1 and Affinity Matured Variants h1B12.1 affinity matured variants were screened for potential liability sequence motifs, including deamidation, oxidation, isomerization, cleavage, hydrolysis, and N-linked glycosylation. IgG proteins should be characterized by the appropriate assays with sufficient sensitivity to confirm the presence or absence of each of the potential post-translational modifications.

Further analysis of protein sequence diversity and sequence prevalence in the final outputs were used to select five lead h1B12.1 improved variants which received the name of h1B12-AM1 to AM5 (Table 22a).

TABLE 22a h1B12.1 affinity matured clones; nomenclature from scFv to IgG

| Affinity matured scFv | output | HC plasmid | LC plasmid | Affinity matured full length IgG name |
|---|---|---|---|---|
| 13 | h1B12 | pHybE-hCg1mut-h1B12-13 | pHybE-hCk-h1B12-13 | h1B12-AM1 |
| 21* | rHC + LC | pHybE-hCg1mut-h1B12-21 | pHybE-hCk-h1B12-21 | h1B12-AM2 |
| 34 | M1S3-2 | pHybE-hCg1mut-h1B12-34 | pHybE-hCk-h1B12-34 | h1B12-AM3 |

TABLE 22a-continued h1B12.1 affinity matured clones; nomenclature from scFv to IgG

| Affinity matured scFv | output | HC plasmid | LC plasmid | Affinity matured full length IgG name |
|---|---|---|---|---|
| A1 | M1S4 | pHybE-hCg1mut-h1B12-A1 | pHybE-hCk-h1B12-A1 | h1B12-AM4 |
| A3 |  | pHybE-hCg1mut-h1B12-A3 | pHybE-hCk-h1B12-A3 | h1B12-AM5 |

*Clone 21 is found in both outputs

Example 13. Generation of h1B12.1 Affinity-Matured IgGs

Following the identification of 5 affinity-matured versions of 1B12.1, each of the 5 variable domain sequences were expressed as a monoclonal IgG1/k mut (234,235) antibody. Each antibody was tested by ELISA to determine if the affinity had been improved to both human and cyno IL-1β, and the chimeric mouse/human 1B12 IgG1/k mut (234,235) was used as a comparator in these assays (Table 22b). All five affinity matured mAbs had $EC_{50}$ values <0.05 nM against human and cyno IL-1β (values are comparable to one another) and have improved affinity compared to chimeric 1B12 (Table 22c).

TABLE 22b

Information and expression data and on affinity-matured h1B12.1 mAbs

| mAb | Identifier | Lot | Titer (ug/mL) | mg mAb purified from 200 mL supernatant | SEC (% monomer) |
|---|---|---|---|---|---|
| h1B12-AM-1 | PR-1354589 | 1851887 | 23 | 5.0 | 98.5 |
| h1B12-AM-2 | PR-1354591 | 1851889 | 128 | 23.2 | 99 |
| h1B12-AM-3 | PR-1354592 | 1851890 | 72 | 14.7 | 99 |
| h1B12-AM-4 | PR-1354594 | 1851892 | 67 | 9.5 | 99.5 |
| h1B12-AM-5 | PR-1354603 | 1851902 | 23 | 4.1 | 98 |
| Chimeric 1B12 (mouse/human) | A-867628 | 1274704 | N/A | N/A | N/A |

TABLE 22c

EC50 values generated following analysis of affinity-matured h1B12.1 mAbs by direct-antigen binding ELISA

| | ELISA EC50 (nM) | |
|---|---|---|
| mAb | Human IL-1β | Cyno IL-1β |
| Chimeric 1B12 (mouse/human) | 0.107 | 0.087 |
| h1B12-AM-1 | 0.031 | 0.026 |
| h1B12-AM-2 | 0.026 | 0.034 |
| h1B12-AM-3 | 0.033 | 0.032 |
| h1B12-AM-4 | 0.031 | 0.025 |
| h1B12-AM-5 | 0.028 | 0.031 |

Example 14. Characterization of DVD-Igs Containing Affinity-Matured 1B12 Variable Domains Five DVD-Igs containing affinity-matured 1B12.1 IL-1β-binding domains paired with the IL-1α-binding domain X3 were generated as discussed in Materials and Methods. The total yields after purification of 500 mL culture supernatants and characterization data are shown in Table 23.

TABLE 23

Purification of DVD-Ig molecules in 293 freestyle system

| DVD | Concentration of Purified DVD (mg/mL) | Total yield from 500 mL (mg) | SEC (% monomer) |
|---|---|---|---|
| h1B12.13-SS-X3 | 0.29 | 1.39 | 98 |
| h1B12.21-SS-X3 | 0.56 | 2.52 | 89 |
| h1B12.34-SS-X3 | 0.55 | 3.3 | 94 |
| h1B12.A1-SS-X3 | 0.32 | 2.08 | 95 |
| h1B12.A3-SS-X3 | 0.19 | 0.95 | 96 |

Example 15. Characterization of 5 DVD-Igs Containing Affinity-Matured h1B12.1 Domains by MRC-5 Bioassay and Biacore The potency of the 5 DVD-Igs containing affinity matured h1B12.1 domains to recombinant and native IL-1 antigens was determined using the MRC-5 bioassay as shown in Table 24. The binding kinetics of the DVD-Igs to recombinant human and cynomolgus IL-1α and IL-1β were determined using surface plasmon resonance. The affinity determinations are shown in Table 25. In some cases, the off-rate could not be determined as they reached the limit of detection of the instrument. For these samples (indicated with a star), the overall affinity was calculated assuming the off-rate to be $1 \times 10^{-6}$.

TABLE 24

Potency of DVD-Igs containing affinity-matured 1B12.1 variable domains in MRC-5 bioassay

| | Potency (IC50) pM | | | | | |
|---|---|---|---|---|---|---|
| | Human | | Cynomolgus | | Native | |
| DVD-Ig | IL-1α | IL-1β | IL-1α | IL-1β | IL-1α | IL-1β |
| h1B12.13-SS-X3 PR-1358316 | 45.4 | 55.9 | 2439 | 3.62 | 24.4 | 1.64 |
| h1B12.21-SS-X3 PR-1358317 | 42.8 | 48.6 | 1642 | 1.86 | 72.0 | 1.91 |
| h1B12.34-SS-X3 PR-1358318 | 41.3 | 42.2 | 1895 | 2.13 | 50.4 | 0.998 |
| h1B12.A1-SS-X3 PR-1358319 | 38.6 | 58.6 | 2584 | 4.02 | 50.9 | 2.46 |
| h1B12.A3-SS-X3 PR-1358321 | 44.3 | 51.2 | 1921 | 6.56 | 57.6 | 4.27 |

TABLE 25

Affinity of DVD-Igs containing affinity-matured 1B12.1 variable domains by BIAcore

| Sample | Ligand | $k_a$ (1/Ms) | $k_d$ (1/s) | $K_D$ (M) |
|---|---|---|---|---|
| h1B12.13-SS-X3 | Hu IL-1alpha | 1.4E+05 | 2.9E−06 | 2.1E−11 |
| h1B12.21-SS-X3 | Hu IL-1alpha | 1.4E+05 | 1.6E−05 | 1.2E−10 |
| h1B12.34-SS-X3 | Hu IL-1alpha | 1.4E+05 | 4.2E−06 | 3.0E−11 |
| h1B12.A1-SS-X3 | Hu IL-1alpha | 1.8E+05 | 3.6E−05 | 2.0E−10 |
| h1B12.A3-SS-X3 | Hu IL-1alpha | 1.5E+05 | 1.6E−06 | 1.0E−11 |
| h1B12.13-SS-X3 | Hu IL-1beta | 2.3E+07 | 5.1E−06 | 2.2E−13 |
| h1B12.21-SS-X3 | Hu IL-1beta | 2.5E+07 | 5.1E−06 | 2.0E−13 |
| h1B12.34-SS-X3 | Hu IL-1beta | 3.9E+07 | *<1E−06 | *<2.6E−14 |
| h1B12.A1-SS-X3 | Hu IL-1beta | 1.1E+07 | 1.0E−05 | 9.8E−13 |
| h1B12.A3-SS-X3 | Hu IL-1beta | 2.6E+07 | 1.3E−05 | 5.0E−13 |
| h1B12.13-SS-X3 | Cyno IL-1alpha | 1.0E+05 | 2.3E−04 | 2.3E−09 |
| h1B12.21-SS-X3 | Cyno IL-1alpha | 1.0E+05 | 2.1E−04 | 2.0E−09 |
| h1B12.34-SS-X3 | Cyno IL-1alpha | 1.0E+05 | 2.4E−04 | 2.3E−09 |
| h1B12.A1-SS-X3 | Cyno IL-1alpha | 1.3E+05 | 3.5E−04 | 2.6E−09 |
| h1B12.A3-SS-X3 | Cyno IL-1alpha | 1.1E+05 | 2.7E−04 | 2.4E−09 |
| h1B12.13-SS-X3 | Cyno IL-1beta | 1.2E+07 | 1.7E−05 | 1.5E−12 |
| h1B12.21-SS-X3 | Cyno IL-1beta | 1.1E+07 | 1.8E−05 | 1.6E−12 |
| h1B12.34-SS-X3 | Cyno IL-1beta | 1.8E+07 | 1.2E−05 | 6.7E−13 |
| h1B12.A1-SS-X3 | Cyno IL-1beta | 5.3E+06 | 9.6E−06 | 1.8E−12 |
| h1B12.A3-SS-X3 | Cyno IL-1beta | 1.3E+07 | 1.3E−05 | 1.0E−12 |

Example 16. Preformulation Studies

Two DVD-Igs (h1B12.13-SS-X3 and h1B12.A3-SS-X3) were scaled up to approximately 30 mg for a preformulation analysis and results are shown in Table 26. The assays were performed in 15 mM histidine pH 6 with a DVD-Ig concentration of 50 mg/mL. Table 26 indicates concentrating h1B12.13-SS-X3 was faster than concentrating h1B12.A3-SS-X3 even though h1B12.13-SS-X3 had much higher viscosity. Additional preliminary studies (e.g. formulation in water) suggested higher ionic strength may reduce viscosity to acceptable levels (<10 cPs). All other properties (storage stability, freeze-thaw stability, serum stability) were within typical monoclonal antibody ranges.

TABLE 26

Preformulation data on two DVD-Igs

| | High Conc. Accelerated Stability Δ (% M) loss @ T21 d, 40° C. | High Conc. Freeze Thaw Stability Δ (% HMW) post 4 freeze thaw cycles | Viscosity (at 80 mg/mL) cPs @ 20° C. | Serum Stability % HMW/day | High Conc. 5° C. Stability Δ (% M) loss @ 5° C. |
|---|---|---|---|---|---|
| h1B12.13-SS-X3 | 6.1% | −1.8% | 160 | 0.24% | 0.01% @ 23 days |
| h1B12.A3-SS-X3 | 7.0% | −0.1% | 16 | 0.12% | 0.01% @ 23 days |

Figure 4:
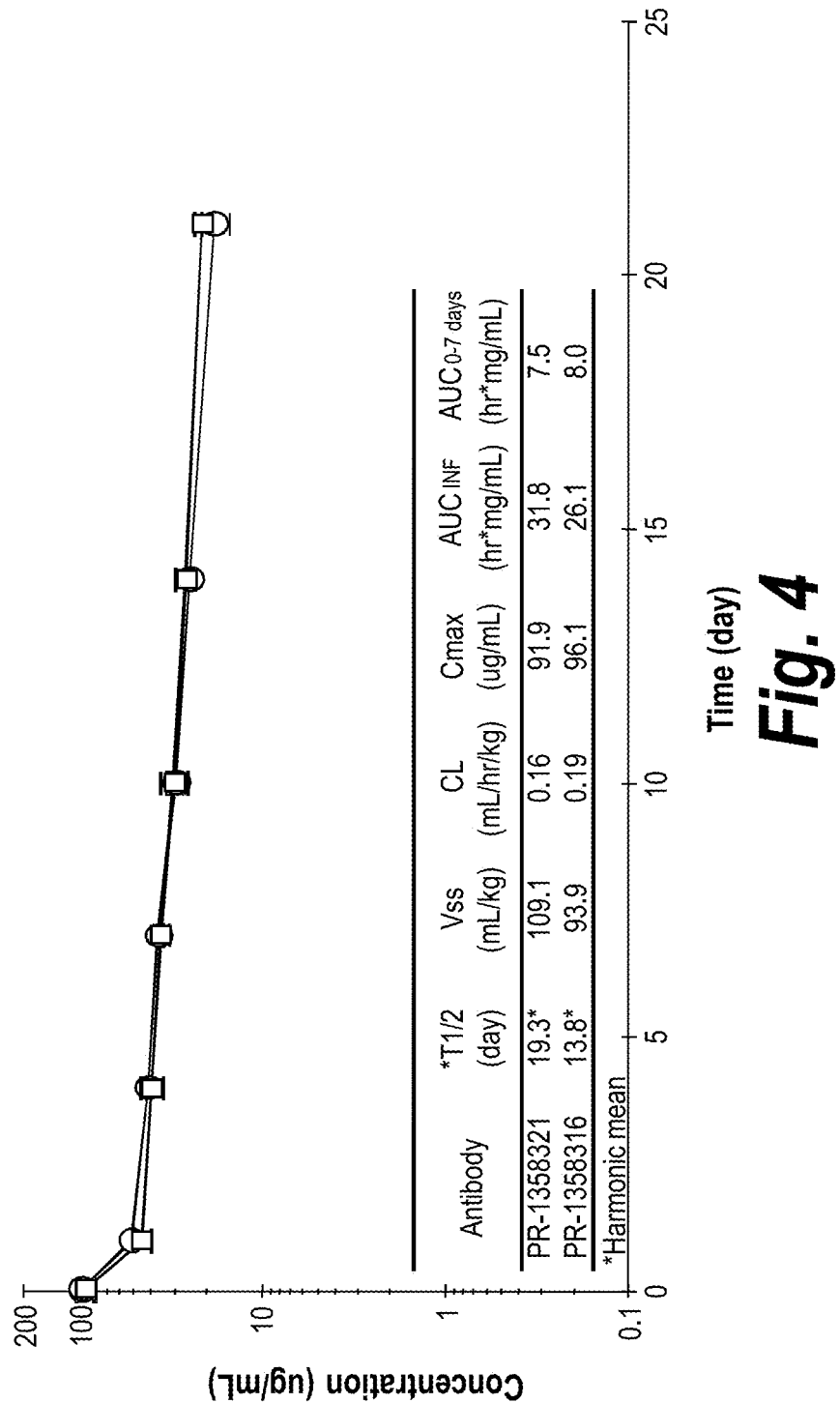
FIG. 4 is a line graph showing pharmacokinetic profiles of IL-1 α/β DVDs after a single 5 mg/kg IV dose in CD-1 mice.
Figure 5:
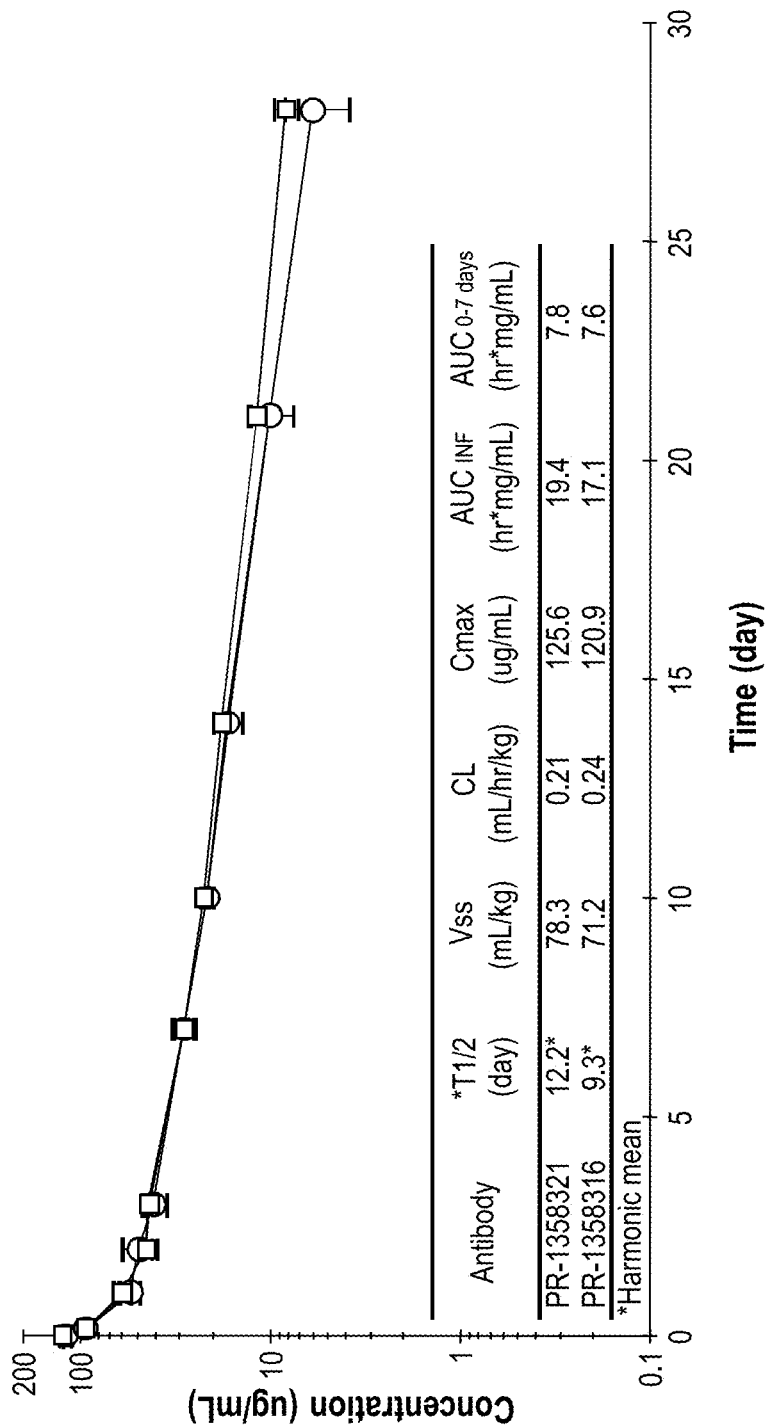
FIG. 5 is a line graph showing pharmacokinetic profiles of IL-1 α/β DVDs after a single 4 mg/kg IV dose in SD rats.

The two DVD-Igs (h1B12.13-SS-X3, PR-1358316 and h1B12.A3-SS-X3, PR-1358321) were also characterized in a single-dose rodent PK study and results are shown in FIG. 4 and FIG. 5.

Example 17. Pharmacokinetic Studies

PR-1358321 and PR-1358316 were administered to CD-1 mice and Sprague-Dawley rats by slow intravenous bolus dose injection at a 4 or 5 mg/kg (rat and mice respectively) dose. Blood samples were collected from each mouse at 1, 24 and 96 hours and 7, 10, 14 and 21 days post dose. Blood samples were collected from each rat at 0.25, 4, and 24 hours and 2, 3, 7, 10, 14, 21 and 28 days post dose. All samples were stored at −80° C. until analysis. Serum samples were analyzed using a IL-1α/β hybrid MSD assay employing a biotinylated rhIL-1 beta for capture and Sulfo-Tag labeled human IL-1alpha for detection. The assay was carried out in 1% final serum concentration. The lower limit of quantitation (LLOQ) was 0.15 μg/mL for both mouse and rat studies.

Standard curve fitting and data evaluation was performed using XLfit4 software with a four-parameter logistic fit. Plates passed when at least ⅔ of the QC's were within 30% of the expected values. Pharmacokinetic parameters for each animal were calculated using WinNonlin software Version 5.0.1 (Pharsight Corporation, Mountain View, Calif.) by non-compartmental analysis using linear trapezoidal fit (NCA Models #201 for IV dosing). For calculations in WinNonlin, the time of dosing was defined as Day 0 Time 0 hr.

Both DVD-Igs demonstrated low clearance (0.16 and 0.19 mL/h/kg) with small volumes of distribution (109 and 94 mL/kg) and long half-lives (19 and 14 days) in CD-1 mouse. In Sprague-Dawley rats, both DVDs also displayed low CL (0.21 and 0.24 mL/h/kg) and small volume of distribution (78 and 71 mL/kg), with PR-1358316 and PR-1358321 displaying a half-life respectively (9 and 12 days).

The invention claimed is:

1. A binding protein that specifically binds to both IL-1α and IL-1β, said binding protein comprising an IL-1β antigen binding domain comprising six CDRs, wherein the six CDRs are CDR-H1, CDR-H2, CDR-H3, CDR-L1, CDR-L2, and CDR-L3, as defined below:
the CDR-H1 comprises the amino acid sequence of residues 31-35 of SEQ ID NO:34;
the CDR-H2 comprises the amino acid sequence of residues 50-65 of SEQ ID NO:34;
the CDR-H3 comprises the amino acid sequence of residues 98-111 of SEQ ID NO:34;
the CDR-L1 comprises the amino acid sequence of residues 24-34 of SEQ ID NO:348;
the CDR-L2 comprises the amino acid sequence of residues 50-56 of SEQ ID NO:348; and
the CDR-L3 comprises the amino acid sequence of residues 89-97 of SEQ ID NO:348,
wherein the binding protein comprises a heavy chain variable domain and a light chain variable domain that binds IL-1α and a heavy chain variable domain and a light chain variable domain that binds IL-1β.

2. The binding protein according to claim 1, wherein the heavy chain variable domain that binds IL-1β comprises the amino acid sequence of SEQ ID NO:34.

3. The binding protein according to claim 1, wherein the light chain variable domain that binds IL-1β comprises the amino acid sequence of SEQ ID NO: 348.

4. The binding protein according to claim 1, wherein the heavy chain variable domain that binds IL-1β comprises the amino acid sequence of SEQ ID NO: 34; and wherein the light chain variable domain that binds IL-1β comprises the amino acid sequence of SEQ ID NO: 348.

5. The binding protein according to claim 4, wherein the heavy chain variable domain that binds IL-1α comprises the amino acid sequence of SEQ ID NO: 128, and wherein the light chain variable domain that binds IL-1α comprises the amino acid sequence of SEQ ID NO: 129.

6. The binding protein according to claim 4, wherein the binding protein further comprises an IgG1 Fc region comprising the amino acid sequence of SEQ ID NO: 73 and an Ig kappa constant region comprising the amino acid sequence of SEQ ID NO: 74.

7. The binding protein according to claim 5, wherein the binding protein further comprises an IgG1 Fc region comprising the amino acid sequence of SEQ ID NO: 73 and an Ig kappa constant region comprising the amino acid sequence of SEQ ID NO: 74.

8. A composition comprising a binding protein as described in claim 5 and a pharmaceutically acceptable carrier.

9. A composition comprising a binding protein as described in claim 4 and a pharmaceutically acceptable carrier.

10. The binding protein according claim 1, further comprising an IL-1α antigen binding domain comprising a CDR-H1 comprising an amino acid sequence of SEQ ID NO:132, a CDR-H2 comprising an amino acid sequence of SEQ ID NO:133, and a CDR-H3 comprising an amino acid sequence of SEQ ID NO:134, a CDR-L1 comprising an amino acid sequence of SEQ ID NO:135, a CDR-L2 comprising an amino acid sequence of SEQ ID NO:136, and a CDR-L3 comprising an amino acid sequence of SEQ ID NO:137.

11. The binding protein according to claim 10, wherein the binding protein further comprises an IgG1 Fc region comprising the amino acid sequence of SEQ ID NO: 73 and an Ig kappa constant region comprising the amino acid sequence of SEQ ID NO: 74.

12. A composition comprising a binding protein as described in claim 10 and a pharmaceutically acceptable carrier.

13. The binding protein according to claim 1, wherein the binding protein further comprises a Fc region selected from the group consisting of an Fc region from an IgG1, an IgG1 LL to AA 234, 235 mutant, IgG2, IgG3, IgG4, IgA, IgM, IgE, and IgD.

14. A binding protein conjugate comprising a binding protein as described in claim 1, said binding protein conjugate further comprising an agent selected from the group consisting of: an immunoadhesion molecule, an imaging agent, a therapeutic agent, and a cytotoxic agent.

15. A composition comprising a binding protein as described in claim 1 and a pharmaceutically acceptable carrier.

16. The binding protein according to claim 1, wherein the heavy chain variable domain that binds IL-1α comprises the amino acid sequence of SEQ ID NO: 128.

17. The binding protein according to claim 1, wherein the light chain variable domain that binds IL-1α comprises the amino acid sequence of SEQ ID NO: 129.

18. The binding protein according to claim 1, wherein the heavy chain variable domain that binds IL-1α comprises the amino acid sequence of SEQ ID NO: 128, and wherein the light chain variable domain that binds IL-1α comprises the amino acid sequence of SEQ ID NO: 129.

19. The binding protein according to claim 1, wherein the binding protein further comprises an IgG1 Fc region comprising the amino acid sequence of SEQ ID NO: 73 and an Ig kappa constant region comprising the amino acid sequence of SEQ ID NO: 74.

20. A binding protein that specifically binds to both IL-1α and IL-1β, comprising first and second polypeptide chains, wherein the first polypeptide chain comprises the amino acid sequence of SEQ ID NO: 52, and wherein the second polypeptide chain comprises the amino acid sequence of SEQ ID NO: 53.

21. A binding protein conjugate comprising a binding protein as described in claim 20, said binding protein conjugate further comprising an agent selected from the group consisting of an immunoadhesion molecule, an imaging agent, a therapeutic agent, and a cytotoxic agent.

22. A composition comprising a binding protein as described in claim 20, and a pharmaceutically acceptable carrier.

23. A binding protein that specifically binds to both IL-1α and IL-1β, comprising first and second polypeptide chains, wherein the first polypeptide chain comprises from N terminus to C terminus the amino acid sequences of SEQ ID NOs: 52 and 73, and wherein the second polypeptide chain comprises from N terminus to C terminus the amino acid sequences of SEQ ID NOs: 53 and 74.

24. A composition comprising a binding protein as described in claim 23 and a pharmaceutically acceptable carrier.

* * * * *

```
                         SEQUENCE LISTING

<160> NUMBER OF SEQ ID NOS: 433

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MOD_RES
<222> LOCATION: (1)..(1)
<223> OTHER INFORMATION: Asp or Glu
<220> FEATURE:
<221> NAME/KEY: MOD_RES
<222> LOCATION: (2)..(2)
<223> OTHER INFORMATION: Tyr or Phe

<400> SEQUENCE: 1

Xaa Xaa Gly Val Ser
1               5

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MOD_RES
<222> LOCATION: (5)..(5)
<223> OTHER INFORMATION: Ser or Gly

<400> SEQUENCE: 2

Leu Ile Trp Gly Xaa Gly Asp Thr Tyr Tyr Asn Ser Pro Leu Lys Ser
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence:
      Synthetic peptide
<220> FEATURE:
<221> NAME/KEY: MOD_RES
<222> LOCATION: (2)..(2)
<223> OTHER INFORMATION: Thr or Arg
<220> FEATURE:
<221> NAME/KEY: MOD_RES
<222> LOCATION: (4)..(4)
<223> OTHER INFORMATION: Leu or Ile
<220> FEATURE:
<221> NAME/KEY: MOD_RES
<222> LOCATION: (6)..(6)
<223> OTHER INFORMATION: Ala or Gly
<220> FEATURE:
<221> NAME/KEY: MOD_RES
<222> LOCATION: (11)..(11)
<223> OTHER INFORMATION: Ser or Gly

<400> SEQUENCE: 3

Gln Xaa Asn Xaa Trp Xaa Tyr Asp Leu Tyr Xaa Met Asp Tyr
1               5                   10
```

```
<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala or Thr
<220> FEATURE:
<221> NAME/KEY: MOD_RES
<222> LOCATION: (4)..(4)
<223> OTHER INFORMATION: Gln or Thr
<220> FEATURE:
<221> NAME/KEY: MOD_RES
<222> LOCATION: (8)..(8)
<223> OTHER INFORMATION: Asp or Met
<220> FEATURE:
<221> NAME/KEY: MOD_RES
<222> LOCATION: (10)..(10)
<223> OTHER INFORMATION: Leu or Met

<400> SEQUENCE: 4

Gln Xaa Ser Xaa Asp Ile Asp Xaa Asp Xaa Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu or Gln
<220> FEATURE:
<221> NAME/KEY: MOD_RES
<222> LOCATION: (2)..(2)
<223> OTHER INFORMATION: Ala or Gly
<220> FEATURE:
<221> NAME/KEY: MOD_RES
<222> LOCATION: (3)..(3)
<223> OTHER INFORMATION: Ser or Met
<220> FEATURE:
<221> NAME/KEY: MOD_RES
<222> LOCATION: (4)..(4)
<223> OTHER INFORMATION: Ile, Lys or Thr
<220> FEATURE:
<221> NAME/KEY: MOD_RES
<222> LOCATION: (6)..(6)
<223> OTHER INFORMATION: Arg, Trp or Pro

<400> SEQUENCE: 5

Xaa Xaa Xaa Xaa Leu Xaa Pro
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (5)..(5)
```

```
<223> OTHER INFORMATION: Ser, Trp or Arg
<220> FEATURE:
<221> NAME/KEY: MOD_RES
<222> LOCATION: (6)..(6)
<223> OTHER INFORMATION: Phe or Leu

<400> SEQUENCE: 6

Leu Gln Xaa Asp Xaa Xaa Pro Leu Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Tyr Gly Val Ser
1               5

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Ile Trp Gly Gly Gly Asp Thr Tyr Tyr Asn Ser Pro Leu Lys Ser
1               5                   10                  15

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Thr Asn Ile Trp Ala Tyr Asp Leu Tyr Ser Met Asp Tyr
1               5                   10

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Phe Gly Val Ser
1               5

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Arg Asn Leu Trp Ala Tyr Asp Leu Tyr Gly Met Asp Tyr
```

```
<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Ile Trp Gly Ser Gly Asp Thr Tyr Tyr Asn Ser Pro Leu Lys Ser
1               5                   10                  15

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Thr Asn Leu Trp Ala Tyr Asp Leu Tyr Ser Met Asp Tyr
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Thr Asn Ile Trp Gly Tyr Asp Leu Tyr Gly Met Asp Tyr
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Thr Asn Leu Trp Ala Tyr Asp Leu Tyr Ser Met Asp Tyr
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Thr Ser Thr Asp Ile Asp Asp Asp Leu Asn
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                        peptide

<400> SEQUENCE: 17

Leu Ala Ser Thr Leu Arg Pro
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Gln Ser Asp Arg Leu Pro Leu Thr
1               5

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Thr Ser Gln Asp Ile Asp Met Asp Leu Asn
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Gly Ser Thr Leu Trp Pro
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Gln Thr Asp Ser Phe Pro Leu Thr
1               5

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Ala Ser Gln Asp Ile Asp Asp Asp Leu Asn
1               5                   10

<210> SEQ ID NO 23
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Ala Ser Ile Leu Arg Pro
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Gln Ser Asp Ser Phe Pro Leu Thr
1               5

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Ala Ser Gln Asp Ile Asp Met Asp Leu Asn
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Ala Asn Thr Leu Pro Pro
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Leu Gln Ser Asp Trp Leu Pro Leu Thr
1               5

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28
```

```
Gln Ala Ser Thr Asp Ile Asp Asp Asp Met Asn
1               5                   10
```

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Leu Ala Asn Lys Leu Arg Pro
1               5
```

<210> SEQ ID NO 30
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Ile Trp Ala Tyr Asp Leu Tyr Ser Met Asp Tyr Trp
            100                 105                 110

Gly Gln Gly Thr Leu Val Thr Val Ser Ser
        115                 120
```

<210> SEQ ID NO 31
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Glu Phe
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
```

```
                   85                  90                  95

Lys Gln Arg Asn Leu Trp Ala Tyr Asp Leu Tyr Gly Met Asp Tyr Trp
            100                 105                 110

Gly Gln Gly Thr Leu Val Thr Val Ser Ser
        115                 120

<210> SEQ ID NO 32
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Leu Trp Ala Tyr Asp Leu Tyr Ser Met Asp Tyr Trp
            100                 105                 110

Gly Gln Gly Thr Leu Val Thr Val Ser Ser
        115                 120

<210> SEQ ID NO 33
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Arg Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Ile Trp Gly Tyr Asp Leu Tyr Gly Met Asp Tyr Trp
            100                 105                 110

Gly Gln Gly Thr Leu Val Thr Val Ser Ser
        115                 120
```

```
<210> SEQ ID NO 34
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Gln Thr Asn Leu Trp Ala Tyr Asp Leu Tyr Ser Met Asp Tyr Trp
            100                 105                 110

Gly Gln Gly Thr Leu Val Thr Val Ser Ser
        115                 120

<210> SEQ ID NO 35
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 36
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36
```

```
Asp Ile Gln Met Thr Gln Ser Pro Ser Ser Leu Ser Ala Ser Val Gly
1               5                   10                  15

Asp Arg Val Thr Ile Thr Cys Gln Thr Ser Thr Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Ser Thr Leu Arg Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Leu Pro Leu
                85                  90                  95

Thr Phe Gly Gln Gly Thr Lys Leu Glu Ile Lys Arg
            100                 105

<210> SEQ ID NO 37
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Gln Thr Ser Gln Asp Ile Asp Met Asp
            20                  25                  30

Leu Asn Trp Tyr Gln Gln Lys Pro Gly Lys Ala Pro Lys Leu Leu Ile
        35                  40                  45

Ser Gln Gly Ser Thr Leu Trp Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Thr Asp Ser Phe Pro Leu
                85                  90                  95

Thr Phe Gly Gln Gly Thr Lys Leu Glu Ile Lys Arg
            100                 105

<210> SEQ ID NO 38
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Ser Ile Leu Arg Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80
```

```
Glu Asp Phe Ala Thr Tyr Tyr Cys Leu Gln Ser Asp Ser Phe Pro Leu
                85                  90                  95
Thr Phe Gly Gln Gly Thr Lys Leu Glu Ile Lys Arg
            100                 105

<210> SEQ ID NO 39
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Asp Ile Asp Met Asp
            20                  25                  30
Leu Asn Trp Tyr Gln Gln Lys Pro Gly Lys Ala Pro Lys Leu Leu Ile
        35                  40                  45
Ser Gln Ala Asn Thr Leu Pro Pro Gly Val Pro Ser Arg Phe Ser Gly
    50                  55                  60
Ser Gly Ser Gly Thr Asp Phe Thr Phe Thr Ile Ser Ser Leu Gln Pro
65                  70                  75                  80
Glu Asp Phe Ala Thr Tyr Tyr Cys Leu Gln Ser Asp Trp Leu Pro Leu
                85                  90                  95
Thr Phe Gly Gln Gly Thr Lys Leu Glu Ile Lys Arg
            100                 105

<210> SEQ ID NO 40
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Met Thr Gln Ser Pro Ser Ser Leu Ser Ala Ser Val Gly
1               5                   10                  15
Asp Arg Val Thr Ile Thr Cys Gln Ala Ser Thr Asp Ile Asp Asp Asp
            20                  25                  30
Met Asn Trp Tyr Gln Gln Lys Pro Gly Lys Ala Pro Lys Leu Leu Ile
        35                  40                  45
Ser Leu Ala Asn Lys Leu Arg Pro Gly Val Pro Ser Arg Phe Ser Gly
    50                  55                  60
Ser Gly Ser Gly Thr Asp Phe Thr Phe Thr Ile Ser Ser Leu Gln Pro
65                  70                  75                  80
Glu Asp Phe Ala Thr Tyr Tyr Cys Leu Gln Thr Asp Ser Phe Pro Leu
                85                  90                  95
Thr Phe Gly Gln Gly Thr Lys Leu Glu Ile Lys Arg
            100                 105

<210> SEQ ID NO 41
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 41

```
Asp Thr Gln Met Thr Gln Ser Pro Ser Ser Leu Ser Ala Ser Val Gly
1               5                   10                  15

Asp Arg Val Thr Ile Thr Cys Ile Thr Ser Thr Asp Ile Asp Val Asp
            20                  25                  30

Met Asn Trp Tyr Gln Gln Lys Pro Gly Lys Pro Lys Leu Leu Ile
        35                  40                  45

Ser Gln Gly Asn Thr Leu Arg Pro Gly Val Pro Ser Arg Phe Ser Ser
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Asn Leu Pro Leu
                85                  90                  95

Thr Phe Gly Gln Gly Thr Lys Leu Glu Ile Lys Arg
            100                 105
```

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

```
Thr Val Ala Ala Pro
1               5
```

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

```
Ala Ser Thr Lys Gly Pro
1               5
```

<210> SEQ ID NO 44
<211> LENGTH: 250
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
```

```
                    85                  90                  95
Lys Gln Thr Asn Ile Trp Ala Tyr Asp Leu Tyr Ser Met Asp Tyr Trp
                100                 105                 110

Gly Gln Gly Thr Leu Val Thr Val Ser Ser Ala Ser Thr Lys Gly Pro
            115                 120                 125

Gln Val Gln Leu Val Glu Ser Gly Gly Gly Val Val Gln Pro Gly Arg
        130                 135                 140

Ser Leu Arg Leu Ser Cys Thr Ala Ser Gly Phe Thr Phe Ser Met Phe
145                 150                 155                 160

Gly Val His Trp Val Arg Gln Ala Pro Gly Lys Gly Leu Glu Trp Val
                165                 170                 175

Ala Ala Val Ser Tyr Asp Gly Ser Asn Lys Tyr Tyr Ala Glu Ser Val
            180                 185                 190

Lys Gly Arg Phe Thr Ile Ser Arg Asp Asn Ser Lys Asn Ile Leu Phe
        195                 200                 205

Leu Gln Met Asp Ser Leu Arg Leu Glu Asp Thr Ala Val Tyr Tyr Cys
    210                 215                 220

Ala Arg Gly Arg Pro Lys Val Val Ile Pro Ala Pro Leu Ala His Trp
225                 230                 235                 240

Gly Gln Gly Thr Leu Val Thr Phe Ser Ser
                245                 250

<210> SEQ ID NO 45
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Gln Thr Ser Thr Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Ser Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Leu Pro Leu
                85                  90                  95

Thr Phe Gly Gln Gly Thr Lys Leu Glu Ile Lys Arg Thr Val Ala Ala
            100                 105                 110

Pro Asp Ile Gln Met Thr Gln Ser Pro Ser Ser Val Ser Ala Ser Val
        115                 120                 125

Gly Asp Arg Val Thr Ile Thr Cys Arg Ala Ser Gln Gly Ile Ser Ser
    130                 135                 140

Trp Leu Ala Trp Tyr Gln Gln Lys Pro Gly Lys Ala Pro Lys Leu Leu
145                 150                 155                 160

Ile Tyr Glu Ala Ser Asn Leu Glu Thr Gly Val Pro Ser Arg Phe Ser
                165                 170                 175

Gly Ser Gly Ser Gly Ser Asp Phe Thr Leu Thr Ile Ser Ser Leu Gln
            180                 185                 190
```

Pro Glu Asp Phe Ala Thr Tyr Tyr Cys Gln Gln Thr Ser Ser Phe Leu
            195                 200                 205

Leu Ser Phe Gly Gly Gly Thr Lys Val Glu His Lys Arg
    210                 215                 220

<210> SEQ ID NO 46
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Glu Phe
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Ala Tyr Asp Leu Tyr Gly Met Asp Tyr Trp
            100                 105                 110

Gly Gln Gly Thr Leu Val Thr Val Ser Ser Ala Ser Thr Lys Gly Pro
        115                 120                 125

Gln Val Gln Leu Val Glu Ser Gly Gly Gly Val Val Gln Pro Gly Arg
    130                 135                 140

Ser Leu Arg Leu Ser Cys Thr Ala Ser Gly Phe Thr Phe Ser Met Phe
145                 150                 155                 160

Gly Val His Trp Val Arg Gln Ala Pro Gly Lys Gly Leu Glu Trp Val
                165                 170                 175

Ala Ala Val Ser Tyr Asp Gly Ser Asn Lys Tyr Tyr Ala Glu Ser Val
            180                 185                 190

Lys Gly Arg Phe Thr Ile Ser Arg Asp Asn Ser Lys Asn Ile Leu Phe
        195                 200                 205

Leu Gln Met Asp Ser Leu Arg Leu Glu Asp Thr Ala Val Tyr Tyr Cys
    210                 215                 220

Ala Arg Gly Arg Pro Lys Val Val Ile Pro Ala Pro Leu Ala His Trp
225                 230                 235                 240

Gly Gln Gly Thr Leu Val Thr Phe Ser Ser
                245                 250

<210> SEQ ID NO 47
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Gln Met Thr Gln Ser Pro Ser Ser Leu Ser Ala Ser Val Gly
1               5                   10                  15

```
Asp Arg Val Thr Ile Thr Cys Gln Thr Ser Gln Asp Ile Asp Met Asp
            20                  25                  30

Leu Asn Trp Tyr Gln Gln Lys Pro Gly Lys Ala Pro Lys Leu Leu Ile
         35                  40                  45

Ser Gln Gly Ser Thr Leu Trp Pro Gly Val Pro Ser Arg Phe Ser Gly
 50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Thr Asp Ser Phe Pro Leu
                85                  90                  95

Thr Phe Gly Gln Gly Thr Lys Leu Glu Ile Lys Arg Thr Val Ala Ala
            100                 105                 110

Pro Asp Ile Gln Met Thr Gln Ser Pro Ser Ser Val Ser Ala Ser Val
        115                 120                 125

Gly Asp Arg Val Thr Ile Thr Cys Arg Ala Ser Gln Gly Ile Ser Ser
130                 135                 140

Trp Leu Ala Trp Tyr Gln Gln Lys Pro Gly Lys Ala Pro Lys Leu Leu
145                 150                 155                 160

Ile Tyr Glu Ala Ser Asn Leu Glu Thr Gly Val Pro Ser Arg Phe Ser
                165                 170                 175

Gly Ser Gly Ser Gly Ser Asp Phe Thr Leu Thr Ile Ser Ser Leu Gln
            180                 185                 190

Pro Glu Asp Phe Ala Thr Tyr Tyr Cys Gln Gln Thr Ser Ser Phe Leu
        195                 200                 205

Leu Ser Phe Gly Gly Gly Thr Lys Val Glu His Lys Arg
210                 215                 220

<210> SEQ ID NO 48
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
         35                  40                  45

Gly Leu Ile Trp Gly Ser Gly Asp Thr Tyr Tyr Asn Ser Pro Leu Lys
 50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Leu Trp Ala Tyr Asp Leu Tyr Ser Met Asp Tyr Trp
            100                 105                 110

Gly Gln Gly Thr Leu Val Thr Val Ser Ala Ser Thr Lys Gly Pro
        115                 120                 125

Gln Val Gln Leu Val Glu Ser Gly Gly Gly Val Val Gln Pro Gly Arg
130                 135                 140

Ser Leu Arg Leu Ser Cys Thr Ala Ser Gly Phe Thr Phe Ser Met Phe
145                 150                 155                 160
```

Gly Val His Trp Val Arg Gln Ala Pro Gly Lys Gly Leu Glu Trp Val
                165                 170                 175

Ala Ala Val Ser Tyr Asp Gly Ser Asn Lys Tyr Tyr Ala Glu Ser Val
            180                 185                 190

Lys Gly Arg Phe Thr Ile Ser Arg Asp Asn Ser Lys Asn Ile Leu Phe
        195                 200                 205

Leu Gln Met Asp Ser Leu Arg Leu Glu Asp Thr Ala Val Tyr Tyr Cys
210                 215                 220

Ala Arg Gly Arg Pro Lys Val Val Ile Pro Ala Pro Leu Ala His Trp
225                 230                 235                 240

Gly Gln Gly Thr Leu Val Thr Phe Ser Ser
            245                 250

<210> SEQ ID NO 49
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Ser Ile Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Ser Phe Pro Leu
                85                  90                  95

Thr Phe Gly Gln Gly Thr Lys Leu Glu Ile Lys Arg Thr Val Ala Ala
            100                 105                 110

Pro Asp Ile Gln Met Thr Gln Ser Pro Ser Val Ser Ala Ser Val
        115                 120                 125

Gly Asp Arg Val Thr Ile Thr Cys Arg Ala Ser Gln Gly Ile Ser Ser
    130                 135                 140

Trp Leu Ala Trp Tyr Gln Gln Lys Pro Gly Lys Ala Pro Lys Leu Leu
145                 150                 155                 160

Ile Tyr Glu Ala Ser Asn Leu Glu Thr Gly Val Pro Ser Arg Phe Ser
                165                 170                 175

Gly Ser Gly Ser Gly Ser Asp Phe Thr Leu Thr Ile Ser Ser Leu Gln
            180                 185                 190

Pro Glu Asp Phe Ala Thr Tyr Tyr Cys Gln Gln Thr Ser Ser Phe Leu
        195                 200                 205

Leu Ser Phe Gly Gly Gly Thr Lys Val Glu His Lys Arg
    210                 215                 220

<210> SEQ ID NO 50
<211> LENGTH: 250
<212> TYPE: PRT
<213> ORGANISM: Artificial Sequence
<220> FEATURE:
<223> OTHER INFORMATION: Description of Artificial Sequence: Synthetic

<400> SEQUENCE: 50

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Arg Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Ile Trp Gly Tyr Asp Leu Tyr Gly Met Asp Tyr Trp
            100                 105                 110

Gly Gln Gly Thr Leu Val Thr Val Ser Ser Ala Ser Thr Lys Gly Pro
        115                 120                 125

Gln Val Gln Leu Val Glu Ser Gly Gly Val Val Gln Pro Gly Arg
    130                 135                 140

Ser Leu Arg Leu Ser Cys Thr Ala Ser Gly Phe Thr Phe Ser Met Phe
145                 150                 155                 160

Gly Val His Trp Val Arg Gln Ala Pro Gly Lys Gly Leu Glu Trp Val
                165                 170                 175

Ala Ala Val Ser Tyr Asp Gly Ser Asn Lys Tyr Tyr Ala Glu Ser Val
            180                 185                 190

Lys Gly Arg Phe Thr Ile Ser Arg Asp Asn Ser Lys Asn Ile Leu Phe
        195                 200                 205

Leu Gln Met Asp Ser Leu Arg Leu Glu Asp Thr Ala Val Tyr Tyr Cys
    210                 215                 220

Ala Arg Gly Arg Pro Lys Val Val Ile Pro Ala Pro Leu Ala His Trp
225                 230                 235                 240

Gly Gln Gly Thr Leu Val Thr Phe Ser Ser
                245                 250
```

<210> SEQ ID NO 51
<211> LENGTH: 221
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Met Asp
            20                  25                  30

Leu Asn Trp Tyr Gln Gln Lys Pro Gly Lys Ala Pro Lys Leu Leu Ile
        35                  40                  45

Ser Gln Ala Asn Thr Leu Pro Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Trp Leu Pro Leu
```

```
            85                  90                  95
Thr Phe Gly Gln Gly Thr Lys Leu Glu Ile Lys Arg Thr Val Ala Ala
            100                 105                 110

Pro Asp Ile Gln Met Thr Gln Ser Pro Ser Ser Val Ser Ala Ser Val
            115                 120                 125

Gly Asp Arg Val Thr Ile Thr Cys Arg Ala Ser Gln Gly Ile Ser Ser
        130                 135                 140

Trp Leu Ala Trp Tyr Gln Gln Lys Pro Gly Lys Ala Pro Lys Leu Leu
145                 150                 155                 160

Ile Tyr Glu Ala Ser Asn Leu Glu Thr Gly Val Pro Ser Arg Phe Ser
                165                 170                 175

Gly Ser Gly Ser Gly Ser Asp Phe Thr Leu Thr Ile Ser Ser Leu Gln
            180                 185                 190

Pro Glu Asp Phe Ala Thr Tyr Tyr Cys Gln Gln Thr Ser Ser Phe Leu
        195                 200                 205

Leu Ser Phe Gly Gly Gly Thr Lys Val Glu His Lys Arg
    210                 215                 220

<210> SEQ ID NO 52
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Gln Thr Asn Leu Trp Ala Tyr Asp Leu Tyr Ser Met Asp Tyr Trp
            100                 105                 110

Gly Gln Gly Thr Leu Val Thr Val Ser Ser Ala Ser Thr Lys Gly Pro
        115                 120                 125

Gln Val Gln Leu Val Glu Ser Gly Gly Val Val Gln Pro Gly Arg
    130                 135                 140

Ser Leu Arg Leu Ser Cys Thr Ala Ser Gly Phe Thr Phe Ser Met Phe
145                 150                 155                 160

Gly Val His Trp Val Arg Gln Ala Pro Gly Lys Gly Leu Glu Trp Val
                165                 170                 175

Ala Ala Val Ser Tyr Asp Gly Ser Asn Lys Tyr Tyr Ala Glu Ser Val
            180                 185                 190

Lys Gly Arg Phe Thr Ile Ser Arg Asp Asn Ser Lys Asn Ile Leu Phe
        195                 200                 205

Leu Gln Met Asp Ser Leu Arg Leu Glu Asp Thr Ala Val Tyr Tyr Cys
    210                 215                 220
```

```
Ala Arg Gly Arg Pro Lys Val Val Ile Pro Ala Pro Leu Ala His Trp
225                 230                 235                 240

Gly Gln Gly Thr Leu Val Thr Phe Ser Ser
                245                 250

<210> SEQ ID NO 53
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp Asp
                20                  25                  30

Leu Asn Trp Tyr Gln Gln Lys Pro Gly Lys Ala Pro Lys Leu Leu Ile
            35                  40                  45

Ser Leu Gly Ser Thr Leu Arg Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Leu Pro Leu
                85                  90                  95

Thr Phe Gly Gln Gly Thr Lys Leu Glu Ile Lys Arg Thr Val Ala Ala
            100                 105                 110

Pro Asp Ile Gln Met Thr Gln Ser Pro Ser Ser Val Ser Ala Ser Val
        115                 120                 125

Gly Asp Arg Val Thr Ile Thr Cys Arg Ala Ser Gln Gly Ile Ser Ser
    130                 135                 140

Trp Leu Ala Trp Tyr Gln Gln Lys Pro Gly Lys Ala Pro Lys Leu Leu
145                 150                 155                 160

Ile Tyr Glu Ala Ser Asn Leu Glu Thr Gly Val Pro Ser Arg Phe Ser
                165                 170                 175

Gly Ser Gly Ser Gly Ser Asp Phe Thr Leu Thr Ile Ser Ser Leu Gln
            180                 185                 190

Pro Glu Asp Phe Ala Thr Tyr Tyr Cys Gln Gln Thr Ser Ser Phe Leu
        195                 200                 205

Leu Ser Phe Gly Gly Gly Thr Lys Val Glu His Lys Arg
    210                 215                 220

<210> SEQ ID NO 54
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
                20                  25                  30

Gly Val Ser Trp Ile Arg Gln Pro Pro Gly Lys Gly Leu Glu Trp Leu
            35                  40                  45
```

```
Gly Leu Ile Trp Gly Gly Gly Asp Thr Tyr Tyr Asn Ser Pro Leu Lys
 50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser Ala Ser Thr Lys Gly Pro
            115                 120                 125

Gln Val Gln Leu Val Glu Ser Gly Gly Val Val Gln Pro Gly Arg
130                 135                 140

Ser Leu Arg Leu Ser Cys Thr Ala Ser Gly Phe Thr Phe Ser Met Phe
145                 150                 155                 160

Gly Val His Trp Val Arg Gln Ala Pro Gly Lys Gly Leu Glu Trp Val
                165                 170                 175

Ala Ala Val Ser Tyr Asp Gly Ser Asn Lys Tyr Tyr Ala Glu Ser Val
                180                 185                 190

Lys Gly Arg Phe Thr Ile Ser Arg Asp Asn Ser Lys Asn Ile Leu Phe
            195                 200                 205

Leu Gln Met Asp Ser Leu Arg Leu Glu Asp Thr Ala Val Tyr Tyr Cys
210                 215                 220

Ala Arg Gly Arg Pro Lys Val Val Ile Pro Ala Pro Leu Ala His Trp
225                 230                 235                 240

Gly Gln Gly Thr Leu Val Thr Phe Ser Ser
                245                 250

<210> SEQ ID NO 55
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Thr Gln Val Thr Gln Ser Pro Ser Ser Leu Ser Ala Ser Val Gly
1               5                  10                  15

Asp Arg Val Thr Ile Thr Cys Ile Thr Ser Thr Asp Ile Asp Val Asp
                20                  25                  30

Met Asn Trp Tyr Gln Gln Lys Pro Gly Lys Pro Pro Lys Leu Leu Ile
            35                  40                  45

Ser Gln Gly Asn Thr Leu Arg Pro Gly Val Pro Ser Arg Phe Ser Ser
 50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Ser Asp Asn Leu Pro Leu
                 85                  90                  95

Thr Phe Gly Gln Gly Thr Lys Leu Glu Ile Lys Arg Thr Val Ala Ala
            100                 105                 110

Pro Asp Ile Gln Met Thr Gln Ser Pro Ser Ser Val Ser Ala Ser Val
            115                 120                 125

Gly Asp Arg Val Thr Ile Thr Cys Arg Ala Ser Gln Gly Ile Ser Ser
130                 135                 140

Trp Leu Ala Trp Tyr Gln Gln Lys Pro Gly Lys Ala Pro Lys Leu Leu
145                 150                 155                 160
```

Ile Tyr Glu Ala Ser Asn Leu Glu Thr Gly Val Pro Ser Arg Phe Ser
            165                 170                 175

Gly Ser Gly Ser Gly Ser Asp Phe Thr Leu Thr Ile Ser Ser Leu Gln
        180                 185                 190

Pro Glu Asp Phe Ala Thr Tyr Tyr Cys Gln Gln Thr Ser Ser Phe Leu
        195                 200                 205

Leu Ser Phe Gly Gly Gly Thr Lys Val Glu His Lys Arg
    210                 215                 220

<210> SEQ ID NO 56
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
gaggtacaac ttcaagaatc tggtccaggg cttgtgaagc ctagtgaaac actgtcactg      60
acttgtaccg tgtccggatt tagcctgtcc gactacggag tttcatggat tcgacagccc     120
cccgggaaag gtctggagtg gctcgggctg atctggggtg gtggagacac atattacaat     180
tcccctctga atccaggct accatcagc aaggataact caaaaagcca gtttcattg        240 aagctgagtt ccgtgactgc cgccgacacg gcggtctatt attgtgcaaa acagaggacc     300
ctgtggggat atgacctcta cggaatggac tattggggcc aaggcacact tgtgaccgtg     360
tccagt                                                                366

<210> SEQ ID NO 57
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
gacactcaaa tgacacagtc cccatcatct ttgtccgcga gtgttgggga cagagtaact      60
attacttgca taaccagcac tgatatagac gtggacatga actggtatca gcagaagcct     120
ggcaagccgc caaaactgct tatctctcaa ggcaataccc tgcgacccgg cgtgccttct     180
agattcagct ctagcggaag cggaaccgat tttaccttca ctatctcaag cctccagccc     240
gaagacttcg ccacctacta ttgtctgcag agcgataacc tccccttgac tttcgggcaa     300
ggtacgaagc ttgagatcaa gcgt                                            324

<210> SEQ ID NO 58
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
gaggtacaac ttcaagaatc tggtccaggg cttgtgaagc ctagtgaaac actgtcactg      60
acttgtaccg tgtccggatt tagcctgagc gactacggag tttcatggat tcgacagcct     120
ccagggaaag gtctggagtg gatcgggctg atctggggca gcggagatac atactacaat     180
tcccctctga atccaggct accatcagc aaggataact caaaaagcca gtttcattg        240

```
aagctgagtt ccgtgactgc cgccgacacg gcggtctatt attgtgcaaa acagacgaac      300
atctgggcgt acgacctcta ctccatggac tattggggcc aaggcacact tgtgaccgtg      360
tccagtgcta gcactaaagg accgcaggtg cagctggtgg aaagcggcgg cggcgtggtg      420
cagccgggcc gcagcctgcg cctgagctgc accgcgagcg gctttacctt tagcatgttt      480
ggcgtgcatt gggtgcgcca ggcgccgggc aaaggcctgg aatgggtggc ggcggtgagc      540
tatgatggca gcaacaaata ttatgcggaa agcgtgaaag gccgctttac cattagccgc      600
gataacagca aaacattct gtttctgcag atggatagcc tgcgcctgga agataccgcg       660
gtgtattatt gcgcgcgcgg ccgcccgaaa gtggtgattc cggcgccgct ggcgcattgg      720
ggccagggca ccctggtgac ctttagcagc                                       750

<210> SEQ ID NO 59
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
gacattcaaa tgacacagtc cccatcatct ttgtccgcga gtgttgggga cagagtaact       60
attacttgcc aaaccagtac tgatatagac gacgacctga actggtatca gcagaagcct      120
ggcaaggcgc caaaactgct tatctctctc gccagtacgc tgcgcccggg cgtgccttct      180
agattcagcg gcagcggaag cggaaccgat tttaccttca ctatctcaag cctccagccc      240
gaagacttcg ccacctacta ttgtctgcag agtgataggt tgcccttgac tttcgggcaa      300
ggtacgaagc ttgagatcaa gcgtaccgtc gcagctcctg atattcagat gcccagagc       360 ccgagcagcg tgagcgcgag cgtgggcgat cgcgtgacca ttacctgccg cgcgagccag      420
ggcattagca gctggctggc gtggtatcag cagaaaccgg gcaaagcgcc gaaactgctg      480
atttatgaag cgagcaacct ggaaaccggc gtgccgagcc gctttagcgg cagcggcagc      540
ggcagcgatt ttaccctgac cattagcagc ctgcagccgg aagatttgc gacctattat       600 tgccagcaga ccagcagctt tctgctgagc tttggcggcg gcaccaaagt ggaacataaa      660
cgc                                                                    663

<210> SEQ ID NO 60
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
gaggtacaac ttcaagaatc tggtccaggg cttgtgaagc ctagtgaaac actgtcactg       60
acttgtaccg tgtccggatt tagcctgagc gagttcggag tttcatggat tcgacagcct      120
ccagggaaag gtctggagtg gatcgggctg atctggggcg gggagacac atactacaat       180 tcccctctga atccaggcta ccatcagc aaggataact caaaaagcca gtttcattg        240 aagctgagtt ccgtgactgc cgccgacacg gcggtctatt attgtgcaaa acagaggaac      300
ctgtgggcgt acgatttgta cggcatggac tattggggcc aaggcacact tgtgaccgtg      360
tccagtgcta gcactaaagg accgcaggtg cagctggtgg aaagcggcgg cggcgtggtg      420
```

| | |
|---|---|
| cagccgggcc gcagcctgcg cctgagctgc accgcgagcg gctttaccct tagcatgttt | 480 |
| ggcgtgcatt gggtgcgcca ggcgccgggc aaaggcctgg aatgggtggc ggcggtgagc | 540 |
| tatgatggca gcaacaaata ttatgcggaa agcgtgaaag gccgctttac cattagccgc | 600 |
| gataacagca aaaacattct gtttctgcag atggatagcc tgcgcctgga agataccgcg | 660 |
| gtgtattatt gcgcgcgcgg ccgcccgaaa gtggtgattc cggcgccgct ggcgcattgg | 720 |
| ggccagggca ccctggtgac ctttagcagc | 750 |

<210> SEQ ID NO 61
<211> LENGTH: 663
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 61

| | |
|---|---|
| gacattcaaa tgacacagtc cccatcatct ttgtccgcga gtgttgggga cagagtaact | 60 |
| attacttgcc aaaccagcca agatatagac atggacctga actggtatca gcagaagcct | 120 |
| ggcaaggcgc caaaactgct tatctctcag ggcagtacgc tgtggccggg cgtgccttct | 180 |
| agattcagcg gcagcggaag cggaaccgat tttaccttca ctatctcaag cctccagccc | 240 |
| gaagacttcg ccacctacta ttgtctgcag acggatagtt ttcccttgac tttcgggcaa | 300 |
| ggtacgaagc ttgagatcaa gcgtaccgtc gcagctcctg atattcagat gacccagagc | 360 |
| ccgagcagcc tgagcgcgag cgtgggcgat cgcgtgacca ttacctgccg cgcgagccag | 420 |
| ggcattagca gctggctggc gtggtatcag cagaaaccgg gcaaagcgcc gaaactgctg | 480 |
| atttatgaag cgagcaacct ggaaaccggc gtgccgagcc gctttagcgg cagcggcagc | 540 |
| ggcagcgatt ttaccctgac cattagcagc ctgcagccgg aagattttgc gacctattat | 600 |
| tgccagcaga ccagcagctt tctgctgagc tttggcggcg gcaccaaagt ggaacataaa | 660 |
| cgc | 663 |

<210> SEQ ID NO 62
<211> LENGTH: 750
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 62

| | |
|---|---|
| gaggtacaac ttcaagaatc tggtccaggg cttgtgaagc ctagtgaaac actgtcactg | 60 |
| acttgtaccg tgtccggatt tagcctgagc gactacggag tttcatggat tcgacagcct | 120 |
| ccagggaaag gtctggagtg gatcgggctg atctgggggt cgggagatac atactacaat | 180 |
| tcccctctga atccaggct taccatcagc aaggatacct caaaaagcca agtttcattg | 240 |
| aagctgagtt ccgtgactgc cgccgacacg gcggtctatt attgtgcaaa acagacgaac | 300 |
| ctgtgggcgt acgacctcta cagcatggac tattgggggcc aaggcacact tgtgaccgtg | 360 |
| tccagtgcta gcactaaagg accgcaggtg cagctggtgg aaagcggcgg cggcgtggtg | 420 |
| cagccgggcc gcagcctgcg cctgagctgc accgcgagcg gctttaccct tagcatgttt | 480 |
| ggcgtgcatt gggtgcgcca ggcgccgggc aaaggcctgg aatgggtggc ggcggtgagc | 540 |
| tatgatggca gcaacaaata ttatgcggaa agcgtgaaag gccgctttac cattagccgc | 600 |
| gataacagca aaaacattct gtttctgcag atggatagcc tgcgcctgga agataccgcg | 660 |

```
gtgtattatt gcgcgcgcgg ccgcccgaaa gtggtgattc cggcgccgct ggcgcattgg    720
ggccagggca ccctggtgac ctttagcagc                                     750

<210> SEQ ID NO 63
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
gacattcaaa tgacacagtc cccatcatct ttgtccgcga gtgttgggga cagagtaact     60
attacttgcc aagccagcca agatatagac gacgacctga actggtatca gcagaagcct    120
ggcaaggcgc caaaactgct tatctctctg gccagtatcc tgcgcccggg cgtgccttct    180
agattcagcg gcagcggaag cggaaccgat tttaccttca ctatctcaag cctccagccc    240
gaagacttcg ccacctacta ttgtctgcag agtgacagtt tccccttgac tttcgggcaa    300
ggtacgaagc ttgagatcaa gcgtaccgtc gcagctcctg atattcagat gacccagagc    360
ccgagcagcc tgagcgcgag cgtgggcgat cgcgtgacca ttacctgccg cgcgagccag    420
ggcattagca gctggctggc gtggtatcag cagaaaccgg gcaaagcgcc gaaactgctg    480
atttatgaag cgagcaacct ggaaaccggc gtgccgagcc gctttagcgg cagcggcagc    540
ggcagcgatt ttaccctgac cattagcagc ctgcagccgg aagattttgc gacctattat    600
tgccagcaga ccagcagctt tctgctgagc tttggcggcg gcaccaaagt ggaacataaa    660
cgc                                                                  663

<210> SEQ ID NO 64
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
gaggtacaac ttcaagaatc tggtccaggg cttgtgaagc ctagtgaaac actgtcactg     60
acttgtaccg tgtccggatt tagcctgagg gactacggag tttcatggat tcgacagcct    120
ccagggaaag gtctggagtg gctcgggctg atctggggga gcggagacac atactacaat    180
tcccctctga aatccaggct taccatcagc aaggatacct caaaaagcca gtttcattg     240 aagctgagtt ccgtgactgc cgccgacacg gcggtctatt attgtgcaaa acagacgaac    300
atctggggct acgatctcta cggcatggac tattggggcc aaggcacact tgtgaccgtg    360
tccagtgcta gcactaaagg accgcaggtg cagctggtgg aaagcggcgg cggcgtggtg    420
cagccgggcc gcagcctgcg cctgagctgc accgcgagcg gctttacctt tagcatgttt    480
ggcgtgcatt gggtgcgcca ggcgccgggc aaaggcctgg aatgggtggc ggcggtgagc    540
tatgatggca gcaacaaata ttatgcggaa agcgtgaaag gccgctttac cattagccgc    600
gataacagca aaaacattct gtttctgcag atggatagcc tgcgcctgga agataccgcg    660
gtgtattatt gcgcgcgcgg ccgcccgaaa gtggtgattc cggcgccgct ggcgcattgg    720
ggccagggca ccctggtgac ctttagcagc                                     750

<210> SEQ ID NO 65
```

<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

| | |
|---|---|
| gacattcaaa tgacacagtc cccatcatct ttgtccgcga gtgttgggga cagagtaact | 60 |
| attacttgcc aagccagcca agatatagac atggacctga actggtatca gcagaagcct | 120 |
| ggcaaggcgc caaaactgct tatctctcag gccaatacgc tgcccccggg cgtgccttct | 180 |
| agattcagcg gcagcggaag cggaaccgat tttaccttca ctatctcaag cctccagccc | 240 |
| gaagacttcg ccacctacta ttgtctgcag agtgattggt tgcccttgac tttcgggcaa | 300 |
| ggtacgaagc ttgagatcaa gcgtaccgtc gcagctcctg atattcagat gacccagagc | 360 |
| ccgagcagcg tgagcgcgag cgtgggcgat cgcgtgacca ttacctgccg cgcgagccag | 420 |
| ggcattagca gctggctggc gtggtatcag cagaaaccgg gcaaagcgcc gaaactgctg | 480 |
| atttatgaag cgagcaacct ggaaaccggc gtgccgagcc gctttagcgg cagcggcagc | 540 |
| ggcagcgatt ttaccctgac cattagcagc ctgcagccgg aagattttgc gacctattat | 600 |
| tgccagcaga ccagcagctt tctgctgagc tttggcggcg gcaccaaagt ggaacataaa | 660 |
| cgc | 663 |

<210> SEQ ID NO 66
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

| | |
|---|---|
| gaggtacaac ttcaagaatc tggtccaggg cttgtgaagc ctagtgaaac actgtcactg | 60 |
| acttgtaccg tgtccggatt tagcctgagc gactacggag tttcatggat tcgacagcct | 120 |
| ccagggaaag gtctggagtg gatcgggctc atctgggcg ggggagatac atactacaat | 180 |
| tcccctctga atccaggct taccatcagc aaggataact caaaaagcca gtttcattg | 240 |
| aagctgagtt ccgtgactgc cgccgacacg gcggtctatt attgtgcaag acagacgaac | 300 |
| ctgtgggcgt acgacttgta cagcatggac tattggggcc aaggcacact tgtgaccgtg | 360 |
| tccagtgcta gcactaaagg accgcaggtg cagctggtgg aaagcggcgg cggcgtggtg | 420 |
| cagccgggcc gcagcctgcg cctgagctgc accgcgagcg gctttacctt tagcatgttt | 480 |
| ggcgtgcatt gggtgcgcca ggcgccgggc aaaggcctgg aatgggtggc ggcggtgagc | 540 |
| tatgatggca gcaacaaata ttatgcggaa agcgtgaaag ccgctttac cattagccgc | 600 |
| gataacagca aaacattct gtttctgcag atggatagcc tgcgcctgga agataccgcg | 660 |
| gtgtattatt gcgcgcgcgg ccgcccgaaa gtggtgattc cggcgccgct ggcgcattgg | 720 |
| ggccagggca ccctggtgac ctttagcagc | 750 |

<210> SEQ ID NO 67
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
gacattcaaa tgacacagtc cccatcatct ttgtccgcga gtgttgggga cagagtaact    60
attacttgcc aagccagcac tgatatagac gacgacctga actggtatca gcagaagcct   120
ggcaaggcgc caaaactgct tatctctctg ggcagtaccc tgcggcccgg cgtgccttct   180
agattcagcg gcagcggaag cggaaccgat tttaccttca ctatctcaag cctccagccc   240
gaagacttcg ccacctacta ttgtctgcag agtgataggt tgcccttgac tttcgggcaa   300
ggtacgaagc ttgagatcaa gcgtaccgtc gcagctcctg atattcagat gacccagagc   360
ccgagcagcg tgagcgcgag cgtgggcgat cgcgtgacca ttacctgccg cgcgagccag   420
ggcattagca gctggctggc gtggtatcag cagaaaccgg gcaaagcgcc gaaactgctg   480
atttatgaag cgagcaacct ggaaaccggg gtgccgagcc gctttagcgg cagcggcagc   540
ggcagcgatt ttaccctgac cattagcagc ctgcagccgg aagattttgc gacctattat   600
tgccagcaga ccagcagctt tctgctgagc tttggcggcg gcaccaaagt ggaacataaa   660
cgc                                                                 663
```

<210> SEQ ID NO 68
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

```
gaggtacaac ttcaagaatc tggtccaggg cttgtgaagc ctagtgaaac actgtcactg    60
acttgtaccg tgtccggatt tagcctgtcc gactacggag tttcatggat tcgacagccc   120
cccgggaaag gtctggagtg gctcgggctg atctggggtg gtggagacac atattacaat   180
tcccctctga aatccaggct taccatcagc aaggataact caaaaagcca agtttcattg   240
aagctgagtt ccgtgactgc cgccgacacg gcggtctatt attgtgcaaa acagaggacc   300
ctgtggggat atgacctcta cggaatggac tattggggcc aaggcacact tgtgaccgtg   360
tccagtgcct caacaaaagg gcctcaggtg cagctggtgg aaagcggcgg cggcgtggtg   420
cagccgggcc gcagcctgcg cctgagctgc accgcgagcg gctttacctt tagcatgttt   480
ggcgtgcatt gggtgcgcca ggcgccgggc aaaggcctgg aatgggtggc ggcggtgagc   540
tatgatggca gcaacaaata ttatgcggaa agcgtgaaag gccgctttac cattagccgc   600
gataacagca aaaacattct gtttctgcag atggatagcc tgcgcctgga agataccgcg   660
gtgtattatt gcgcgcgcgg ccgcccgaaa gtggtgattc cggcgccgct ggcgcattgg   720
ggccagggca ccctggtgac ctttagcagc                                    750
```

<210> SEQ ID NO 69
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

```
gacactcaag tgacacagtc cccatcatct ttgtccgcga gtgttgggga cagagtaact    60
attacttgca taaccagcac tgatatagac gtggacatga actggtatca gcagaagcct   120
ggcaagccgc caaaactgct tatctctcaa ggcaatatcc tgcgacccgg cgtgccttct   180
```

```
agattcagct ctagcggaag cggaaccgat tttaccttca ctatctcaag cctccagccc    240
gaagacttcg ccacctacta ttgtctgcag agcgataacc tccccttgac tttcgggcaa    300
ggtacgaagc ttgagatcaa gcgtacggtg gctgcaccag atattcagat gacccagagc    360
ccgagcagcg tgagcgcgag cgtgggcgat cgcgtgacca ttacctgccg cgcgagccag    420
ggcattagca gctggctggc gtggtatcag cagaaaccgg gcaaagcgcc gaaactgctg    480
atttatgaag cgagcaacct ggaaaccggc gtgccagagcc gctttagcgg cagcggcagc    540
ggcagcgatt ttaccctgac cattagcagc ctgcagccgg aagatttttgc gacctattat    600 tgccagcaga ccagcagctt tctgctgagc tttggcggcg gcaccaaagt ggaacataaa    660
cgc                                                                   663
```

```
<210> SEQ ID NO 70
<211> LENGTH: 159
<212> TYPE: PRT
<213> ORGANISM: Homo sapiens

<400> SEQUENCE: 70
```

Ser Ala Pro Phe Ser Phe Leu Ser Asn Val Lys Tyr Asn Phe Met Arg
1               5                   10                  15

Ile Ile Lys Tyr Glu Phe Ile Leu Asn Asp Ala Leu Asn Gln Ser Ile
                20                  25                  30

Ile Arg Ala Asn Asp Gln Tyr Leu Thr Ala Ala Ala Leu His Asn Leu
            35                  40                  45

Asp Glu Ala Val Lys Phe Asp Met Gly Ala Tyr Lys Ser Ser Lys Asp
50                  55                  60

Asp Ala Lys Ile Thr Val Ile Leu Arg Ile Ser Lys Thr Gln Leu Tyr
65                  70                  75                  80

Val Thr Ala Gln Asp Glu Asp Gln Pro Val Leu Leu Lys Glu Met Pro
                85                  90                  95

Glu Ile Pro Lys Thr Ile Thr Gly Ser Glu Thr Asn Leu Leu Phe Phe
            100                 105                 110

Trp Glu Thr His Gly Thr Lys Asn Tyr Phe Thr Ser Val Ala His Pro
        115                 120                 125

Asn Leu Phe Ile Ala Thr Lys Gln Asp Tyr Trp Val Cys Leu Ala Gly
    130                 135                 140

Gly Pro Pro Ser Ile Thr Asp Phe Gln Ile Leu Glu Asn Gln Ala
145                 150                 155

```
<210> SEQ ID NO 71
<211> LENGTH: 153
<212> TYPE: PRT
<213> ORGANISM: Homo sapiens

<400> SEQUENCE: 71
```

Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
                20                  25                  30

Gly Gln Asp Met Glu Gln Val Val Phe Ser Met Ser Phe Val Gln
            35                  40                  45

Gly Glu Glu Ser Asn Asp Lys Ile Pro Val Ala Leu Gly Leu Lys Glu
50                  55                  60

Lys Asn Leu Tyr Leu Ser Cys Val Leu Lys Asp Asp Lys Pro Thr Leu
65                  70                  75                  80

```
Gln Leu Glu Ser Val Asp Pro Lys Asn Tyr Pro Lys Lys Met Glu
                85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
            115                 120                 125

Asn Met Pro Val Phe Leu Gly Gly Thr Lys Gly Gly Gln Asp Ile Thr
            130                 135                 140

Asp Phe Thr Met Gln Phe Val Ser Ser
145                 150

<210> SEQ ID NO 72
<211> LENGTH: 330
<212> TYPE: PRT
<213> ORGANISM: Homo sapiens

<400> SEQUENCE: 72

Ala Ser Thr Lys Gly Pro Ser Val Phe Phe Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
```

```
              290                 295                 300
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 73
<211> LENGTH: 330
<212> TYPE: PRT
<213> ORGANISM: Homo sapiens

<400> SEQUENCE: 73

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 74
<211> LENGTH: 106
<212> TYPE: PRT
<213> ORGANISM: Homo sapiens

<400> SEQUENCE: 74

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 75
<211> LENGTH: 105
<212> TYPE: PRT
<213> ORGANISM: Homo sapiens

<400> SEQUENCE: 75

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 76

Phe Gly Xaa Gly
1

<210> SEQ ID NO 77
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Glu Trp Ile Gly
1               5

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 78

Trp Gly Xaa Gly
1

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Gly Gly Gly Ser Gly
1               5

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Gly Ser Gly Gly
1               5

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Gly Gly Gly Ser Gly Gly Gly Gly Ser
1               5                   10

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 82

Gly Gly Ser Gly Gly Gly Gly Ser Gly
1               5

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Gly Ser Gly Gly Gly Gly Ser Gly Ser
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Gly Ser Gly Gly Gly Gly Ser Gly Gly Gly Gly Ser
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Gly Gly Gly Ser Gly Gly Gly Gly Ser Gly Gly Gly Gly
1               5                   10

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Gly Gly Gly Ser Gly Gly Gly Gly Ser Gly Gly Gly Gly Ser
1               5                   10                  15

<210> SEQ ID NO 87
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ala Ser Thr Lys Gly Pro Ser Val Phe Pro Leu Ala Pro
1               5                   10

<210> SEQ ID NO 88
<211> LENGTH: 6
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Thr Val Ala Ala Pro
1               5

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Thr Val Ala Ala Pro Ser Val Phe Ile Phe Pro Pro
1               5                   10

<210> SEQ ID NO 90
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Thr Val Ala Ala Pro Ser Val Phe Ile Phe Pro Pro
1               5                   10

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Lys Thr Thr Pro Lys Leu Glu Glu Gly Glu Phe Ser Glu Ala Arg
1               5                   10                  15

<210> SEQ ID NO 92
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ala Lys Thr Thr Pro Lys Leu Glu Glu Gly Glu Phe Ser Glu Ala Arg
1               5                   10                  15

Val

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

```
Ala Lys Thr Thr Pro Lys Leu Gly Gly
1               5

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ser Ala Lys Thr Thr Pro Lys Leu Gly Gly
1               5                   10

<210> SEQ ID NO 95
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ser Ala Lys Thr Thr Pro
1               5

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Ala Asp Ala Ala Pro
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Arg Ala Asp Ala Ala Pro Thr Val Ser
1               5

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Ala Asp Ala Ala Ala Ala Gly Gly Pro Gly Ser
1               5                   10

<210> SEQ ID NO 99
<211> LENGTH: 27
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 99

Arg Ala Asp Ala Ala Ala Ala Gly Gly Gly Gly Ser Gly Gly Gly Gly
1               5                   10                  15

Ser Gly Gly Gly Gly Ser Gly Gly Gly Gly Ser
            20                  25

<210> SEQ ID NO 100
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Ala Lys Thr Thr Pro Lys Leu Glu Glu Gly Glu Phe Ser Glu Ala
1               5                   10                  15

Arg Val

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ala Asp Ala Ala Pro
1               5

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ala Asp Ala Ala Pro Thr Val Ser Ile Phe Pro Pro
1               5                   10

<210> SEQ ID NO 103
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gln Pro Lys Ala Ala Pro
1               5

<210> SEQ ID NO 104
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 104

Gln Pro Lys Ala Ala Pro Ser Val Thr Leu Phe Pro Pro
1               5                   10

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Lys Thr Thr Pro Pro
1               5

<210> SEQ ID NO 106
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ala Lys Thr Thr Pro Pro Ser Val Thr Pro Leu Ala Pro
1               5                   10

<210> SEQ ID NO 107
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ala Lys Thr Thr Ala Pro
1               5

<210> SEQ ID NO 108
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ala Lys Thr Thr Ala Pro Ser Val Tyr Pro Leu Ala Pro
1               5                   10

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Glu Asn Lys Val Glu Tyr Ala Pro Ala Leu Met Ala Leu Ser
1               5                   10                  15

<210> SEQ ID NO 110
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 110

Gly Pro Ala Lys Glu Leu Thr Pro Leu Lys Glu Ala Lys Val Ser
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly His Glu Ala Ala Ala Val Met Gln Val Gln Tyr Pro Ala Ser
1               5                   10                  15

<210> SEQ ID NO 112
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
accgtgtcca gtgcctcaac aaaagggcct caggtgcagc tggtggaaag              50

<210> SEQ ID NO 113
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
cagctgcacc tgaggccctt ttgttgaggc actggacacg gtcacaagtg              50

<210> SEQ ID NO 114
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
cttgagatca agcgtacggt ggctgcacca gatattcaga tgacccagag              50

<210> SEQ ID NO 115
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
ggtcatctga atatctggtg cagccaccgt acgcttgatc tcaagcttcg              50

<210> SEQ ID NO 116
<211> LENGTH: 60
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116 ctggctttttt cttgtcgcga ttttaaaagg tgtccagtgc gaggtacaac ttcaagaatc    60

<210> SEQ ID NO 117
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gctgggcctg ctgctgctgt ggttccccgg ctcgcgatgc gacactcaag tgacacagtc    60

<210> SEQ ID NO 118
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
agggtgccag ggggaagacc gatgggccct tggtcgacgc                          40

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
cctttattag ccagaggtcg aggtc                                          25

<210> SEQ ID NO 120
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120 tggcttttc ttgtcgcgat tttaaaaggt gtccagtgcg aggtacaact tcaagaatct    60
ggtccaggg                                                            69

<210> SEQ ID NO 121
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
gctttccacc agctgcacct gcggtccttt agtgctagca ctggacacgg tcacaagtgt    60
gccttggcc                                                            69
```

<210> SEQ ID NO 122
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
acacttgtga ccgtgtccag tgctagcact aaaggaccgc aggtgcagct ggtggaaagc      60
ggcggcggcg tg                                                          72

<210> SEQ ID NO 123
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
gggtgccagg gggaagaccg atgggccctt ggtcgacgcg ctgctaaagg tcaccagggt      60
gccctggccc ca                                                          72

<210> SEQ ID NO 124
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
ctgggcctgc tgctgctgtg gttccccggc tcgcgatgcg acattcaaat gacacagtcc      60
ccatcatctt tg                                                          72

<210> SEQ ID NO 125
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gctctgggtc atctgaatat caggagctgc gacggtacgc ttgatctcaa gcttcgtacc      60
ttgcccgaaa gt                                                          72

<210> SEQ ID NO 126
<211> LENGTH: 78
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
caaggtacga agcttgagat caagcgtacc gtcgcagctc ctgatattca gatgacccag      60
agcccgagca gcgtgagc                                                    78

<210> SEQ ID NO 127
<211> LENGTH: 69
<212> TYPE: DNA

<213> ORGANISM: Artificial Sequence
<220> FEATURE:
<223> OTHER INFORMATION: Description of Artificial Sequence: Synthetic primer

<400> SEQUENCE: 127

```
gaagatgaag acagatggtg cagccaccgt gcgtttatgt tccactttgg tgccgccgcc      60
aaagctcag                                                              69
```

<210> SEQ ID NO 128
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 128

```
Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Met Phe
            20                  25                  30

Gly Val His Trp Val Arg Gln Ala Pro Gly Lys Gly Leu Glu Trp Val
        35                  40                  45

Ala Ala Val Ser Tyr Asp Gly Ser Asn Lys Tyr Tyr Ala Glu Ser Val
    50                  55                  60

Lys Gly Arg Phe Thr Ile Ser Arg Asp Asn Ser Lys Asn Ile Leu Phe
65                  70                  75                  80

Leu Gln Met Asp Ser Leu Arg Leu Glu Asp Thr Ala Val Tyr Tyr Cys
                85                  90                  95

Ala Arg Gly Arg Pro Lys Val Val Ile Pro Ala Pro Leu Ala His Trp
            100                 105                 110

Gly Gln Gly Thr Leu Val Thr Phe Ser Ser
        115                 120
```

<210> SEQ ID NO 129
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 129

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Asn Leu Glu Thr Gly Val Pro Ser Arg Phe Ser Gly
    50                  55                  60

Ser Gly Ser Gly Ser Asp Phe Thr Leu Thr Ile Ser Ser Leu Gln Pro
65                  70                  75                  80

Glu Asp Phe Ala Thr Tyr Tyr Cys Gln Gln Thr Ser Ser Phe Leu Leu
                85                  90                  95

Ser Phe Gly Gly Gly Thr Lys Val Glu His Lys Arg
            100                 105
```

```
<210> SEQ ID NO 130
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
gcgatgcgac actcaaatga cacagtcccc atc                                33

<210> SEQ ID NO 131
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
gatggggact gtgtcatttg agtgtcgcat cgc                                33

<210> SEQ ID NO 132
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Met Phe Gly Val His
1               5

<210> SEQ ID NO 133
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Val Ser Tyr Asp Gly Ser Asn Lys Tyr Tyr Ala Glu Ser Val Lys
1               5                   10                  15

Gly

<210> SEQ ID NO 134
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Arg Pro Lys Val Val Ile Pro Ala Pro Leu Ala His
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135
```

```
Arg Ala Ser Gln Gly Ile Ser Ser Trp Leu Ala
1               5                   10

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Glu Ala Ser Asn Leu Glu Thr
1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gln Gln Thr Ser Ser Phe Leu Leu Ser
1               5

<210> SEQ ID NO 138
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Ile Thr Ser Thr Asp Ile Asp Val Asp
            20                  25                  30

Met Asn Trp Tyr Gln Gln Lys Pro Gly Lys Pro Pro Lys Leu Leu Ile
        35                  40                  45

Ser Gln Gly Asn Thr Leu Arg Pro Gly Val Pro Ser Arg Phe Ser Ser
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Asn Leu Pro Leu
                85                  90                  95

Thr Phe Gly Gln Gly Thr Lys Leu Glu Ile Lys Arg
            100                 105

<210> SEQ ID NO 139
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Gln Thr Ser Gln Asp Ile Asp Met Asp
```

```
                20                  25                  30
Leu Asn Trp Tyr Gln Gln Lys Pro Gly Lys Ala Pro Lys Leu Leu Ile
            35                  40                  45

Ser Gln Gly Ser Thr Leu Trp Pro Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Thr Asp Ser Phe Pro Leu
                85                  90                  95

Thr Phe Gly Gln Gly Thr Lys Leu Glu Ile Lys Arg
            100                 105
```

<210> SEQ ID NO 140
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

```
Gly Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Met Asn Trp Tyr Gln Gln Lys Pro Gly Lys Ala Pro Lys Leu Leu Ile
            35                  40                  45

Ser Leu Ala Ser Met Leu Arg Pro Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Ser Phe Pro Leu
                85                  90                  95

Thr Phe Gly Gln Gly Thr Lys Leu Glu Ile Lys Arg
            100                 105
```

<210> SEQ ID NO 141
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

```
Gly Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Met Asn Trp Tyr Gln Gln Lys Pro Gly Lys Ala Pro Lys Leu Leu Ile
            35                  40                  45

Ser Leu Ala Ser Met Leu Arg Pro Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Ser Phe Pro Leu
                85                  90                  95

Thr Phe Gly Gln Gly Thr Lys Leu Glu Ile Lys Arg
```

-continued

<210> SEQ ID NO 142
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp Asp
            20                  25                  30

Met Asn Trp Tyr Gln Gln Lys Pro Gly Lys Ala Pro Lys Leu Leu Ile
        35                  40                  45

Ser Leu Ala Asn Lys Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Thr Asp Ser Phe Pro Leu
                85                  90                  95

Thr Phe Gly Gln Gly Thr Lys Leu Glu Ile Lys Arg
            100                 105

<210> SEQ ID NO 143
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Asn Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Ser Trp Leu Pro Leu
                85                  90                  95

Thr Phe Gly Gln Gly Thr Lys Leu Glu Ile Lys Arg
            100                 105

<210> SEQ ID NO 144
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Gly Ser Thr Leu Arg Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Leu Phe Pro
                85                  90                  95

Leu Thr Phe Gly Gln Gly Thr Lys Leu Glu Ile Lys Arg
            100                 105

<210> SEQ ID NO 145
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Asn Thr Leu Arg Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Ser Phe Pro Leu
                85                  90                  95

Thr Phe Gly Gln Gly Thr Lys Leu Glu Ile Lys Arg
            100                 105

<210> SEQ ID NO 146
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Glu, His, Tyr, Asn, Gly, Val or Gln
<220> FEATURE:
<221> NAME/KEY: MOD_RES
<222> LOCATION: (2)..(2)
<223> OTHER INFORMATION: Tyr, Phe, Asp, Asn, His or Ser

<400> SEQUENCE: 146

Xaa Xaa Gly Val Ser
1               5

<210> SEQ ID NO 147
<211> LENGTH: 16
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu, Val, Arg, Gly, Phe, Trp, Met or Ile
<220> FEATURE:
<221> NAME/KEY: MOD_RES
<222> LOCATION: (3)..(3)
<223> OTHER INFORMATION: Trp, Gly, Leu, Tyr, Ser, Arg, Glu or Ala
<220> FEATURE:
<221> NAME/KEY: MOD_RES
<222> LOCATION: (4)..(4)
<223> OTHER INFORMATION: Gly, Val, Arg, Trp, Leu, Asp or Ser
<220> FEATURE:
<221> NAME/KEY: MOD_RES
<222> LOCATION: (5)..(5)
<223> OTHER INFORMATION: Gly, Arg, Val, Trp, Ser, Leu, Ile, Glu or Asp
<220> FEATURE:
<221> NAME/KEY: MOD_RES
<222> LOCATION: (7)..(7)
<223> OTHER INFORMATION: Asp, Gly, Glu, Val, Ser, Ala, Lys, Asp, Tyr or
      Gln
<220> FEATURE:
<221> NAME/KEY: MOD_RES
<222> LOCATION: (9)..(9)
<223> OTHER INFORMATION: Tyr, Phe, Ser, Asp, Val, Thr or His

<400> SEQUENCE: 147

Xaa Ile Xaa Xaa Xaa Gly Xaa Thr Xaa Tyr Asn Ser Pro Leu Lys Ser
1               5                   10                  15

<210> SEQ ID NO 148
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln, Asp, Lys, Pro, His, Ala, Tyr, Val or Thr
<220> FEATURE:
<221> NAME/KEY: MOD_RES
<222> LOCATION: (2)..(2)
<223> OTHER INFORMATION: Arg, Thr, Met, Ser, Ile, Trp, Pro, Asn or Lys
<220> FEATURE:
<221> NAME/KEY: MOD_RES
<222> LOCATION: (3)..(3)
<223> OTHER INFORMATION: Thr, Arg, Asn, Tyr, Trp, Val, Met or Lys
<220> FEATURE:
<221> NAME/KEY: MOD_RES
<222> LOCATION: (4)..(4)
<223> OTHER INFORMATION: Leu, Met, Arg, Ile, Gly, Trp, Gln, His, Phe or
      Ala
<220> FEATURE:
<221> NAME/KEY: MOD_RES
<222> LOCATION: (5)..(5)
<223> OTHER INFORMATION: Trp, Ser, Gly, Arg, Val, Leu, Lys, Ala, Tyr or
      Thr
<220> FEATURE:
<221> NAME/KEY: MOD_RES
<222> LOCATION: (6)..(6)
<223> OTHER INFORMATION: Gly, Ala, Arg, Val, Thr, Pro, Asn, Glu or Asp
<220> FEATURE:
<221> NAME/KEY: MOD_RES
<222> LOCATION: (7)..(7)
<223> OTHER INFORMATION: Tyr, Phe, Asn, Asp, His or Ser
<220> FEATURE:
<221> NAME/KEY: MOD_RES
<222> LOCATION: (8)..(8)
<223> OTHER INFORMATION: Asp, Gln, His, Ala, Val, Leu or Lys
<220> FEATURE:
<221> NAME/KEY: MOD_RES
<222> LOCATION: (9)..(9)
<223> OTHER INFORMATION: Leu, Ile, Phe, Ser, Met or Gly
```

```
<220> FEATURE:
<221> NAME/KEY: MOD_RES
<222> LOCATION: (10)..(10)
<223> OTHER INFORMATION: Tyr, Asn, Val or Asp
<220> FEATURE:
<221> NAME/KEY: MOD_RES
<222> LOCATION: (11)..(11)
<223> OTHER INFORMATION: Ser, Gly, Ala, Arg, Asp or Trp

<400> SEQUENCE: 148

Xaa Xaa Xaa Xaa Xaa Xaa Xaa Xaa Xaa Xaa Xaa Met Asp Tyr
1               5                   10

<210> SEQ ID NO 149
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile or Gln
<220> FEATURE:
<221> NAME/KEY: MOD_RES
<222> LOCATION: (2)..(2)
<223> OTHER INFORMATION: Thr or Ala
<220> FEATURE:
<221> NAME/KEY: MOD_RES
<222> LOCATION: (4)..(4)
<223> OTHER INFORMATION: Thr or Gln
<220> FEATURE:
<221> NAME/KEY: MOD_RES
<222> LOCATION: (7)..(7)
<223> OTHER INFORMATION: Asp, Pro, Tyr, Asn, Gln or Leu
<220> FEATURE:
<221> NAME/KEY: MOD_RES
<222> LOCATION: (8)..(8)
<223> OTHER INFORMATION: Asp, Val, Pro, Ala or Phe
<220> FEATURE:
<221> NAME/KEY: MOD_RES
<222> LOCATION: (9)..(9)
<223> OTHER INFORMATION: Asp, Ala, Pro, Asn, Tyr or Val
<220> FEATURE:
<221> NAME/KEY: MOD_RES
<222> LOCATION: (10)..(10)
<223> OTHER INFORMATION: Leu or Met

<400> SEQUENCE: 149

Xaa Xaa Ser Xaa Asp Ile Xaa Xaa Xaa Xaa Asn
1               5                   10

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu, Ser or Tyr
<220> FEATURE:
<221> NAME/KEY: MOD_RES
<222> LOCATION: (2)..(2)
<223> OTHER INFORMATION: Gly, Ala, Gln, His, Pro, Lys or Arg
<220> FEATURE:
<221> NAME/KEY: MOD_RES
<222> LOCATION: (3)..(3)
<223> OTHER INFORMATION: Ser, Asn, Gly or Ala
<220> FEATURE:
<221> NAME/KEY: MOD_RES
<222> LOCATION: (4)..(4)
```

```
<223> OTHER INFORMATION: Thr, Lys, Asn or Ser
<220> FEATURE:
<221> NAME/KEY: MOD_RES
<222> LOCATION: (6)..(6)
<223> OTHER INFORMATION: Arg, Thr, Ser, Ile, Met or Ala
<220> FEATURE:
<221> NAME/KEY: MOD_RES
<222> LOCATION: (7)..(7)
<223> OTHER INFORMATION: Pro, Leu, Ser or Thr

<400> SEQUENCE: 150

Xaa Xaa Xaa Xaa Leu Xaa Xaa
1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu or Gln
<220> FEATURE:
<221> NAME/KEY: MOD_RES
<222> LOCATION: (3)..(3)
<223> OTHER INFORMATION: Thr, Ser, Trp, Arg, Lys, Gly or Val
<220> FEATURE:
<221> NAME/KEY: MOD_RES
<222> LOCATION: (4)..(4)
<223> OTHER INFORMATION: Asp, Gly, Lys or Val
<220> FEATURE:
<221> NAME/KEY: MOD_RES
<222> LOCATION: (5)..(5)
<223> OTHER INFORMATION: Ser, Asn, Glu, Arg, Met or Gly
<220> FEATURE:
<221> NAME/KEY: MOD_RES
<222> LOCATION: (6)..(6)
<223> OTHER INFORMATION: Phe, Leu, Gly or Asp
<220> FEATURE:
<221> NAME/KEY: MOD_RES
<222> LOCATION: (7)..(7)
<223> OTHER INFORMATION: Pro or Ala

<400> SEQUENCE: 151

Xaa Gln Xaa Xaa Xaa Xaa Xaa Leu Thr
1               5

<210> SEQ ID NO 152
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Gly Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80
```

```
Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 153
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Leu Trp Gly Tyr Asp Leu Tyr Ser Met Asp Tyr Trp
            100                 105                 110

Gly Gln Gly Thr Leu Val Thr Val Ser Ser
        115                 120

<210> SEQ ID NO 154
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Glu Phe
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120
```

<210> SEQ ID NO 155
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asn Phe
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 156
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Gly Tyr
            20                  25                  30

Gly Val Ser Trp Ile Arg Gln Pro Pro Gly Lys Gly Leu Glu Trp Leu
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 157
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Lys Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Ile Trp Ala Tyr Asp Leu Tyr Ser Met Asp Tyr Trp
            100                 105                 110

Gly Gln Gly Thr Leu Val Thr Val Ser Ser
        115                 120

<210> SEQ ID NO 158
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Tyr Asp Met Tyr Gly Met Asp Tyr Trp
            100                 105                 110

Gly Gln Gly Thr Leu Val Thr Val Ser Ser
        115                 120

<210> SEQ ID NO 159
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Phe
            20                  25                  30

Gly Val Ser Trp Ile Arg Gln Pro Pro Gly Lys Gly Leu Glu Trp Leu

```
                    35                  40                  45
Gly Leu Ile Trp Gly Gly Gly Asp Thr Tyr Tyr Asn Ser Pro Leu Lys
         50                  55                  60
Ser Arg Leu Thr Ile Ser Lys Asp Asn Ser Lys Ser Gln Val Ser Leu
 65                  70                  75                  80
Lys Leu Ser Ser Val Thr Ala Ala Asp Thr Ala Val Tyr Tyr Cys Ala
                 85                  90                  95
Lys Gln Thr Asn Leu Trp Ala Tyr Asp Leu Tyr Ser Met Asp Tyr Trp
             100                 105                 110
Gly Gln Gly Thr Leu Val Thr Val Ser Ser
         115                 120

<210> SEQ ID NO 160
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Glu Val Gln Leu Gln Glu Ser Gly Pro Gly Leu Val Lys Pro Ser Glu
 1               5                  10                  15
Thr Leu Ser Leu Thr Cys Thr Val Ser Gly Phe Ser Leu Ser Gly Tyr
                 20                  25                  30
Gly Val Ser Trp Ile Arg Gln Pro Pro Gly Lys Gly Leu Glu Trp Ile
             35                  40                  45
Gly Leu Ile Trp Gly Ser Gly Asp Thr Tyr Tyr Asn Ser Pro Leu Lys
         50                  55                  60
Ser Arg Leu Thr Ile Ser Lys Asp Asn Ser Lys Ser Gln Val Ser Leu
 65                  70                  75                  80
Lys Leu Ser Ser Val Thr Ala Ala Asp Thr Ala Val Tyr Tyr Cys Ala
                 85                  90                  95
Lys Gln Arg Thr Leu Trp Gly Tyr Asp Leu Tyr Gly Met Asp Tyr Trp
             100                 105                 110
Gly Gln Gly Thr Leu Val Thr Val Ser Ser
         115                 120

<210> SEQ ID NO 161
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Glu Val Gln Leu Gln Glu Ser Gly Pro Gly Leu Val Lys Pro Ser Glu
 1               5                  10                  15
Thr Leu Ser Leu Thr Cys Thr Val Ser Gly Phe Ser Leu Ser Asp Tyr
                 20                  25                  30
Gly Val Ser Trp Ile Arg Gln Pro Pro Gly Lys Gly Leu Glu Trp Ile
             35                  40                  45
Gly Leu Ile Trp Gly Gly Gly Asp Thr Tyr Tyr Asn Ser Pro Leu Lys
         50                  55                  60
Ser Arg Leu Thr Ile Ser Lys Asp Asn Ser Lys Ser Gln Val Ser Leu
 65                  70                  75                  80
Lys Leu Ser Ser Val Thr Ala Ala Asp Thr Ala Val Tyr Tyr Cys Ala
```

```
                        85                  90                  95

Arg Gln Arg Asn Ile Trp Ala Tyr Asp Leu Tyr Gly Met Asp Tyr Trp
            100                 105                 110

Gly Gln Gly Thr Leu Val Thr Val Ser Ser
        115                 120

<210> SEQ ID NO 162
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Asn Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 163
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Val Trp Gly Tyr Asp Leu Tyr Gly Met Asp Tyr Trp
            100                 105                 110

Gly Gln Gly Thr Leu Val Thr Val Ser Ser
        115                 120
```

```
<210> SEQ ID NO 164
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164
```

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys His Arg Asn Ile Trp Gly Tyr Asp Leu Tyr Gly Met Asp Tyr Trp
            100                 105                 110

Gly Gln Gly Thr Leu Val Thr Val Ser Ser
        115                 120

```
<210> SEQ ID NO 165
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165
```

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Glu Phe
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

```
<210> SEQ ID NO 166
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166
```

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Phe
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 167
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Ser Asn Val Trp Gly Tyr Asp Leu Tyr Ser Met Asp Tyr Trp
            100                 105                 110

Gly Gln Gly Thr Leu Val Thr Val Ser Ser
        115                 120

<210> SEQ ID NO 168
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

```
Gly Leu Ile Trp Gly Gly Gly Asp Thr Tyr Tyr Asn Ser Pro Leu Lys
        50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Lys Gln Ile Asn Ile Trp Gly Tyr Asp Leu Tyr Gly Met Asp Tyr Trp
            100                 105                 110

Gly Gln Gly Thr Leu Val Thr Val Ser Ser
            115                 120

<210> SEQ ID NO 169
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Glu Val Gln Leu Gln Glu Ser Gly Pro Gly Leu Val Lys Pro Ser Glu
  1               5                  10                  15

Thr Leu Ser Leu Thr Cys Thr Val Ser Gly Phe Ser Leu Ser Asp Tyr
                 20                  25                  30

Gly Val Ser Trp Ile Arg Gln Pro Pro Gly Lys Gly Leu Glu Trp Leu
             35                  40                  45

Gly Leu Ile Trp Gly Gly Gly Asp Thr Tyr Tyr Asn Ser Pro Leu Lys
        50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Arg Gln Asn Thr Arg Trp Gly Asp Leu Tyr Gly Met Asp Tyr Trp
            100                 105                 110

Gly Gln Gly Thr Leu Val Thr Val Ser Ser
            115                 120

<210> SEQ ID NO 170
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Glu Val Gln Leu Gln Glu Ser Gly Pro Gly Leu Val Lys Pro Ser Glu
  1               5                  10                  15

Thr Leu Ser Leu Thr Cys Thr Val Ser Gly Phe Ser Leu Ser Asp Tyr
                 20                  25                  30

Gly Val Ser Trp Ile Arg Gln Pro Pro Gly Lys Gly Leu Glu Trp Ile
             35                  40                  45

Gly Leu Ile Trp Gly Gly Gly Asp Thr Tyr Tyr Asn Ser Pro Leu Lys
        50                  55                  60

Ser Arg Leu Thr Ile Ser Lys Asp Thr Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95
```

Lys Gln Arg Asn Leu Trp Gly Tyr Asp Leu Tyr Ser Met Asp Tyr Trp
            100                 105                 110

Gly Gln Gly Thr Leu Val Thr Val Ser Ser
        115                 120

<210> SEQ ID NO 171
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Gly Tyr
            20                  25                  30

Gly Val Ser Trp Ile Arg Gln Pro Pro Gly Lys Gly Leu Glu Trp Leu
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 172
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Arg Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 173

<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Asn Asn Val Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 174
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys His Arg Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 175
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Glu Tyr
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 176
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Gln Thr Asn Leu Trp Ala Tyr Asp Leu Tyr Ser Met Asp Tyr Trp
            100                 105                 110

Gly Gln Gly Thr Leu Val Thr Val Ser Ser
        115                 120

<210> SEQ ID NO 177
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
        50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 178
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Arg Glu Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
        50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 179
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
        50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

```
Lys Gln Arg Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 180
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Ile Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 181
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 182
<211> LENGTH: 122
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Phe
            20                  25                  30

Gly Val Ser Trp Ile Arg Gln Pro Pro Gly Lys Gly Leu Glu Trp Leu
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 183
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Arg Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 184
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Glu Val Gln Leu Gln Glu Ser Gly Pro Gly Leu Val Lys Pro Ser Glu
```

```
                1               5                   10                  15
Thr Leu Ser Leu Thr Cys Thr Val Ser Gly Phe Ser Leu Arg Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
        50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 185
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
        50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Ile Trp Ala Tyr Asp Leu Tyr Ser Met Asp Tyr Trp
            100                 105                 110

Gly Gln Gly Thr Leu Val Thr Val Ser Ser
        115                 120

<210> SEQ ID NO 186
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
```

```
                    50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                    85                  90                  95

Lys Gln Thr Asn Val Trp Gly Tyr Asp Leu Tyr Gly Met Asp Tyr Trp
                100                 105                 110

Gly Gln Gly Thr Leu Val Thr Val Ser Ser
            115                 120

<210> SEQ ID NO 187
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ser Glu Phe
                20                  25                  30

Gly Val Ser Trp Ile Arg Gln Pro Pro Gly Lys Gly Leu Glu Trp Ile
            35                  40                  45

Gly Leu Ile Trp Gly Ser Gly Asp Thr Tyr Tyr Asn Ser Pro Leu Lys
     50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
                100                 105                 110

Gly Gln Gly Thr Leu Val Thr Val Ser Ser
            115                 120

<210> SEQ ID NO 188
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ser Asp Phe
                20                  25                  30

Gly Val Ser Trp Ile Arg Gln Pro Pro Gly Lys Gly Leu Glu Trp Ile
            35                  40                  45

Gly Leu Ile Trp Gly Gly Gly Asp Thr Tyr Tyr Asn Ser Pro Leu Lys
     50                  55                  60

Ser Arg Leu Thr Ile Ser Lys Asp Thr Ser Lys Ser Gln Val Ser Leu
 65                  70                  75                  80

Lys Leu Ser Ser Val Thr Ala Ala Asp Thr Ala Val Tyr Tyr Cys Ala
                85                  90                  95

Lys Gln Ser Asn Leu Trp Gly Tyr Asp Leu Tyr Ser Met Asp Tyr Trp
```

Gly Gln Gly Thr Leu Val Thr Val Ser Ser
        115                 120

<210> SEQ ID NO 189
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Glu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 190
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Lys Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Ile Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 191
<211> LENGTH: 122
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 191

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Gln Asn Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 192
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asn Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Val Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 193
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Asn Arg Asn Ile Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 194
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Met Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Leu Trp Ala Tyr Asp Leu Tyr Ser Met Asp Tyr Trp
            100                 105                 110

Gly Gln Gly Thr Leu Val Thr Val Ser Ser
        115                 120

<210> SEQ ID NO 195
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

```
Ser Arg Leu Thr Ile Ser Lys Asp Thr Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 196
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ser Glu Tyr
                 20                  25                  30

Gly Val Ser Trp Ile Arg Gln Pro Pro Gly Lys Gly Leu Glu Trp Ile
            35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Lys Asn Arg Asn Leu Trp Gly Tyr Asp Leu Tyr Ser Met Asp Tyr Trp
            100                 105                 110

Gly Gln Gly Thr Leu Val Thr Val Ser Ser
        115                 120

<210> SEQ ID NO 197
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Gly Glu Tyr
                 20                  25                  30

Gly Val Ser Trp Ile Arg Gln Pro Pro Gly Lys Gly Leu Glu Trp Leu
            35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Lys Gln Arg Thr Leu Trp Gly Tyr Asp Leu Tyr Gly Met Asp Tyr Trp
            100                 105                 110
```

Gly Gln Gly Thr Leu Val Thr Val Ser Ser
        115                 120

<210> SEQ ID NO 198
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Glu Phe
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 199
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Arg Gly Tyr
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Ile Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 200
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Gly Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Leu Trp Ala Tyr Asp Leu Tyr Ser Met Asp Tyr Trp
            100                 105                 110

Gly Gln Gly Thr Leu Val Thr Val Ser Ser
        115                 120

<210> SEQ ID NO 201
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Gln Arg Asn Leu Trp Ala Tyr Asp Leu Tyr Thr Met Asp Tyr Trp
            100                 105                 110

Gly Gln Gly Thr Leu Val Thr Val Ser Ser
        115                 120

<210> SEQ ID NO 202
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Glu Val Gln Leu Gln Glu Ser Gly Pro Gly Leu Val Lys Pro Ser Glu
1               5                   10                  15

```
Thr Leu Ser Leu Thr Cys Thr Val Ser Gly Phe Ser Leu Arg Asp Tyr
             20                  25                  30

Gly Val Ser Trp Ile Arg Gln Pro Pro Gly Lys Gly Leu Glu Trp Ile
         35                  40                  45

Gly Leu Ile Trp Gly Gly Gly Asp Thr Tyr Tyr Asn Ser Pro Leu Lys
     50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Lys Gln Thr Asn Leu Trp Ala Tyr Asp Leu Tyr Thr Met Asp Tyr Trp
            100                 105                 110

Gly Gln Gly Thr Leu Val Thr Val Ser Ser
        115                 120
```

<210> SEQ ID NO 203
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

```
Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Asp Tyr
             20                  25                  30

Gly Val Ser Trp Ile Arg Gln Pro Pro Gly Lys Gly Leu Glu Trp Ile
         35                  40                  45

Gly Met Ile Trp Gly Ser Gly Asp Thr Tyr Tyr Asn Ser Pro Leu Lys
     50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120
```

<210> SEQ ID NO 204
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

```
Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Gly Glu Phe
             20                  25                  30

Gly Val Ser Trp Ile Arg Gln Pro Pro Gly Lys Gly Leu Glu Trp Ile
         35                  40                  45

Gly Leu Ile Trp Gly Gly Gly Asp Thr Tyr Tyr Asn Ser Pro Leu Lys
     50                  55                  60
```

-continued

```
Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120
```

<210> SEQ ID NO 205
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

```
Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Glu Phe
             20                  25                  30

Gly Val Ser Trp Ile Arg Gln Pro Pro Gly Lys Gly Leu Glu Trp Ile
         35                  40                  45

Gly Leu Ile Trp Gly Ser Gly Asp Thr Tyr Tyr Asn Ser Pro Leu Lys
     50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Lys Gln Thr Asn Leu Trp Ala Tyr Asp Leu Tyr Ser Met Asp Tyr Trp
            100                 105                 110

Gly Gln Gly Thr Leu Val Thr Val Ser Ser
        115                 120
```

<210> SEQ ID NO 206
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

```
Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ser Glu Tyr
             20                  25                  30

Gly Val Ser Trp Ile Arg Gln Pro Pro Gly Lys Gly Leu Glu Trp Leu
         35                  40                  45

Gly Leu Ile Trp Gly Gly Gly Asp Thr Tyr Tyr Asn Ser Pro Leu Lys
     50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Lys Gln Thr Asn Val Trp Gly Tyr Asp Leu Tyr Gly Met Asp Tyr Trp
            100                 105                 110
```

-continued

Gly Gln Gly Thr Leu Val Thr Val Ser Ser
        115                 120

<210> SEQ ID NO 207
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Glu Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 208
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Asn Arg Asn Ile Trp Gly Val Asp Leu Tyr Gly Met Asp Tyr Trp
            100                 105                 110

Gly Gln Gly Thr Leu Val Thr Val Ser Ser
        115                 120

<210> SEQ ID NO 209
<211> LENGTH: 122
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 209

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 210
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 210

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Gln Asn Asn Val Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 211
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 211

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr

```
                    20                  25                  30
Gly Val Ser Trp Ile Arg Gln Pro Gly Lys Gly Leu Glu Trp Ile
            35                  40                  45

Gly Leu Ile Trp Gly Ser Gly Asp Thr Tyr Tyr Asn Ser Pro Leu Lys
 50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Tyr Asp Leu Tyr Gly Met Asp Tyr Trp
                100                 105                 110

Gly Gln Gly Thr Leu Val Thr Val Ser Ser
            115                 120

<210> SEQ ID NO 212
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ser Asp Tyr
                20                  25                  30

Gly Val Ser Trp Ile Arg Gln Pro Gly Lys Gly Leu Glu Trp Ile
            35                  40                  45

Gly Leu Ile Trp Gly Gly Gly Asp Thr Tyr Tyr Asn Ser Pro Leu Lys
 50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                85                  90                  95

Lys Gln Asn Asn Val Trp Gly Tyr Asp Leu Tyr Gly Met Asp Tyr Trp
                100                 105                 110

Gly Gln Gly Thr Leu Val Thr Val Ser Ser
            115                 120

<210> SEQ ID NO 213
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ser Asp Tyr
                20                  25                  30

Gly Val Ser Trp Ile Arg Gln Pro Gly Lys Gly Leu Glu Trp Ile
            35                  40                  45

Gly Leu Ile Trp Gly Gly Gly Asp Thr Tyr Tyr Asn Ser Pro Leu Lys
 50                  55                  60

Ser Arg Leu Thr Ile Ser Lys Asp Thr Ser Lys Ser Gln Val Ser Leu
```

```
                65                  70                  75                  80
Lys Leu Ser Ser Val Thr Ala Ala Asp Thr Ala Val Tyr Tyr Cys Ala
                    85                  90                  95

Lys Gln Thr Asn Leu Trp Gly Tyr Asp Leu Tyr Ser Met Asp Tyr Trp
                    100                 105                 110

Gly Gln Gly Thr Leu Val Thr Val Ser Ser
            115                 120

<210> SEQ ID NO 214
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
                20                  25                  30

Gly Val Ser Trp Ile Arg Gln Pro Pro Gly Lys Gly Leu Glu Trp Leu
            35                  40                  45

Gly Leu Ile Trp Gly Gly Gly Asp Thr Tyr Tyr Asn Ser Pro Leu Lys
        50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                    85                  90                  95

Lys Gln Thr Asn Leu Trp Gly Tyr Asp Leu Tyr Gly Met Asp Tyr Trp
                    100                 105                 110

Gly Gln Gly Thr Leu Val Thr Val Ser Ser
            115                 120

<210> SEQ ID NO 215
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
                20                  25                  30

Gly Val Ser Trp Ile Arg Gln Pro Pro Gly Lys Gly Leu Glu Trp Ile
            35                  40                  45

Gly Leu Ile Trp Gly Ser Gly Asp Thr Tyr Tyr Asn Ser Pro Leu Lys
        50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                    85                  90                  95

Lys Gln Arg Asn Leu Trp Gly Tyr Asp Leu Tyr Gly Met Asp Tyr Trp
                    100                 105                 110

Gly Gln Gly Thr Leu Val Thr Val Ser Ser
```

115             120

<210> SEQ ID NO 216
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 217
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Lys Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 218
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 218

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 219
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Leu Trp Ala Tyr Asp Leu Tyr Ser Met Asp Tyr Trp
            100                 105                 110

Gly Gln Gly Thr Leu Val Thr Val Ser Ser
        115                 120

<210> SEQ ID NO 220
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asp Tyr
            20                  25                  30

-continued

Gly Val Ser Trp Ile Arg Gln Pro Gly Lys Gly Leu Glu Trp Ile
            35                  40                  45

Gly Leu Ile Trp Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Ala Tyr Asp Leu Tyr Gly Met Asp Tyr Trp
            100                 105                 110

Gly Gln Gly Thr Leu Val Thr Val Ser Ser
        115                 120

<210> SEQ ID NO 221
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Gly Lys Gly Leu Glu Trp Ile
            35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Val Arg Asn Val Trp Gly Tyr Asp Leu Tyr Thr Met Asp Tyr Trp
            100                 105                 110

Gly Gln Gly Thr Leu Val Thr Val Ser Ser
        115                 120

<210> SEQ ID NO 222
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Gly Asp Phe
            20                  25                  30

Gly Val Ser Trp Ile Arg Gln Pro Gly Lys Gly Leu Glu Trp Ile
            35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

```
Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 223
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Glu Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Ile Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 224
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Asn Asn Val Trp Gly Tyr Asp Leu Tyr Gly Met Asp Tyr Trp
            100                 105                 110

Gly Gln Gly Thr Leu Val Thr Val Ser Ser
        115                 120
```

<210> SEQ ID NO 225
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 225

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Gly Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Tyr Asp Leu Tyr Gly Met Asp Tyr Trp
            100                 105                 110

Gly Gln Gly Thr Leu Val Thr Val Ser Ser
        115                 120
```

<210> SEQ ID NO 226
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 226

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Ala Tyr Asp Leu Tyr Gly Met Asp Tyr Trp
            100                 105                 110

Gly Gln Gly Thr Leu Val Thr Val Ser Ser
        115                 120
```

<210> SEQ ID NO 227
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 227

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Glu Phe
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Leu Trp Ala Tyr Asp Leu Tyr Ser Met Asp Tyr Trp
            100                 105                 110

Gly Gln Gly Thr Leu Val Thr Val Ser Ser
        115                 120

<210> SEQ ID NO 228
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Asn Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Ile Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 229
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Arg Asp Tyr
            20                  25                  30

Gly Val Ser Trp Ile Arg Gln Pro Pro Gly Lys Gly Leu Glu Trp Leu
             35                  40                  45

Gly Leu Ile Trp Gly Ser Gly Asp Thr Tyr Tyr Asn Ser Pro Leu Lys
         50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                 85                  90                  95

Lys Gln Arg Asn Leu Trp Gly Tyr Asp Leu Tyr Gly Met Asp Tyr Trp
            100                 105                 110

Gly Gln Gly Thr Leu Val Thr Val Ser Ser
            115                 120

<210> SEQ ID NO 230
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
            35                  40                  45

Gly Leu Ile Trp Gly Ser Gly Asp Thr Tyr Tyr Asn Ser Pro Leu Lys
         50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                 85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
            115                 120

<210> SEQ ID NO 231
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Glu Tyr
            20                  25                  30

Gly Val Ser Trp Ile Arg Gln Pro Pro Gly Lys Gly Leu Glu Trp Ile
            35                  40                  45

Gly Leu Ile Trp Gly Gly Gly Asp Thr Tyr Tyr Asn Ser Pro Leu Lys
         50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 232
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 233
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Gln Arg Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 234
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Met Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 235
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Asn Arg Asn Val Trp Gly Tyr Asp Met Tyr Ala Met Asp Tyr Trp
            100                 105                 110

Gly Gln Gly Thr Leu Val Thr Val Ser Ser
        115                 120

<210> SEQ ID NO 236
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Arg Asp Phe
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Val Arg Asn Leu Trp Gly Tyr Asp Met Tyr Thr Met Asp Tyr Trp
            100                 105                 110

Gly Gln Gly Thr Leu Val Thr Val Ser Ser
        115                 120

<210> SEQ ID NO 237
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Glu Phe
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 238
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu

```
                    35                  40                  45

Gly Leu Ile Trp Gly Gly Gly Asp Thr Tyr Tyr Asn Ser Pro Leu Lys
        50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Ile Asn Leu Trp Gly Tyr Asp Leu Tyr Gly Met Asp Tyr Trp
            100                 105                 110

Gly Gln Gly Thr Leu Val Thr Val Ser Ser
            115                 120

<210> SEQ ID NO 239
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
                20                  25                  30

Gly Val Asp Trp Ile Arg Gln Pro Pro Gly Lys Gly Leu Glu Trp Ile
            35                  40                  45

Gly Leu Ile Trp Gly Gly Gly Asp Thr Tyr Tyr Asn Ser Pro Leu Lys
        50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
            115                 120

<210> SEQ ID NO 240
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
                20                  25                  30

Gly Val Ser Trp Ile Arg Gln Pro Pro Gly Lys Gly Leu Glu Trp Leu
            35                  40                  45

Gly Leu Ile Trp Gly Gly Gly Asp Thr Tyr Tyr Asn Ser Pro Leu Lys
        50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
```

85                  90                  95

Lys Gln Arg Asn Leu Trp Gly Tyr Asp Leu Tyr Ser Met Asp Tyr Trp
                100                 105                 110

Gly Gln Gly Thr Leu Val Thr Val Ser Ser
        115                 120

<210> SEQ ID NO 241
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
                20                  25                  30

Gly Val Ser Trp Ile Arg Gln Pro Pro Gly Lys Gly Leu Glu Trp Leu
            35                  40                  45

Gly Leu Ile Trp Gly Gly Asp Thr Tyr Tyr Asn Ser Pro Leu Lys
        50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Ala Tyr Asp Leu Tyr Gly Met Asp Tyr Trp
                100                 105                 110

Gly Gln Gly Thr Leu Val Thr Val Ser Ser
        115                 120

<210> SEQ ID NO 242
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Phe
                20                  25                  30

Gly Val Ser Trp Ile Arg Gln Pro Pro Gly Lys Gly Leu Glu Trp Ile
            35                  40                  45

Gly Leu Ile Trp Gly Gly Asp Thr Tyr Tyr Asn Ser Pro Leu Lys
        50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Leu Trp Ala Tyr Asp Leu Tyr Ser Met Asp Tyr Trp
                100                 105                 110

Gly Gln Gly Thr Leu Val Thr Val Ser Ser
        115                 120

```
<210> SEQ ID NO 243
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser His Tyr
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 244
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 245
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245
```

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Arg Glu Tyr
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Val Arg Asn Leu Trp Gly Tyr Asp Met Tyr Thr Met Asp Tyr Trp
            100                 105                 110

Gly Gln Gly Thr Leu Val Thr Val Ser Ser
        115                 120

<210> SEQ ID NO 246
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (113)..(113)
<223> OTHER INFORMATION: Any amino acid

<400> SEQUENCE: 246

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Tyr Asp Leu Tyr Gly Met Asp Tyr Trp
            100                 105                 110

Xaa Gln Gly Thr Leu Val Thr Val Ser Ser
        115                 120

<210> SEQ ID NO 247
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Glu Tyr

```
                    20                  25                  30
Gly Val Ser Trp Ile Arg Gln Pro Gly Lys Gly Leu Glu Trp Leu
            35                  40                  45

Gly Leu Ile Trp Gly Gly Gly Asp Thr Tyr Tyr Asn Ser Pro Leu Lys
 50                  55                  60

Ser Arg Leu Thr Ile Ser Lys Asp Thr Ser Lys Ser Gln Val Ser Leu
 65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 248
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ser Asn Tyr
            20                  25                  30

Gly Val Ser Trp Ile Arg Gln Pro Gly Lys Gly Leu Glu Trp Ile
            35                  40                  45

Gly Leu Ile Trp Gly Gly Gly Asp Thr Tyr Tyr Asn Ser Pro Leu Lys
 50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 249
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ser Asp Tyr
            20                  25                  30

Gly Val Ser Trp Ile Arg Gln Pro Gly Lys Gly Leu Glu Trp Ile
            35                  40                  45

Gly Leu Ile Trp Gly Ser Gly Asp Thr Tyr Tyr Asn Ser Pro Leu Lys
 50                  55                  60

Ser Arg Leu Thr Ile Ser Lys Asp Asn Ser Lys Ser Gln Val Ser Leu
```

```
              65                  70                  75                  80
Lys Leu Ser Ser Val Thr Ala Ala Asp Thr Ala Val Tyr Tyr Cys Ala
                    85                  90                  95

Lys Gln Arg Thr Leu Trp Gly Tyr Asp Leu Tyr Gly Met Asp Tyr Trp
                100                 105                 110

Gly Gln Gly Thr Leu Val Thr Val Ser Ser
        115                 120

<210> SEQ ID NO 250
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asp Tyr
                20                  25                  30

Gly Val Ser Trp Ile Arg Gln Pro Pro Gly Lys Gly Leu Glu Trp Ile
            35                  40                  45

Gly Leu Ile Trp Gly Gly Gly Asp Thr Tyr Tyr Asn Ser Pro Leu Lys
        50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
                100                 105                 110

Gly Gln Gly Thr Leu Val Thr Val Ser Ser
        115                 120

<210> SEQ ID NO 251
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Gly Asp Tyr
                20                  25                  30

Gly Val Ser Trp Ile Arg Gln Pro Pro Gly Lys Gly Leu Glu Trp Ile
            35                  40                  45

Gly Leu Ile Trp Gly Ser Gly Asp Thr Tyr Tyr Asn Ser Pro Leu Lys
        50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
                100                 105                 110

Gly Gln Gly Thr Leu Val Thr Val Ser Ser
```

115           120

<210> SEQ ID NO 252
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asn Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Gln Arg Asn Leu Trp Ala Tyr Asp Leu Tyr Thr Met Asp Tyr Trp
            100                 105                 110

Gly Gln Gly Thr Leu Val Thr Val Ser Ser
        115                 120

<210> SEQ ID NO 253
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Gln Arg Asn Ile Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 254
<211> LENGTH: 122
<212> TYPE: PRT
<213> ORGANISM: Artificial Sequence
<220> FEATURE:
<223> OTHER INFORMATION: Description of Artificial Sequence: Synthetic -continued

```
      polypeptide

<400> SEQUENCE: 254

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Phe
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Ile Trp Gly Tyr Asp Leu Tyr Ser Met Asp Tyr Trp
            100                 105                 110

Gly Gln Gly Thr Leu Val Thr Val Ser Ser
        115                 120

<210> SEQ ID NO 255
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Phe
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Leu Trp Ala Tyr Asp Leu Tyr Ser Met Asp Tyr Trp
            100                 105                 110

Gly Gln Gly Thr Leu Val Thr Val Ser Ser
        115                 120

<210> SEQ ID NO 256
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30
```

Gly Val Ser Trp Ile Arg Gln Pro Gly Lys Gly Leu Glu Trp Ile
            35                  40                  45

Gly Leu Ile Trp Gly Gly Gly Asp Thr Tyr Tyr Asn Ser Pro Leu Lys
 50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Lys Gln Ser Asn Ile Trp Ala Tyr Asp Leu Tyr Ser Met Asp Tyr Trp
                100                 105                 110

Gly Gln Gly Thr Leu Val Thr Val Ser Ser
            115                 120

<210> SEQ ID NO 257
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ser Asp Tyr
                 20                  25                  30

Gly Val Ser Trp Ile Arg Gln Pro Pro Gly Lys Gly Leu Glu Trp Leu
            35                  40                  45

Gly Leu Ile Trp Gly Gly Gly Asp Thr Tyr Tyr Asn Ser Pro Leu Lys
 50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Arg Gln Asn Asn Glu Trp Gly Tyr Asp Leu Tyr Gly Met Asp Tyr Trp
                100                 105                 110

Gly Gln Gly Thr Leu Val Thr Val Ser Ser
            115                 120

<210> SEQ ID NO 258
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ser Asp Tyr
                 20                  25                  30

Gly Val Ser Trp Ile Arg Gln Pro Pro Gly Lys Gly Leu Glu Trp Leu
            35                  40                  45

Gly Leu Ile Trp Gly Gly Gly Asp Thr Tyr Tyr Asn Ser Pro Leu Lys
 50                  55                  60

Ser Arg Leu Thr Ile Ser Lys Asp Asn Ser Lys Ser Gln Val Ser Leu
 65                  70                  75                  80

```
Lys Leu Ser Ser Val Thr Ala Ala Asp Thr Ala Val Tyr Tyr Cys Ala
                85                  90                  95

Lys Gln Arg Asn Ile Trp Gly Ile Asp Leu Tyr Gly Met Asp Tyr Trp
            100                 105                 110

Gly Gln Gly Thr Leu Val Thr Val Ser Ser
        115                 120

<210> SEQ ID NO 259
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Asp His Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 260
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Ile Trp Gly Val Asp Met Phe Gly Met Asp Tyr Trp
            100                 105                 110

Gly Gln Gly Thr Leu Val Thr Val Ser Ser
        115                 120
```

<210> SEQ ID NO 261
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 262
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Lys Phe
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 263
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Arg Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Leu Trp Ala Tyr Asp Leu Tyr Ser Met Asp Tyr Trp
            100                 105                 110

Gly Gln Gly Thr Leu Val Thr Val Ser Ser
        115                 120

<210> SEQ ID NO 264
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 265
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Gly Lys Gly Leu Glu Trp Ile
            35                  40                  45

Gly Leu Ile Trp Gly Gly Gly Asp Thr Tyr Tyr Asn Ser Pro Leu Lys
 50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Arg Gln Arg Asn Leu Trp Ala Tyr Asp Leu Tyr Thr Met Asp Tyr Trp
            100                 105                 110

Gly Gln Gly Thr Leu Val Thr Val Ser Ser
            115                 120

<210> SEQ ID NO 266
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Arg Asp Tyr
            20                  25                  30

Gly Val Ser Trp Ile Arg Gln Pro Gly Lys Gly Leu Glu Trp Ile
            35                  40                  45

Gly Leu Ile Trp Gly Gly Gly Asp Thr Tyr Tyr Asn Ser Pro Leu Lys
 50                  55                  60

Ser Arg Leu Thr Ile Ser Lys Asp Thr Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
            115                 120

<210> SEQ ID NO 267
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ser Asp Tyr
            20                  25                  30

Gly Val Ser Trp Ile Arg Gln Pro Gly Lys Gly Leu Glu Trp Ile
            35                  40                  45

Gly Leu Ile Trp Gly Ser Gly Asp Thr Tyr Tyr Asn Ser Pro Leu Lys
 50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                85                  90                  95

Lys Gln Arg Asn Ile Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 268
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Phe
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 269
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
        35                  40                  45

Gly Leu Ile Trp Glu Gly Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 270
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Glu Cys
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 271
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Val Trp Gly Val Asp Leu Tyr Gly Met Asp Tyr Trp
            100                 105                 110

Gly Gln Gly Thr Leu Val Thr Val Ser Ser
        115                 120

<210> SEQ ID NO 272
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 272

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Arg Glu Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Ile Trp Gly Tyr Asp Leu Tyr Ser Met Asp Tyr Trp
            100                 105                 110

Gly Gln Gly Thr Leu Val Thr Val Ser Ser
        115                 120

<210> SEQ ID NO 273
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Glu Phe
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 274
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
```

```
                35                  40                  45
Gly Leu Ile Trp Gly Gly Gly Asp Thr Tyr Tyr Asn Ser Pro Leu Lys
         50                  55                  60
Ser Arg Leu Thr Ile Ser Lys Asp Asn Ser Lys Ser Gln Val Ser Leu
 65                  70                  75                  80
Lys Leu Ser Ser Val Thr Ala Ala Asp Thr Ala Val Tyr Tyr Cys Ala
                 85                  90                  95
Lys Gln Arg Thr Leu Trp Gly Tyr Asp Leu Tyr Gly Met Asp Tyr Trp
                100                 105                 110
Gly Gln Gly Thr Leu Val Thr Val Ser Ser
                115                 120

<210> SEQ ID NO 275
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Glu Val Gln Leu Gln Glu Ser Gly Pro Gly Leu Val Lys Pro Ser Glu
 1               5                  10                  15
Thr Leu Ser Leu Thr Cys Thr Val Ser Gly Phe Ser Leu Ser Asp Tyr
                 20                  25                  30
Gly Val Ser Trp Ile Arg Gln Pro Pro Gly Lys Gly Leu Glu Trp Ile
                 35                  40                  45
Gly Leu Ile Trp Gly Gly Gly Asp Thr Tyr Tyr Asn Ser Pro Leu Lys
         50                  55                  60
Ser Arg Leu Thr Ile Ser Lys Asp Asn Ser Lys Ser Gln Val Ser Leu
 65                  70                  75                  80
Lys Leu Ser Ser Val Thr Ala Ala Asp Thr Ala Val Tyr Tyr Cys Ala
                 85                  90                  95
Lys Gln Arg Asn Leu Trp Gly Tyr Asp Leu Tyr Gly Met Asp Tyr Trp
                100                 105                 110
Gly Gln Gly Thr Leu Val Thr Val Ser Ser
                115                 120

<210> SEQ ID NO 276
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Glu Val Gln Leu Gln Glu Ser Gly Pro Gly Leu Val Lys Pro Ser Glu
 1               5                  10                  15
Thr Leu Ser Leu Thr Cys Thr Val Ser Gly Phe Ser Leu Ser Asp Tyr
                 20                  25                  30
Gly Val Ser Trp Ile Arg Gln Pro Pro Gly Lys Gly Leu Glu Trp Leu
                 35                  40                  45
Gly Leu Ile Trp Gly Gly Gly Asp Thr Tyr Tyr Asn Ser Pro Leu Lys
         50                  55                  60
Ser Arg Leu Thr Ile Ser Lys Asp Asn Ser Lys Ser Gln Val Ser Leu
 65                  70                  75                  80
Lys Leu Ser Ser Val Thr Ala Ala Asp Thr Ala Val Tyr Tyr Cys Ala
```

```
                    85                  90                  95

Lys Gln Arg Asn Ile Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 277
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Gly Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 278
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Phe
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Phe Asp Leu Tyr Gly Met Asp Tyr Trp
            100                 105                 110

Gly Gln Gly Thr Leu Val Thr Val Ser Ser
        115                 120
```

<210> SEQ ID NO 279
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (113)..(113)
<223> OTHER INFORMATION: Any amino acid

<400> SEQUENCE: 279

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Ile Trp Gly Tyr Asp Leu Tyr Gly Met Asp Tyr Trp
            100                 105                 110

Xaa Gln Gly Thr Leu Val Thr Val Ser Ser
        115                 120

<210> SEQ ID NO 280
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Glu Phe
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Ala Tyr Asp Leu Tyr Gly Met Asp Tyr Trp
            100                 105                 110

Gly Gln Gly Thr Leu Val Thr Val Ser Ser
        115                 120

<210> SEQ ID NO 281
<211> LENGTH: 122
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 281

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Lys Glu Tyr
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 282
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Tyr Asp Leu Tyr Thr Met Asp Tyr Trp
            100                 105                 110

Gly Gln Gly Thr Leu Val Thr Val Ser Ser
        115                 120

<210> SEQ ID NO 283
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser His Tyr

```
                20                  25                  30

Gly Val Ser Trp Ile Arg Gln Pro Gly Lys Gly Leu Glu Trp Ile
            35                  40                  45

Gly Leu Ile Trp Gly Gly Gly Asp Thr Tyr Tyr Asn Ser Pro Leu Lys
 50                  55                  60

Ser Arg Leu Thr Ile Ser Lys Asp Thr Ser Lys Ser Gln Val Ser Leu
 65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 284
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ser Asp Phe
                20                  25                  30

Gly Val Ser Trp Ile Arg Gln Pro Gly Lys Gly Leu Glu Trp Ile
            35                  40                  45

Gly Leu Ile Trp Gly Gly Gly Asp Thr Tyr Tyr Asn Ser Pro Leu Lys
 50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 285
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Gly Glu His
                20                  25                  30

Gly Val Ser Trp Ile Arg Gln Pro Gly Lys Gly Leu Glu Trp Ile
            35                  40                  45

Gly Ile Ile Trp Gly Gly Gly Asp Thr Tyr Tyr Asn Ser Pro Leu Lys
 50                  55                  60

Ser Arg Leu Thr Ile Ser Lys Asp Thr Ser Lys Ser Gln Val Ser Leu
```

```
                65                  70                  75                  80
Lys Leu Ser Ser Val Thr Ala Ala Asp Thr Ala Val Tyr Tyr Cys Ala
                    85                  90                  95

Lys Gln Arg Asn Leu Trp Gly Tyr Asp Leu Tyr Gly Met Asp Tyr Trp
                100                 105                 110

Gly Gln Gly Thr Leu Val Thr Val Ser Ser
        115                 120

<210> SEQ ID NO 286
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
                20                  25                  30

Gly Val Ser Trp Ile Arg Gln Ser Pro Gly Lys Gly Leu Glu Trp Leu
            35                  40                  45

Gly Leu Ile Trp Gly Gly Gly Asp Thr Tyr Tyr Asn Ser Pro Leu Lys
        50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                    85                  90                  95

Lys Gln Arg Asn Leu Trp Gly Tyr Asp Leu Tyr Gly Met Asp Tyr Trp
                100                 105                 110

Gly Gln Gly Thr Leu Val Thr Val Ser Ser
        115                 120

<210> SEQ ID NO 287
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Gly Glu Tyr
                20                  25                  30

Gly Val Ser Trp Ile Arg Gln Pro Pro Gly Lys Gly Leu Glu Trp Leu
            35                  40                  45

Gly Leu Ile Trp Gly Gly Gly Asp Thr Tyr Tyr Asn Ser Pro Leu Lys
        50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                    85                  90                  95

Lys Gln Arg Asn Ile Trp Gly Tyr Asp Leu Tyr Gly Met Asp Tyr Trp
                100                 105                 110

Gly Gln Gly Thr Leu Val Thr Val Ser Ser
```

115                 120

<210> SEQ ID NO 288
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Arg Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Ser Asn Val Trp Gly Tyr Asp Leu Tyr Ser Met Asp Tyr Trp
            100                 105                 110

Gly Gln Gly Thr Leu Val Thr Val Ser Ser
        115                 120

<210> SEQ ID NO 289
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Glu Tyr
            20                  25                  30

Gly Val Ser Trp Ile Arg Gln Pro Pro Gly Lys Gly Leu Glu Trp Ile
        35                  40                  45

Gly Leu Ile Trp Gly Ser Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Ala Tyr Asp Leu Tyr Gly Met Asp Tyr Trp
            100                 105                 110

Gly Gln Gly Thr Leu Val Thr Val Ser Ser
        115                 120

<210> SEQ ID NO 290
<211> LENGTH: 122
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 290

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys His Arg Asn Leu Trp Gly Phe Asp Leu Tyr Gly Met Asp Tyr Trp
            100                 105                 110

Gly Gln Gly Thr Leu Val Thr Val Ser Ser
        115                 120

<210> SEQ ID NO 291
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Ile Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 292
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Glu Tyr
            20                  25                  30

```
Gly Val Ser Trp Ile Arg Gln Pro Pro Gly Lys Gly Leu Glu Trp Ile
            35                  40                  45

Gly Leu Ile Trp Gly Gly Gly Asp Thr Tyr Tyr Asn Ser Pro Leu Lys
        50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120
```

<210> SEQ ID NO 293
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Glu Asp
            20                  25                  30

Leu Asn Trp Tyr Gln Gln Lys Pro Gly Lys Ala Pro Lys Leu Leu Ile
        35                  40                  45

Ser Leu Ala Ser Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Thr Asp Ser Phe Pro Leu
                85                  90                  95

Thr Phe Gly Gln Gly Thr Lys Leu Glu Ile Lys
            100                 105
```

<210> SEQ ID NO 294
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp Asp
            20                  25                  30

Met Asn Trp Tyr Gln Gln Lys Pro Gly Lys Ala Pro Lys Leu Leu Ile
        35                  40                  45

Ser Leu Ala Asn Lys Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Ser Leu Pro Leu
                85                  90                  95
```

```
Thr Phe Gly Gln Gly Thr Lys Leu Glu Ile Lys
            100                 105

<210> SEQ ID NO 295
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Asp Ile Gln Met Thr Gln Ser Pro Ser Ser Leu Ser Ala Ser Val Gly
1               5                   10                  15

Asp Arg Val Thr Ile Thr Cys Gln Thr Ser Gln Asp Ile Asp Asp Asp
            20                  25                  30

Met Asn Trp Tyr Gln Gln Lys Pro Gly Lys Ala Pro Lys Leu Leu Ile
        35                  40                  45

Ser Ser Ala Ser Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Lys Glu Lys Leu Pro Leu
                85                  90                  95

Thr Phe Gly Gln Gly Thr Lys Leu Glu Ile Lys
            100                 105

<210> SEQ ID NO 296
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Phe Asp
            20                  25                  30

Leu Asn Trp Tyr Gln Gln Lys Pro Gly Lys Ala Pro Lys Leu Leu Ile
        35                  40                  45

Ser Gln Ala Ser Thr Leu Ser Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Glu Lys Leu Pro Leu
                85                  90                  95

Thr Phe Gly Gln Gly Thr Lys Leu Glu Ile Lys
            100                 105

<210> SEQ ID NO 297
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297
```

Asp Ile Gln Met Thr Gln Ser Pro Ser Ser Leu Ser Ala Ser Val Gly
1               5                   10                  15

Asp Arg Val Thr Ile Thr Cys Gln Thr Ser Thr Asp Ile Asp Glu Asp
            20                  25                  30

Leu Asn Trp Tyr Gln Gln Lys Pro Gly Lys Ala Pro Lys Leu Leu Ile
        35                  40                  45

Ser Leu Ala Asn Asn Leu His Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Gly Asp Arg Leu Pro Leu
                85                  90                  95

Thr Phe Gly Gln Gly Thr Lys Leu Glu Ile Lys
            100                 105

<210> SEQ ID NO 298
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Gly Ser Thr Leu Gln Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Leu Pro Leu
                85                  90                  95

Thr Phe Gly Gln Gly Thr Lys Leu Glu Ile Lys
            100                 105

<210> SEQ ID NO 299
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Asp Ile Gln Met Thr Gln Ser Pro Ser Ser Leu Ser Ala Ser Val Gly
1               5                   10                  15

Asp Arg Val Thr Ile Thr Cys Gln Thr Ser Gln Asp Ile Asp Asp Asp
            20                  25                  30

Met Asn Trp Tyr Gln Gln Lys Pro Gly Lys Ala Pro Lys Leu Leu Ile
        35                  40                  45

Ser Leu Gly Ser His Leu Arg Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Phe Pro Leu
                85                  90                  95

Thr Phe Gly Gln Gly Thr Lys Leu Glu Ile Lys
            100                 105

<210> SEQ ID NO 300
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Asp Ile Gln Met Thr Gln Ser Pro Ser Ser Leu Ser Ala Ser Val Gly
1               5                   10                  15

Asp Arg Val Thr Ile Thr Cys Gln Thr Ser Gln Asp Ile Asp Glu Asp
            20                  25                  30

Leu Asn Trp Tyr Gln Gln Lys Pro Gly Lys Ala Pro Lys Leu Leu Ile
        35                  40                  45

Ser Leu Ala Ser Asn Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Leu Pro Leu
                85                  90                  95

Thr Phe Gly Gln Gly Thr Lys Leu Glu Ile Lys
            100                 105

<210> SEQ ID NO 301
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Val Asp
            20                  25                  30

Leu Asn Trp Tyr Gln Gln Lys Pro Gly Lys Ala Pro Lys Leu Leu Ile
        35                  40                  45

Ser Gln Ala Asn Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Trp Leu Pro Leu
                85                  90                  95

Thr Phe Gly Gln Gly Thr Lys Leu Glu Ile Lys
            100                 105

<210> SEQ ID NO 302
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 302

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Glu Asp
            20                  25                  30

Leu Asn Trp Tyr Gln Gln Lys Pro Gly Lys Ala Pro Lys Leu Leu Ile
        35                  40                  45

Ser Leu Ala Ser Thr Leu Pro Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Phe Pro Leu
                85                  90                  95

Thr Phe Gly Gln Gly Thr Lys Leu Glu Ile Lys
            100                 105

<210> SEQ ID NO 303
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Asp Ile Gln Met Thr Gln Ser Pro Ser Ser Leu Ser Ala Ser Val Gly
1               5                   10                  15

Asp Arg Val Thr Ile Thr Cys Gln Thr Ser Gln Asp Ile Asp Glu Asp
            20                  25                  30

Leu Asn Trp Tyr Gln Gln Lys Pro Gly Lys Ala Pro Lys Leu Leu Ile
        35                  40                  45

Ser Gln Ala Ser Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Glu Arg Leu Pro Leu
                85                  90                  95

Thr Phe Gly Gln Gly Thr Lys Leu Glu Ile Lys
            100                 105

<210> SEQ ID NO 304
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp
            20                  25                  30

Met Asn Trp Tyr Gln Gln Lys Pro Gly Lys Ala Pro Lys Leu Leu Ile
        35                  40                  45

Ser Leu Ala Ser Ser Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro

```
                65                  70                  75                  80
Glu Asp Phe Ala Thr Tyr Tyr Cys Leu Gln Val Asp Gly Leu Pro Leu
                    85                  90                  95

Thr Phe Gly Gln Gly Thr Lys Leu Glu Ile Lys
                100                 105

<210> SEQ ID NO 305
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
                20                  25                  30

Leu Asn Trp Tyr Gln Gln Lys Pro Gly Lys Ala Pro Lys Leu Leu Ile
            35                  40                  45

Ser Leu Ala Ser Thr Leu Trp Pro Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Ser Leu Pro Leu
                    85                  90                  95

Thr Phe Gly Gln Gly Thr Lys Leu Glu Ile Lys
                100                 105

<210> SEQ ID NO 306
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
                20                  25                  30

Leu Asn Trp Tyr Gln Gln Lys Pro Gly Lys Ala Pro Lys Leu Leu Ile
            35                  40                  45

Ser Gln Ala Ser Thr Leu Gly Pro Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Asp Arg Val Pro Leu
                    85                  90                  95

Thr Phe Gly Gln Gly Thr Lys Leu Glu Ile Lys
                100                 105

<210> SEQ ID NO 307
<211> LENGTH: 107
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 307

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Glu Asp
            20                  25                  30

Met Asn Trp Tyr Gln Gln Lys Pro Gly Lys Ala Pro Lys Leu Leu Ile
        35                  40                  45

Ser Gln Ala Asn Lys Leu Arg Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Asp Arg Val Pro Leu
                85                  90                  95

Thr Phe Gly Gln Gly Thr Lys Leu Glu Ile Lys
            100                 105

<210> SEQ ID NO 308
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Gly Ser Thr Leu Gln Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Asp Ser Phe Pro Leu
                85                  90                  95

Thr Phe Gly Gln Gly Thr Lys Leu Glu Ile Lys
            100                 105

<210> SEQ ID NO 309
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

Asp Ile Gln Met Thr Gln Ser Pro Ser Ser Leu Ser Ala Ser Val Gly
1               5                   10                  15

Asp Arg Val Thr Ile Thr Cys Gln Thr Ser Thr Asp Ile Asp Asp Asp
            20                  25                  30

Met Asn Trp Tyr Gln Gln Lys Pro Gly Lys Ala Pro Lys Leu Leu Ile
        35                  40                  45

Ser Leu Ala Ser Thr Leu Arg Pro Gly Val Pro Ser Arg Phe Ser Gly
    50                  55                  60

-continued

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Ser Trp Leu Pro Leu
                85                  90                  95

Thr Phe Gly Gln Gly Thr Lys Leu Glu Ile Lys
            100                 105

<210> SEQ ID NO 310
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp Asp
            20                  25                  30

Met Asn Trp Tyr Gln Gln Lys Pro Gly Lys Ala Pro Lys Leu Leu Ile
        35                  40                  45

Ser Leu Ala Asn Lys Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Thr Asp Ser Phe Pro Leu
                85                  90                  95

Thr Phe Gly Gln Gly Thr Lys Leu Glu Ile Lys
            100                 105

<210> SEQ ID NO 311
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Ser Thr Leu Trp Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Ser Phe Pro Leu
                85                  90                  95

Thr Phe Gly Gln Gly Thr Lys Leu Glu Ile Lys
            100                 105

<210> SEQ ID NO 312
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Asp Ile Gln Met Thr Gln Ser Pro Ser Ser Leu Ser Ala Ser Val Gly
1               5                   10                  15

Asp Arg Val Thr Ile Thr Cys Gln Thr Ser Thr Asp Ile Asp Asp Asp
            20                  25                  30

Leu Asn Trp Tyr Gln Gln Lys Pro Gly Lys Ala Pro Lys Leu Leu Ile
        35                  40                  45

Ser Gln Gly Ser Thr Leu Arg Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Asp Arg Val Pro Leu
                85                  90                  95

Thr Phe Gly Gln Gly Thr Lys Leu Glu Ile Lys
            100                 105

<210> SEQ ID NO 313
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Met Asp
            20                  25                  30

Met Asn Trp Tyr Gln Gln Lys Pro Gly Lys Ala Pro Lys Leu Leu Ile
        35                  40                  45

Ser Leu Gly Asn Ile Leu Arg Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Ser Phe Pro Leu
                85                  90                  95

Thr Phe Gly Gln Gly Thr Lys Leu Glu Ile Lys
            100                 105

<210> SEQ ID NO 314
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Val Asp
            20                  25                  30

Met Asn Trp Tyr Gln Gln Lys Pro Gly Lys Ala Pro Lys Leu Leu Ile
        35                  40                  45

Ser Leu Ala Ser Lys Leu Arg Pro Gly Val Pro Ser Arg Phe Ser Gly
            50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Val Glu Arg Phe Pro Leu
                 85                  90                  95

Thr Phe Gly Gln Gly Thr Lys Leu Glu Ile Lys
            100                 105

<210> SEQ ID NO 315
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Asp Ile Gln Met Thr Gln Ser Pro Ser Ser Leu Ser Ala Ser Val Gly
 1               5                  10                  15

Asp Arg Val Thr Ile Thr Cys Gln Ala Ser Thr Asn Ile Asp Asp Asp
            20                  25                  30

Met Asn Trp Tyr Gln Gln Lys Pro Gly Lys Ala Pro Lys Leu Leu Ile
            35                  40                  45

Ser Leu Ala Asn Met Leu Arg Pro Gly Val Pro Ser Arg Phe Ser Gly
            50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Gly Asp Arg Leu Pro Leu
                 85                  90                  95

Thr Phe Gly Gln Gly Thr Lys Leu Glu Ile Lys
            100                 105

<210> SEQ ID NO 316
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Asp Glu Asp
            20                  25                  30

Leu Asn Trp Tyr Gln Gln Lys Pro Gly Lys Ala Pro Lys Leu Leu Ile
            35                  40                  45

Ser Leu Ala Ser Thr Leu Arg Pro Gly Val Pro Ser Arg Phe Ser Gly
            50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Ser Asp Asn Leu Pro Leu
                 85                  90                  95

Thr Phe Gly Gln Gly Thr Lys Leu Glu Ile Lys
            100                 105

<210> SEQ ID NO 317
<211> LENGTH: 107

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Met Asn Trp Tyr Gln Gln Lys Pro Gly Lys Ala Pro Lys Leu Leu Ile
        35                  40                  45

Ser Leu Ala Ser Thr Leu Arg Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Ser Leu Pro Leu
                85                  90                  95

Thr Phe Gly Gln Gly Thr Lys Leu Glu Ile Lys
            100                 105

<210> SEQ ID NO 318
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Glu Asp
            20                  25                  30

Leu Asn Trp Tyr Gln Gln Lys Pro Gly Lys Ala Pro Lys Leu Leu Ile
        35                  40                  45

Ser Leu Ala Asn Ile Leu Arg Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Phe Pro Leu
                85                  90                  95

Thr Phe Gly Gln Gly Thr Lys Leu Glu Ile Lys
            100                 105

<210> SEQ ID NO 319
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Asp Ile Gln Met Thr Gln Ser Pro Ser Ser Leu Ser Ala Ser Val Gly
1               5                   10                  15

Asp Arg Val Thr Ile Thr Cys Ile Thr Ser Thr Asp Ile Asp Asp Asp
            20                  25                  30

Met Asn Trp Tyr Gln Gln Lys Pro Gly Lys Ala Pro Lys Leu Leu Ile

```
                35                  40                  45
Ser Gln Ala Ser Thr Leu Arg Pro Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Val Asp Arg Val Pro Leu
                 85                  90                  95

Thr Phe Gly Gln Gly Thr Lys Leu Glu Ile Lys
            100                 105
```

<210> SEQ ID NO 320
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Asp Met Asp
             20                  25                  30

Leu Asn Trp Tyr Gln Gln Lys Pro Gly Lys Ala Pro Lys Leu Leu Ile
         35                  40                  45

Ser Gln Gly Ser Thr Leu Trp Pro Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Val Glu Arg Phe Pro Leu
                 85                  90                  95

Thr Phe Gly Gln Gly Thr Lys Leu Glu Ile Lys
            100                 105
```

<210> SEQ ID NO 321
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Thr Asp Ile Asp Met Asp
             20                  25                  30

Leu Asn Trp Tyr Gln Gln Lys Pro Gly Lys Ala Pro Lys Leu Leu Ile
         35                  40                  45

Ser Gln Ala Asn Thr Leu Arg Pro Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Val Asp Arg Met Pro Leu
                 85                  90                  95

Thr Phe Gly Gln Gly Thr Lys Leu Glu Ile Lys
            100                 105
```

```
<210> SEQ ID NO 322
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp Asp
            20                  25                  30

Met Asn Trp Tyr Gln Gln Lys Pro Gly Lys Ala Pro Lys Leu Leu Ile
        35                  40                  45

Ser Gln Ala Asn Met Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Leu Pro Leu
                85                  90                  95

Thr Phe Gly Gln Gly Thr Lys Leu Glu Ile Lys
            100                 105

<210> SEQ ID NO 323
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Gly Ser Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Thr Asp Ser Phe Pro Leu
                85                  90                  95

Thr Phe Gly Gln Gly Thr Lys Leu Glu Ile Lys
            100                 105

<210> SEQ ID NO 324
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Glu Asp
            20                  25                  30
```

```
Leu Asn Trp Tyr Gln Gln Lys Pro Gly Lys Ala Pro Lys Leu Leu Ile
            35                  40                  45

Ser Leu Ala Asn Ile Leu Arg Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Leu Pro Leu
                85                  90                  95

Thr Phe Gly Gln Gly Thr Lys Leu Glu Ile Lys
            100                 105

<210> SEQ ID NO 325
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Asp Ile Gln Met Thr Gln Ser Pro Ser Ser Leu Ser Ala Ser Val Gly
1               5                   10                  15

Asp Arg Val Thr Ile Thr Cys Gln Thr Ser Gln Asp Ile Asp Glu Asp
            20                  25                  30

Leu Asn Trp Tyr Gln Gln Lys Pro Gly Lys Ala Pro Lys Leu Leu Ile
            35                  40                  45

Ser Leu Ala Ser Thr Leu Arg Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Asp Ser Phe Pro Leu
                85                  90                  95

Thr Phe Gly Gln Gly Thr Lys Leu Glu Ile Lys
            100                 105

<210> SEQ ID NO 326
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp Asp
            20                  25                  30

Leu Asn Trp Tyr Gln Gln Lys Pro Gly Lys Ala Pro Lys Leu Leu Ile
            35                  40                  45

Ser Leu Gly Ser Thr Leu Arg Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Met Pro Leu
                85                  90                  95

Thr Phe Gly Gln Gly Thr Lys Leu Glu Ile Lys
            100                 105
```

```
<210> SEQ ID NO 327
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Val Asp
            20                  25                  30

Met Asn Trp Tyr Gln Gln Lys Pro Gly Lys Ala Pro Lys Leu Leu Ile
        35                  40                  45

Ser Gln Gly Ser Thr Leu Pro Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ile Asp Arg Leu Pro Leu
                85                  90                  95

Thr Phe Gly Gln Gly Thr Lys Val Glu Ile Lys Arg
            100                 105

<210> SEQ ID NO 328
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 328

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp Asp
            20                  25                  30

Met Asn Trp Tyr Gln Gln Lys Pro Gly Lys Ala Pro Lys Leu Leu Ile
        35                  40                  45

Ser Leu Ala Asn Lys Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Leu Pro Leu
                85                  90                  95

Thr Phe Gly Gln Gly Thr Lys Leu Glu Ile Lys
            100                 105

<210> SEQ ID NO 329
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Asp Ile Gln Met Thr Gln Ser Pro Ser Ser Leu Ser Ala Ser Val Gly
1               5                   10                  15
```

```
Asp Arg Val Thr Ile Thr Cys Gln Ala Ser Thr Ile Asp Asp Asp
            20                  25                  30

Leu Asn Trp Tyr Gln Gln Lys Pro Gly Lys Ala Pro Lys Leu Leu Ile
        35                  40                  45

Ser Leu Gly Ser Ser Leu Trp Pro Gly Val Pro Ser Arg Phe Ser Gly
 50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Gly Asp Ser Met Pro Leu
                85                  90                  95

Thr Phe Gly Gln Gly Thr Lys Leu Glu Ile Lys
                100                 105
```

<210> SEQ ID NO 330
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp Asp
            20                  25                  30

Met Asn Trp Tyr Gln Gln Lys Pro Gly Lys Ala Pro Lys Leu Leu Ile
        35                  40                  45

Ser Leu Ala Asn Lys Leu Arg Pro Gly Val Pro Ser Arg Phe Ser Gly
 50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Phe Pro Leu
                85                  90                  95

Thr Phe Gly Gln Gly Thr Lys Leu Glu Ile Lys
                100                 105
```

<210> SEQ ID NO 331
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

```
Asp Ile Gln Met Thr Gln Ser Pro Ser Ser Leu Ser Ala Ser Val Gly
1               5                   10                  15

Asp Arg Val Thr Ile Thr Cys Gln Thr Ser Thr Asp Ile Asp Val Asp
            20                  25                  30

Met Asn Trp Tyr Gln Gln Lys Pro Gly Lys Ala Pro Lys Leu Leu Ile
        35                  40                  45

Ser Leu Ala Ser Thr Leu Arg Pro Gly Val Pro Ser Arg Phe Ser Gly
 50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Phe Pro Leu
                85                  90                  95
```

Thr Phe Gly Gln Gly Thr Lys Leu Glu Ile Lys
            100                 105

<210> SEQ ID NO 332
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

Asp Ile Gln Met Thr Gln Ser Pro Ser Ser Leu Ser Ala Ser Val Gly
1               5                   10                  15

Asp Arg Val Thr Ile Thr Cys Gln Thr Ser Thr Asp Ile Asp Asp Asp
            20                  25                  30

Met Asn Trp Tyr Gln Gln Lys Pro Gly Lys Ala Pro Lys Leu Leu Ile
        35                  40                  45

Ser Gln Gly Ser Leu Leu Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Ser Asp Arg Leu Pro Leu
                85                  90                  95

Thr Phe Gly Gln Gly Thr Lys Leu Glu Ile Lys
            100                 105

<210> SEQ ID NO 333
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Val Asp
            20                  25                  30

Met Asn Trp Tyr Gln Gln Lys Pro Gly Lys Ala Pro Lys Leu Leu Ile
        35                  40                  45

Ser Leu Gly Asn Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Leu Pro Leu
                85                  90                  95

Thr Phe Gly Gln Gly Thr Lys Leu Glu Ile Lys
            100                 105

<210> SEQ ID NO 334
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Asp Ile Gln Met Thr Gln Ser Pro Ser Ser Leu Ser Ala Ser Val Gly

```
  1               5                  10                 15
Asp Arg Val Thr Ile Thr Cys Gln Ala Ser Thr Asp Ile Asp Asp Asp
            20                  25                 30

Met Asn Trp Tyr Gln Gln Lys Pro Gly Lys Ala Pro Lys Leu Leu Ile
        35                  40                 45

Ser Leu Ala Ser Thr Leu Trp Pro Gly Val Pro Ser Arg Phe Ser Gly
    50                  55                 60

Ser Gly Ser Gly Thr Asp Phe Thr Phe Thr Ile Ser Ser Leu Gln Pro
65                  70                 75                 80

Glu Asp Phe Ala Thr Tyr Tyr Cys Leu Gln Gly Asp Ser Leu Pro Leu
                85                  90                 95

Thr Phe Gly Gln Gly Thr Lys Leu Glu Ile Lys
            100                 105
```

<210> SEQ ID NO 335
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

```
Asp Ile Gln Met Thr Gln Ser Pro Ser Ser Leu Ser Ala Ser Val Gly
1               5                  10                 15

Asp Arg Val Thr Ile Thr Cys Gln Ala Ser Gln Asp Ile Asp Asp Asp
            20                  25                 30

Leu Asn Trp Tyr Gln Gln Lys Pro Gly Lys Ala Pro Lys Leu Leu Ile
        35                  40                 45

Ser Leu Ala Asn Thr Leu Arg Pro Gly Val Pro Ser Arg Phe Ser Gly
    50                  55                 60

Ser Gly Ser Gly Thr Asp Phe Thr Phe Thr Ile Ser Ser Leu Gln Pro
65                  70                 75                 80

Glu Asp Phe Ala Thr Tyr Tyr Cys Leu Gln Ser Ser Trp Leu Pro Leu
                85                  90                 95

Thr Phe Gly Gln Gly Thr Lys Leu Glu Ile Lys
            100                 105
```

<210> SEQ ID NO 336
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

```
Asp Ile Gln Met Thr Gln Ser Pro Ser Ser Leu Ser Ala Ser Val Gly
1               5                  10                 15

Asp Arg Val Thr Ile Thr Cys Thr Ser Thr Asp Ile Asp Asp Asp
            20                  25                 30

Leu Asn Trp Tyr Gln Gln Lys Pro Gly Lys Ala Pro Lys Leu Leu Ile
        35                  40                 45

Ser Leu Ala Ser Thr Leu Arg Pro Gly Val Pro Ser Arg Phe Ser Gly
    50                  55                 60

Ser Gly Ser Gly Thr Asp Phe Thr Phe Thr Ile Ser Ser Leu Gln Pro
65                  70                 75                 80

Glu Asp Phe Ala Thr Tyr Tyr Cys Leu Gln Ser Asp Arg Val Pro Leu
```

```
                85                  90                  95

Thr Phe Gly Gln Gly Thr Lys Leu Glu Ile Lys
            100                 105

<210> SEQ ID NO 337
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 337

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Asn Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Ser Leu Pro Leu
                85                  90                  95

Thr Phe Gly Gln Gly Thr Lys Leu Glu Ile Lys
            100                 105

<210> SEQ ID NO 338
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Asn Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Lys Met Pro Leu
                85                  90                  95

Thr Phe Gly Gln Gly Thr Lys Leu Glu Ile Lys
            100                 105

<210> SEQ ID NO 339
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339
```

```
Asp Ile Gln Met Thr Gln Ser Pro Ser Ser Leu Ser Ala Ser Val Gly
1               5                   10                  15

Asp Arg Val Thr Ile Thr Cys Gln Thr Ser Gln Asp Ile Asp Val Asp
            20                  25                  30

Met Asn Trp Tyr Gln Gln Lys Pro Gly Lys Ala Pro Lys Leu Leu Ile
        35                  40                  45

Ser Leu Gly Ser Thr Leu Arg Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Leu Pro Leu
                85                  90                  95

Thr Phe Gly Gln Gly Thr Lys Leu Glu Ile Lys
            100                 105

<210> SEQ ID NO 340
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Asp Ile Gln Met Thr Gln Ser Pro Ser Ser Leu Ser Ala Ser Val Gly
1               5                   10                  15

Asp Arg Val Thr Ile Thr Cys Gln Thr Ser Thr Asp Ile Asp Phe Asp
            20                  25                  30

Met Asn Trp Tyr Gln Gln Lys Pro Gly Lys Ala Pro Lys Leu Leu Ile
        35                  40                  45

Ser Gln Gly Ser Met Leu Arg Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Asp Arg Val Pro Leu
                85                  90                  95

Thr Phe Gly Gln Gly Thr Lys Leu Glu Ile Lys
            100                 105

<210> SEQ ID NO 341
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Any amino acid

<400> SEQUENCE: 341

Asp Ile Gln Met Thr Gln Ser Pro Ser Ser Leu Ser Ala Ser Val Gly
1               5                   10                  15

Asp Arg Val Thr Ile Thr Xaa Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Asn Thr Leu Arg Pro Gly Val Pro Ser Arg Phe Ser Gly
```

```
                50                  55                  60
Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Ser Asp Arg Leu Pro Leu
                 85                  90                  95

Thr Phe Gly Gln Gly Thr Lys Leu Glu Ile Lys
               100                 105
```

<210> SEQ ID NO 342
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: Any amino acid

<400> SEQUENCE: 342

```
Asp Ile Gln Met Thr Gln Ser Pro Ser Ser Leu Ser Ala Ser Val Gly
  1               5                  10                  15

Asp Arg Val Thr Ile Thr Cys Gln Xaa Ser Gln Asp Ile Asp Asp Asp
                 20                  25                  30

Leu Asn Trp Tyr Gln Gln Lys Pro Gly Lys Ala Pro Lys Leu Leu Ile
             35                  40                  45

Ser Leu Ala Ser Ile Leu Arg Pro Gly Val Pro Ser Arg Phe Ser Gly
         50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Ser Asp Ser Phe Pro Leu
                 85                  90                  95

Thr Phe Gly Gln Gly Thr Lys Leu Glu Ile Lys
               100                 105
```

<210> SEQ ID NO 343
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 343

```
Asp Ile Gln Met Thr Gln Ser Pro Ser Ser Leu Ser Ala Ser Val Gly
  1               5                  10                  15

Asp Arg Val Thr Ile Thr Cys Gln Ala Ser Thr Asp Ile Asp Ile Asp
                 20                  25                  30

Met Asn Trp Tyr Gln Gln Lys Pro Gly Lys Ala Pro Lys Leu Leu Ile
             35                  40                  45

Ser Leu Gly Ser Ile Leu Arg Pro Gly Val Pro Ser Arg Phe Ser Gly
         50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Gln Gln Gly Asp Arg Phe Pro Leu
                 85                  90                  95

Thr Phe Gly Gln Gly Thr Lys Leu Glu Ile Lys
               100                 105
```

<210> SEQ ID NO 344
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 344

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Ser Ile Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Asp Ser Phe Pro Leu
                85                  90                  95

Thr Phe Gly Gln Gly Thr Lys Leu Glu Ile Lys
            100                 105

<210> SEQ ID NO 345
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 345

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Ser Ile Leu Arg His Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Ser Phe Pro Leu
                85                  90                  95

Thr Phe Gly Gln Gly Thr Lys Leu Glu Ile Lys
            100                 105

<210> SEQ ID NO 346
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 346

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Glu Asp

```
                20                  25                  30

Leu Asn Trp Tyr Gln Gln Lys Pro Gly Lys Ala Pro Lys Leu Leu Ile
            35                  40                  45

Ser Leu Ala Asn Ile Leu Arg Pro Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Val Asp Met Leu Pro Leu
                85                  90                  95

Thr Phe Gly Gln Gly Thr Lys Leu Glu Ile Lys
            100                 105

<210> SEQ ID NO 347
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

Asp Ile Gln Met Thr Gln Ser Pro Ser Ser Leu Ser Ala Ser Val Gly
 1               5                  10                  15

Asp Arg Val Thr Ile Thr Cys Gln Thr Ser Thr Asp Ile Asp Asp Asp
                20                  25                  30

Leu Asn Trp Tyr Gln Gln Lys Pro Gly Lys Ala Pro Lys Leu Leu Ile
            35                  40                  45

Ser Gln Ala Ser Thr Leu Arg Pro Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Val Asp Arg Val Pro Leu
                85                  90                  95

Thr Phe Gly Gln Gly Thr Lys Leu Glu Ile Lys
            100                 105

<210> SEQ ID NO 348
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Asp Ile Gln Met Thr Gln Ser Pro Ser Ser Leu Ser Ala Ser Val Gly
 1               5                  10                  15

Asp Arg Val Thr Ile Thr Cys Gln Ala Ser Thr Asp Ile Asp Asp Asp
                20                  25                  30

Leu Asn Trp Tyr Gln Gln Lys Pro Gly Lys Ala Pro Lys Leu Leu Ile
            35                  40                  45

Ser Leu Gly Ser Thr Leu Arg Pro Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Ser Asp Arg Leu Pro Leu
                85                  90                  95

Thr Phe Gly Gln Gly Thr Lys Leu Glu Ile Lys
```

```
                            100                 105

<210> SEQ ID NO 349
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Asp Ile Gln Met Thr Gln Ser Pro Ser Ser Leu Ser Ala Ser Val Gly
1               5                   10                  15

Asp Arg Val Thr Ile Thr Cys Gln Thr Ser Thr Asp Ile Asp Val Asp
            20                  25                  30

Met Asn Trp Tyr Gln Gln Lys Pro Gly Lys Ala Pro Lys Leu Leu Ile
        35                  40                  45

Ser Gln Ala Ser Thr Leu Ile Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Glu Arg Leu Pro Leu
                85                  90                  95

Thr Phe Gly Gln Gly Thr Lys Leu Glu Ile Lys
            100                 105

<210> SEQ ID NO 350
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Asp Ile Gln Met Thr Gln Ser Pro Ser Ser Leu Ser Ala Ser Val Gly
1               5                   10                  15

Asp Arg Val Thr Ile Thr Cys Gln Thr Ser Thr Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Ser Lys Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Asp Ser Phe Pro Leu
                85                  90                  95

Thr Phe Gly Gln Gly Thr Lys Leu Glu Ile Lys
            100                 105

<210> SEQ ID NO 351
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 351

Asp Ile Gln Met Thr Gln Ser Pro Ser Ser Leu Ser Ala Ser Val Gly
1               5                   10                  15
```

-continued

```
Asp Arg Val Thr Ile Thr Cys Gln Ala Ser Thr Asp Ile Asp Glu Asp
            20                  25                  30

Leu Asn Trp Tyr Gln Gln Lys Pro Gly Lys Ala Pro Lys Leu Leu Ile
        35                  40                  45

Ser Leu Ala Ser Thr Leu Arg Pro Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Thr Asp Ser Phe Pro Leu
                85                  90                  95

Thr Phe Gly Gln Gly Thr Lys Leu Glu Ile Lys
            100                 105

<210> SEQ ID NO 352
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 352

Asp Ile Gln Met Thr Gln Ser Pro Ser Ser Leu Ser Ala Ser Val Gly
1               5                  10                  15

Asp Arg Val Thr Ile Thr Cys Gln Thr Ser Asp Ile Asp Glu Asp
            20                  25                  30

Met Asn Trp Tyr Gln Gln Lys Pro Gly Lys Ala Pro Lys Leu Leu Ile
        35                  40                  45

Ser Leu Ala Ser Met Leu Arg Pro Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Gly Asp Arg Leu Pro Leu
                85                  90                  95

Thr Phe Gly Gln Gly Thr Lys Leu Glu Ile Lys
            100                 105

<210> SEQ ID NO 353
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 353

Asp Ile Gln Met Thr Gln Ser Pro Ser Ser Leu Ser Ala Ser Val Gly
1               5                  10                  15

Asp Arg Val Thr Ile Thr Cys Gln Ala Ser Thr Asp Ile Asp Ala Asp
            20                  25                  30

Leu Asn Trp Tyr Gln Gln Lys Pro Gly Lys Ala Pro Lys Leu Leu Ile
        35                  40                  45

Ser Gln Ala Asn Thr Leu Trp Pro Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Val Asp Arg Phe Pro Leu
                85                  90                  95
```

Thr Phe Gly Gln Gly Thr Lys Leu Glu Ile Lys
            100                 105

<210> SEQ ID NO 354
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Ile Asp
            20                  25                  30

Met Asn Trp Tyr Gln Gln Lys Pro Gly Lys Ala Pro Lys Leu Leu Ile
        35                  40                  45

Ser Leu Gly Ser Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Gly Asp Lys Phe Pro Leu
                85                  90                  95

Thr Phe Gly Gln Gly Thr Lys Leu Glu Ile Lys
            100                 105

<210> SEQ ID NO 355
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Met Asp
            20                  25                  30

Leu Asn Trp Tyr Gln Gln Lys Pro Gly Lys Ala Pro Lys Leu Leu Ile
        35                  40                  45

Ser Gln Ala Ser Ser Leu Thr Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Glu Lys Leu Pro Leu
                85                  90                  95

Thr Phe Gly Gln Gly Thr Lys Leu Glu Ile Lys
            100                 105

<210> SEQ ID NO 356
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

```
Asp Ile Gln Met Thr Gln Ser Pro Ser Ser Leu Ser Ala Ser Val Gly
1               5                   10                  15

Asp Arg Val Thr Ile Thr Cys Gln Thr Ser Gln Asp Ile Asp Ala Asp
            20                  25                  30

Leu Asn Trp Tyr Gln Gln Lys Pro Gly Lys Ala Pro Lys Leu Leu Ile
        35                  40                  45

Ser Gln Ala Ser Lys Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Glu Ser Leu Pro Leu
                85                  90                  95

Thr Phe Gly Gln Gly Thr Lys Leu Glu Ile Lys
            100                 105
```

<210> SEQ ID NO 357
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 357

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Gly Ser Thr Leu Ser Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Asp Trp Leu Pro Leu
                85                  90                  95

Thr Phe Gly Gln Gly Thr Lys Leu Glu Ile Lys
            100                 105
```

<210> SEQ ID NO 358
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 358

```
Asp Ile Gln Met Thr Gln Ser Pro Ser Ser Leu Ser Ala Ser Val Gly
1               5                   10                  15

Asp Arg Val Thr Ile Thr Cys Gln Thr Ser Thr Asp Ile Asp Asp Asp
            20                  25                  30

Leu Asn Trp Tyr Gln Gln Lys Pro Gly Lys Ala Pro Lys Leu Leu Ile
        35                  40                  45

Ser Gln Ala Ser Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80
```

Glu Asp Phe Ala Thr Tyr Tyr Cys Leu Gln Val Asp Arg Met Pro Leu
                85                  90                  95

Thr Phe Gly Gln Gly Thr Lys Leu Glu Ile Lys
            100                 105

<210> SEQ ID NO 359
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

Asp Ile Gln Met Thr Gln Ser Pro Ser Ser Leu Ser Ala Ser Val Gly
1               5                   10                  15

Asp Arg Val Thr Ile Thr Cys Gln Val Ser Gln Ile Asp Asp Asp
            20                  25                  30

Leu Asn Trp Tyr Gln Gln Lys Pro Gly Lys Ala Pro Lys Leu Leu Ile
            35                  40                  45

Ser Leu Ala Ser Thr Leu Trp Pro Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Gly Asp Ser Leu Pro Leu
                85                  90                  95

Thr Phe Gly Gln Gly Thr Lys Leu Glu Ile Lys
            100                 105

<210> SEQ ID NO 360
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 360

Asp Ile Gln Met Thr Gln Ser Pro Ser Ser Leu Ser Ala Ser Val Gly
1               5                   10                  15

Asp Arg Val Thr Ile Thr Cys Gln Thr Ser Thr Asp Ile Asp Val Asp
            20                  25                  30

Met Asn Trp Tyr Gln Gln Lys Pro Gly Lys Ala Pro Lys Leu Leu Ile
            35                  40                  45

Ser Gln Ala Asn Ile Leu Ser Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Glu Lys Leu Pro Leu
                85                  90                  95

Thr Phe Gly Gln Gly Thr Lys Leu Glu Ile Lys
            100                 105

<210> SEQ ID NO 361
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361

Asp Ile Arg Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Met Asp
            20                  25                  30

Leu Asn Trp Tyr Gln Gln Lys Pro Gly Lys Ala Pro Lys Leu Leu Ile
        35                  40                  45

Ser Gln Ala Ser Thr Leu Leu Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ile Asp Glu Leu Pro Leu
                85                  90                  95

Thr Phe Gly Gln Gly Thr Lys Leu Glu Ile Lys
            100                 105

<210> SEQ ID NO 362
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 362

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Glu Asp
            20                  25                  30

Met Asn Trp Tyr Gln Gln Lys Pro Gly Lys Ala Pro Lys Leu Leu Ile
        35                  40                  45

Ser Gln Ala Ser Thr Leu Gly Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Asp Ser Phe Pro Leu
                85                  90                  95

Thr Phe Gly Gln Gly Thr Lys Leu Glu Ile Lys
            100                 105

<210> SEQ ID NO 363
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 363

Asp Ile Gln Met Thr Gln Ser Pro Ser Ser Leu Ser Ala Ser Val Gly
1               5                   10                  15

Asp Arg Val Thr Ile Thr Cys Ile Thr Ser Gln Asp Ile Asp Glu Asp
            20                  25                  30

Leu Asn Trp Tyr Gln Gln Lys Pro Gly Lys Ala Pro Lys Leu Leu Ile
        35                  40                  45

Ser Leu Ala Ser Thr Leu Leu Pro Gly Val Pro Ser Arg Phe Ser Gly
50                  55                  60

Ser Gly Ser Gly Thr Asp Phe Thr Phe Thr Ile Ser Ser Leu Gln Pro

```
              65                  70                  75                  80
Glu Asp Phe Ala Thr Tyr Tyr Cys Leu Gln Ser Asp Arg Leu Pro Leu
                    85                  90                  95
Thr Phe Gly Gln Gly Thr Lys Leu Glu Ile Lys
                100                 105

<210> SEQ ID NO 364
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

Asp Ile Gln Met Thr Gln Ser Pro Ser Ser Leu Ser Ala Ser Val Gly
1               5                   10                  15
Asp Arg Val Thr Ile Thr Cys Gln Ala Ser Thr Asp Ile Asp Asp Asp
                20                  25                  30
Leu Asn Trp Tyr Gln Gln Lys Pro Gly Lys Ala Pro Lys Leu Leu Ile
            35                  40                  45
Ser Leu Ala Ser Met Leu Gly Pro Gly Val Pro Ser Arg Phe Ser Gly
        50                  55                  60
Ser Gly Ser Gly Thr Asp Phe Thr Phe Thr Ile Ser Ser Leu Gln Pro
65                  70                  75                  80
Glu Asp Phe Ala Thr Tyr Tyr Cys Leu Gln Thr Asp Ser Phe Pro Leu
                    85                  90                  95
Thr Phe Gly Gln Gly Thr Lys Leu Glu Ile Lys
                100                 105

<210> SEQ ID NO 365
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 365

Asp Ile Gln Met Thr Gln Ser Pro Ser Ser Leu Ser Ala Ser Val Gly
1               5                   10                  15
Asp Arg Val Thr Ile Thr Cys Gln Ala Ser Thr Asp Ile Asp Asp Asp
                20                  25                  30
Leu Asn Trp Tyr Gln Gln Lys Pro Gly Lys Ala Pro Lys Leu Leu Ile
            35                  40                  45
Ser Leu Gly Ser Ile Leu Arg Pro Gly Val Pro Ser Arg Phe Ser Gly
        50                  55                  60
Ser Gly Ser Gly Thr Asp Phe Thr Phe Thr Ile Ser Ser Leu Gln Pro
65                  70                  75                  80
Glu Asp Phe Ala Thr Tyr Tyr Cys Gln Gln Gly Asp Arg Phe Pro Leu
                    85                  90                  95
Thr Phe Gly Gln Gly Thr Lys Leu Glu Ile Lys
                100                 105

<210> SEQ ID NO 366
<211> LENGTH: 107
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 366

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp Asp
            20                  25                  30

Leu Asn Trp Tyr Gln Gln Lys Pro Gly Lys Ala Pro Lys Leu Leu Ile
        35                  40                  45

Ser Ser Ala Asn Thr Leu Leu Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Lys Glu Lys Leu Pro Leu
                85                  90                  95

Thr Phe Gly Gln Gly Thr Lys Leu Glu Ile Lys
            100                 105

<210> SEQ ID NO 367
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 367

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Ser Thr Leu Trp Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Phe Pro Leu
                85                  90                  95

Thr Phe Gly Gln Gly Thr Lys Leu Glu Ile Lys
            100                 105

<210> SEQ ID NO 368
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 368

Asp Ile Gln Met Thr Gln Ser Pro Ser Ser Leu Ser Ala Ser Val Gly
1               5                   10                  15

Asp Arg Val Thr Ile Thr Cys Thr Ser Gln Asp Ile Asp Met Asp
            20                  25                  30

Leu Asn Trp Tyr Gln Gln Lys Pro Gly Lys Ala Pro Lys Leu Leu Ile
        35                  40                  45

Ser Gln Gly Ser Thr Leu Trp Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Thr Asp Ser Phe Pro Leu
                85                  90                  95

Thr Phe Gly Gln Gly Thr Lys Leu Glu Ile Lys
            100                 105

<210> SEQ ID NO 369
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 369

Gly Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Met Asn Trp Tyr Gln Gln Lys Pro Gly Lys Ala Pro Lys Leu Leu Ile
        35                  40                  45

Ser Leu Ala Ser Met Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Ser Phe Pro Leu
                85                  90                  95

Thr Phe Gly Gln Gly Thr Lys Leu Glu Ile Lys
            100                 105

<210> SEQ ID NO 370
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 370

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Ser Ile Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ile Asp Ser Phe Pro Leu
                85                  90                  95

Thr Phe Gly Gln Gly Thr Lys Leu Glu Ile Lys
            100                 105

<210> SEQ ID NO 371
<211> LENGTH: 107
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 371

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Ser Asn Leu Arg Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Ser Phe Pro Leu
                85                  90                  95

Thr Phe Gly Gln Gly Thr Lys Leu Glu Ile Lys
            100                 105

<210> SEQ ID NO 372
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 372

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Glu Asp
            20                  25                  30

Leu Asn Trp Tyr Gln Gln Lys Pro Gly Lys Ala Pro Lys Leu Leu Ile
        35                  40                  45

Ser Gln Gly Ser Thr Leu Trp Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Gly Asp Arg Leu Pro Leu
                85                  90                  95

Thr Phe Gly Gln Gly Thr Lys Leu Glu Ile Lys
            100                 105

<210> SEQ ID NO 373
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 373

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Thr Asp
            20                  25                  30

Leu Asn Trp Tyr Gln Gln Lys Pro Gly Lys Ala Pro Lys Leu Leu Ile
        35                  40                  45
```

-continued

Ser Gln Ala Ser Thr Leu Phe Pro Gly Val Pro Ser Arg Phe Ser Gly
            50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Trp Leu Pro Leu
                85                  90                  95

Thr Phe Gly Gln Gly Thr Lys Leu Glu Ile Lys
            100                 105

<210> SEQ ID NO 374
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 374

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
            35                  40                  45

Ser Leu Ala Ser Ile Leu Arg Pro Gly Val Pro Ser Arg Phe Ser Gly
            50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Ser Phe Pro Leu
                85                  90                  95

Thr Phe Gly Gln Gly Thr Lys Leu Glu Ile Lys
            100                 105

<210> SEQ ID NO 375
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 375

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Val Asp
            20                  25                  30

Leu Asn Trp Tyr Gln Gln Lys Pro Gly Lys Ala Pro Lys Leu Leu Ile
            35                  40                  45

Ser Leu Gly Asn Ile Leu Arg Pro Gly Val Pro Ser Arg Phe Ser Gly
            50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Leu Pro Leu
                85                  90                  95

Thr Phe Gly Gln Gly Thr Lys Leu Glu Ile Lys
            100                 105

<210> SEQ ID NO 376
<211> LENGTH: 107

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 376

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Asn Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Phe Pro Leu
                85                  90                  95

Thr Phe Gly Gln Gly Thr Lys Leu Glu Ile Lys
            100                 105

<210> SEQ ID NO 377
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 377

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Ser Thr Leu Trp Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Asp Arg Phe Pro Leu
                85                  90                  95

Thr Phe Gly Gln Gly Thr Lys Leu Glu Ile Lys
            100                 105

<210> SEQ ID NO 378
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 378

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
```

```
            35                  40                  45

Ser Leu Ala Ser Asn Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Trp Leu Pro Leu
                85                  90                  95

Thr Phe Gly Gln Gly Thr Lys Leu Glu Ile Lys
            100                 105

<210> SEQ ID NO 379
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 379

Asp Ile Gln Met Thr Gln Ser Pro Ser Ser Leu Ser Ala Ser Val Gly
1               5                   10                  15

Asp Arg Val Thr Ile Thr Cys Gln Thr Ser Thr Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Ser Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Leu Pro Leu
                85                  90                  95

Thr Phe Gly Gln Gly Thr Lys Leu Glu Ile Lys
            100                 105

<210> SEQ ID NO 380
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 380

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Gly Ser Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Phe Pro Leu
                85                  90                  95

Thr Phe Gly Gln Gly Thr Lys Leu Glu Ile Lys
            100                 105
```

-continued

```
<210> SEQ ID NO 381
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 381

Asp Ile Gln Met Thr Gln Ser Pro Ser Ser Leu Ser Ala Ser Val Gly
1               5                   10                  15

Asp Arg Val Thr Ile Thr Cys Gln Thr Ser Thr Asp Ile Asp Val Asp
            20                  25                  30

Leu Asn Trp Tyr Gln Gln Lys Pro Gly Lys Ala Pro Lys Leu Leu Ile
        35                  40                  45

Ser Gln Ala Ser Thr Leu His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Glu Arg Leu Pro Leu
                85                  90                  95

Thr Phe Gly Gln Gly Thr Lys Leu Glu Ile Lys
            100                 105

<210> SEQ ID NO 382
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 382

Asp Ile Gln Met Thr Gln Ser Pro Ser Ser Leu Ser Ala Ser Val Gly
1               5                   10                  15

Asp Arg Val Thr Ile Thr Cys Gln Thr Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Gln Ala Ser Thr Leu Phe Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Gly Asp Arg Leu Pro Leu
                85                  90                  95

Thr Phe Gly Gln Gly Thr Lys Leu Glu Ile Lys
            100                 105

<210> SEQ ID NO 383
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 383

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp Asp
            20                  25                  30
```

```
Leu Asn Trp Tyr Gln Gln Lys Pro Gly Lys Ala Pro Lys Leu Leu Ile
            35                  40                  45

Ser Leu Ala Asn Met Leu His Pro Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Ser Asp Arg Phe Pro Leu
                 85                  90                  95

Thr Phe Gly Gln Gly Thr Lys Leu Glu Ile Lys
            100                 105
```

<210> SEQ ID NO 384
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 384

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
            35                  40                  45

Ser Leu Ala Ser Thr Leu Arg Pro Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Ser Asp Ser Phe Pro Leu
                 85                  90                  95

Thr Phe Gly Gln Gly Thr Lys Leu Glu Ile Lys
            100                 105
```

<210> SEQ ID NO 385
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 385

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
            35                  40                  45

Ser Leu Gly Ser Thr Leu Gln Pro Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Val Asp Trp Leu Pro Leu
                 85                  90                  95

Thr Phe Gly Gln Gly Thr Lys Leu Glu Ile Lys
            100                 105
```

<210> SEQ ID NO 386
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 386

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Asn Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Ser Phe Pro Leu
                85                  90                  95

Thr Phe Gly Gln Gly Thr Lys Leu Glu Ile Lys
            100                 105

<210> SEQ ID NO 387
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 387

Asp Ile Gln Met Thr Gln Ser Pro Ser Ser Leu Ser Ala Ser Val Gly
1               5                   10                  15

Asp Arg Val Thr Ile Thr Cys Gln Thr Ser Gln Asp Ile Asp Asp Asp
            20                  25                  30

Met Asn Trp Tyr Gln Gln Lys Pro Gly Lys Ala Pro Lys Leu Leu Ile
        35                  40                  45

Ser Leu Ala Ser Met Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Leu Pro Leu
                85                  90                  95

Thr Phe Gly Gln Gly Thr Lys Leu Glu Ile Lys
            100                 105

<210> SEQ ID NO 388
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 388

Asp Ile Gln Met Thr Gln Ser Pro Ser Ser Leu Ser Ala Ser Val Gly
1               5                   10                  15

Asp Arg Val Thr Ile Thr Cys Gln Thr Ser Gln Asp Ile Asp Asp
            20                  25                  30

Met Asn Trp Tyr Gln Gln Lys Pro Gly Lys Ala Pro Lys Leu Leu Ile
        35                  40                  45

Ser Gln Gly Ser Ser Leu Leu Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Asp Arg Val Pro Leu
                85                  90                  95

Thr Phe Gly Gln Gly Thr Lys Leu Glu Ile Lys
            100                 105

<210> SEQ ID NO 389
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 389

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp
            20                  25                  30

Leu Asn Trp Tyr Gln Gln Lys Pro Gly Lys Ala Pro Lys Leu Leu Ile
        35                  40                  45

Ser Leu Ala Ser Thr Leu Trp Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Leu Pro Leu
                85                  90                  95

Thr Phe Gly Gln Gly Thr Lys Leu Glu Ile Lys
            100                 105

<210> SEQ ID NO 390
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 390

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp
            20                  25                  30

Met Asn Trp Tyr Gln Gln Lys Pro Gly Lys Ala Pro Lys Leu Leu Ile
        35                  40                  45

Ser Gln Ala Ser Thr Leu Ile Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Asp Ser Phe Pro Leu
                85                  90                  95

```
Thr Phe Gly Gln Gly Thr Lys Leu Glu Ile Lys
            100                 105

<210> SEQ ID NO 391
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 391

Asp Ile Gln Met Thr Gln Ser Pro Ser Ser Leu Ser Ala Ser Val Gly
1               5                   10                  15

Asp Arg Val Thr Ile Thr Cys Gln Thr Ser Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Ser Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Ser Phe Pro Leu
                85                  90                  95

Thr Phe Gly Gln Gly Thr Lys Leu Glu Ile Lys
            100                 105

<210> SEQ ID NO 392
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 392

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Ser Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Phe Pro Leu
                85                  90                  95

Thr Phe Gly Gln Gly Thr Lys Leu Glu Ile Lys
            100                 105

<210> SEQ ID NO 393
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 393

Asp Ile Gln Met Thr Gln Ser Pro Ser Ser Leu Ser Ala Ser Val Gly
```

```
                1               5                  10                    15
Asp Arg Val Thr Ile Thr Cys Ile Ala Ser Thr Asp Ile Asp Asp
                    20                  25                  30

Met Asn Trp Tyr Gln Gln Lys Pro Gly Lys Ala Pro Lys Leu Leu Ile
        35                  40                  45

Ser Leu Ala Ser Ile Leu Arg Pro Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Leu Pro Leu
                    85                  90                  95

Thr Phe Gly Gln Gly Thr Lys Leu Glu Ile Lys
            100                 105
```

<210> SEQ ID NO 394
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 394

```
Asp Ile Gln Met Thr Gln Ser Pro Ser Ser Leu Ser Ala Ser Val Gly
1               5                   10                  15

Asp Arg Val Thr Ile Thr Cys Gln Thr Ser Thr Asp Ile Asp Val Asp
                    20                  25                  30

Leu Asn Trp Tyr Gln Gln Lys Pro Gly Lys Ala Pro Lys Leu Leu Ile
        35                  40                  45

Ser Leu Ala Asn Thr Leu Arg Pro Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Phe Pro Leu
                    85                  90                  95

Thr Phe Gly Gln Gly Thr Lys Leu Glu Ile Lys
            100                 105
```

<210> SEQ ID NO 395
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 395

```
Asp Ile Gln Met Thr Gln Ser Pro Ser Ser Leu Ser Ala Ser Val Gly
1               5                   10                  15

Asp Arg Val Thr Ile Thr Cys Gln Thr Ser Gln Asp Ile Asp Asp Asp
                    20                  25                  30

Met Asn Trp Tyr Gln Gln Lys Pro Gly Lys Ala Pro Lys Leu Leu Ile
        35                  40                  45

Ser Leu Gly Ser Thr Leu Trp Pro Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Gly Asp Ser Leu Pro Leu
```

Thr Phe Gly Gln Gly Thr Lys Leu Glu Ile Lys
            100                 105

<210> SEQ ID NO 396
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 396

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Ser Thr Leu Trp Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Gly Glu Arg Phe Pro Leu
                85                  90                  95

Thr Phe Gly Gln Gly Thr Lys Leu Glu Ile Lys
            100                 105

<210> SEQ ID NO 397
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 397

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Ser Thr Leu Trp Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Gly Asp Ser Leu Pro Leu
                85                  90                  95

Thr Phe Gly Gln Gly Thr Lys Leu Glu Ile Lys
            100                 105

<210> SEQ ID NO 398
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 398

-continued

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Glu Asp
            20                  25                  30

Met Asn Trp Tyr Gln Gln Lys Pro Gly Lys Ala Pro Lys Leu Leu Ile
        35                  40                  45

Ser Ser Ala Asn Ile Leu Pro Arg Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Lys Glu Arg Leu Pro Leu
                85                  90                  95

Thr Phe Gly Gln Gly Thr Lys Leu Glu Ile Lys
            100                 105

<210> SEQ ID NO 399
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 399

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Met Asp
            20                  25                  30

Met Asn Trp Tyr Gln Gln Lys Pro Gly Lys Ala Pro Lys Leu Leu Ile
        35                  40                  45

Ser Gln Ala Ser Thr Leu Arg Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Thr Glu Arg Phe Pro Leu
                85                  90                  95

Thr Phe Gly Gln Gly Thr Lys Leu Glu Ile Lys
            100                 105

<210> SEQ ID NO 400
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 400

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Ala Asp
            20                  25                  30

Leu Asn Trp Tyr Gln Gln Lys Pro Gly Lys Ala Pro Lys Leu Leu Ile
        35                  40                  45

Ser Leu Gly Ser Thr Leu Arg Pro Gly Val Ser Ser Arg Phe Ser Gly
50                  55                  60

Ser Gly Ser Gly Thr Asp Phe Thr Phe Thr Ile Ser Ser Leu Gln Pro
65                  70                  75                  80

```
Glu Asp Phe Ala Thr Tyr Tyr Cys Leu Gln Val Asp Lys Phe Pro Leu
                85                  90                  95

Thr Phe Gly Gln Gly Thr Lys Leu Glu Ile Lys
            100                 105

<210> SEQ ID NO 401
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 401

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Val Asp
                20                  25                  30

Leu Asn Trp Tyr Gln Gln Lys Pro Gly Lys Ala Pro Lys Leu Leu Ile
            35                  40                  45

Ser Leu Ala Asn Thr Leu His Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Glu Arg Phe Pro Leu
                85                  90                  95

Thr Phe Gly Gln Gly Thr Lys Leu Glu Ile Lys
            100                 105

<210> SEQ ID NO 402
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 402

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp Asp
                20                  25                  30

Leu Asn Trp Tyr Gln Gln Lys Pro Gly Lys Ala Pro Lys Leu Leu Ile
            35                  40                  45

Ser His Gly Ser Thr Leu Gln His Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Asp Arg Leu Pro Leu
                85                  90                  95

Thr Phe Gly Gln Gly Thr Lys Leu Glu Ile Lys
            100                 105

<210> SEQ ID NO 403
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 403

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Gly Asn Thr Leu His Pro Gly Val Pro Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Ser Asp Arg Leu Pro Leu
                85                  90                  95

Thr Phe Gly Gln Gly Thr Lys Leu Glu Ile Lys
            100                 105

<210> SEQ ID NO 404
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 404

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Glu Asp
            20                  25                  30

Leu Asn Trp Tyr Gln Gln Lys Pro Gly Lys Ala Pro Lys Leu Leu Ile
        35                  40                  45

Ser Leu Ala Ser Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Asp Ser Phe Pro Leu
                85                  90                  95

Thr Phe Gly Gln Gly Thr Lys Leu Glu Ile Lys
            100                 105

<210> SEQ ID NO 405
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 405

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Ala Asn Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Ser Phe Pro Leu
                85                  90                  95

Thr Phe Gly Gln Gly Thr Lys Leu Glu Ile Lys
            100                 105

<210> SEQ ID NO 406
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 406

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Glu Asp
                20                  25                  30

Leu Asn Trp Tyr Gln Gln Lys Pro Gly Lys Ala Pro Lys Leu Leu Ile
            35                  40                  45

Ser Leu Ala Asn Asn Leu Arg Pro Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ile Glu Arg Leu Pro Leu
                85                  90                  95

Thr Phe Gly Gln Gly Thr Lys Leu Glu Ile Lys
            100                 105

<210> SEQ ID NO 407
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 407

Asp Ile Gln Met Thr Gln Ser Pro Ser Ser Leu Ser Ala Ser Val Gly
1               5                   10                  15

Asp Arg Val Thr Ile Thr Cys Gln Thr Ser Thr Asp Ile Asp Asp Asp
                20                  25                  30

Met Asn Trp Tyr Gln Gln Lys Pro Gly Lys Ala Pro Lys Leu Leu Ile
            35                  40                  45

Ser Leu Ala Asn Asn Leu Arg Pro Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Cys Asp Arg Leu Pro Leu
                85                  90                  95

Thr Phe Gly Gln Gly Thr Lys Leu Glu Ile Lys
            100                 105

<210> SEQ ID NO 408
<211> LENGTH: 107
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 408

Asp Ile Gln Met Thr Gln Ser Pro Ser Ser Leu Ser Ala Ser Val Gly
1               5                   10                  15

Asp Arg Val Thr Ile Thr Cys Gln Val Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Gly Ser Thr Leu Gln Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Leu Pro Leu
                85                  90                  95

Thr Phe Gly Gln Gly Thr Lys Leu Glu Ile Lys
            100                 105

<210> SEQ ID NO 409
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 409

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Gly Ser Lys Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Asp Ser Phe Pro Leu
                85                  90                  95

Thr Phe Gly Gln Gly Thr Lys Leu Glu Ile Lys
            100                 105

<210> SEQ ID NO 410
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 410

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Glu Asp
            20                  25                  30

Leu Asn Trp Tyr Gln Gln Lys Pro Gly Lys Ala Pro Lys Leu Leu Ile
        35                  40                  45

Ser Leu Ala Ser Lys Leu Arg Pro Gly Val Pro Ser Arg Phe Ser Gly 50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Ser Asp Arg Phe Pro Leu
                 85                  90                  95

Thr Phe Gly Gln Gly Thr Lys Leu Glu Ile Lys
            100                 105

<210> SEQ ID NO 411
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 411

Asp Ile Gln Met Thr Gln Ser Pro Ser Ser Leu Ser Ala Ser Val Gly
 1               5                  10                  15

Asp Arg Val Thr Ile Thr Cys Gln Ala Ser Thr Asp Ile Asp Val Asp
                 20                  25                  30

Leu Asn Trp Tyr Gln Gln Lys Pro Gly Lys Ala Pro Lys Leu Leu Ile
             35                  40                  45

Ser Gln Ala Ser Thr Leu Pro Pro Gly Val Pro Ser Arg Phe Ser Gly
         50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Ser Asp Ser Leu Pro Leu
                 85                  90                  95

Thr Phe Gly Gln Gly Thr Lys Leu Glu Ile Lys
            100                 105

<210> SEQ ID NO 412
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 412

Asp Ile Gln Met Thr Gln Ser Pro Ser Ser Leu Ser Ala Ser Val Gly
 1               5                  10                  15

Asp Arg Val Thr Ile Thr Cys Gln Ala Ser Thr Asp Ile Asp Asp Asp
                 20                  25                  30

Leu Asn Trp Tyr Gln Gln Lys Pro Gly Lys Ala Pro Lys Leu Leu Ile
             35                  40                  45

Ser Leu Ala Ser Thr Leu Arg Pro Gly Val Pro Ser Arg Phe Ser Gly
         50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Ser Asp Arg Phe Pro Leu
                 85                  90                  95

Thr Phe Gly Gln Gly Thr Lys Leu Glu Ile Lys
            100                 105

<210> SEQ ID NO 413
<211> LENGTH: 107
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 413

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp Asp
            20                  25                  30

Met Asn Trp Tyr Gln Gln Lys Pro Gly Lys Ala Pro Lys Leu Leu Ile
        35                  40                  45

Ser Leu Gly Ser Lys Leu Trp Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Asn Leu Pro Leu
                85                  90                  95

Thr Phe Gly Gln Gly Thr Lys Leu Glu Ile Lys
            100                 105

<210> SEQ ID NO 414
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 414

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Thr Asp
            20                  25                  30

Met Asn Trp Tyr Gln Gln Lys Pro Gly Lys Ala Pro Lys Leu Leu Ile
        35                  40                  45

Tyr Asp Ala Asn Thr Leu Arg Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Lys Asp Arg Leu Pro Leu
                85                  90                  95

Thr Phe Gly Gln Gly Thr Lys Leu Glu Ile Lys
            100                 105

<210> SEQ ID NO 415
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 415

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Val Asp
            20                  25                  30

Met Asn Trp Tyr Gln Gln Lys Pro Gly Lys Ala Pro Lys Leu Leu Ile
        35                  40                  45

Ser Leu Ala Ser Lys Leu Arg Pro Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Asp Ser Phe Pro Leu
                85                  90                  95

Thr Phe Gly Gln Gly Thr Lys Leu Glu Ile Lys
            100                 105

<210> SEQ ID NO 416
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 416

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Ala Asp
                20                  25                  30

Leu Asn Trp Tyr Gln Gln Lys Pro Gly Lys Ala Pro Lys Leu Leu Ile
            35                  40                  45

Ser Leu Ala Ser Lys Leu Arg Pro Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Val Asp Ser Phe Pro Leu
                85                  90                  95

Thr Phe Gly Gln Gly Thr Lys Leu Glu Ile Lys
            100                 105

<210> SEQ ID NO 417
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 417

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Asp Asp
                20                  25                  30

Met Asn Trp Tyr Gln Gln Lys Pro Gly Lys Ala Pro Lys Leu Leu Ile
            35                  40                  45

Ser Leu Ala Ser Thr Leu Arg Pro Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Gly Asp Ser Leu Pro Leu
                85                  90                  95

Thr Phe Gly Gln Gly Thr Lys Leu Glu Ile Lys
            100                 105

<210> SEQ ID NO 418

```
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 418

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Gly Ser Thr Leu Arg Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Ser Leu Pro Leu
                85                  90                  95

Thr Phe Gly Gln Gly Thr Lys Leu Glu Ile Lys
            100                 105

<210> SEQ ID NO 419
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 419

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Glu Asp
            20                  25                  30

Leu Asn Trp Tyr Gln Gln Lys Pro Gly Lys Ala Pro Lys Leu Leu Ile
        35                  40                  45

Ser Leu Ala Asn Asn Leu Arg Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Arg Phe Pro Leu
                85                  90                  95

Thr Phe Gly Gln Gly Thr Lys Leu Glu Ile Lys
            100                 105

<210> SEQ ID NO 420
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 420

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30
```

Gly Val Ser Trp Ile Arg Gln Pro Gly Lys Gly Leu Glu Trp Leu
            35                  40                  45

Gly Leu Ile Trp Gly Gly Gly Asp Thr Tyr Tyr Asn Ser Pro Leu Lys
 50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Lys Gln Arg Thr Leu Trp Gly Tyr Asp Leu Tyr Gly Met Asp Tyr Trp
                100                 105                 110

Gly Gln Gly Thr Leu Val Thr Val Ser Ser
            115                 120

<210> SEQ ID NO 421
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 421

Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ser Glu Phe
                 20                  25                  30

Gly Val Ser Trp Ile Arg Gln Pro Pro Gly Lys Gly Leu Glu Trp Ile
            35                  40                  45

Gly Leu Ile Trp Gly Gly Gly Asp Thr Tyr Tyr Asn Ser Pro Leu Lys
 50                  55                  60

Ser Arg Leu Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Lys Gln Arg Asn Leu Trp Ala Tyr Asp Leu Tyr Gly Met Asp Tyr Trp
                100                 105                 110

Gly Gln Gly Thr Leu Val Thr Val Ser Ser
            115                 120

<210> SEQ ID NO 422
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 422

Glu Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ser Asp Tyr
                 20                  25                  30

Gly Val Ser Trp Ile Arg Gln Pro Pro Gly Lys Gly Leu Glu Trp Leu
            35                  40                  45

Gly Leu Ile Trp Gly Gly Gly Asp Thr Tyr Tyr Asn Ser Pro Leu Lys
 50                  55                  60

Ser Arg Leu Thr Ile Ser Lys Asp Asn Ser Lys Ser Gln Val Ser Leu
 65                  70                  75                  80

```
Lys Leu Ser Ser Val Thr Ala Ala Asp Thr Ala Val Tyr Tyr Cys Ala
                85                  90                  95

Lys Gln Arg Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 423
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 424
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 424

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Asn Asn Val Trp Gly Tyr Asp Leu Tyr Gly Met Asp Tyr Trp
            100                 105                 110

Gly Gln Gly Thr Leu Val Thr Val Ser Ser
        115                 120
```

<210> SEQ ID NO 425
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 425

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Glu Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Val Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 426
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 426

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Glu Phe
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Thr Asn Leu Trp Ala Tyr Asp Leu Tyr Ser Met Asp Tyr Trp
            100                 105                 110

Gly Gln Gly Thr Leu Val Thr Val Ser Ser
        115                 120

<210> SEQ ID NO 427
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide -continued

<400> SEQUENCE: 427

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Ile
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Asn Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 428
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 428

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Gly Asp Thr Tyr Tyr Asn Ser Pro Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Leu Val Thr Val Ser Ser
        115                 120

<210> SEQ ID NO 429
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 429

Asp Thr Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Asp Val Asp
            20                  25                  30

Met Asn Trp Tyr Gln Gln Lys Pro Gly Lys Pro Pro Lys Leu Leu Ile

```
                35                  40                  45
Ser Gln Gly Asn Thr Leu Arg Pro Gly Val Pro Ser Arg Phe Ser Ser
        50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Ser Asp Asn Leu Pro Leu
                85                  90                  95

Thr Phe Gly Gln Gly Thr Lys Leu Glu Ile Lys
            100                 105

<210> SEQ ID NO 430
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(9)
<223> OTHER INFORMATION: Any amino acid

<400> SEQUENCE: 430

Cys Xaa Xaa Xaa Xaa Xaa Xaa Xaa Xaa
1               5

<210> SEQ ID NO 431
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Phe or Gly
<220> FEATURE:
<221> NAME/KEY: MOD_RES
<222> LOCATION: (30)..(30)
<223> OTHER INFORMATION: Ser, Arg, Gly, Asn, Ile, Thr, Met or Lys
<220> FEATURE:
<221> NAME/KEY: MOD_RES
<222> LOCATION: (31)..(31)
<223> OTHER INFORMATION: Asp, Glu, His, Tyr, Asn, Gly, Val or Gln
<220> FEATURE:
<221> NAME/KEY: MOD_RES
<222> LOCATION: (32)..(32)
<223> OTHER INFORMATION: Tyr, Asp, Asn, His, Ser or Phe
<220> FEATURE:
<221> NAME/KEY: MOD_RES
<222> LOCATION: (48)..(48)
<223> OTHER INFORMATION: Leu or Ile
<220> FEATURE:
<221> NAME/KEY: MOD_RES
<222> LOCATION: (50)..(50)
<223> OTHER INFORMATION: Leu, Val, Arg, Gly, Phe, Trp, Met or Ile
<220> FEATURE:
<221> NAME/KEY: MOD_RES
<222> LOCATION: (52)..(52)
<223> OTHER INFORMATION: Trp, Gly, Leu, Tyr, Ser, Arg, Glu or Ala
<220> FEATURE:
<221> NAME/KEY: MOD_RES
<222> LOCATION: (53)..(53)
<223> OTHER INFORMATION: Gly, Val, Arg, Trp, Leu, Asp or Ser
<220> FEATURE:
<221> NAME/KEY: MOD_RES
<222> LOCATION: (54)..(54)
<223> OTHER INFORMATION: Gly, Arg, Val, Trp, Ser, Leu, Ile, Glu or Asp
<220> FEATURE:
<221> NAME/KEY: MOD_RES
<222> LOCATION: (56)..(56)
```

```
<223> OTHER INFORMATION: Asp, Gly, Glu, Val, Ser, Ala, Lys, Gln or Tyr
<220> FEATURE:
<221> NAME/KEY: MOD_RES
<222> LOCATION: (58)..(58)
<223> OTHER INFORMATION: Tyr, Phe, Ser, Asp, Val, Thr or His
<220> FEATURE:
<221> NAME/KEY: MOD_RES
<222> LOCATION: (68)..(68)
<223> OTHER INFORMATION: Thr or Val
<220> FEATURE:
<221> NAME/KEY: MOD_RES
<222> LOCATION: (70)..(70)
<223> OTHER INFORMATION: Ser or Thr
<220> FEATURE:
<221> NAME/KEY: MOD_RES
<222> LOCATION: (97)..(97)
<223> OTHER INFORMATION: Lys or Arg
<220> FEATURE:
<221> NAME/KEY: MOD_RES
<222> LOCATION: (98)..(98)
<223> OTHER INFORMATION: Gln, Thr, Asp, Lys, Pro, His, Ala, Tyr or Val
<220> FEATURE:
<221> NAME/KEY: MOD_RES
<222> LOCATION: (99)..(99)
<223> OTHER INFORMATION: Arg, Thr, Met, Ser, Ile, Trp, Pro, Asn or Lys
<220> FEATURE:
<221> NAME/KEY: MOD_RES
<222> LOCATION: (100)..(100)
<223> OTHER INFORMATION: Thr, Lys, Arg, Asn, Tyr, Trp, Val or Met
<220> FEATURE:
<221> NAME/KEY: MOD_RES
<222> LOCATION: (101)..(101)
<223> OTHER INFORMATION: Leu, Ala, Met, Arg, Ile, Gly, Trp, Gln, His or
      Phe
<220> FEATURE:
<221> NAME/KEY: MOD_RES
<222> LOCATION: (102)..(102)
<223> OTHER INFORMATION: Trp, Ser, Gly, Arg, Val, Leu, Lys, Ala, Tyr or
      Thr
<220> FEATURE:
<221> NAME/KEY: MOD_RES
<222> LOCATION: (103)..(103)
<223> OTHER INFORMATION: Gly, Ala, Arg, Val, Thr, Pro, Asn, Glu or Asp
<220> FEATURE:
<221> NAME/KEY: MOD_RES
<222> LOCATION: (104)..(104)
<223> OTHER INFORMATION: Tyr, Phe, Asn, Asp, His or Ser
<220> FEATURE:
<221> NAME/KEY: MOD_RES
<222> LOCATION: (105)..(105)
<223> OTHER INFORMATION: Asp, Gln, Lys, His, Ala, Val or Leu
<220> FEATURE:
<221> NAME/KEY: MOD_RES
<222> LOCATION: (106)..(106)
<223> OTHER INFORMATION: Leu, Gly, Ile, Phe, Ser or Met
<220> FEATURE:
<221> NAME/KEY: MOD_RES
<222> LOCATION: (107)..(107)
<223> OTHER INFORMATION: Tyr, Asn, Asp, Val or Ser
<220> FEATURE:
<221> NAME/KEY: MOD_RES
<222> LOCATION: (108)..(108)
<223> OTHER INFORMATION: Gly, Ala, Arg, Asp or Trp

<400> SEQUENCE: 431

Glu Val Gln Leu Gln Glu Ser Gly Pro Gly Leu Val Lys Pro Ser Glu
1               5                   10                  15

Thr Leu Ser Leu Thr Cys Thr Val Ser Gly Xaa Ser Leu Xaa Xaa Xaa
            20                  25                  30

Gly Val Ser Trp Ile Arg Gln Pro Pro Gly Lys Gly Leu Glu Trp Xaa
        35                  40                  45

Gly Xaa Ile Xaa Xaa Xaa Gly Xaa Thr Xaa Tyr Asn Ser Pro Leu Lys
    50                  55                  60

Ser Arg Leu Xaa Ile Xaa Lys Asp Asn Ser Lys Ser Gln Val Ser Leu
```

```
                65                  70                  75                  80
Lys Leu Ser Ser Val Thr Ala Ala Asp Thr Ala Val Tyr Tyr Cys Ala
                        85                  90                  95

Xaa Xaa Xaa Xaa Xaa Xaa Xaa Xaa Xaa Xaa Xaa Xaa Met Asp Tyr Trp
            100                 105                 110

Gly Gln Gly Thr Leu Val Thr Val Ser Ser
        115                 120
```

<210> SEQ ID NO 432
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Thr or Ile
<220> FEATURE:
<221> NAME/KEY: MOD_RES
<222> LOCATION: (4)..(4)
<223> OTHER INFORMATION: Val or Met
<220> FEATURE:
<221> NAME/KEY: MOD_RES
<222> LOCATION: (24)..(24)
<223> OTHER INFORMATION: Ile or Gln
<220> FEATURE:
<221> NAME/KEY: MOD_RES
<222> LOCATION: (25)..(25)
<223> OTHER INFORMATION: Thr or Ala
<220> FEATURE:
<221> NAME/KEY: MOD_RES
<222> LOCATION: (27)..(27)
<223> OTHER INFORMATION: Thr or Gln
<220> FEATURE:
<221> NAME/KEY: MOD_RES
<222> LOCATION: (30)..(30)
<223> OTHER INFORMATION: Asp, Pro, Tyr, Asn, Gln or Leu
<220> FEATURE:
<221> NAME/KEY: MOD_RES
<222> LOCATION: (31)..(31)
<223> OTHER INFORMATION: Val, Pro, Ala or Phe
<220> FEATURE:
<221> NAME/KEY: MOD_RES
<222> LOCATION: (32)..(32)
<223> OTHER INFORMATION: Asp, Ala, Pro, Asn, Tyr or Val
<220> FEATURE:
<221> NAME/KEY: MOD_RES
<222> LOCATION: (43)..(43)
<223> OTHER INFORMATION: Pro or Ala
<220> FEATURE:
<221> NAME/KEY: MOD_RES
<222> LOCATION: (49)..(49)
<223> OTHER INFORMATION: Ser or Tyr
<220> FEATURE:
<221> NAME/KEY: MOD_RES
<222> LOCATION: (50)..(50)
<223> OTHER INFORMATION: Gln, His, Pro, Lys or Arg
<220> FEATURE:
<221> NAME/KEY: MOD_RES
<222> LOCATION: (51)..(51)
<223> OTHER INFORMATION: Gly or Ala
<220> FEATURE:
<221> NAME/KEY: MOD_RES
<222> LOCATION: (52)..(52)
<223> OTHER INFORMATION: Asn or Ser
<220> FEATURE:
<221> NAME/KEY: MOD_RES
<222> LOCATION: (53)..(53)
<223> OTHER INFORMATION: Thr, Ser, Ile, Met or Ala
<220> FEATURE:
<221> NAME/KEY: MOD_RES
<222> LOCATION: (55)..(55)
<223> OTHER INFORMATION: Arg, Leu, Pro, Trp, Gln or His

```
<220> FEATURE:
<221> NAME/KEY: MOD_RES
<222> LOCATION: (56)..(56)
<223> OTHER INFORMATION: Pro, Leu, Ser or Thr
<220> FEATURE:
<221> NAME/KEY: MOD_RES
<222> LOCATION: (64)..(64)
<223> OTHER INFORMATION: Ser or Gly
<220> FEATURE:
<221> NAME/KEY: MOD_RES
<222> LOCATION: (89)..(89)
<223> OTHER INFORMATION: Leu or Gln
<220> FEATURE:
<221> NAME/KEY: MOD_RES
<222> LOCATION: (91)..(91)
<223> OTHER INFORMATION: Ser, Trp, Arg, Lys, Gly or Val
<220> FEATURE:
<221> NAME/KEY: MOD_RES
<222> LOCATION: (92)..(92)
<223> OTHER INFORMATION: Asp, Gly, Lys or Val
<220> FEATURE:
<221> NAME/KEY: MOD_RES
<222> LOCATION: (93)..(93)
<223> OTHER INFORMATION: Asn, Glu, Arg, Met or Gly
<220> FEATURE:
<221> NAME/KEY: MOD_RES
<222> LOCATION: (94)..(94)
<223> OTHER INFORMATION: Leu, Gly, Asp or Phe
<220> FEATURE:
<221> NAME/KEY: MOD_RES
<222> LOCATION: (95)..(95)
<223> OTHER INFORMATION: Pro or Ala

<400> SEQUENCE: 432

Asp Xaa Gln Xaa Thr Gln Ser Pro Ser Ser Leu Ser Ala Ser Val Gly
1               5                   10                  15

Asp Arg Val Thr Ile Thr Cys Xaa Xaa Ser Xaa Asp Ile Xaa Xaa Xaa
            20                  25                  30

Met Asn Trp Tyr Gln Gln Lys Pro Gly Lys Xaa Pro Lys Leu Leu Ile
        35                  40                  45

Xaa Xaa Xaa Xaa Xaa Leu Xaa Xaa Gly Val Pro Ser Arg Phe Ser Xaa
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Xaa Gln Xaa Xaa Xaa Xaa Xaa Leu
                85                  90                  95

Thr Phe Gly Gln Gly Thr Lys Leu Glu Ile Lys
            100                 105

<210> SEQ ID NO 433
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 433

Asp Ile Gln Met Thr Gln Ser Pro Ser Ser Leu Ser Ala Ser Val Gly
1               5                   10                  15

Asp Arg Val Thr Ile Thr Cys Gln Ala Ser Thr Asp Ile Asp Asp Asp
            20                  25                  30

Leu Asn Trp Tyr Gln Gln Lys Pro Gly Lys Ala Pro Lys Leu Leu Ile
        35                  40                  45

Ser Leu Gly Ser Thr Leu Arg Pro Gly Val Pro Ser Arg Phe Ser Gly
50                  55                  60
```

-continued

```
Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Ser Asp Ser Leu Pro Leu
                 85                  90                  95

Thr Phe Gly Gln Gly Thr Lys Leu Glu Ile Lys Arg
            100                 105
```